United States Patent
Torrens et al.

(10) Patent No.: US 8,207,156 B2
(45) Date of Patent: Jun. 26, 2012

(54) SUBSTITUTED PYRAZOLINE COMPOUNDS, THEIR PREPARATION AND USE AS MEDICAMENTS

(75) Inventors: Antoni Torrens, Barcelona (ES); Jordi Quintana, Barcelona (ES); Helmut Buschmann, Barcelona (ES); Albert Dordal, Barcelona (ES); Josep Mas, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 13/036,533

(22) Filed: Feb. 28, 2011

(65) Prior Publication Data
US 2011/0160181 A1 Jun. 30, 2011

Related U.S. Application Data

(62) Division of application No. 11/457,730, filed on Jul. 14, 2006, now Pat. No. 7,897,589.

(60) Provisional application No. 60/705,433, filed on Aug. 5, 2005.

(30) Foreign Application Priority Data

Jul. 15, 2005 (EP) .................................. 05384018

(51) Int. Cl.
A61K 31/397 (2006.01)
A61K 31/55 (2006.01)
A61K 31/5377 (2006.01)
A61K 31/496 (2006.01)
A61K 31/473 (2006.01)
A61K 31/4725 (2006.01)
A61K 31/454 (2006.01)
A61K 31/4155 (2006.01)

(52) U.S. Cl. .......... 514/210.18; 514/217.09; 514/236.5; 514/254.05; 514/296; 514/307; 514/326; 514/406

(58) Field of Classification Search ............ 514/210.18, 514/326, 236.5, 406, 217.09, 254.05, 307, 514/296
See application file for complete search history.

(56) References Cited

U.S. PATENT DOCUMENTS

| | | | |
|---|---|---|---|
| 5,017,596 A | 5/1991 | Colombo et al. | |
| 5,849,931 A | 12/1998 | Frigola-Constansa et al. | |
| 6,118,009 A | 9/2000 | Torrens-Jover et al. | |
| 6,187,930 B1 | 2/2001 | Torrens-Jover et al. | |
| 6,410,582 B1 | 6/2002 | Merce-Vidal et al. | |
| 6,509,367 B1 | 1/2003 | Martin et al. | |
| 6,610,737 B1 | 8/2003 | Garzon et al. | |
| 6,956,033 B2 | 10/2005 | Ogaw et al. | |
| 2002/0058816 A1 | 5/2002 | Kordik et al. | |
| 2002/0156104 A1 | 10/2002 | Adams et al. | |
| 2003/0022925 A1 | 1/2003 | Merce-Vidal et al. | |
| 2003/0153569 A1 | 8/2003 | Adams et al. | |
| 2004/0092535 A1 | 5/2004 | Barsanti et al. | |
| 2005/0137251 A1 | 6/2005 | Garzon et al. | |
| 2005/0171179 A1 | 8/2005 | Lange et al. | |
| 2005/0222138 A1 | 10/2005 | Ohhata et al. | |
| 2005/0282798 A1 | 12/2005 | Lazzari et al. | |
| 2006/0020010 A1 | 1/2006 | Altisen et al. | |
| 2006/0052315 A1 | 3/2006 | Leung et al. | |
| 2006/0106014 A1 | 5/2006 | Boddupalli et al. | |
| 2006/0128673 A1 | 6/2006 | Firnges et al. | |
| 2006/0172019 A1 | 8/2006 | Ralston et al. | |
| 2006/0189658 A1 | 8/2006 | Cuberes Altisen et al. | |
| 2006/0194843 A1 | 8/2006 | Berdini et al. | |
| 2007/0073056 A1 | 3/2007 | Torrens et al. | |
| 2009/0131497 A1 | 5/2009 | Torrens Jover et al. | |

FOREIGN PATENT DOCUMENTS

| | | |
|---|---|---|
| GB | 1209326 | 10/1970 |
| JP | 02-117605 | 5/1990 |
| WO | 8805046 A2 | 7/1988 |
| WO | 8806583 A1 | 9/1988 |
| WO | 9203421 A2 | 3/1992 |
| WO | 0076503 A1 | 12/2000 |
| WO | 02080909 A1 | 10/2002 |
| WO | 2004060882 A1 | 7/2004 |
| WO | 2004078261 A1 | 9/2004 |
| WO | 2006077414 A1 | 7/2006 |
| WO | 2006077419 A1 | 7/2006 |
| WO | 2006077425 A1 | 7/2006 |
| WO | 2006077428 A1 | 7/2006 |

OTHER PUBLICATIONS

Vippagunta et al., Crystalline Solids, Advanced Drug Delivery Reviews, 48, pp. 3-26, 2001.*
Anthony R. West, Solid Solutions, Solid State Chemistry and its applications, pp. 358 & 365, 1988.*
"Autism," [retrieved on May 14, 2008]. Retrieved online via Internet, URL: http://www.nlm.nih.gov/medlineplus/autism.html.*
"Anxiety," [retrieved on May 14, 2008]. Retrieved online via Internet, URL: http://www.nlm.nih.gov/medlineplus/anxiety.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
International Search Report for International Application PCT/EP2005/001659, dated Jul. 29, 2005.
HTTP://mojo.calyx.net/~olsen/MEDICAL/IOM/iom115054635.html (25 pages), 2007.
HTTP:/www.norml.org/index.cfm?Group_ID=7282&wtm_format=print (2 pages), 2007.
HTTP:/www.nlm.nih.gov/medlineplus/ency/article.001553.htm (3 pages), 2011.

(Continued)

Primary Examiner — Kamal Saeed
Assistant Examiner — Kristin Bianchi
(74) Attorney, Agent, or Firm — Banner & Witcoff, Ltd.

(57) ABSTRACT

The present invention relates to substituted pyrazoline compounds, methods for their preparation, medicaments comprising these compounds as well as their use for the preparation of a medicament for the treatment of humans and animals.

1 Claim, No Drawings

OTHER PUBLICATIONS

HTTP:/www.webmd.com/diet/tc/Obesity-Overview (3 pages), 2011.

HTTP:/health.yahoo.com/topic/addiction/abuse/article.pt/Psychology_Today_articles_pto_term_alcohol (6 pages), 2007.

HTTP:/www.mayoclinic.com/health/alzheimers-disease/DS00161/DSECTION=3 (15 pages), 2011.

HTTP:/www.medindia.net/patients/patientinfo/Alzheimers_treatment.htm (2 pages), 2011.

Alpermann, H.G. et al. "Pharmacological Effects of Hoe 249: A New Potential Antidepressant" Drug Development Research vol. 25: pp. 267-282 (1992).

Alzheimers Association, Alzheimers Disease Facts & Figures 2007 (2 pages).

Chan et al., "N-substituted Pyrazoline-type Insecticides" ACS Symposium Series, No. 800, pp. 144-155 (2002).

Chawla et al., "Challenges in Polymorphism of Pharmaceuticals", CRIPS vol. 5, No. 1, Jan.-Mar. 2004.

Columbo, G. et al. "Appetite Suppression and Weight Loss after the Cannabinoid Antagonist SR 141716" Life Sciences, vol. 63, No. 8, pp. 113-117 (1998).

Compton, David R. et al. "In-Vivo Characterization of a Specific Cannabinoid Receptor Antagonist (SR141716A): Inhibition of Δ9—Tetrahydracannabinol-Induced Responsed and Apparent Agonist Activity" Journal of Pharmacology and Experimental Thearpeutics, vol. 277, No. 2, pp. 586-594 (1996).

Desmedt, L.K.C. et al. "Anticonvulsive Properties of Cinnarizine and Flunarizine in Rats and Mice" Arzneim-Forsch (Drug Res) vol. 25, No. 9 pp. 1408-1413 (1975).

Dujardin G. et al. "A Straightforward Route to E-γ-Aryl-α-oxobutenoic Esters by One-step Acid-Catalysed Crononisation of Pyruvates" Synlett, No. 1, pp. 147-149 (2001).

Hollister, L.E. "Health Aspects in Cannabis" Pharmocological Review, vol. 38, No. 1 pp. 1-20 (1986).

Howlett, A.C. et al. "International Union of Pharmacology XXVII, Classification of Cannabinoid Receptors" Pharmacological Reviews vol. 54, pp. 161-202 (2002).

Lin S. et al. "Regioselective Friedel-Crafts Acylation with Unsymmetrically Substituted Furandicarboxylic Acid Anhydride and Furan Acid Chloride: Syntheses of 4-Substituted 3-Arylcarbonyl-2-Phenylfuran and 3-Substituted 4-Arlycarbonly-2-Phenylfuran" Heterocycles vol. 55, No. 2, pp. 265-277 (2001).

Megard et al. "A Co-Culture Based Model of Human Blood-Brain Barrier: Application to Active Transport of Indinavire and In-Vivo-in-Vitro Correlation", Brain Research vol. 927, pp. 153-167, (2002).

Meier et al. "Insecticidal Dihydropyrazoles with Reduced Lipophilicity" ACS Symposium Series No. 504 pp. 313-326 (1992).

Meyer et al., "1,5-Diaryl-2,3-Pyrrolidinediones—Phenylhydrazine Derivatives" Jnl. Org. Chem. vol. 22: pp. 1565-1567 (1957).

Muccioli G.G. et al. "Latest Advances in Cannabinoid Receptor Antagonists and Inverse Agonists" Expert Opinion on Therapeutic Patents, vol. 16, No. 10, pp. 1405-1423 (2006).

Murphy L. et al. "Consroe and Sandyk Potential Role of Cannabinoids for Therapy of Neurological Disorders" pp. 459-524 CRC Press (1992).

Newman et al., "Solid-state analysis of teh active pharmaceutical ingredient in drug products", DDT vol. 8, No. 19, pp. 898-905 (Oct. 2003).

Pascual Alfons, "Synthese des 5-[(Acetylhydrazono)-(4-chlorophenyl)-methyl]thiophen-2-yl-esters der Trifluormethethansulfonsäure" J. Prakt. Chem 341, No. 7 pp. 695-700 (1999).

Pearson D.E. and Buehler, C.A. Friedel-Crafts Acylations with Little or No Catalysts' Synthesis No. 10, pp. 533-542 (Oct. 1972).

Rao, P.D. et al. "Rational Syntheses of Porphyrins Bearing up to Four Different Meso Substituents" J. Org. Chem. vol. 65 pp. 7323-7344 (2000).

Ross, Ruth A. et al. "Agonist-Inverse Agonist Characterization at CB1 and CB2 Cannanbinoid Receptors of L-759633, L-759656 and AM630" British Journal of Pharmacology vol. 126, pp. 665-672 (1999).

Seth, Renu et al. "Progress in Drug Research" Chemistry and Pharmacology of Cannabis, vol. 36, pp. 71-115 (1991).

Slavinska, B. et al. "New Way for the Preparation of 4-Phenyl-2-Oxobytyric Acid Ethyl Ester" Synthetic Communications vol. 26 No. 11 pp. 2229-2233 (1996).

Tamura, Kenji et al. "One-Pot Synthesis of Trifluoroacetimidoly Halides" Jnl. Org. Chem. vol. 58 pp. 32-35 (1993).

Thomas, B.F.et al., "Synthesis of Long-Chain Amide Analogs of the Cannabinoid CB1 Receptor Antagonist N-(piperidinyl)-5-(4-chlorophenly)-1-(2,4-dichlorophenyl)-4-methyl-1H-pyrazole-3-carboxamide(SR141716) with Unique Binding Selctives and Pharmacological Activities", Bioorganic & Medicinal Chemistry, vol. 13, No. 18, pp. 5463-5474 (2005).

Torrens et al., 2007:82492 CAPLUS (3 pages).

Woolfe, G. et al., "The Evaluation of the Analgesic Action of Pethidine Hydrochloride (Demerol)", Jnl of Pharmacology and Experimental Therapeutics vol. 80 pp. 300-307 (1944).

Zips et al. "New Anticancer Agents: In-Vitro and In-Vivo" In Vivo vol. 19, pp. 1-7 (2005).

* cited by examiner

SUBSTITUTED PYRAZOLINE COMPOUNDS, THEIR PREPARATION AND USE AS MEDICAMENTS

CROSS-REFERENCE TO RELATED APPLICATIONS

This application is a divisional of U.S. patent application Ser. No. 11/457,730, filed Jul. 14, 2006, now U.S. Pat. No. 7,897,589, which claims priority to U.S. Provisional Patent Application Ser. No. 60/705,433, filed Aug. 5, 2005, and European Patent Application No. 05384018, filed Jul. 15, 2005. All of these applications are hereby incorporated by reference in their entireties.

FIELD OF THE INVENTION

The present invention relates to substituted pyrazoline compounds, methods for their preparation, medicaments comprising these compounds as well as their use for the preparation of a medicament for the treatment of humans and animals.

BACKGROUND OF THE INVENTION

Cannabinoids are compounds, which are derived from the cannabis sativa plant which is commonly known as marijuana. The most active chemical compound of the naturally occurring cannabinoids is tetrahydrocannabinol (THC), particularly $\Delta^9$-THC.

These naturally occurring cannabinoids as well as their synthetic analogues promote their physiological effects via binding to specific G-coupled receptors, the so-called cannabinoid-receptors.

At present, two distinct types of receptors that bind both the naturally occurring and synthetic cannabinoids have been identified and cloned. These receptors, which are designated $CB_1$ and $CB_2$ are involved in a variety of physiological or pathophysiological processes in humans and animals, e.g. processes related to the central nervous system, immune system, cardiovascular system, endocrinous system, respiratory system, the gastrointestinal tract or to reproduction, as described for example, in Hollister, Pharm. Rev. 38, 1986, 1-20; Reny and Singha, Prog. Drug. Res., 36, 71-114, 1991; Consroe and Sandyk, in Marijuana/Cannabinoids, Neurobiology and Neurophysiology, 459, Murphy L. and Barthe A. Eds., CRC Press, 1992.

Therefore, compounds, which have a high binding affinity for these cannabinoid receptors and which are suitable for modulating these receptors are useful in the prevention and/or treatment of cannabinoid-receptor related disorders.

In particular, the $CB_1$-receptor is involved in many different food-intake related disorders such as bulimia or obesity, including obesity associated with type II diabetes (non-insulin-dependent diabetes) and thus, compounds suitable for regulating this receptor may be used in the prophylaxis and/or treatment of these disorders.

SUMMARY OF THE INVENTION

Thus, it was an object of the present invention to provide novel compounds for use as active substances in medicaments. In particular, these active substances should be suitable for the modulation of cannabinoid receptors, more particularly for the modulation of cannabinoid 1 ($CB_1$) receptors.

Said object was achieved by providing the substituted pyrazoline compounds of general formula I given below, their stereoisomers, corresponding salts and corresponding solvates thereof.

It has been found that these compounds have a high affinity for cannabinoid receptors, particularly for the $CB_1$-receptor, and that they act as modulators e.g. antagonists, inverse agonists or agonists on these receptors. They are therefore suitable for the prophylaxis and/or treatment of various disorders related to the central nervous system, the immune system, the cardiovascular system, the endocrinous system, the respiratory system, the gastrointestinal tract or reproduction in humans and/or animals, preferably humans including infants, children and grown-ups.

DETAILED DESCRIPTION OF THE INVENTION

Thus, in one of its aspects the present invention relates to substituted pyrazoline compounds of general formula I,

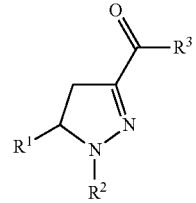

I wherein
$R^1$ represents an unsubstituted or at least mono-substituted phenyl radical;
$R^2$ represents an unsubstituted or at least mono-substituted phenyl radical;
$R^3$ represents an unsubstituted or at least mono-substituted radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl,
a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$C_{1-6}$-alkyl substituted with one or more hydroxy groups, —$C_{1-6}$-alkyl substituted with one or more chlorine atoms, —$C_{1-6}$-alkyl substituted with one or more methoxy and/or ethoxy groups, —O—$C_{1-6}$-alkyl substituted with one or more methoxy and/or ethoxy groups, —S—$C_{1-6}$-alkyl, —C(=O)—O—$C_{1-6}$-alkyl, —O—C(=O)—$C_{1-6}$-alkyl, —SCF$_3$, —SCF$_2$H, —SCFH$_2$, —SH, —SO$_3$H, —NH—C(=O)—$C_{1-6}$-alkyl, —N($C_{1-6}$-alkyl)-C(=O)—$C_{1-6}$-alkyl, —CHO, —C(=O)—$C_{1-6}$-perfluoroalkyl, —C(=S)—NH—$C_{1-6}$-alkyl, —CF$_2$H, —CFH$_2$, —C(=O)—NH—NR$^C$R$^D$, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —NR$^A$R$^B$, —($C_{1-5}$-alkylene)-NR$^A$R$^B$, —S(=O)$_2$—NH—$C_{1-6}$-alkyl, —S(=O)$_2$—NH-phenyl, cyclopropyl, cyclobutyl, cyclopentyl, cyclohexyl, pyrrolidinyl, piperidinyl, thiophenyl, phenoxy and benzyl;

whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —$C_{1-6}$-alkyl, —O—$C_{1-6}$-alkyl, —O—CF$_3$ and —S—CF$_3$;

a —NR$^4$R$^5$ moiety or a —O—R$^6$ moiety;

R$^4$ represents a hydrogen atom or a saturated or unsaturated, unsubstituted or at least mono-substituted aliphatic radical;

R$^5$ represents an unsubstituted or at least mono-substituted radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —O-methyl, —O-ethyl, —O-n-propyl, —O-isopropyl, —O-n-butyl, —O-isobutyl, —O-tert-butyl, —O-n-pentyl and —O-n-hexyl;

a substituted radical selected from the group consisting of methyl, ethyl, n-propyl, isopropyl, n-butyl, sec-butyl, tert-butyl, n-pentyl, n-hexyl, n-heptyl and n-octyl, which is substituted with 1, 2, 3, 4, 5, 6, 7, 8 or 9 substituents independently selected from the group consisting of —NH—$C_{1-6}$-alkyl, —N($C_{1-6}$-alkyl)$_2$, —C(=O)—O—$C_{1-6}$-alkyl and —NH—C(=O)—$C_{1-6}$-alkyl;

an unsubstituted or at least mono-substituted radical selected from the group consisting of adamantyl, cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydrocarbazolyl, 9H-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$C_{1-6}$-alkyl substituted with one or more hydroxy groups, —$C_{1-6}$-alkyl substituted with one or more chlorine atoms, —$C_{1-6}$-alkyl substituted with one or more methoxy and/or ethoxy groups, —O—$C_{1-6}$-alkyl substituted with one or more methoxy and/or ethoxy groups, —S—$C_{1-6}$-alkyl, —C(=O)—O—$C_{1-6}$-alkyl, —O—C(=O)—$C_{1-6}$-alkyl, —SCF$_3$, —SCF$_2$H, —SCFH$_2$, —SH, —SO$_3$H, —NH—C(=O)—$C_{1-6}$-alkyl, —N($C_{1-6}$-alkyl)-C(=O)—$C_{1-6}$-alkyl, —CHO, —C(=O)—$C_{1-6}$-perfluoroalkyl, —C(=S)—NH—$C_{1-6}$-alkyl, —CF$_2$H, —CFH$_2$, —C(=O)—NH—NR$^C$R$^D$, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —NR$^A$R$^B$, —($C_{1-5}$-alkylene)-NR$^A$R$^B$, —S(=O)$_2$—NH—$C_{1-6}$-alkyl, —S(=O)$_2$—NH-phenyl, cyclopropyl, cyclobutyl, cyclopentyl, cyclohexyl, pyrrolidinyl, piperidinyl, thiophenyl, phenoxy, —O-Benzyl, and benzyl;

whereby in each case the cyclic moieties cyclopropyl, cyclobutyl, cyclopentyl, phenyl, cyclohexyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —$C_{1-6}$-alkyl, —O—$C_{1-6}$-alkyl, —O—CF$_3$ and —S—CF$_3$;

a saturated or unsaturated, unsubstituted or at least mono-substituted, optionally at least one heteroatom as a ring member containing cycloaliphatic radical, which is bonded via an unsubstituted or at least mono-substituted alkylene group, alkenylene group or alkinylene group may be condensed with an unsubstituted or at least mono-substituted mono- or polycyclic ring system and/or may be bridged by at least one unsubstituted or at least mono-substituted alkylene group;

a —NR$^7$R$^8$ moiety; a —P(=O)(OR$^9$)$_2$ moiety; a —C(=O)—OR$^{10}$ moiety; a —C(=O)—NH—R$^{11}$ moiety or a —C(=O)—R$^{12}$ moiety;

R$^6$ represents an unsubstituted or at least mono-substituted $C_{5-16}$ alkyl radical, $C_{2-16}$ alkenyl radical or $C_{2-16}$ alkinyl radical;

or a saturated or unsaturated, unsubstituted or at least mono-substituted, optionally at least one heteroatom as a ring member containing cycloaliphatic radical, which may be condensed with an unsubstituted or at least mono-substituted mono- or polycyclic ring system and/or may be bridged by at least one unsubstituted or at least mono-substituted alkylene group;

a —P(=O)(OR$^9$)$_2$ moiety; a —C(=O)—OR$^{10}$ moiety; a —C(=O)—NH—R$^{11}$ moiety or a —C(=O)—R$^{12}$ moiety;

R$^7$ represents a hydrogen atom or a saturated or unsaturated, unsubstituted or at least mono-substituted aliphatic radical;

R$^8$ represents an unsubstituted or at least mono-substituted radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —O-methyl, —O-ethyl, —O-n-propyl, —O-isopropyl, —O-n-butyl, —O-isobutyl, —O-tert-butyl, —O-n-pentyl and —O-n-hexyl;

a substituted radical selected from the group consisting of methyl, ethyl, n-propyl, isopropyl, n-butyl, sec-butyl, tert-butyl, n-pentyl, n-hexyl, n-heptyl and n-octyl, which is substituted with 1, 2, 3, 4, 5, 6, 7, 8 or 9 substituents independently selected from the group consisting of —NH—$C_{1-6}$-alkyl, —N($C_{1-6}$-alkyl)$_2$, —C(═O)—O—$C_{1-6}$-alkyl and —NH—C(═O)—$C_{1-6}$-alkyl;

an unsubstituted or at least mono-substituted radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (═S), —$C_{1-6}$-alkyl substituted with one or more hydroxy groups, —$C_{1-6}$-alkyl substituted with one or more chlorine atoms, —$C_{1-6}$-alkyl substituted with one or more methoxy and/or ethoxy groups, —O—$C_{1-6}$-alkyl substituted with one or more methoxy and/or ethoxy groups, —S—$C_{1-6}$-alkyl, —C(═O)—O—$C_{1-6}$-alkyl, —O—C(═O)—$C_{1-6}$-alkyl, —SCF$_3$, —SCF$_2$H, —SCFH$_2$, —SH, —SO$_3$H, —NH—C(═O)—$C_{1-6}$-alkyl, —N($C_{1-6}$-alkyl)-C(═O)—$C_{1-6}$-alkyl, —CHO, —C(═O)—$C_{1-6}$-perfluoroalkyl, —C(═S)—NH—$C_{1-6}$-alkyl, —CF$_2$H, —CFH$_2$, —C(═O)—NH—NR$^C$R$^D$, —S(═O)$_2$-phenyl, —($C_{1-5}$-alkylene)-S—$C_{1-6}$-alkyl, —($C_{1-5}$-alkylene)-S(═O)—$C_{1-6}$-alkyl, —($C_{1-5}$-alkylene)-S(═O)$_2$—$C_{1-6}$-alkyl, —NR$^A$R$^B$, —($C_{1-5}$-alkylene)-NR$^A$R$^B$, —S(═O)$_2$—NH—$C_{1-6}$-alkyl, —S(═O)$_2$—NH-phenyl, cyclopropyl, cyclobutyl, cyclopentyl, cyclohexyl, pyrrolidinyl, piperidinyl, thiophenyl, phenoxy and benzyl;

whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —$C_{1-6}$-alkyl, —O—$C_{1-6}$-alkyl, —O—CF$_3$ and —S—CF$_3$;

or a saturated or unsaturated, unsubstituted or at least mono-substituted, optionally at least one heteroatom as a ring member containing cycloaliphatic radical, which is bonded via an unsubstituted or at least mono-substituted alkylene group, alkenylene group or alkinylene group may be condensed with an unsubstituted or at least mono-substituted mono- or polycyclic ring system and/or may be bridged by at least one unsubstituted or at least mono-substituted alkylene group;

R$^9$, R$^{10}$, R$^{11}$ and R$^{12}$, independently of one another, in each case represent a saturated or unsaturated, unsubstituted or at least mono-substituted aliphatic radical;

or an unsubstituted or at least mono-substituted aryl or heteroaryl radical, which may be condensed with an unsubstituted or at least mono-substituted mono- or polycyclic ring system and/or may be bonded via an unsubstituted or at least mono-substituted alkylene group, alkenylene group or alkinylene group;

R$^A$ and R$^B$, independently of one another, in each case represent —$C_{1-6}$-alkyl or R$^A$ and R$^B$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different $C_{1-6}$ alkyl radicals; and R$^C$ and R$^D$, independently of one another, in each case represent hydrogen, —$C_{1-6}$-alkyl, —C(═O)—O—$C_{1-6}$-alkyl, $C_{3-8}$-cycloalkyl, —($C_{1-5}$-alkylene)-$C_{3-8}$-cycloalkyl, —($C_{1-6}$-alkylene)-O—$C_{1-6}$-alkyl or —$C_{1-6}$-alkyl substituted with one or more hydroxy groups or R$^C$ and R$^D$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —$C_{1-6}$-alkyl, —C(═O)—$C_{1-6}$-alkyl, —C(═O)—O—$C_{1-6}$-alkyl, —C(═O)—NH—$C_{1-6}$-alkyl, —C(═S)—NH—$C_{1-6}$-alkyl, oxo (═O), —$C_{1-6}$-alkyl substituted with one or more hydroxy groups, —($C_{1-6}$-alkylene)-O—$C_{1-6}$-alkyl and —C(═O)—NH$_2$;

optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

If one or more of the residues R$^1$ to R$^{12}$ and R$^A$, R$^B$, R$^C$ and R$^D$ represents or comprises an aryl, phenyl or heteroaryl radical, which may be substituted, unless defined otherwise, preferably said aryl, phenyl or heteroaryl radical may optionally be substituted with 1, 2, 3, 4 or 5 substituent(s) independently selected from the group consisting of $C_{1-6}$-perfluoralkyl, —$C_{1-6}$-alkyl substituted with one or more methoxy and/or ethoxy groups, —$C_{1-6}$-alkyl, —$C_{1-6}$-alkyl substituted with one or more hydroxy groups, —$C_{1-6}$-alkyl substituted with one or more chlorine atoms, —O—$C_{1-6}$-alkyl, —O—$C_{1-6}$-alkyl substituted with one or more methoxy and/or ethoxy groups, —S—$C_{1-6}$-alkyl, —C(═O)—OH, —C(═O)—O—$C_{1-6}$-alkyl, —O—C(═O)—$C_{1-6}$-alkyl, F, Cl, Br, I, —CN, —OCF$_3$, —O—$C_2$F$_5$, —O—$C_3$F$_7$, —O—$C_4$F$_9$, —SCF$_3$, —SCF$_3$, —SCF$_2$H, —SCFH$_2$, —OH, —SH, —SO$_3$H, —NH—C(═O)—$C_{1-6}$-alkyl, —N($C_{1-6}$-alkyl)-C(═O)—$C_{1-6}$-alkyl, —NO$_2$, —CHO, —C(═O)—$C_{1-6}$-alkyl, —C(═O)—$C_{1-6}$-perfluoroalkyl, —C(═S)—NH—$C_{1-6}$-alkyl, —CF$_2$H, —CFH$_2$, —C(═O)—NR$^K$R$^L$, —C(═O)—NH—NR$^G$R$^H$, —S(═O)—$C_{1-6}$-alkyl, —S(═O)$_2$—$C_{1-6}$-alkyl, —S(═O)$_2$-phenyl, —($C_{1-5}$-alkylene)-S—$C_{1-6}$-alkyl, —($C_{1-6}$-alkylene)-S(═O)—$C_{1-6}$-alkyl, —($C_{1-6}$-alkylene)-S(═O)$_2$—$C_{1-6}$-alkyl, —NR$^E$R$^F$, —($C_{1-5}$-alkylene)-NR$^E$R$^F$, —S(═O)—NH$_2$, —S(═O)$_2$—NH—$C_{1-6}$-alkyl, —S(═O)$_2$—NH-phenyl, —NH—S(═O)$_2$—$C_{1-6}$-alkyl, cyclopropyl, cyclobutyl, cyclopentyl, cyclohexyl, pyrrolidinyl, piperidinyl, phenyl, thiophenyl, phenoxy and benzyl;

whereby in each case the cyclic moieties cyclopropyl, cyclobutyl, cyclopentyl, cyclohexyl, pyrrolidinyl, piperidinyl, phenyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —C$_{1-6}$-alkyl, —O—C$_{1-6}$-alkyl, —O—CF$_3$ and —S—CF$_3$ and whereby R$^K$, R$^L$, R$^E$ and R$^F$, independently of one another, represent hydrogen or —C$_{1-6}$-alkyl or R$^K$ and R$^L$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different C$_{1-6}$ alkyl radicals and whereby R$^G$ and R$^H$, independently of one another, represent hydrogen, —C$_{1-6}$-alkyl, —C(=O)—O—C$_{1-6}$-alkyl, C$_{3-8}$-cycloalkyl, —(C$_{1-6}$-alkylene)-C$_{3-8}$-cycloalkyl, —(C$_{1-6}$-alkylene)-O—C$_{1-6}$-alkyl or —C$_{1-6}$-alkyl substituted with one or more hydroxy groups or R$^G$ and R$^H$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —C$_{1-6}$-alkyl, —C(=O)—C$_{1-6}$-alkyl, —C(=O)—O—C$_{1-6}$-alkyl, —C(=O)—NH—C$_{1-6}$-alkyl, —C(=S)—NH—C$_{1-6}$-alkyl, oxo (=O), —C$_{1-6}$-alkyl substituted with one or more hydroxy groups, —(C$_{1-6}$-alkylene)-O—C$_{1-6}$-alkyl and —C(=O)—NH$_2$.

More preferably said phenyl, aryl and heteroaryl radicals may optionally be substituted with 1, 2, 3, 4 or 5 substituent(s) independently selected from the group consisting of —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, cyclopropyl, cyclobutyl, cyclopentyl, cyclohexyl, pyrrolidinyl, piperidinyl, phenyl, thiophenyl, phenoxy and benzyl, whereby said thiophenyl radical can be substituted with 1, 2 or 3 substituent(s) independently selected from the group consisting of F, Cl, Br, methyl, ethyl and n-propyl.

Preferred aryl radicals which are optionally at least mono-substituted are phenyl and naphthyl (1- and 2-naphthyl).

Preferably the heteroatoms which are present as ring members in the heteroaryl radical may, unless defined otherwise, independently be selected from the group consisting of nitrogen, oxygen and sulfur. More preferably a heteroaryl radical is 5- to 14-membered and may comprise 1, 2, 3 or 4 heteroatoms independently selected from the group consisting of nitrogen, oxygen and sulfur.

Preferred heteroaryl radicals which are unsubstituted or at least mono-substituted are pyridinyl, furyl (furanyl), thienyl (thiophenyl), pyrrolyl, oxazolyl, isoxazolyl, thiazolyl, isothiazolyl, imidazolyl, pyrazolyl, oxadiazolyl, thiadiazolyl, triazolyl, pyridazinyl, indolyl, isoindolyl, pyrimidinyl, pyrazinyl, quinolinyl, isoquinolinyl, benzo[b]furanyl, benzo[b]thiophenyl, benzo[2,1,3]thiadiazolyl, [1,2,3]-benzothiadiazolyl, [2,1,3]-benzoxadiazolyl, [1,2,3]-benzoxadiazolyl, benzoxazolyl, benzthiazolyl, benzisoxazolyl, benzisothiazolyl, imidazo[2,1-b]thiazolyl, 2H-chromenyl, pyranyl, indazolyl and quinazolinyl.

Preferred aryl and heteroaryl radicals which are condensed with a mono- or polycyclic ring system are [1,3]-benzodioxolyl, [1,4]-benzodioxanyl, [1,2,3,4]-tetrahydronaphthyl, (2,3)-dihydro-1H-cyclopenta[b]indolyl, [1,2,3,4]-tetrahydroquinolinyl, [1,2,3,4]-tetrahydroisoquinolinyl, [1,2,3,4]-tetrahydroquinazolinyl and [3,4]-dihydro-2H-benzo[1,4]oxazinyl.

If one or more of the residues R$^1$ to R$^{12}$ or R$^A$, R$^B$, R$^C$ and R$^D$ represents or comprises a saturated or unsaturated, optionally at least one heteroatom as a ring member containing cycloaliphatic radical, preferably a C$_{3-18}$ cycloaliphatic radical, a heterocyclic ring, preferably a 4- to 10-membered heterocyclic ring, a C$_{3-16}$ cycloalkyl radical, a C$_{4-16}$ cycloalkenyl radical, a C$_{4-16}$ heterocycloalkyl radical, or a C$_{5-16}$ heterocycloalkenyl radical, which may be substituted, unless defined otherwise, preferably said cycloaliphatic radical, heterocyclic ring, C$_{3-16}$ cycloalkyl radical, C$_{4-16}$ cycloalkenyl radical, C$_{4-16}$ heterocycloalkyl radical, or C$_{5-16}$ heterocycloalkenyl radical, may in each case optionally be substituted with 1, 2, 3, 4 or 5 substituent(s) independently selected from the group consisting of oxo (=O), thioxo (=S), C$_{1-6}$-perfluoralkyl, —C$_{1-6}$-alkyl, —C$_{1-6}$-alkyl substituted with one or more hydroxy groups, —C$_{1-6}$-alkyl substituted with one or more chlorine atoms, —C$_{1-6}$-alkyl substituted with one or more methoxy and/or ethoxy groups, —O—C$_{1-6}$-alkyl, —O—C$_{1-6}$-alkyl substituted with one or more methoxy and/or ethoxy groups, —S—C$_{1-6}$-alkyl, —C(=O)—OH, —C(=O)—O—C$_{1-6}$-alkyl, —O—C(=O)—C$_{1-6}$-alkyl, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—C$_{1-6}$-alkyl, —N(C$_{1-6}$-alkyl)-C(=O)—C$_{1-6}$-alkyl, —NO$_2$, —CHO, —C(=O)—C$_{1-6}$-alkyl, —C(=O)—C$_{1-6}$-perfluoroalkyl, —C(=S)—NH—C$_{1-6}$-alkyl, —CF$_2$H, —CFH$_2$, —C(=O)—NR$^K$R$^L$, —C(=O)—NH—NR$^G$R$^H$, —S(=O)—C$_{1-6}$-alkyl, —S(=O)$_2$—C$_{1-6}$-alkyl, —S(=O)$_2$-phenyl, —(C$_{1-5}$-alkylene)-S—C$_{1-6}$-alkyl, —(C$_{1-5}$-alkylene)-S(=O)—C$_{1-6}$-alkyl, —(C$_{1-5}$-alkylene)-S(=O)$_2$—C$_{1-6}$-alkyl, —NR$^E$R$^F$, —(C$_{1-5}$-alkylene)-NR$^E$R$^F$, —S(=O)—NH$_2$, —S(=O)$_2$—NH—C$_{1-6}$-alkyl, —S(=O)$_2$—NH-phenyl, —NH—S(=O)$_2$—C$_{1-6}$-alkyl, cyclopropyl, cyclobutyl, cyclopentyl, cyclohexyl, pyrrolidinyl, piperidinyl, phenyl, thiophenyl, phenoxy and benzyl;
whereby in each case the cyclic moieties cyclopropyl, cyclobutyl, cyclopentyl, cyclohexyl, pyrrolidinyl, piperidinyl, phenyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —C$_{1-6}$-alkyl, —O—C$_{1-6}$-alkyl, —O—CF$_3$ and —S—CF$_3$ and
whereby R$^K$, R$^L$, R$^E$ and R$^F$, independently of one another, represent hydrogen or —C$_{1-6}$-alkyl or R$^K$ and R$^L$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different C$_{1-6}$ alkyl radicals
and whereby R$^G$ and R$^H$, independently of one another, represent hydrogen, —C$_{1-6}$-alkyl, —C(=O)—O—C$_{1-6}$-alkyl, C$_{3-8}$-cycloalkyl, —(C$_{1-5}$-alkylene)-C$_{3-8}$-cycloalkyl, —(C$_{1-6}$-alkylene)-O—C$_{1-6}$-alkyl or —C$_{1-6}$-alkyl substituted with one or more hydroxy groups or R$^G$ and R$^H$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —C$_{1-6}$-alkyl, —C(=O)—C$_{1-6}$-alkyl, —C(=O)—O—C$_{1-6}$-alkyl, —C(=O)—NH—C$_{1-6}$-alkyl, —C(=S)—NH—C$_{1-6}$-alkyl, oxo (=O), —C$_{1-6}$-alkyl substituted with one or more hydroxy groups, —(C$_{1-6}$-alkylene)-O—C$_{1-6}$-alkyl and —C(=O)—NH$_2$.

More preferably said cycloaliphatic radicals, heterocyclic rings, C$_{3-16}$ cycloalkyl radicals, C$_{4-16}$ cycloalkenyl radicals, C$_{4-16}$ heterocycloalkyl radicals, or C$_{5-16}$ heterocycloalkenyl radicals may optionally be substituted with 1, 2, 3, 4 or 5 substituent(s) independently selected from the group consisting of oxo (=O), thioxo (=S), —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(OH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, cyclopropyl, cyclobutyl, cyclopentyl, cyclohexyl, pyrrolidinyl, piperidinyl, phenyl, thiophenyl, phenoxy and benzyl, whereby said thiophenyl radical can be substituted with 1, 2 or 3 substituents independently selected from the group consisting of F, Cl, Br, methyl, ethyl and n-propyl.

If one or more of the residues R$^1$ to R$^{12}$ or R$^A$, R$^B$, R$^C$ and R$^D$ represents or comprises a cycloaliphatic radical, preferably a C$_{3-16}$ cycloaliphatic radical, which contains one or more heteroatoms as ring members, unless defined otherwise, each of these heteroatoms may preferably be selected from the group consisting of nitrogen, oxygen and sulfur. More preferably a cycloaliphatic group may optionally contain 1, 2, 3 or 4 heteroatom(s) independently selected from the group consisting of N, O and S as ring members.

Suitable saturated or unsaturated, optionally at least one heteroatom as ring member containing cycloaliphatic radicals may preferably be selected from the group consisting of cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentenyl, cyclohexenyl, cycloheptenyl, cyclooctenyl, pyrrolidinyl, piperidinyl, piperazinyl, homopiperazinyl, morpholinyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl and (1,3)-dioxolanyl.

Suitable saturated or unsaturated, optionally at least one heteroatom as ring member containing cycloaliphatic radicals which are condensed with an unsubstituted or at least mono-substituted mono- or polycyclic ring system may preferably be selected from the group consisting of indolinyl, isoindolinyl, decahydronaphthyl, (1,2,3,4)-tetrahydroquinolinyl, (1,2,3,4)-tetrahydroisoquinolinyl, (1,2,3,4)-tetrahydronaphthyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl and (1,2,3,4)-tetrahydroquinoxazlinyl.

Preferably a cycloaliphatic radical, a C$_{3-16}$ cycloalkyl radical, a C$_{4-16}$ cycloalkenyl radical, a C$_{4-16}$ heterocycloalkyl radical or a C$_{5-16}$ heterocycloalkenyl radical may be bridged by 1, 2 or 3 unsubstituted or at least mono-substituted alkylene group(s).

Suitable saturated or unsaturated, optionally at least one heteroatom as ring member containing cycloaliphatic radicals which are bridged by at least one unsubstituted or at least mono-substituted alkylene group may preferably be selected from the group consisting of adamantyl, bicyclo[2.2.1]heptyl, bicyclo[3.1.1]heptyl, norbornenyl and 8-aza-bicyclo[3.2.1]octyl.

A suitable saturated or unsaturated, optionally at least one heteroatom as ring member containing cycloaliphatic radical which together with a saturated or unsaturated, unsubstituted or at least mono-substituted cycloaliphatic radical forms a spirocyclic residue via a common ring atom is 8-aza-spiro[4.5]decanyl.

A mono- or polycyclic ring system according to the present invention—if not defined otherwise—means a mono- or polycyclic hydrocarbon ring system, preferably a mono- or bicyclic ring system, that may be saturated, unsaturated or aromatic. Each of its different rings may show a different degree of saturation, i.e. they may be saturated, unsaturated or aromatic. Optionally each of the rings of the mono- or bicyclic ring system may contain one or more, preferably 1, 2 or 3, heteroatom(s) as ring member(s), which may be identical or different and which can preferably be selected from the group consisting of nitrogen, oxygen and sulfur. The rings of the mono- or bicyclic ring system are preferably 5-, 6- or 7-membered.

The term "condensed" according to the present invention means that a ring or ring system is attached to another ring or ring system, whereby the terms "annulated" or "annelated" are also used by those skilled in the art to designate this kind of attachment.

If one or more of the residues $R^1$ to $R^{12}$ comprises a mono- or polycyclic ring system, which may be substituted, unless defined otherwise, preferably said mono- or polycyclic ring system may optionally be substituted with 1, 2, 3, 4 or 5 substituent(s) independently selected from the group consisting of oxo (=O), thioxo (=S), $C_{1-6}$-perfluoralkyl, —$C_{1-6}$-alkyl, —$C_{1-6}$-alkyl substituted with one or more hydroxy groups, —$C_{1-6}$-alkyl substituted with one or more chlorine atoms, —$C_{1-6}$-alkyl substituted with one or more methoxy and/or ethoxy groups, —O—$C_{1-6}$-alkyl, —O—$C_{1-6}$-alkyl substituted with one or more methoxy and/or ethoxy groups, —S—$C_{1-6}$-alkyl, —C(=O)—OH, —C(=O)—O—$C_{1-6}$-alkyl, —O—C(=O)—$C_{1-6}$-alkyl, F, Cl, Br, I, —CN, —OCF$_3$, —O—$C_2F_5$, —O—$C_3F_7$, —O—$C_4F_9$, —SCF$_3$, —SCF$_2$H, —SCFH$_2$, —OH, —SH, —SO$_3$H, —NH—C(=O)—$C_{1-6}$-alkyl, —N($C_{1-6}$-alkyl)-C(=O)—$C_{1-6}$-alkyl, —NO$_2$, —CHO, —C(=O)—$C_{1-6}$-alkyl, —C(=O)—$C_{1-6}$-perfluoroalkyl, —C(=S)—NH—$C_{1-6}$-alkyl, —CF$_2$H, —CFH$_2$, —C(=O)—NR$^K$R$^L$, —C(=O)—NH—NR$^G$R$^H$, —S(=O)—$C_{1-6}$-alkyl, —S(=O)$_2$—$C_{1-6}$-alkyl, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —NR$^E$R$^F$, —($C_{1-5}$-alkylene)-NR$^E$R$^F$, —S(=O)—NH$_2$, —S(=O)$_2$—NH—$C_{1-6}$-alkyl, —S(=O)$_2$—NH-phenyl, —NH—S(=O)$_2$—$C_{1-6}$-alkyl, cyclopropyl, cyclobutyl, cyclopentyl, cyclohexyl, pyrrolidinyl, piperidinyl, phenyl, thiophenyl, phenoxy and benzyl;
whereby in each case the cyclic moieties cyclopropyl, cyclobutyl, cyclopentyl, cyclohexyl, pyrrolidinyl, piperidinyl, phenyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —$C_{1-6}$-alkyl, —O—$C_{1-6}$-alkyl, —O—CF$_3$ and —S—CF$_3$ and
whereby $R^K$, $R^L$, $R^E$ and $R^F$, independently of one another, represent hydrogen or —$C_{1-6}$-alkyl or $R^K$ and $R^L$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different $C_{1-6}$ alkyl radicals
and whereby $R^G$ and $R^H$, independently of one another, represent hydrogen, —$C_{1-6}$-alkyl, —C(=O)—O—$C_{1-6}$-alkyl, $C_{3-8}$-cycloalkyl, —($C_{1-5}$-alkylene)-$C_{3-8}$-cycloalkyl, —($C_{1-6}$-alkylene)-O—$C_{1-6}$-alkyl or —$C_{1-6}$-alkyl substituted with one or more hydroxy groups or $R^G$ and $R^H$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —$C_{1-6}$-alkyl, —C(=O)—$C_{1-6}$-alkyl, —C(=O)—O—$C_{1-6}$-alkyl, —C(=O)—NH—$C_{1-6}$-alkyl, —C(=S)—NH—$C_{1-6}$-alkyl, oxo (=O), —$C_{1-6}$-alkyl substituted with one or more hydroxy groups, —($C_{1-6}$-alkylene)-O—$C_{1-6}$-alkyl and —C(=O)—NH$_2$.

More preferably said mono- or polycyclic ring system may optionally be substituted with 1, 2, 3, 4 or 5 substituent(s) independently selected from the group consisting of oxo (=O), thioxo (=S), —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, cyclopropyl, cyclobutyl, cyclopentyl, cyclohexyl, pyrrolidinyl, piperidinyl, phenyl, thiophenyl, phenoxy and benzyl, whereby said thiophenyl radical can be substituted with 1, 2 or 3 substituents independently selected from the group consisting of F, Cl, Br, methyl, ethyl and n-propyl.

If one or more of the residues $R^4$ to $R^{12}$ represent or comprise a saturated or unsaturated, unsubstituted or at least mono-substituted aliphatic radical, preferably a $C_{1-16}$ aliphatic radical, said aliphatic radical may be linear or branched.

Preferably aliphatic radicals, $C_{1-16}$ alkyl radicals, $C_{2-16}$ alkenyl radical and $C_{2-16}$ alkinyl radicals, unless defined otherwise, may optionally be substituted with 1, 2, 3, 4, 5, 6, 7, 8 or 9 substituents independently selected from the group consisting of —OH, F, Cl, Br, I, —O—$C_{1-6}$-alkyl, —OCF$_3$, —O—C$_2$F$_5$, —O—C$_3$F$_7$, —O—C$_4$F$_9$, —CF$_3$, —C$_2$F$_5$, —$C_3F_7$, —$C_4F_9$, —$NH_2$, —NH—$C_{1-6}$-alkyl, —N($C_{1-6}$-alkyl)$_2$, —C(=O)—OH, —C(=O)—O—$C_{1-6}$-alkyl, —C(=O)—$NH_2$, —C(=O)—NH—$C_{1-6}$-alkyl, —C(=O)—N($C_{1-6}$-alkyl)$_2$, —CN, —$NO_2$, —S(=O)—$NH_2$, —CHO, —C(=O)—$C_{1-6}$-alkyl, —S(=O)—$C_{1-6}$-alkyl, —S(=O)$_2$—$C_{1-6}$-alkyl, —NH—S(=O)—$C_{1-6}$-alkyl, —NH—C(=O)—O—$C_{1-6}$-alkyl and —NH—C(=O)—$C_{1-6}$-alkyl.

More preferably aliphatic radicals, $C_{1-16}$ alkyl radicals, $C_{2-16}$ alkenyl radical and $C_{2-16}$ alkinyl radicals may optionally be substituted with 1, 2, 3, 4, 5, 6, 7, 8 or 9 substituents independently selected from the group consisting of —OH, F, Cl, Br, I, —O—$CH_3$, —O—$C_2H_5$, —O—$CH_2$—$CH_2$—$CH_3$, —O—CH($CH_3$)$_2$, —O—$CH_2$—$CH_2$—$CH_2$—$CH_3$, —O—C($CH_3$)$_3$, —$NH_2$, —NH—$CH_3$, —NH—$C_2H_5$, —N($CH_3$)$_2$, —N($C_2H_5$)$_2$, —CN, —$NO_2$, —NH—C(=O)—$CH_3$, —NH—C(=O)—$C_2H_5$, —NH—C(=O)—C($CH_3$)$_3$, —NH—C(=O)—O—$CH_3$, —NH—C(=O)—O—$C_2H_5$, —NH—C(=O)—O—C($CH_3$)$_3$, —C(=O)—NH—$CH_3$, —C(=O)—NH—$C_2H_5$, —C(=O)—NH—C($CH_3$)$_3$, —C(=O)—N($CH_3$)$_2$, —C(=O)—N($C_2H_5$)$_2$, —C(=O)—OH, —C(=O)—O—$CH_3$, —C(=O)—O—$C_2H_5$, —C(=O)—O—C($CH_3$)$_3$, —C(=O)—$CH_3$, —C(=O)—$C_2H_5$ and —C(=O)—C($CH_3$)$_3$.

Suitable alkyl radicals, preferably $C_{1-16}$ alkyl radicals, are selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, n-nonyl, n-decyl, n-undecyl, n-dodecyl, n-tridecyl, n-tetradecyl, n-pentadecycl and n-hexadecyl.

Suitable at least mono-substituted alkyl radicals are selected from the group consisting of —$CF_3$, —$CH_2F$, —$CF_2H$, —$CH_2$—O—$CH_3$, —$C_2F_5$, —$CH_2$—$CH_2$—F, —$CH_2$—CN, —$CH_2$—OH, —$CH_2$—$CH_2$—CN, —$CH_2$—$CH_2$—OH, —$CH_2$—$CH_2$—$OCH_3$, —$CH_2$—$CH_2$—$CH_2$—CN, —$CH_2$—$CH_2$—$CH_2$—OH, —$CH_2$—$CH_2$—$CH_2$—O—$CH_3$, —$CH_2$—$CH_2$—$CH_2$—$CH_2$—O—$CH_3$, —$CH_2$—$NH_2$, —$CH_2$—N($CH_3$)$_2$, —$CH_2$—N($C_2H_5$)$_2$, —$CH_2$—$CH$—$NH_2$, —$CH_2$—$CH_2$—N($CH_3$)$_2$, —$CH_2$—$CH_2$—N($C_2H_5$)$_2$, —$CH_2$—$CH_2$—$CH_2$—$NH_2$, —$CH_2$—$CH_2$—$CH_2$—N($CH_3$)$_2$ and —$CH_2$—$CH_2$—$CH_2$—N($C_2H_5$)$_2$.

An alkenyl radical according to the present invention comprises at least one carbon-carbon double bond. Suitable alkenyl radicals, preferably $C_{2-16}$ alkenyl radicals, are selected from the group consisting of vinyl, n-propenyl, n-butenyl, n-pentenyl, n-hexenyl, n-heptenyl, n-octenyl, n-nonenyl, n-decenyl, n-undecenyl, n-dodecenyl, n-tridecenyl, n-tetradecenyl, n-pentadecenyl and n-hexadecenyl.

An alkinyl radical comprises at least one carbon-carbon triple bond. Suitable alkinyl radicals, preferably $C_{2-16}$ alkinyl radicals, are selected from the group consisting of ethinyl, propinyl, n-butinyl, n-pentinyl, n-hexinyl, n-octinyl, n-noninyl, n-decinyl, n-undecinyl, n-dodecinyl, n-tridecinyl, n-tetradecinyl, n-pentadecinyl and n-hexadecinyl.

If any of the substituents represents an alkylene group, an alkenylene group or an alkinylene group, which may be substituted, said alkylene group, alkenylene group or alkinylene group may—if not defined otherwise—be unsubstituted or substituted by one or more substituents, preferably unsubstituted or substituted with 1, 2 or 3 substituent(s). Said substituent(s) may preferably be selected independently from the group consisting of —O—$C_{1-6}$-alkyl, —S—$C_{1-6}$-alkyl, —F, Cl, Br, I, —CN, —$CF_3$, —$OCF_3$, —$SCF_3$, —OH, —SH, —$SO_3H$, —$NH_2$, —NH($C_{1-6}$-alkyl), —N($C_{1-6}$-alkyl)$_2$ and phenyl. More preferably said substituent(s) may be selected from the group consisting of —F, Cl, Br, I, —CN, —$CF_3$, —$OCF_3$, —$SCF_3$, —OH, —SH, —$SO_3H$, —$NH_2$, —NH—$CH_3$, —N($CH_3$)$_2$, —O—$CH_3$ and —O—$C_2H_5$. An alkenylene group comprises at least one carbon-carbon double bond, an alkinylene group comprises at least one carbon-carbon triple bond.

Suitable alkylene groups, preferably $C_{1-5}$-alkylene groups, include —($CH_2$)—, —CH($CH_3$)—, —CH(phenyl), —($CH_2$)$_2$—, —($CH_2$)$_3$—, —($CH_2$)$_4$—, —($CH_2$)$_5$— and —($CH_2$)$_6$—, suitable alkenylene groups, preferably $C_{2-5}$-alkenylene groups, include —CH=CH—, —$CH_2$—CH=CH— and —CH=CH—$CH_2$— and suitable alkinylene groups, preferably $C_{2-5}$-alkinylene groups, include —C≡C—, —$CH_2$—C≡C— and —C≡C—$CH_2$—.

Preferred are substituted pyrazoline compounds of general formula I given above, wherein $R^1$ represents an unsubstituted or at least mono-substituted phenyl radical;

$R^2$ represents an unsubstituted or at least mono-substituted phenyl radical;

$R^3$ represents an unsubstituted or at least mono-substituted radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$C_{1-6}$-alkyl substituted with one or more hydroxy groups, —$C_{1-6}$-alkyl substituted with one or more chlorine atoms, —$C_{1-6}$-alkyl substituted with one or more methoxy and/or ethoxy groups, —O—$C_{1-6}$-alkyl substituted with one or more methoxy and/or ethoxy groups, —S—$C_{1-6}$-alkyl, —C(=O)—O—$C_{1-6}$-alkyl, —O—C(=O)—$C_{1-6}$-alkyl, —$SCF_3$, —$SCF_2H$, —$SCFH_2$, —SH, —$SO_3H$, —NH—C(=O)—$C_{1-6}$-alkyl, —N($C_{1-6}$-alkyl)-C(=O)—$C_{1-6}$-alkyl, —CHO, —C(=O)—$C_{1-6}$-perfluoroalkyl, —C(=S)—NH—$C_{1-6}$-alkyl, —$CF_2H$, —$CFH_2$, —C(=O)—NH—$NR^CR^D$, —S(=O)$_2$-phenyl, —($C_{1-6}$-alkylene)-S—$C_{1-6}$-alkyl, —($C_{1-6}$-alkylene)-S(=O)—$C_{1-6}$-alkyl, —($C_{1-6}$-alkylene)-S(=O)$_2$—$C_{1-6}$-alkyl, —$NR^AR^B$, —($C_{1-5}$-alkylene)-$NR^AR^B$, —S(=O)$_2$—NH—$C_{1-6}$-alkyl, —S(=O)$_2$—NH-phenyl, cyclopropyl, cyclobutyl, cyclopentyl, cyclohexyl, pyrrolidinyl, piperidinyl, thiophenyl, phenoxy and benzyl;

whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —C$_{1-6}$-alkyl, —O—C$_{1-6}$-alkyl, —O—CF$_3$ and —S—CF$_3$;

a —NR$^4$R$^5$ moiety or a —O—R$^6$ moiety;

R$^4$ represents a hydrogen atom or an unsubstituted or at least mono-substituted C$_{1-16}$ alkyl radical, C$_{2-16}$ alkenyl radical or C$_{2-16}$ alkinyl radical;

R$^5$ represents an unsubstituted or at least mono-substituted radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —O-methyl; —O-ethyl, —O-n-propyl, —O-isopropyl, —O-n-butyl, —O-isobutyl, —O-tert-butyl, —O-n-pentyl and —O-n-hexyl;

a substituted radical selected from the group consisting of methyl, ethyl, n-propyl, isopropyl, n-butyl, sec-butyl, tert-butyl, n-pentyl, n-hexyl, n-heptyl and n-octyl, which is substituted with 1, 2, 3, 4, 5, 6, 7, 8 or 9 substituents independently selected from the group consisting of —NH—C$_{1-6}$-alkyl, —N(C$_{1-6}$-alkyl)$_2$, —C(=O)—O—C$_{1-6}$-alkyl and —NH—C(=O)—C$_{1-6}$-alkyl;

an unsubstituted or at least mono-substituted radical selected from the group consisting of adamantyl, cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydrocarbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —C$_{1-6}$-alkyl substituted with one or more hydroxy groups, —C$_{1-6}$-alkyl substituted with one or more chlorine atoms, —C$_{1-6}$-alkyl substituted with one or more methoxy and/or ethoxy groups, —O—C$_{1-6}$-alkyl substituted with one or more methoxy and/or ethoxy groups, —S—C$_{1-6}$-alkyl, —C(=O)—O—C$_{1-6}$-alkyl, —O—C(=O)—C$_{1-6}$-alkyl, —SCF$_3$, —SCF$_2$H, —SCFH$_2$, —SH, —SO$_3$H, —NH—C(=O)—C$_{1-6}$-alkyl, —N(C$_{1-6}$-alkyl)-C(=O)—C$_{1-6}$-alkyl, —CHO, —C(=O)—C$_{1-6}$-perfluoroalkyl, —C(=S)—NH—C$_{1-6}$-alkyl, —CF$_2$H, —CFH$_2$, —C(=O)—NH—NR$^C$R$^D$, —S(=O)$_2$-phenyl, —(C$_{1-5}$-alkylene)-S—C$_{1-6}$-alkyl, —(C$_{1-5}$-alkylene)-S(=O)—C$_{1-6}$-alkyl, —(C$_{1-5}$-alkylene)-S(=O)$_2$—C$_{1-6}$-alkyl, —NR$^A$R$^B$, —(C$_{1-5}$-alkylene)-NR$^A$R$^B$, —S(=O)$_2$—NH—C$_{1-6}$-alkyl, —S(=O)$_2$—NH-phenyl, cyclopropyl, cyclobutyl, cyclopentyl, cyclohexyl, pyrrolidinyl, piperidinyl, thiophenyl, phenoxy, —O-Benzyl, and benzyl;

whereby in each case the cyclic moieties cyclopropyl, cyclobutyl, cyclopentyl, phenyl, cyclohexyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —C$_{1-6}$-alkyl, —O—C$_{1-6}$-alkyl, —O—CF$_3$ and —S—CF$_3$;

an unsubstituted or at least mono-substituted C$_{3-16}$ cycloalkyl radical or C$_{4-16}$ cycloalkenyl radical, which in each case is bonded via an unsubstituted or at least mono-substituted C$_{1-5}$ alkylene group, C$_{2-5}$ alkenylene group or C$_{2-5}$ alkinylene group and/or may be condensed with an unsubstituted or at least mono-substituted mono- or polycyclic ring system and/or may be bridged by at least one unsubstituted or at least mono-substituted C$_{1-5}$ alkylene group;

or an unsubstituted or at least mono-substituted C$_{4-16}$ heterocycloalkyl radical or C$_{5-16}$ heterocycloalkenyl radical, which in each case is bonded via an unsubstituted or at least mono-substituted C$_{1-5}$ alkylene group, C$_{2-5}$ alkenylene group or C$_{2-5}$ alkinylene group and/or may be condensed with an unsubstituted or at least mono-substituted mono- or polycyclic ring system and/or may be bridged by at least one unsubstituted or at least mono-substituted C$_{1-5}$ alkylene group;

a —NR$^7$R$^8$ moiety; a —P(=O)(OR$^9$)$_2$ moiety; a —C(=O)—OR$^{10}$ moiety; a —C(=O)—NH—R$^{11}$ moiety or a —C(=O)—R$^{12}$ moiety;

R$^6$ represents an unsubstituted or at least mono-substituted C$_{5-16}$ alkyl radical, C$_{2-16}$ alkenyl radical or C$_{2-16}$ alkinyl radical;

an unsubstituted or at least mono-substituted C$_{3-16}$ cycloalkyl radical or C$_{4-16}$ cycloalkenyl radical, which in each case may be condensed with an unsubstituted or at least mono-substituted mono- or polycyclic ring system and/or may be bridged by at least one unsubstituted or at least mono-substituted C$_{1-5}$ alkylene group;

an unsubstituted or at least mono-substituted C$_{4-16}$ heterocycloalkyl radical or C$_{5-16}$ heterocycloalkenyl radical, which in each case may be condensed with an unsubstituted or at least mono-substituted mono- or polycyclic ring system and/or may be bridged by at least one unsubstituted or at least mono-substituted C$_{1-5}$ alkylene group;

a —P(=O)(OR$^9$)$_2$ moiety; a —C(=O)—OR$^{10}$ moiety; a —C(=O)—NH—R$^{11}$ moiety or a —C(=O)—R$^{12}$ moiety;

R$^7$ represents a hydrogen atom or an unsubstituted or at least mono-substituted C$_{1-16}$ alkyl radical, C$_{2-16}$ alkenyl radical or C$_{2-16}$ alkinyl radical;

R$^8$ represents an unsubstituted or at least mono-substituted radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —O-methyl, —O-ethyl, —O-n-propyl, —O-isopropyl, —O-n-butyl, —O-isobutyl, —O-tert-butyl, —O-n-pentyl and —O-n-hexyl;

a substituted radical selected from the group consisting of methyl, ethyl, n-propyl, isopropyl, n-butyl, sec-butyl, tert-butyl, n-pentyl, n-hexyl, n-heptyl and n-octyl, which is substituted with 1, 2, 3, 4, 5, 6, 7, 8 or 9 substituents independently selected from the group consisting of —NH—$C_{1-6}$-alkyl, —N($C_{1-6}$-alkyl)$_2$, —C(=O)—O—$C_{1-6}$-alkyl and —NH—C(=O)—$C_{1-6}$-alkyl;

an unsubstituted or at least mono-substituted radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$C_{1-6}$-alkyl substituted with one or more hydroxy groups, —$C_{1-6}$-alkyl substituted with one or more chlorine atoms, —$C_{1-6}$-alkyl substituted with one or more methoxy and/or ethoxy groups, —O—$C_{1-6}$-alkyl substituted with one or more methoxy and/or ethoxy groups, —S—$C_{1-6}$-alkyl, —C(=O)—O—$C_{1-6}$-alkyl, —O—C(=O)—$C_{1-6}$-alkyl, —SCF$_3$, —SCF$_2$H, —SCFH$_2$, —SH, —SO$_3$H, —NH—C(=O)—$C_{1-6}$-alkyl, —N($C_{1-6}$-alkyl)-C(=O)—$C_{1-6}$-alkyl, —CHO, —C(=O)—$C_{1-6}$-perfluoroalkyl, —C(=S)—NH—$C_{1-6}$-alkyl, —CF$_2$H, —CFH$_2$, —C(=O)—NH—NR$^C$R$^D$, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —NR$^A$R$^B$, —($C_{1-5}$-alkylene)-NR$^A$R$^B$, —S(=O)$_2$—NH—$C_{1-6}$-alkyl, —S(=O)$_2$—NH-phenyl, cyclopropyl, cyclobutyl, cyclopentyl, cyclohexyl, pyrrolidinyl, piperidinyl, thiophenyl, phenoxy and benzyl;

whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —$C_{1-6}$-alkyl, —O—$C_{1-6}$-alkyl, —O—CF$_3$ and —S—CF$_3$;

an unsubstituted or at least mono-substituted $C_{3-16}$ cycloalkyl radical or $C_{4-16}$ cycloalkenyl radical, which in each case is bonded via an unsubstituted or at least mono-substituted $C_{1-5}$ alkylene group, $C_{2-5}$ alkenylene group or $C_{2-5}$ alkinylene group and/or may be condensed with an unsubstituted or at least mono-substituted mono- or polycyclic ring system and/or may be bridged by at least one unsubstituted or at least mono-substituted $C_{1-5}$ alkylene group;

or an unsubstituted or at least mono-substituted $C_{4-16}$ heterocycloalkyl radical or $C_{5-16}$ heterocycloalkenyl radical, which in each case is bonded via an unsubstituted or at least mono-substituted $C_{1-5}$ alkylene group, $C_{2-5}$ alkenylene group or $C_{2-5}$ alkinylene group and/or may be condensed with an unsubstituted or at least mono-substituted mono- or polycyclic ring system and/or may be bridged by at least one unsubstituted or at least mono-substituted $C_{1-5}$ alkylene group;

$R^9$, $R^{10}$, $R^{11}$ and $R^{12}$, independently of one another, in each case represent an optionally at least mono-substituted $C_{5-16}$ alkyl radical, $C_{2-16}$ alkenyl radical or $C_{2-16}$ alkinyl radical;

an unsubstituted or at least mono-substituted 6- or 10-membered aryl radical, which may be condensed with an unsubstituted or at least mono-substituted mono- or polycyclic ring system and/or may be bonded via an unsubstituted or at least mono-substituted $C_{1-5}$ alkylene group, $C_{2-5}$ alkenylene group or $C_{2-5}$ alkinylene group;

an unsubstituted or at least mono-substituted 5- to 14-membered heteroaryl radical, which may be condensed with an unsubstituted or at least mono-substituted mono- or polycyclic ring system and/or may be bonded via an unsubstituted or at least mono-substituted $C_{1-5}$ alkylene group, $C_{2-5}$ alkenylene group or $C_{2-5}$ alkinylene group;

$R^A$ and $R^B$, independently of one another, in each case represent hydrogen or —$C_{1-6}$-alkyl or $R^A$ and $R^B$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different $C_{1-6}$ alkyl radicals; and $R^C$ and $R^D$, independently of one another, in each case represent hydrogen, —$C_{1-6}$-alkyl, —C(=O)—O—$C_{1-6}$-alkyl, $C_{3-8}$-cycloalkyl, —($C_{1-5}$-alkylene)-$C_{3-8}$-cycloalkyl, —($C_{1-6}$-alkylene)-O—$C_{1-6}$-alkyl or —$C_{1-6}$-alkyl substituted with one or more hydroxy groups or $R^C$ and $R^D$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —$C_{1-6}$-alkyl, —C(=O)—$C_{1-6}$-alkyl, —C(=O)—O—$C_{1-6}$-alkyl, —C(=O)—NH—$C_{1-6}$-alkyl, —C(=S)—NH—$C_{1-6}$-alkyl, oxo (=O), —$C_{1-6}$-alkyl substituted with one or more hydroxy groups, —($C_{1-6}$-alkylene)-O—$C_{1-6}$-alkyl and —C(=O)—NH$_2$;

whereby the rings of the aforementioned ring system are in each case independently of one another 5- 6- or 7-membered and may in each case independently of one another optionally contain 1, 2 or 3 heteroatom(s) independently selected from the group consisting of nitrogen, oxygen and sulfur;

the aforementioned heteroaryl radicals in each case optionally contain 1, 2, 3 or 4 heteroatom(s) independently selected from the group consisting of nitrogen, oxygen and sulfur as ring member(s);

the aforementioned heterocycloalkyl radicals and heterocycloalkenyl radicals in each case optionally contain 1, 2, 3 or 4 heteroatom(s) independently selected from the group consisting of nitrogen, oxygen and sulfur as ring member(s);

optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

Preferred are substituted pyrazoline compounds of general formula I given above, wherein $R^1$ and $R^2$, independently of one another, in each case represent a phenyl radical which may be substituted with 1, 2, 3, 4 or 5 substituent(s) independently selected from the group consisting of —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —$C(OCH_3)(C_2H_5)_2$, —$C(OCH_3)(CH_3)_2$, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—C($CH_3$)$_3$, —C(=O)—OH, —C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—$C(CH_3)_3$, —$NO_2$, —CHO, —C(=O)—$CH_3$, —C(=O)—$C_2H_5$, —C(=O)—$C(CH_3)_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—N($CH_3$)$_2$, —C(=O)—N($C_2H_5$)$_2$, —C(=O)—NH—NH—$CH_3$, —C(=O)—NH—NH—$C_2H_5$, —C(=O)—NH—$NH_2$, —C(=O)—NH—N($CH_3$)$_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —S(=O)$_2$-phenyl, —$NH_2$, —NH—$CH_3$, —NH—$C_2H_5$, —N($CH_3$)$_2$, —N($C_2H_5$)$_2$, —$CH_2$—N($CH_3$)$_2$, —($CH_2$)-morpholinyl, —($CH_2$)-piperidinyl, —($CH_2$)-piperazinyl, —($CH_2$)—N($C_2H_5$)$_2$, —$CH_2$—N($C_3H_7$)$_2$, —$CH_2$—N($C_4H_9$)$_2$, —$CH_2$—N($CH_3$)($C_2H_5$), —S(=O)—$NH_2$, —S(=O)$_2$—NH—$CH_3$, —S(=O)$_2$—NH-phenyl, —NH—S(=O)$_2$—$CH_3$, cyclopropyl, cyclobutyl, cyclopentyl, cyclohexyl, pyrrolidinyl, piperidinyl, phenyl, thiophenyl, phenoxy and benzyl, whereby in each case the cyclic moieties cyclopropyl, cyclobutyl, cyclopentyl, cyclohexyl, pyrrolidinyl, piperidinyl, phenyl, thiophenyl, phenoxy and benzyl may optionally be substituted with 1, 2 or 3 substituent(s) independently selected from the group consisting of F, Cl, Br, methyl, ethyl and n-propyl; and $R^3$ to $R^{12}$ and $R^A$, $R^B$, $R^C$ and $R^D$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preference is also given to substituted pyrazoline compounds of general formula I given above, wherein $R^3$ represents a radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, which may optionally be substituted with 1, 2, 3, 4 or 5 substituent(s) independently selected from the group consisting of oxo (=O), thioxo (=S), —$CF_3$, —$C_2F_5$, —$C_3F_7$, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —$C(OCH_3)(C_2H_5)_2$, —$C(OCH_3)(CH_3)_2$, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—C($CH_3$)$_3$, —C(=O)—OH, —C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—$C(CH_3)_3$, —$NO_2$, —CHO, —C(=O)—$CH_3$, —C(=O)—$C_2H_5$, —C(=O)—$C(CH_3)_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—N($CH_3$)$_2$, —C(=O)—N($C_2H_5$)$_2$, —C(=O)—NH—NH—$CH_3$, —C(=O)—NH—NH—$C_2H_5$, —C(=O)—NH—$NH_2$, —C(=O)—NH—N($CH_3$)$_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —S(=O)$_2$-phenyl, —$NH_2$, —NH—$CH_3$, —NH—$C_2H_5$, —N($CH_3$)$_2$, —N($C_2H_5$)$_2$, —$CH_2$—N($CH_3$)$_2$, —($CH_2$)-morpholinyl, —($CH_2$)-piperidinyl, —($CH_2$)-piperazinyl, —($CH_2$)—N($C_2H_5$)$_2$, —$CH_2$—N($C_3H_7$)$_2$, —$CH_2$—N($C_4H_9$)$_2$, —$CH_2$—N($CH_3$)($C_2H_5$), —S(=O)—$NH_2$, —S(=O)$_2$—NH—$CH_3$, —S(=O)$_2$—NH-phenyl, —NH—S(=O)$_2$—$CH_3$, cyclopropyl, cyclobutyl, cyclopentyl, cyclohexyl, pyrrolidinyl, piperidinyl, phenyl, thiophenyl, phenoxy and benzyl, whereby in each case the cyclic moieties cyclopropyl, cyclobutyl, cyclopentyl, cyclohexyl, pyrrolidinyl, piperidinyl, phenyl, thiophenyl, phenoxy and benzyl may optionally be substituted with 1, 2 or 3 substituent(s) independently selected from the group consisting of F, Cl, Br, methyl, ethyl and n-propyl; a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$CH_2$—OH, —$CH_2$—$CH_2$—OH, —$OH_2$—$CH_2$—$CH_2$—OH, —$CH_2Cl$, —$CHCl_2$, —$C_2H_4Cl$, —O—$CH_2$—O—$CH_3$, —O—$CH_2$—$CH_2$—O—

CH$_3$, —O—CH$_2$—O—C$_2$H$_5$, —C(OCH$_3$)(C$_2$H$_5$)$_2$, —C(OCH$_3$)(CH$_3$)$_2$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, —SCF$_3$, —SCF$_2$H, —SCFH$_2$, —SH, —SO$_3$H, —NH—C(=O)—CH$_3$, —NH—C(=O)—C$_2$H$_5$, —NH—C(=O)—C(CH$_3$)$_3$, —CHO, —C(=O)—CF$_3$, —C(=O)—C$_2$F$_5$, —C(=O)—C$_3$F$_7$, —CF$_2$H, —CFH$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)$_2$-phenyl, —(C$_{1-5}$-alkylene)-S—C$_{1-6}$-alkyl, —(C$_{1-6}$-alkylene)-S(=O)—C$_{1-6}$-alkyl, —(C$_{1-5}$-alkylene)-S(=O)$_2$—C$_{1-6}$-alkyl, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), cyclopropyl, cyclobutyl, cyclopentyl, cyclohexyl, pyrrolidinyl, piperidinyl, thiophenyl, phenoxy and benzyl; whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —C$_{1-6}$-alkyl, —O—C$_{1-6}$-alkyl, —O—CF$_3$ and —S—CF$_3$;

a —NR$^4$R$^5$ moiety or a —O—R$^6$ moiety;

and R$^1$, R$^2$, R$^4$ to R$^{12}$ and R$^A$, R$^B$, R$^C$ and R$^D$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preferred are substituted pyrazoline compounds of general formula I given above, wherein R$^4$ represents a hydrogen atom or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, n-nonyl, n-decyl, n-undecyl, n-dodecyl, n-tridecyl, n-tetradecyl, n-pentadecycl, n-hexadecyl, —CF$_3$, —CH$_2$F, —CF$_2$H, —CH$_2$—O—CH$_3$, —C$_2$F$_5$, —CH$_2$—CH$_2$—F, —CH$_2$—CN, —CH$_2$—OH, —CH$_2$—CH$_2$—CN, —CH$_2$—CH$_2$—OH, —CH$_2$—CH$_2$—OCH$_3$, —CH$_2$—CH$_2$—CH$_2$—CN, —CH$_2$—CH$_2$—CH$_2$—OH, —CH$_2$—CH$_2$—CH$_2$—O—CH$_3$, —CH$_2$—CH$_2$—CH$_2$—CH$_2$—O—CH$_3$, —CH$_2$—NH$_2$, —CH$_2$—N(CH$_3$)$_2$, —CH$_2$—CH—NH$_2$, —CH$_2$—CH$_2$—N(CH$_3$)$_2$, —CH$_2$—CH$_2$—N(C$_2$H$_5$)$_2$, —CH$_2$—CH$_2$—CH$_2$—NH$_2$, —CH$_2$—CH$_2$—CH$_2$—N(CH$_3$)$_2$ and —CH$_2$—CH$_2$—CH$_2$—N(C$_2$H$_5$)$_2$;

and R$^1$ to R$^3$, R$^5$ to R$^{12}$ and R$^A$, R$^B$, R$^C$ and R$^D$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preferred are substituted pyrazoline compounds of general formula I given above, wherein R$^5$ represents a radical selected from the group consisting of 2-pentyl, 3-pentyl, neopentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —O-methyl, —O-ethyl, —O-n-propyl, —O-isopropyl, —O-n-butyl, —O-isobutyl, —O-tert-butyl, —O-n-pentyl, —O-n-hexyl, —CH$_2$—N(CH$_3$)$_2$, —CH$_2$—N(C$_2$H$_5$)$_2$, —CH$_2$—CH$_2$—N(CH$_3$)$_2$, —CH$_2$—CH$_2$—N(C$_2$H$_5$)$_2$, —CH$_2$—CH$_2$—CH$_2$—N(CH$_3$)$_2$ and —CH$_2$—CH$_2$—CH$_2$—N(C$_2$H$_5$)$_2$;

a radical selected from the group consisting of adamantyl, cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, which may optionally be substituted with 1, 2, 3, 4 or 5 substituent(s) independently selected from the group consisting of oxo (=O), thioxo (=S), —CF$_3$, —C$_2$F$_5$, —C$_3$F$_7$, —C$_4$F$_9$, —CH$_2$Cl, —CHCl$_2$, —C$_2$H$_4$Cl, methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, F, Cl, Br, I, —CN, —OCF$_3$, —O—C$_2$F$_5$, —O—C$_3$F$_7$, —O—C$_4$F$_9$, —SCF$_3$, —SCF$_2$H, —SCFH$_2$, —OH, —SH, —SO$_3$H, —NH—C(=O)—CH$_3$, —NH—C(=O)—C$_2$H$_5$, —NH—C(=O)—C(CH$_3$)$_3$, —NO$_2$, —CHO, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—C$_3$F$_7$, —C(=S)—NH—CH$_3$, —C(=S)—NH—C$_2$H$_5$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —S(=O)$_2$-phenyl, —NH$_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)— piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, cyclopropyl, cyclobutyl, cyclopentyl, cyclohexyl, pyrrolidinyl, piperidinyl, phenyl, thiophenyl, phenoxy and benzyl, whereby in each case the cyclic moieties cyclopropyl, cyclobutyl, cyclopentyl, cyclohexyl, pyrrolidinyl, piperidinyl, phenyl, thiophenyl, phenoxy and benzyl may optionally be substituted with 1, 2 or 3 substituent(s) independently selected from the group consisting of F, Cl, Br, methyl, ethyl and n-propyl;

a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —CH$_2$—OH, —CH$_2$—CH$_2$—OH, —OH$_2$—CH$_2$—CH$_2$—OH, —CH$_2$Cl, —CHCl$_2$, —C$_2$H$_4$Cl, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —S—CH$_3$, —S—C$_2$H$_5$, —S—CH$_2$—CH$_2$—CH$_3$, —S—CH(CH$_3$)$_2$, —S—CH$_2$—CH$_2$—CH$_3$, —S—C(CH$_3$)$_3$, C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, —SCF$_3$, —SCF$_2$H, —SCFH$_2$, —SH, —SO$_3$H, —NH—C(=O)—CH$_3$, —NH—C(=O)—C$_2$H$_5$, —NH—C(=O)—C(CH$_3$)$_3$, —CHO, —C(=O)—CF$_3$, —C(=O)—C$_2$F$_5$, —C(=O)—C$_3$F$_7$, —CF$_2$H, —CFH$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)$_2$-phenyl, —(C$_{1-5}$-alkylene)-S—C$_{1-6}$-alkyl, —(C$_{1-5}$-alkylene)-S(=O)—C$_{1-6}$-alkyl, —(C$_{1-5}$-alkylene)-S(=O)$_2$—C$_{1-6}$-alkyl, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), cyclopropyl, cyclobutyl, cyclopentyl, cyclohexyl, pyrrolidinyl, piperidinyl, thiophenyl, phenoxy, —O-Benzyl, and benzyl; whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —C$_{1-6}$-alkyl, —O—C$_{1-6}$-alkyl, —O—CF$_3$ and —S—CF$_3$;

a radical selected from the group consisting of (1,2,3,4)-tetrahydronaphthyl, (2,3)-dihydro-1H-cyclopenta[b]indolyl, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentenyl, cyclohexenyl, cycloheptenyl, cyclooctenyl, pyrrolidinyl, piperidinyl, piperazinyl, homopiperazinyl, morpholinyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, bicyclo[2.2.1]heptyl, bicyclo[3.1.1]heptyl and norbornenyl, which is bonded via a —(CH$_2$)—, —(CH$_2$)—(CH$_2$)—, —(CH$_2$)—(CH$_2$)—(CH$_2$)— or —CH=CH-group and/or may optionally be substituted with 1, 2, 3, 4 or 5 substituent(s) independently selected from the group consisting of oxo (=O), thioxo (=S), —CF$_3$, methyl, ethyl, n-propyl, isopropyl, n-butyl, isobutyl, 2-butyl, tert-butyl, n-pentyl, 2-pentyl, n-hexyl, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —S—CH$_3$, —S—C$_2$H$_5$, —S—CH$_2$—CH$_2$—CH$_3$, —S—CH(CH$_3$)$_2$, —S—CH$_2$—CH$_2$—CH$_3$, —S—C(CH$_3$)$_3$, F, Cl, Br, I, —CN, —OCF$_3$, —SCF$_3$, —SCF$_2$H, —SCFH$_2$, —OH, —SH, —NO$_2$, —CHO, —C(=O)—CH$_3$, —C(=O)—C$_2$H$_5$, —C(=O)—C(CH$_3$)$_3$, —C(=O)—OH, —C(=O)—O—CH$_3$, —C(=O)—O—C$_2$H$_5$, —C(=O)—O—C(CH$_3$)$_3$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —NH$_2$, —NH—CH$_3$, —NH—C$_2$H$_5$, —N(CH$_3$)$_2$, —N(C$_2$H$_5$)$_2$, cyclopentyl, cyclohexyl, pyrrolidinyl and piperidinyl;

a —NR$^7$R$^8$ moiety; a —P(=O)(OR$^9$)$_2$ moiety; a —C(=O)—OR$^{10}$ moiety; a —C(=O)—NH—R$^{11}$ moiety or a —C(=O)—R$^{12}$ moiety;

and R$^1$ to R$^4$, R$^6$ to R$^{12}$ and R$^A$, R$^B$, R$^C$ and R$^D$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preference is also given to substituted pyrazoline compounds of general formula I given above, wherein R$^6$ represents a radical selected from the group consisting of n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, n-nonyl, n-decyl, n-undecyl, n-dodecyl, n-tridecyl, n-tetradecyl, n-pentadecycl and n-hexadecyl;

a radical selected from the group consisting of (1,2,3,4)-tetrahydronaphthyl, (2,3)-dihydro-1H-cyclopenta[b]indolyl, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentenyl, cyclohexenyl, cycloheptenyl, cyclooctenyl, pyrrolidinyl, piperidinyl, piperazinyl, homopiperazinyl, morpholinyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, bicyclo[2.2.1]heptyl, bicyclo[3.1.1]heptyl and norbornenyl, which may optionally be substituted with 1, 2, 3, 4 or 5 substituent(s) independently selected from the group consisting of oxo (=O), thioxo (=S), $-CF_3$, methyl, ethyl, n-propyl, isopropyl, n-butyl, isobutyl, 2-butyl, tert-butyl, n-pentyl, 2-pentyl, n-hexyl, $-O-CH_3$, $-O-C_2H_5$, $-O-CH_2-CH_2-CH_3$, $-O-CH(CH_3)_2$, $-O-CH_2-CH_2-CH_2-CH_3$, $-O-C(CH_3)_3$, $-O-CH_2-O-CH_3$, $-O-CH_2-CH_2-O-CH_3$, $-O-CH_2-O-C_2H_5$, $-C(OCH_3)(C_2H_5)_2$, $-C(OCH_3)(CH_3)_2$, $-S-CH_3-$, $-S-C_2H_5$, $-S-CH_2-CH_2-CH_3$, $-S-CH(CH_3)_2$, $-S-CH_2-CH_2-CH_2-CH_3$, $-S-C(CH_3)_3$, F, Cl, Br, I, $-CN$, $-OCF_3$, $-SCF_3$, $-SCF_2H$, $-SCFH_2$, $-OH$, $-SH$, $-NO_2$, $-CHO$, $-C(=O)-CH_3$, $-C(=O)-C_2H_5$, $-C(=O)-C(CH_3)_3$, $-C(=O)-OH$, $-C(=O)-O-CH_3$, $-C(=O)-O-C_2H_5$, $-C(=O)-O-C(CH_3)_3$, $-CF_2H$, $-CFH_2$, $-C(=O)-NH_2$, $-C(=O)-NH-CH_3$, $-C(=O)-NH-C_2H_5$, $-C(=O)-NH-C_3H_7$, $-C(=O)-N(CH_3)_2$, $-C(=O)-N(C_2H_5)_2$, $-S(=O)-CH_3$, $-S(=O)-C_2H_5$, $-S(=O)-C_3H_7$, $-S(=O)_2-CH_3$, $-S(=O)_2-C_2H_5$, $-S(=O)_2-C_3H_7$, $-NH_2$, $-NH-CH_3$, $-NH-C_2H_5$, $-N(CH_3)_2$, $-N(C_2H_5)_2$, cyclopentyl, cyclohexyl, pyrrolidinyl and piperidinyl; a $-P(=O)(OR^9)_2$ moiety; a $-C(=O)-OR^{10}$ moiety; a $-C(=O)-NH-R^{11}$ moiety or a $-C(=O)-R^{12}$ moiety; and $R^1$ to $R^5$, $R^7$ to $R^{12}$ and $R^A$, $R^B$, $R^C$ and $R^D$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preferred are substituted pyrazoline compounds of general formula I given above, wherein $R^7$ represents a hydrogen atom or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, n-nonyl, n-decyl, n-undecyl, n-dodecyl, n-tridecyl, n-tetradecyl, n-pentadecycl, n-hexadecyl, $-CF_3$, $-CH_2F$, $-CF_2H$, $-CH_2-O-CH_3$, $-C_2F_5$, $-CH_2-CH_2-F$, $-CH_2-CN$, $-CH_2-OH$, $-CH_2-CH_2-CN$, $-CH_2-CH_2-OH$, $-CH_2-CH_2-OCH_3$, $-CH_2-CH_2-CH_2-CN$, $-CH_2-CH_2-CH_2-OH$, $-CH_2-CH_2-CH_2-O-CH_3$, $-CH_2-CH_2-CH_2-CH_2-O-CH_3$, $-CH_2-NH_2$, $-CH_2-N(CH_3)_2$, $-CH_2-CH-NH_2$, $-CH_2-CH_2-N(CH_3)_2$, $-CH_2-CH_2-N(C_2H_5)_2$, $-CH_2-CH_2-CH_2-NH_2$, $-CH_2-CH_2-CH_2-N(CH_3)_2$ and $-CH_2-CH_2-CH_2-N(C_2H_5)_2$;
and $R^1$ to $R^6$, $R^8$ to $R^{12}$ and $R^A$, $R^B$, $R^C$ and $R^D$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preference is also given substituted pyrazoline compounds of general formula I given above, wherein $R^8$ represents a radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, $-O$-methyl, $-O$-ethyl, $-O$-n-propyl, $-O$-isopropyl, $-O$-n-butyl, $-O$-isobutyl, $-O$-tert-butyl, $-O$-n-pentyl, $-O$-n-hexyl, $-CH_2-N(CH_3)_2$, $-CH_2-N(C_2H_5)_2$, $-CH_2-CH_2-N(CH_3)_2$, $-CH_2-CH_2-N(C_2H_5)_2$, $-CH_2-CH_2-CH_2-N(CH_3)_2$ and $-CH_2-CH_2-CH_2-N(C_2H_5)_2$;
a radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydro-pyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, which may optionally be substituted with 1, 2, 3, 4 or 5 substituent(s) independently selected from the group consisting of oxo (=O), thioxo (=S), $-CF_3$, $-C_2F_5$, $-C_3F_7$, $-C_4F_9$, $-CH_2Cl$, $-CHCl_2$, $-C_2H_4Cl$, methyl, ethyl, n-propyl, isopropyl, n-butyl, isobutyl, 2-butyl, tert-butyl, n-pentyl, 2-pentyl, n-hexyl, $-CH_2-OH$, $-CH_2-CH_2-OH$, $-CH_2-CH_2-CH_2-OH$, $-O-CH_2-O-CH_3$, $-O-CH_2-CH_2-O-CH_3$, $-O-CH_2-O-C_2H_5$, $-C(OCH_3)(C_2H_5)_2$, $-C(OCH_3)(OH_3)_2$, $-O-CH_3$, $-O-C_2H_5$, $-O-CH_2-CH_2-CH_3$, $-O-CH(CH_3)_2$, $-O-CH_2-CH_2-CH_2-CH_3$, $-O-C(CH_3)_3$, $-S-CH_3$, $-S-C_2H_5$, $-S-CH_2-CH_2-CH_3$, $-S-CH(CH_3)_2$, $-S-CH_2-CH_2-CH_2-CH_3$, $-S-C(CH_3)_3$, $-C(=O)-OH$, $-C(=O)-O-CH_3$, $-C(=O)-O-C_2H_5$, $-C(=O)-O-C_3H_7$, $-C(=O)-O-C(CH_3)_3$, $-O-C(=O)-CH_3$, $-O-C(=O)-C_2H_5$, $-O-C(=O)-CH(CH_3)_2$, $-O-C(=O)-CH_2-CH_2-CH_3$, $-O-C(=O)-C(CH_3)_3$, F, Cl, Br, I, $-CN$, $-OCF_3$, $-O-C_2F_5$, $-O-C_3F_7$, $-O-C_4F_3$, $-SCF_3$, $-SCF_2H$, $-SCFH_2$, $-OH$, $-SH$, $-SO_3H$, $-NH-C(=O)-CH_3$, $-NH-C(=O)-C_2H_5$, $-NH-C(=O)-C(CH_3)_3$, $-NO_2$, $-CHO$, $-C(=O)-CH_3$, $-C(=O)-C_2H_5$, $-C(=O)-C(CH_3)_3$, $-C(=O)-CF_3$, $-C(=O)-C_2F_5$, $-C(=O)-C_3F_7$, $-C(=S)-NH-CH_3$, $-C(=S)-NH-C_2H_5$, $-CF_2H$, $-CFH_2$, $-C(=O)-NH_2$, $-C(=O)-NH-CH_3$, $-C(=O)-NH-C_2H_5$, $-C(=O)-NH-C_3H_7$, $-C(=O)-N(CH_3)_2$, $-C(=O)-N(C_2H_5)_2$, $-C(=O)-NH-NH-CH_3$, $-C(=O)-NH-NH-C_2H_5$, $-C(=O)-NH-NH_2$, $-C(=O)-NH-N(CH_3)_2$, $-S(=O)-CH_3$, $-S(=O)-C_2H_5$, $-S(=O)-C_3H_7$, $-S(=O)_2-CH_3$, $-S(=O)_2-C_2H_5$, $-S(=O)_2-C_3H_7$, $-S(=O)_2$-phenyl, $-NH_2$, —NH—CH$_3$, —NH—C$_2$H$_5$, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)— piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), —S(=O)—NH$_2$, —S(=O)$_2$—NH—CH$_3$, —S(=O)$_2$—NH-phenyl, —NH—S(=O)$_2$—CH$_3$, cyclopropyl, cyclobutyl, cyclopentyl, cyclohexyl, pyrrolidinyl, piperidinyl, phenyl, thiophenyl, phenoxy and benzyl, whereby in each case the cyclic moieties cyclopropyl, cyclobutyl, cyclopentyl, cyclohexyl, pyrrolidinyl, piperidinyl, phenyl, thiophenyl, phenoxy and benzyl may optionally be substituted with 1, 2 or 3 substituent(s) independently selected from the group consisting of F, Cl, Br, methyl, ethyl and n-propyl; a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —CH$_2$—OH, —CH$_2$—CH$_2$—OH, —CH$_2$—CH$_2$—CH$_2$—OH, —CH$_2$Cl, —CHCl$_2$, —C$_2$H$_4$Cl, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —S—CH$_3$, —S—C$_2$H$_5$, —S—CH$_2$—CH$_2$—CH$_3$, —S—CH(CH$_3$)$_2$, —S—CH$_2$—CH$_2$—CH$_3$, —S—C(CH$_3$)$_3$, C(=O)—O—CH$_3$, —C(=O)—O—C$_2$H$_5$, —C(=O)—O—C$_3$H$_7$, —C(=O)—O—C(CH$_3$)$_3$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —O—C(=O)—C(CH$_3$)$_3$, —SCF$_3$, —SCF$_2$H, —SCFH$_2$, —SH, —SO$_3$H, —NH—C(=O)—CH$_3$, —NH—C(=O)—C$_2$H$_5$, —NH—C(=O)—C(CH$_3$)$_3$, —CHO, —C(=O)—CF$_3$, —C(=O)—C$_2$F$_5$, —C(=O)—C$_3$F$_7$, —CF$_2$H, —CFH$_2$, —C(=O)—NH—NH—CH$_3$, —C(=O)—NH—NH—C$_2$H$_5$, —C(=O)—NH—NH$_2$, —C(=O)—NH—N(CH$_3$)$_2$, —S(=O)$_2$-phenyl, —(C$_{1-5}$-alkylene)-S—C$_{1-6}$-alkyl, —(C$_{1-5}$-alkylene)-S(=O)—C$_{1-6}$-alkyl, —(C$_{1-5}$-alkylene)-S(=O)$_2$—C$_{1-6}$-alkyl, —N(CH$_3$)$_2$, —N(C$_2$H$_5$)$_2$, —CH$_2$—N(CH$_3$)$_2$, —(CH$_2$)-morpholinyl, —(CH$_2$)-piperidinyl, —(CH$_2$)-piperazinyl, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$), cyclopropyl, cyclobutyl, cyclopentyl, cyclohexyl, pyrrolidinyl, piperidinyl, thiophenyl, phenoxy and benzyl; whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —C$_{1-6}$-alkyl, —O—C$_{1-6}$-alkyl, —O—CF$_3$ and —S—CF$_3$;

or a radical selected from the group consisting of (1,2,3,4)-tetrahydronaphthyl, (2,3)-dihydro-1H-cyclopenta[b]indolyl, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentenyl, cyclohexenyl, cycloheptenyl, cyclooctenyl, pyrrolidinyl, piperidinyl, piperazinyl, homopiperazinyl, morpholinyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, bicyclo[2.2.1]heptyl, bicyclo[3.1.1]heptyl and norbornenyl, which is bonded via a —(CH$_2$)—, —(OH$_2$)—(OH$_2$)—, —(OH$_2$)—(OH$_2$)—(CH$_2$)— or —CH=CH-group and/or may optionally be substituted with 1, 2, 3, 4 or 5 substituent(s) independently selected from the group consisting of oxo (=O), thioxo (=S), —CF$_3$, methyl, ethyl, n-propyl, isopropyl, n-butyl, isobutyl, 2-butyl, tert-butyl, n-pentyl, 2-pentyl, n-hexyl, —O—CH$_3$, —O—C$_2$H$_5$, —O—CH$_2$—OH$_2$—OH$_3$, —O—CH(CH$_3$)$_2$, —O—CH$_2$—CH$_2$—CH$_2$—CH$_3$, —O—C(CH$_3$)$_3$, —O—CH$_2$—O—CH$_3$, —O—CH$_2$—OH$_2$—O—OH$_3$, —O—CH$_2$—O—C$_2$H$_5$, —C(OCH$_3$)(C$_2$H$_5$)$_2$, —C(OCH$_3$)(CH$_3$)$_2$, —S—CH$_3$, —S—C$_2$H$_5$, —S—CH$_2$—OH$_2$—OH$_3$, —S—CH(CH$_3$)$_2$, —S—CH$_2$—OH$_2$—OH$_2$—OH$_3$, —S—C(CH$_3$)$_3$, F, Cl, Br, I, —CN, —OCF$_3$, —SCF$_3$, —SCF$_2$H, —SCFH$_2$, —OH, —SH, —NO$_2$, —CHO, —C(=O)—CH$_3$, —C(=O)—C$_2$H$_5$, —C(=O)—C(CH$_3$)$_3$, —C(=O)—OH, —C(=O)—O—CH$_3$, —C(=O)—O—C$_2$H$_5$, —C(=O)—O—C(CH$_3$)$_3$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —S(=O)—CH$_3$, —S(=O)—C$_2$H$_5$, —S(=O)—C$_3$H$_3$, —S(=O)$_2$—CH$_3$, —S(=O)$_2$—C$_2$H$_5$, —S(=O)$_2$—C$_3$H$_7$, —NH$_2$, —NH—CH$_3$, —NH—C$_2$H$_5$, —N(CH$_3$)$_2$, —N(C$_2$H$_5$)$_2$ cyclopentyl, cyclohexyl, pyrrolidinyl and piperidinyl;

and $R^1$ to $R^7$, $R^9$ to $R^{12}$ and $R^A$, $R^B$, $R^C$ and $R^D$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preferred are substituted pyrazoline compounds of general formula I given above, wherein $R^9$, $R^{10}$, $R^{11}$ and $R^{12}$, independently of one another, in each case represent a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, vinyl, n-propenyl, n-butenyl, n-pentenyl, n-hexenyl, ethinyl, propinyl, n-butinyl, n-pentinyl and n-hexinyl, which may optionally be substituted with 1, 2, 3, 4, 5, 6, 7, 8 or 9 substituent(s) independently selected from the group consisting of NH$_2$, —NH—CH$_3$, —NH—C$_2$H$_5$, —N(CH$_3$)$_2$, —N(C$_2$H$_5$)$_2$, —NH—C(=O)—CH$_3$, —NH—C(=O)—C$_2$H$_5$, —NH—C(=O)—C(CH$_3$)$_3$, —NH—C(=O)—O—CH$_3$, —NH—C(=O)—O—C$_2$H$_5$, —NH—C(=O)—O—C(CH$_3$)$_3$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —OH, —C(=O)—OH, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$ and —C(=O)—C(CH$_3$)$_3$;

or a radical selected from the group consisting of phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, oxadiazolyl, thiadiazolyl, triazolyl, pyridazinyl, indolyl and isoindolyl, which may be bonded via a —(CH₂)—, —(CH₂)—(CH₂)—, —(CH₂)—(CH₂)—(CH₂)— or —CH=CH-group and/or may optionally be substituted with 1, 2, 3, 4 or 5 substituent(s) independently selected from the group consisting of —CF₃, methyl, ethyl, n-propyl, isopropyl, n-butyl, isobutyl, 2-butyl, tert-butyl, n-pentyl, 2-pentyl, n-hexyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, F, Cl, Br, I, —CN, —OCF₃, —SCF₃, —SCF₂H, —SCFH₂, —OH, —SH, —NO₂, —CHO, —C(=O)—CH₃, —C(=O)—C₂H₅, —C(=O)—C(CH₃)₃, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —NH₂, —NH—CH₃, —NH—C₂H₅, —N(CH₃)₂, —N(C₂H₅)₂, —O—C(=O)—CH₃, —O—C(=O)—C₂H₅, —O—C(=O)—CH(CH₃)₂, —O—C(=O)—CH₂—CH₂—CH₃, —CH₂—N(CH₃)₂, —(CH₂)—N(C₂H₅)₂, —CH₂—N(C₃H₇)₂, —CH₂—N(C₄H₉)₂, —CH₂—N(CH₃)(C₂H₅) and —(CH₂)-morpholinyl;
and $R^1$ to $R^8$ and $R^A$, $R^B$, $R^C$ and $R^D$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preference is also given to substituted pyrazoline compounds of general formula I given above, wherein $R^A$ and $R^B$, independently of one another, in each case represent hydrogen or methyl, ethyl, n-propyl, isopropyl, n-butyl, sec-butyl, isobutyl and tert-butyl or $R^A$ and $R^B$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl;
and
$R^C$ and $R^D$, independently of one another, in each case represent hydrogen, methyl, ethyl, n-propyl, isopropyl, n-butyl, sec-butyl, isobutyl, tert-butyl, —C(=O)—O—CH₃, —C(=O)—O—C₂H₅, —C(=O)—O—C(CH₃)₃, cyclopropyl, cyclobutyl, cyclopentyl or cyclohexyl or $R^C$ and $R^D$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl;
and $R^1$ to $R^{12}$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preferred are substituted pyrazoline compounds of general formula I given above, wherein
$R^1$ and $R^2$, independently of one another, in each case represent a phenyl radical which may be substituted with 1, 2, 3, 4 or 5 substituent(s) independently selected from the group consisting of —CF₃, —C₂F₅, —C₃F₇, —C₄F₉, —CH₂Cl, —CHCl₂, —C₂H₄Cl, methyl, ethyl, n-propyl, isopropyl, n-butyl, isobutyl, 2-butyl, tert-butyl, n-pentyl, 2-pentyl, n-hexyl, —CH₂—OH, —CH₂—CH₂—OH, —CH₂—CH₂—CH₂—OH, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —O—CH₃, —O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—OH, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —S(=O)₂-phenyl, —NH₂, —NH—CH₃, —NH—C₂H₅, —N(CH₃)₂, —N(C₂H₅)₂, —CH₂—N(CH₃)₂, —(CH₂)-morpholinyl, —(CH₂)-piperidinyl, —(CH₂)-piperazinyl, —(CH₂)—N(C₂H₅)₂, —CH₂—N(C₃H₇)₂, —CH₂—N(C₄H₉)₂, —CH₂—N(CH₃)(C₂H₅), —S(=O)—NH₂, —S(=O)₂—NH—CH₃, —S(=O)₂—NH-phenyl, —NH—S(=O)₂—CH₃, cyclopropyl, cyclobutyl, cyclopentyl, cyclohexyl, pyrrolidinyl, piperidinyl, phenyl, thiophenyl, phenoxy and benzyl, whereby in each case the cyclic moieties cyclopropyl, cyclobutyl, cyclopentyl, cyclohexyl, pyrrolidinyl, piperidinyl, phenyl, thiophenyl, phenoxy and benzyl may optionally be substituted with 1, 2 or 3 substituent(s) independently selected from the group consisting of F, Cl, Br, methyl, ethyl and n-propyl;
$R^3$ represents a radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, which may optionally be substituted with 1, 2, 3, 4 or 5 substituent(s) independently selected from the group consisting of oxo (=O), thioxo (=S), —CF₃, —C₂F₅, —C₃F₇, —C₄F₉, —CH₂Cl, —CHCl₂, —C₂H₄Cl, methyl, ethyl, n-propyl, isopropyl, n-butyl, isobutyl, 2-butyl, tert-butyl, n-pentyl, 2-pentyl, n-hexyl, —CH₂—OH, —CH₂—CH₂—

OH, —CH₂—CH₂—CH₂—OH, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —O—CH₃, —O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—OH, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —S(=O)₂-phenyl, —NH₂, —NH—CH₃, —NH—C₂H₅, —N(CH₃)₂, —N(C₂H₅)₂, —CH₂—N(CH₃)₂, —(CH₂)-morpholinyl, —(CH₂)-piperidinyl, —(CH₂)-piperazinyl, —(CH₂)—N(C₂H₅)₂, —CH₂—N(C₃H₇)₂, —CH₂—N(C₄H₉)₂, —CH₂—N(CH₃)(C₂H₅), —S(=O)—NH₂, —S(=O)₂—NH—CH₃, —S(=O)₂—NH-phenyl, —NH—S(=O)₂—CH₃, cyclopropyl, cyclobutyl, cyclopentyl, cyclohexyl, pyrrolidinyl, piperidinyl, phenyl, thiophenyl, phenoxy and benzyl, whereby in each case the cyclic moieties cyclopropyl, cyclobutyl, cyclopentyl, cyclohexyl, pyrrolidinyl, piperidinyl, phenyl, thiophenyl, phenoxy and benzyl may optionally be substituted with 1, 2 or 3 substituent(s) independently selected from the group consisting of F, Cl, Br, methyl, ethyl and n-propyl; a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —CH₂—OH, —CH₂—CH₂—OH, —OH₂—CH₂—CH₂—OH, —CH₂Cl, —CHCl₂, —C₂H₄Cl, —O—CH₂—O—CH₃, —O—CH₂—CH₂—O—CH₃, —O—OH₂—O—C₂H₅, —C(OCH₃)(C₂H₅)₂, —C(OCH₃)(CH₃)₂, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, —SCF₃, —SCF₂H, —SCFH₂, —SH, —SO₃H, —NH—C(=O)—CH₃, —NH—C(=O)—C₂H₅, —NH—C(=O)—C(CH₃)₃, —CHO, —C(=O)—CF₃, —C(=O)—C₂F₅, —C(=O)—C₃F₇, —CF₂H, —CFH₂, —C(=O)—NH—NH—CH₃, —C(=O)—NH—NH—C₂H₅, —C(=O)—NH—NH₂, —C(=O)—NH—N(CH₃)₂, —S(=O)₂-phenyl, —(C₁₋₅-alkylene)-S—C₁₋₆-alkyl, —(C₁₋₅-alkylene)-S(=O)—C₁₋₆-alkyl, —(C₁₋₅-alkylene)-S(=O)₂—C₁₋₆-alkyl, —N(CH₃)₂, —N(C₂H₅)₂, —CH₂—N(CH₃)₂, —(CH₂)-morpholinyl, —(CH₂)-piperidinyl, —(CH₂)-piperazinyl, —(CH₂)—N(C₂H₅)₂, —CH₂—N(C₃H₇)₂, —CH₂—N(C₄H₉)₂, —CH₂—N(CH₃)(C₂H₅), cyclopropyl, cyclobutyl, cyclopentyl, cyclohexyl, pyrrolidinyl, piperidinyl, thiophenyl, phenoxy and benzyl; whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF₃, —ON, —NO₂, —C₁₋₆-alkyl, —O—C₁₋₆-alkyl, —O—CF₃ and —S—CF₃;

a —NR⁴R⁵ moiety or a —O—R⁶ moiety;

R⁴ represents a hydrogen atom or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, n-nonyl, n-decyl, n-undecyl, n-dodecyl, n-tridecyl, n-tetradecyl, n-pentadecycl, n-hexadecyl, —CF₃, —CH₂F, —CF₂H, —CH₂—O—CH₃, —C₂F₅, —CH₂—CH₂—F, —CH₂—CN, —CH₂—OH, —CH₂—CH₂—CN, —CH₂—CH₂—OH, —CH₂—CH₂—OCH₃, —CH₂—CH₂—CH₂—CN, —CH₂—CH₂—CH₂—OH, —CH₂—CH₂—CH₂—O—CH₃, —CH₂—CH₂—CH₂—CH₂—O—CH₃, —CH₂—NH₂, —CH₂—N(CH₃)₂, —CH₂—CH—NH₂, —CH₂—CH₂—N(CH₃)₂, —CH₂—CH₂—N(C₂H₅)₂, —CH₂—CH₂—CH₂—NH₂, —CH₂—CH₂—CH₂—N(CH₃)₂ and —CH₂—CH₂—CH₂—N(C₂H₅)₂;

R⁵ represents a radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —O-methyl, —O-ethyl, —O-n-propyl, —O-isopropyl, —O-n-butyl, —O-isobutyl, —O-tert-butyl, —O-n-pentyl, —O-n-hexyl, —CH₂—N(CH₃)₂, —CH₂—N(C₂H₅)₂, —CH₂—CH₂—N(CH₃)₂, —CH₂—CH₂—N(C₂H₅)₂, —CH₂—CH₂—CH₂—N(CH₃)₂ and —CH₂—CH₂—CH₂—N(C₂H₅)₂;

a radical selected from the group consisting of adamantyl, cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, which may optionally be substituted with 1, 2, 3, 4 or 5 substituent(s) independently selected from the group consisting of oxo (=O), thioxo (=S), —CF₃, —C₂F₅, —C₃F₇, —$C_4F_9$, —$CH_2Cl$, —$CHCl_2$, —$C_2H_4Cl$, methyl, ethyl, n-propyl, isopropyl, n-butyl, isobutyl, 2-butyl, tert-butyl, n-pentyl, 2-pentyl, n-hexyl, —$CH_2$—OH, —$CH_2$—$CH_2$—OH, —$CH_2$—$CH_2$—$CH_2$—OH, —O—$CH_2$—O—$CH_3$, —O—$CH_2$—$CH_2$—O—$CH_3$, —O—$CH_2$—O—$C_2H_5$, —$C(OCH_3)(C_2H_5)_2$, —$C(OCH_3)(CH_3)_2$, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—$C(CH_3)_3$, —C(=O)—OH, —C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, F, Cl, Br, I, —CN, —$OCF_3$, —O—$C_2F_5$, —O—$C_3F_7$, —O—$C_4F_9$, —$SCF_3$, —$SCF_2H$, —$SCFH_2$, —OH, —SH, —$SO_3H$, —NH—C(=O)—$CH_3$, —NH—C(=O)—$C_2H_5$, —NH—C(=O)—$C(CH_3)_3$, —$NO_2$, —CHO, —C(=O)—$CH_3$, —C(=O)—$C_2H_5$, —C(=O)—$C(CH_3)_3$, —C(=O)—$CF_3$, —C(=O)—$C_2F_5$, —C(=O)—$C_3F_7$, —C(=S)—NH—$CH_3$, —C(=S)—NH—$C_2H_5$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—$N(CH_3)_2$, —C(=O)—$N(C_2H_5)_2$, —C(=O)—NH—NH—$CH_3$, —C(=O)—NH—NH—$C_2H_5$, —C(=O)—NH—$NH_2$, —C(=O)—NH—$N(CH_3)_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —S(=O)$_2$-phenyl, —$NH_2$, —NH—$CH_3$, —NH—$C_2H_5$, —$N(CH_3)_2$, —$N(C_2H_5)_2$, —$CH_2$—$N(CH_3)_2$, —($CH_2$)-morpholinyl, —($CH_2$)-piperidinyl, —($CH_2$)-piperazinyl, —($CH_2$)—$N(C_2H_5)_2$, —$CH_2$—$N(C_3H_7)_2$, —$CH_2$—$N(C_4H_9)_2$, —$CH_2$—$N(CH_3)(C_2H_5)$, —S(=O)—$NH_2$, —S(=O)$_2$—NH—$CH_3$, —S(=O)$_2$—NH-phenyl, —NH—S(=O)$_2$—$CH_3$, cyclopropyl, cyclobutyl, cyclopentyl, cyclohexyl, pyrrolidinyl, piperidinyl, phenyl, thiophenyl, phenoxy and benzyl, whereby in each case the cyclic moieties cyclopropyl, cyclobutyl, cyclopentyl, cyclohexyl, pyrrolidinyl, piperidinyl, phenyl, thiophenyl, phenoxy and benzyl may optionally be substituted with 1, 2 or 3 substituent(s) independently selected from the group consisting of F, Cl, Br, methyl, ethyl and n-propyl;

a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$CH_2$—OH, —$CH_2$—$CH_2$—OH, —$CH_2$—$CH_2$—$CH_2$—OH, —$CH_2Cl$, —$CHCl_2$, —$C_2H_4Cl$, —O—$CH_2$—O—$CH_3$, —O—$CH_2$—$CH_2$—O—$CH_3$, —O—$OH_2$—O—$C_2H_5$, —$C(OCH_3)(C_2H_5)_2$, —$C(OCH_3)(CH_3)_2$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—$C(CH_3)_3$, C(=O)—O—$CH_3$, —C(=O)—O—$C_2H_5$, —C(=O)—O—$C_3H_7$, —C(=O)—O—$C(CH_3)_3$, —O—C(=O)—$CH_3$, —O—C(=O)—$C_2H_5$, —O—C(=O)—$CH(CH_3)_2$, —O—C(=O)—$CH_2$—$CH_2$—$CH_3$, —O—C(=O)—$C(CH_3)_3$, —$SCF_3$, —$SCF_2H$, —$SCFH_2$, —SH, —$SO_3H$, —NH—C(=O)—$CH_3$, —NH—C(=O)—$C_2H_5$, —NH—C(=O)—$C(CH_3)_3$, —CHO, —C(=O)—$CF_3$, —C(=O)—$C_2F_5$, —C(=O)—$C_3F_7$, —$CF_2H$, —$CFH_2$, —C(=O)—NH—NH—$CH_3$, —C(=O)—NH—NH—$C_2H_5$, —C(=O)—NH—$NH_2$, —C(=O)—NH—$N(CH_3)_2$, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —$N(CH_3)_2$, —$N(C_2H_5)_2$, —$CH_2$—$N(CH_3)_2$, —($CH_2$)-morpholinyl, —($CH_2$)-piperidinyl, —($CH_2$)-piperazinyl, —($CH_2$)—$N(C_2H_5)_2$, —$CH_2$—$N(C_3H_7)_2$, —$CH_2$—$N(C_4H_9)_2$, —$CH_2$—$N(CH_3)(C_2H_5)$, cyclopropyl, cyclobutyl, cyclopentyl, cyclohexyl, pyrrolidinyl, piperidinyl, thiophenyl, phenoxy and benzyl; whereby in each case the cyclic moieties cyclopropyl, cyclobutyl, cyclopentyl, cyclohexyl, phenyl, pyrrolidinyl, piperidinyl, thiophenyl, phenoxy, —O-Benzyl and benzyl can optionally be substituted with 1, 2, 3, 4 or 5 substituent(s) independently selected from the group consisting of F, Cl, Br, I, —OH, —$CF_3$, —CN, —$NO_2$, —$C_{1-6}$-alkyl, —O—$C_{1-6}$-alkyl, —O—$CF_3$ and —S—$CF_3$;

a radical selected from the group consisting of (1,2,3,4)-tetrahydronaphthyl, (2,3)-dihydro-1H-cyclopenta[b]indolyl, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentenyl, cyclohexenyl, cycloheptenyl, cyclooctenyl, pyrrolidinyl, piperidinyl, piperazinyl, homopiperazinyl, morpholinyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, bicyclo[2.2.1]heptyl, bicyclo[3.1.1]heptyl and norbornenyl, which is bonded via a —($CH_2$)—, —($CH_2$)—($CH_2$)—, —($CH_2$)—($CH_2$)—($CH_2$)— or —CH=CH-group and/or may optionally be substituted with 1, 2, 3, 4 or 5 substituent(s) independently selected from the group consisting of oxo (=O), thioxo (=S), —$CF_3$, methyl, ethyl, n-propyl, isopropyl, n-butyl, isobutyl, 2-butyl, tert-butyl, n-pentyl, 2-pentyl, n-hexyl, —O—$CH_3$, —O—$C_2H_5$, —O—$CH_2$—$CH_2$—$CH_3$, —O—$CH(CH_3)_2$, —O—$CH_2$—$CH_2$—$CH_2$—$CH_3$, —O—$C(CH_3)_3$, —O—$CH_2$—O—$CH_3$, —O—$CH_2$—$CH_2$—O—$CH_3$, —O—$CH_2$—O—$C_2H_5$, —$C(OCH_3)(C_2H_5)_2$, —$C(OCH_3)(CH_3)_2$, —S—$CH_3$, —S—$C_2H_5$, —S—$CH_2$—$CH_2$—$CH_3$, —S—$CH(CH_3)_2$, —S—$CH_2$—$CH_2$—$CH_2$—$CH_3$, —S—$C(CH_3)_3$, F, Cl, Br, I, —CN, —$OCF_3$, —$SCF_3$, —$SCF_2H$, —$SCFH_2$, —OH, —SH, —$NO_2$, —CHO, —C(=O)—$CH_3$, —C(=O)—$C_2H_5$, —C(=O)—$C(CH_3)_3$, —C(=O)—OH, —C(=O)—O—$CH_3$, —C(=O)—O—$C_2H_5$, —C(=O)—O—$C(CH_3)_3$, —$CF_2H$, —$CFH_2$, —C(=O)—$NH_2$, —C(=O)—NH—$CH_3$, —C(=O)—NH—$C_2H_5$, —C(=O)—NH—$C_3H_7$, —C(=O)—$N(CH_3)_2$, —C(=O)—$N(C_2H_5)_2$, —S(=O)—$CH_3$, —S(=O)—$C_2H_5$, —S(=O)—$C_3H_7$, —S(=O)$_2$—$CH_3$, —S(=O)$_2$—$C_2H_5$, —S(=O)$_2$—$C_3H_7$, —$NH_2$, —NH—$CH_3$, —NH—$C_2H_5$, —$N(CH_3)_2$, —$N(C_2H_5)_2$, cyclopentyl, cyclohexyl, pyrrolidinyl and piperidinyl;

a —$NR^7R^8$ moiety; a —P(=O)(OR$^9$)$_2$ moiety; a —C(=O)—OR$^{10}$ moiety; a —C(=O)—NH—R$^{11}$ moiety or a —C(=O)—R$^{12}$ moiety;

R⁶ represents a radical selected from the group consisting of n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, n-nonyl, n-decyl, n-undecyl, n-dodecyl, n-tridecyl, n-tetradecyl, n-pentadecycl and n-hexadecyl;

a radical selected from the group consisting of (1,2,3,4)-tetrahydronaphthyl, (2,3)-dihydro-1H-cyclopenta[b]indolyl, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentenyl, cyclohexenyl, cycloheptenyl, cyclooctenyl, pyrrolidinyl, piperidinyl, piperazinyl, homopiperazinyl, morpholinyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, bicyclo[2.2.1]heptyl, bicyclo[3.1.1]heptyl and norbornenyl, which may optionally be substituted with 1, 2, 3, 4 or 5 substituent(s) independently selected from the group consisting of oxo (=O), thioxo (=S), —CF₃, methyl, ethyl, n-propyl, isopropyl, n-butyl, isobutyl, 2-butyl, tert-butyl, n-pentyl, 2-pentyl, n-hexyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —S—CH₃, —S—C₂H₅, —S—CH₂—CH₂—CH₃, —S—CH(CH₃)₂, —S—CH₂—CH₂—CH₂—CH₃, —S—C(CH₃)₃, F, Cl, Br, I, —CN, —OCF₃, —SCF₃, —SCF₂H, —SCFH₂, —OH, —SH, —NO₂, —CHO, —C(=O)—CH₃, —C(=O)—C₂H₅, —C(=O)—C(CH₃)₃, —C(=O)—OH, —C(=O)—O—CH₃, —C(=O)—O—C₂H₅, —C(=O)—O—C(CH₃)₃, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —NH₂, —NH—CH₃, —NH—C₂H₅, —N(CH₃)₂, —N(C₂H₅)₂, cyclopentyl, cyclohexyl, pyrrolidinyl and piperidinyl;

a —P(=O)(OR⁹)₂ moiety; a —C(=O)—OR¹⁰ moiety; a —C(=O)—NH—R¹¹ moiety or a —C(=O)—R¹² moiety;

R⁷ represents a hydrogen atom or a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, n-nonyl, n-decyl, n-undecyl, n-dodecyl, n-tridecyl, n-tetradecyl, n-pentadecycl, n-hexadecyl, —CF₃, —CH₂F, —CF₂H, —CH₂—O—CH₃, —C₂F₅, —CH₂—CH₂—F, —CH₂—CN, —CH₂—OH, —CH₂—CH₂—CN, —CH₂—CH₂—OH, —CH₂—CH₂—OCH₃, —CH₂—CH₂—CH₂—CN, —CH₂—CH₂—CH₂—OH, —CH₂—CH₂—CH₂—O—CH₃, —CH₂—CH₂—CH₂—CH₂—O—CH₃, —CH₂—NH₂, —CH₂—N(CH₃)₂, —CH₂—CH—NH₂, —CH₂—CH₂—N(CH₃)₂, —CH₂—CH₂—N(C₂H₅)₂, —CH₂—CH₂—CH₂—NH₂, —CH₂—CH₂—CH₂—N(CH₃)₂ and —CH₂—CH₂—CH₂—N(C₂H₅)₂;

R⁸ represents a radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —O-methyl, —O-ethyl, —O-n-propyl, —O-isopropyl, —O-n-butyl, —O-isobutyl, —O-tert-butyl, —O-n-pentyl, —O-n-hexyl, —CH₂—N(CH₃)₂, —CH₂—N(C₂H₅)₂, —CH₂—CH₂—N(CH₃)₂, —CH₂—CH₂—N(C₂H₅)₂, —CH₂—CH₂—CH₂—N(CH₃)₂ and —CH₂—CH₂—CH₂—N(C₂H₅)₂;

a radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-aza-spiro[4.5]decanyl and (2,3)-dihydro-1H-cyclopenta[b]-indolyl, which may optionally be substituted with 1, 2, 3, 4 or 5 substituent(s) independently selected from the group consisting of oxo (=O), thioxo (=S), —CF₃, —C₂F₅, —C₃F₇, —C₄F₉, —CH₂Cl, —CHCl₂, —C₂H₄Cl, methyl, ethyl, n-propyl, isopropyl, n-butyl, isobutyl, 2-butyl, tert-butyl, n-pentyl, 2-pentyl, n-hexyl, —CH₂—OH, —CH₂—CH₂—OH, —CH₂—CH₂—CH₂—OH, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —O—CH₃, O—C₂H₅, —O—CH₂—CH₂—CH₃, —O—CH(CH₃)₂, —O—CH₂—CH₂—CH₂—CH₃, —O—C(CH₃)₃, —S—CH₃, —S—C₂H₅, —S—CH₂—CH₂—CH₃, —S—CH(CH₃)₂, —S—CH₂—CH₂—CH₂—CH₃, —S—C(CH₃)₃, —C(=O)—OH, —C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, F, Cl, Br, I, —CN, —OCF₃, —O—C₂F₅, —O—C₃F₇, —O—C₄F₉, —SCF₃, —SCF₂H, —SCFH₂, —OH, —SH, —SO₃H, —NH—C(=O)—CH₃, —NH—C(=O)—C₂H₅, —NH—C(=O)—C(CH₃)₃, —NO₂, —CHO, —C(=O)—CH₃, —C(=O)—C₂H₅, —C(=O)—C(CH₃)₃, —C(=O)—CF₃, —C(=O)—C₂F₅, —C(=O)—C₃F₇, —C(=S)—NH—CH₃, —C(=S)—NH—C₂H₅, —CF₂H, —CFH₂, —C(=O)—NH₂, —C(=O)—NH—CH₃, —C(=O)—NH—C₂H₅, —C(=O)—NH—C₃H₇, —C(=O)—N(CH₃)₂, —C(=O)—N(C₂H₅)₂, —C(=O)—NH—NH—CH₃, —C(=O)—NH—NH—C₂H₅, —C(=O)—NH—NH₂, —C(=O)—NH—N(CH₃)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —S(=O)₂-phenyl, —NH₂, —NH—CH₃, —NH—C₂H₅, —N(CH₃)₂, —N(C₂H₅)₂, —CH₂—N(CH₃)₂, —(CH₂)-morpholinyl, —(CH₂)-piperidinyl, —(CH₂)— piperazinyl, —(CH₂)—N(C₂H₅)₂, —CH₂—N(C₃H₇)₂, —CH₂—N(C₄H₉)₂, —CH₂—N(CH₃)(C₂H₅), —S(=O)—NH₂, —S(=O)₂—NH—CH₃, —S(=O)₂—NH-phenyl, —NH—S(=O)₂—CH₃, cyclopropyl, cyclobutyl, cyclopentyl, cyclohexyl, pyrrolidinyl, piperidinyl, phenyl, thiophenyl, phenoxy and benzyl, whereby in each case the cyclic moieties cyclopropyl, cyclobutyl, cyclopentyl, cyclohexyl, pyrrolidinyl, piperidinyl, phenyl, thiophenyl, phenoxy and benzyl may optionally be substituted with 1, 2 or 3 substituent(s) independently selected from the group consisting of F, Cl, Br, methyl, ethyl and n-propyl; a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —CH₂—OH, —CH₂—CH₂—OH, —CH₂—CH₂—CH₂—OH, —CH₂Cl, —CHCl₂, —C₂H₄Cl, —O—CH₂—O—CH₃, —O—CH₂—CH₂—O—CH₃, —O—CH₂—O—C₂H₅, —C(OCH₃)(C₂H₅)₂, —C(OCH₃)(OH₃)₂, —S—CH₃, —S—C₂H₅, —S—CH₂—CH₂—CH₃, —S—CH(CH₃)₂, —S—CH₂—CH₂—CH₂—CH₃, —S—C(CH₃)₃, C(=O)—O—CH₃, —C(=O)—O—C₂H₅, —C(=O)—O—C₃H₇, —C(=O)—O—C(CH₃)₃, —O—C(=O)—CH₃, —O—C(=O)—C₂H₅, —O—C(=O)—CH(CH₃)₂, —O—C(=O)—CH₂—CH₂—CH₃, —O—C(=O)—C(CH₃)₃, —SCF₃, —SCF₂H, —SCFH₂, —SH, —SO₃H, —NH—C(=O)—CH₃, —NH—C(=O)—C₂H₅, —NH—C(=O)—C(CH₃)₃, —CHO, —C(=O)—CF₃, —C(=O)—C₂F₅, —C(=O)—C₃F₇, —CF₂H, —CFH₂, —C(=O)—NH—NH—CH₃, —C(=O)—NH—NH—C₂H₅, —C(=O)—NH—NH₂, —C(=O)—NH—N(CH₃)₂, —S(=O)₂-phenyl, —(C₁₋₅-alkylene)-S—C₁₋₆-alkyl, —(C₁₋₅-alkylene)-S(=O)—C₁₋₆-alkyl, —(C₁₋₅-alkylene)-S(=O)₂—C₁₋₆-alkyl, —N(CH₃)₂, —N(C₂H₅)₂, —CH₂—N(CH₃)₂, —(CH₂)-morpholinyl, —(CH₂)-piperidinyl, —(CH₂)-piperazinyl, —(CH₂)—N(C₂H₅)₂, —CH₂—N(C₃H₇)₂, —CH₂—N(C₄H₉)₂, —CH₂—N(CH₃)(C₂H₅), cyclopropyl, cyclobutyl, cyclopentyl, cyclohexyl, pyrrolidinyl, piperidinyl, thiophenyl, phenoxy and benzyl; whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF₃, —ON, —NO₂, —C₁₋₆-alkyl, —O—C₁₋₆-alkyl, —O—CF₃ and —S—CF₃;

a radical selected from the group consisting of (1,2,3,4)-tetrahydronaphthyl, (2,3)-dihydro-1H-cyclopenta[b]indolyl, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentenyl, cyclohexenyl, cycloheptenyl, cyclooctenyl, pyrrolidinyl, piperidinyl, piperazinyl, homopiperazinyl, morpholinyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydropyranyl, tetrahydrothiopyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, bicyclo[2.2.1]heptyl, bicyclo[3.1.1]heptyl and norbornenyl, which is bonded via a —(CH₂)—, —(CH₂)—(CH₂)—, —(CH₂)—(CH₂)—(CH₂)— or —CH=CH-group and/or may optionally be substituted with 1, 2, 3, 4 or 5 substituent(s) independently selected from the group consisting of oxo (=O), thioxo (=S), —CF₃, methyl, ethyl, n-propyl, isopropyl, n-butyl, isobutyl, 2-butyl, tert-butyl, n-pentyl, 2-pentyl, n-hexyl, —O—CH₃, —O—C₂H₅, —O—CH₂—CH₂—CH₃, —O—CH(CH₃)₂, —O—CH₂—CH₂—CH₂—CH₃, —O—C(CH₃)₃, —O—CH₂—O—CH₃, —O—CH₂—CH₂—O—CH₃, —O—CH₂—O—C₂H₅, —C(OCH₃)(C₂H₅)₂, —C(OCH₃)(CH₃)₂, —S—CH₃, —S—C₂H₅, —S—CH₂—CH₂—CH₃, —S—CH(CH₃)₂, —S—CH₂—CH₂—CH₂—CH₃, —S—C(CH₃)₃, F, Cl, Br, I, —CN, —OCF₃, —SCF₃, —SCF₂H, —SCFH₂, —OH, —SH, —NO₂, —CHO, —C(=O)—CH₃, —C(=O)—C₂H₅, —C(=O)—C(CH₃)₃, —C(=O)—OH, —C(=O)—O—CH₃, —C(=O)—O—C₂H₅, —C(=O)—O—C(CH₃)₃, —CF₂H, —CFH₂, —C(=O)—NH₂, —C(=O)—NH—CH₃, —C(=O)—NH—C₂H₅, —C(=O)—NH—C₃H₇, —O(=O)—N(CH₃)₂, —C(=O)—N(C₂H₅)₂, —S(=O)—CH₃, —S(=O)—C₂H₅, —S(=O)—C₃H₇, —S(=O)₂—CH₃, —S(=O)₂—C₂H₅, —S(=O)₂—C₃H₇, —NH₂, —NH—CH₃, —NH—C₂H₅, —N(CH₃)₂, —N(C₂H₅)₂, cyclopentyl, cyclohexyl, pyrrolidinyl and piperidinyl;

and

R⁹, R¹⁰, R¹¹ and R¹², independently of one another, in each case represent a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, vinyl, n-propenyl, n-butenyl, n-pentenyl, n-hexenyl, ethinyl, propinyl, n-butinyl, n-pentinyl and n-hexinyl, which may optionally be substituted with 1, 2, 3, 4, 5, 6, 7, 8 or 9 substituent(s) independently selected from the group consisting of NH₂, —NH—CH₃, —NH—C₂H₅, —N(CH₃)₂, —N(C₂H₅)₂, —NH—C(=O)—CH₃, —NH—C(=O)—C₂H₅, —NH—C(=O)—C(CH₃)₃, —NH—C(=O)—O—CH₃, —NH—C(=O)—O—C₂H₅, —NH—C(=O)—O—C(CH₃)₃, —C(=O)—NH—CH₃, —C(=O)—NH—C₂H₅, —C(=O)—NH—C(CH₃)₃, —C(=O)—N(CH₃)₂, —C(=O)—N(C₂H₅)₂, —OH, —C(=O)—OH, —C(=O)—O—CH₃, —C(=O)—O—C₂H₅, —C(=O)—O—C(CH₃)₃, —C(=O)—CH₃, —C(=O)—C₂H₅ and —C(=O)—C(CH₃)₃;

or a radical selected from the group consisting of phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, oxadiazolyl, thiadiazolyl, triazolyl, pyridazinyl, indolyl and isoindolyl, which may be bonded via a —(CH$_2$)—, —(CH$_2$)—(CH$_2$)—, —(CH$_2$)—(CH$_2$)—(CH$_2$)— or —CH=CH-group and/or may optionally be substituted with 1, 2, 3, 4 or 5 substituent(s) independently selected from the group consisting of —CF$_3$, methyl, ethyl, n-propyl, isopropyl, n-butyl, isobutyl, 2-butyl, tert-butyl, n-pentyl, 2-pentyl, n-hexyl, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, F, Cl, Br, I, —CN, —OCF$_3$, —SCF$_3$, —SCF$_2$H, —SCFH$_2$, —OH, —SH, —NO$_2$, —CHO, —C(=O)—CH$_3$, —C(=O)—C$_2$H$_5$, —C(=O)—C(CH$_3$)$_3$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —NH$_2$, —NH—CH$_3$, —NH—C$_2$H$_5$, —N(CH$_3$)$_2$, —N(C$_2$H$_5$)$_2$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —CH$_2$—N(CH$_3$)$_2$, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$) and —(CH$_2$)-morpholinyl;

optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

Particularly preferred are substituted pyrazoline compounds of general formula I given above, wherein R$^1$ represents a phenyl radical which may be substituted with 1, 2, 3, 4 or 5 substituent(s) independently selected from the group consisting of —OH, F, Cl, Br, I, —O—CH$_3$ and —O—C$_2$H$_5$;

R$^2$ represents a phenyl radical which may be substituted with 1, 2, 3, 4 or 5 substituent(s) independently selected from the group consisting of F, Cl, Br and I;

R$^3$ represents a radical selected from the group consisting of aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, 8-aza-spiro[4.5]decanyl and (2,3)-dihydro-1H-cyclopenta[b]-indolyl, which may optionally be substituted with 1, 2, 3, 4 or 5 substituent(s) independently selected from the group consisting of oxo (=O), thioxo (=S), methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —CH$_2$—O—CH$_3$, —CH$_2$—O—C$_2$H$_5$ and —OH;

a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of —C(OCH$_3$)(C$_2$H$_5$)$_2$, —C(OCH$_3$)(CH$_3$)$_2$, —C(=O)—O—CH$_3$, —C(=O)—O—C$_2$H$_5$, —C(=O)—O—C$_3$H$_7$, —C(=O)—O—C(CH$_3$)$_3$, —CH$_2$—O—CH$_3$, —CH$_2$—O—C$_2$H$_5$, cyclopropyl, cyclobutyl, cyclopentyl, cyclohexyl, pyrrolidinyl, piperidinyl, thiophenyl, phenoxy and benzyl;

a —NR$^4$R$^5$ moiety
or a —O—R$^6$ moiety;

R$^4$ represents a hydrogen atom;

R$^5$ represents a radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —CH$_2$—N(CH$_3$)$_2$, —CH$_2$—N(C$_2$H$_5$)$_2$, —CH$_2$—CH$_2$—N(CH$_3$)$_2$, —CH$_2$—CH$_2$—N(C$_2$H$_5$)$_2$, —CH$_2$—CH$_2$—CH$_2$—N(CH$_3$)$_2$ and —CH$_2$—CH$_2$—CH$_2$—N(C$_2$H$_5$)$_2$;

a radical selected from the group consisting of adamantyl, bicyclo[2.2.1]heptyl, bicyclo[3.1.1]heptyl, (1,7,7)-trimethyl-bicyclo[2.2.1]heptyl, cyclononyl, cyclodecyl, cycloundecyl, cyclododecyl, cyclotridecyl and cyclotetradecyl;

a radical selected from the group consisting of cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentenyl, cyclohexenyl, cycloheptenyl, cyclooctenyl, pyrrolidinyl, piperidinyl, piperazinyl, homopiperazinyl, morpholinyl, aziridinyl, azetidinyl, imidazolidinyl, thiomorpholinyl, pyrazolidinyl, tetrahydrofuranyl, tetrahydrothiophenyl, azepanyl, diazepanyl and azocanyl, which is bonded via a —(CH$_2$)—, —(CH$_2$)—(CH$_2$)— or —(CH$_2$)—(CH$_2$)—(CH$_2$)-group;

a radical selected from the group consisting of aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydro-indolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, 8-aza-spiro[4.5]decanyl and (2,3)-dihydro-1H-cyclopenta[b]-indolyl, which may optionally be substituted with 1, 2, 3, 4 or 5 substituent(s) independently selected from the group consisting of oxo (=O), thioxo (=S), methyl, ethyl, n-propyl, isopropyl, n-butyl, isobutyl, 2-butyl, tert-butyl, n-pentyl, 2-pentyl, n-hexyl, —CH$_2$—OH, —CH$_2$—CH$_2$—OH, —CH$_2$—CH$_2$—CH$_2$—OH, —O—CH$_2$—O—CH$_3$, —O—CH$_2$—CH$_2$—O—CH$_3$, —O—CH$_2$—O—C$_2$H$_5$, —C(OCH$_3$)(C$_2$H$_5$)$_2$, —C(OCH$_3$)(CH$_3$)$_2$, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —C(=O)—OH, —C(=O)—O—CH$_3$, —C(=O)—O—C$_2$H$_5$, —C(=O)—O—C$_3$H$_7$, —C(=O)—O—C(CH$_3$)$_3$, —CH$_2$—O—CH$_3$, —CH$_2$—O—C$_2$H$_5$ and —OH;

or a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of —C(OCH$_3$)(C$_2$H$_5$)$_2$, —C(OCH$_3$)(CH$_3$)$_2$, —C(=O)—O—CH$_3$, —C(=O)—O—C$_2$H$_5$, —C(=O)—O—C$_3$H$_7$, —C(=O)—O—C(CH$_3$)$_3$, —CH$_2$—O—CH$_3$, —CH$_2$—O—C$_2$H$_5$, cyclopropyl, cyclobutyl, cyclopentyl, cyclohexyl, pyrrolidinyl, piperidinyl, thiophenyl, phenoxy, —O-Benzyl, and benzyl;

R$^6$ represents a —P(=O)(OR$^9$)$_2$ moiety; a —C(=O)—OR$^{10}$ moiety; a —C(=O)—NH—R$^{11}$ moiety or a —C(=O)—R$^{12}$ moiety; and R$^9$, R$^{10}$, R$^{11}$ and R$^{12}$, independently of one another, in each case represent a radical selected from the group consisting of methyl, ethyl, n-propyl, isopropyl, n-butyl, isobutyl, sec-butyl, tert-butyl, n-pentyl, 2-pentyl, 3-pentyl, neo-pentyl, n-hexyl, 2-hexyl, 3-hexyl, n-heptyl, 2-heptyl, 3-heptyl, 4-heptyl, n-octyl, 2-octyl, 3-octyl, 4-octyl, vinyl, n-propenyl, n-butenyl, n-pentenyl, n-hexenyl, ethinyl, propinyl, n-butinyl, n-pentinyl and n-hexinyl, which may optionally be substituted with 1, 2, 3, 4, 5, 6, 7, 8 or 9 substituent(s) independently selected from the group consisting of NH$_2$, —NH—CH$_3$, —NH—C$_2$H$_5$, —N(CH$_3$)$_2$, —N(C$_2$H$_5$)$_2$, —NH—C(=O)—CH$_3$, —NH—C(=O)—C$_2$H$_5$, —NH—C(=O)—C(CH$_3$)$_3$, —NH—C(=O)—O—CH$_3$, —NH—C(=O)—O—C$_2$H$_5$, —NH—C(=O)—O—C(CH$_3$)$_3$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —OH, —C(=O)—OH, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$ and —C(=O)—C(CH$_3$)$_3$;

or a radical selected from the group consisting of phenyl, naphthyl, pyridinyl, furyl (furanyl), thienyl (thiophenyl), pyrrolyl, oxazolyl, isoxazolyl, thiazolyl, isothiazolyl, imidazolyl, pyrazolyl, oxadiazolyl, thiadiazolyl, triazolyl, pyridazinyl, indolyl and isoindolyl, which may be bonded via a —(CH$_2$)—, —(CH$_2$)—(CH$_2$)—, —(CH$_2$)—(CH$_2$)—(CH$_2$)— or —CH=CH-group and/or may optionally be substituted with 1, 2, 3, 4 or 5 substituent(s) independently selected from the group consisting of —CF$_3$, methyl, ethyl, n-propyl, isopropyl, n-butyl, isobutyl, 2-butyl, tert-butyl, n-pentyl, 2-pentyl, n-hexyl, —O—CH$_3$, —O—C$_2$H$_5$, —O—CH$_2$—CH$_2$—CH$_3$, —O—CH(CH$_3$)$_2$, —O—CH$_2$—CH$_2$—CH$_2$—CH$_3$, —O—C(CH$_3$)$_3$, —S—CH$_3$, —S—C$_2$H$_5$, —S—CH$_2$—CH$_2$—CH$_3$, —S—CH(CH$_3$)$_2$, —S—CH$_2$—CH$_2$—CH$_2$—CH$_3$, —S—C(CH$_3$)$_3$, F, Cl, Br, I, —CN, —OCF$_3$, —SCF$_3$, —SCF$_2$H, —SCFH$_2$, —OH, —SH, —NO$_2$, —CHO, —C(=O)—CH$_3$, —C(=O)—C$_2$H$_5$, —C(=O)—C(CH$_3$)$_3$, —CF$_2$H, —CFH$_2$, —C(=O)—NH$_2$, —C(=O)—NH—CH$_3$, —C(=O)—NH—C$_2$H$_5$, —C(=O)—NH—C$_3$H$_7$, —C(=O)—N(CH$_3$)$_2$, —C(=O)—N(C$_2$H$_5$)$_2$, —S(=O)—CH$_3$, —S(=O)—C$_2$H$_5$, —S(=O)—C$_3$H$_7$, —S(=O)$_2$—CH$_3$, —S(=O)$_2$—C$_2$H$_5$, —S(=O)$_2$—C$_3$H$_7$, —NH$_2$, —NH—CH$_3$, —NH—C$_2$H$_5$, —N(CH$_3$)$_2$, —N(C$_2$H$_5$)$_2$, —O—C(=O)—CH$_3$, —O—C(=O)—C$_2$H$_5$, —O—C(=O)—CH(CH$_3$)$_2$, —O—C(=O)—CH$_2$—CH$_2$—CH$_3$, —CH$_2$—N(CH$_3$)$_2$, —(CH$_2$)—N(C$_2$H$_5$)$_2$, —CH$_2$—N(C$_3$H$_7$)$_2$, —CH$_2$—N(C$_4$H$_9$)$_2$, —CH$_2$—N(CH$_3$)(C$_2$H$_5$) and —(CH$_2$)-morpholinyl;

optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

More particularly preferred are substituted pyrazoline compounds of general formula I given above, wherein R$^1$ represents a phenyl radical that is substituted with a hydroxy, fluorine, chlorine, bromine or iodine atom or a —O—CH$_3$-group in the para-(4-)-position of the phenyl radical;

R$^2$ represents a (2,4)-dichloro-phenyl radical;

R$^3$ represents a radical selected from the group consisting of

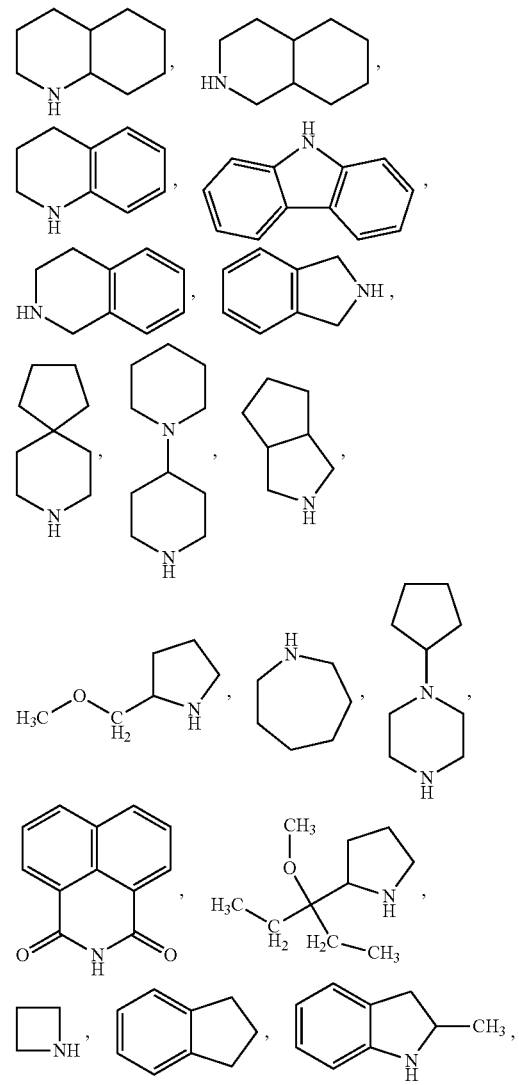

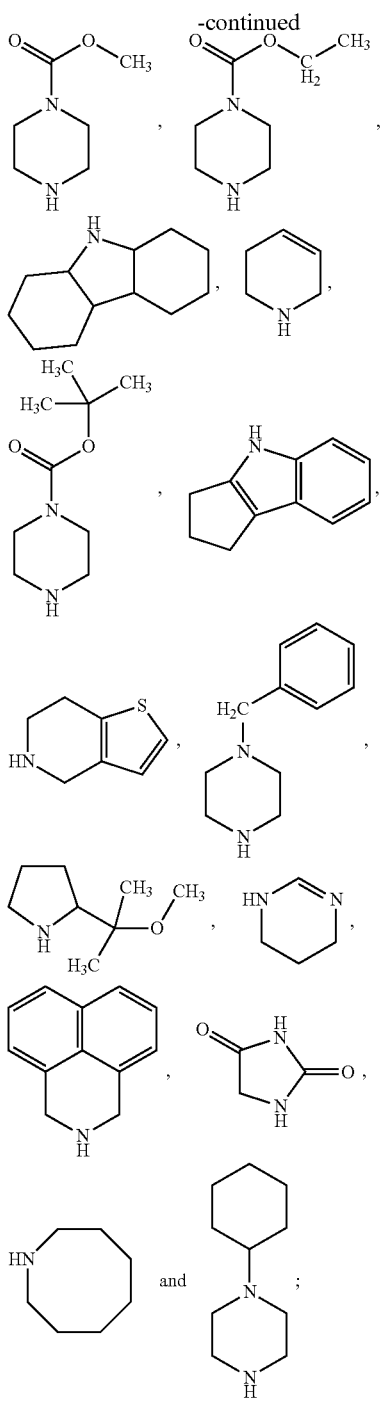

which is in each case bonded to the pyrazoline compound of general formula I in any position of the cyclic part of the aforementioned radicals including the NH-groups, preferably said radicals are bonded to the pyrazoline compound of general formula I at the nitrogen atom of the cyclic part of the aforementioned radicals;
or a —NR⁴R⁵ moiety;
R⁴ represents a hydrogen atom;
R⁵ represents a radical selected from the group consisting of 2-heptyl, 3-heptyl, 4-heptyl, 2-octyl, 3-octyl, 4-octyl, —CH₂—N(CH₃)₂, —CH₂—N(C₂H₅)₂, —CH₂—CH₂—N(CH₃)₂, —CH₂—CH₂—N(C₂H₅)₂, —CH₂—CH₂—CH₂—N(CH₃)₂ and —CH₂—CH₂—CH₂—N(C₂H₅)₂;

a radical selected from the group consisting of adamantyl, bicyclo[2.2.1]heptyl, bicyclo[3.1.1]heptyl, (1,7,7)-trimethyl-bicyclo[2.2.1]heptyl, [1,2,3,4]-tetrahydronaphthyl, cyclononyl, cyclodecyl, cycloundecyl and cyclododecyl;
a radical selected from the group consisting of cyclopropyl, cyclobutyl, cyclopentyl, cyclohexyl, cycloheptyl, cyclooctyl, pyrrolidinyl, piperidinyl, piperazinyl, homopiperazinyl, morpholinyl, azepanyl, diazepanyl and azocanyl, which is bonded via a —(CH₂)—, —(CH₂)—(CH₂)— or —(CH₂)—(CH₂)—(CH₂)-group;
a substituted radical selected from the group consisting of cyclopentyl, cyclohexyl and cycloheptyl which is substituted with a —O-Benzyl radical;
or a radical selected from the group consisting of

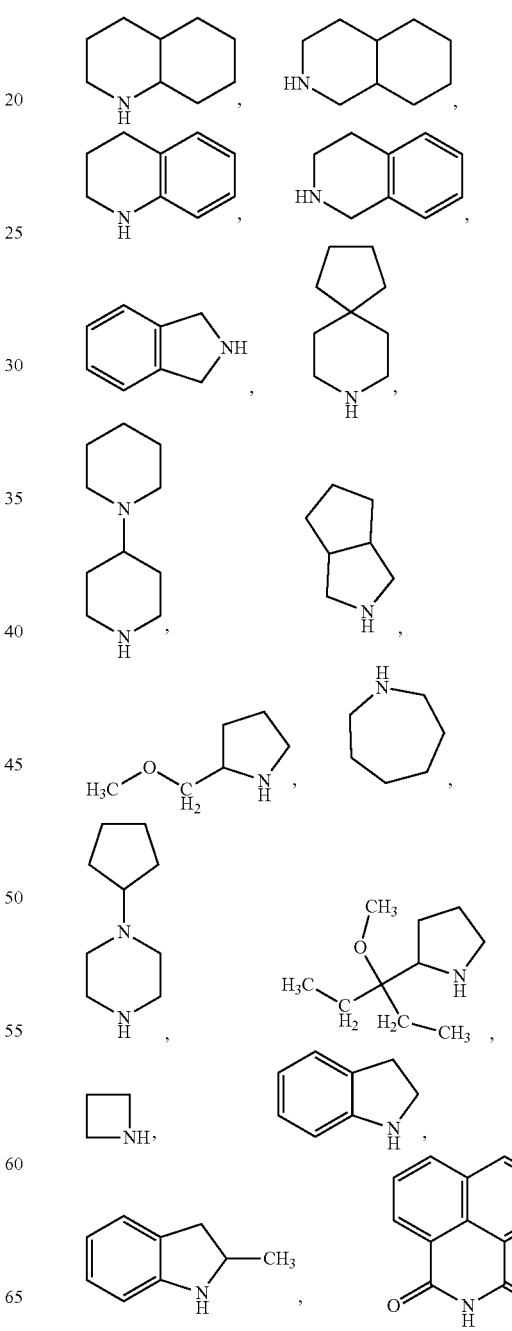

-continued

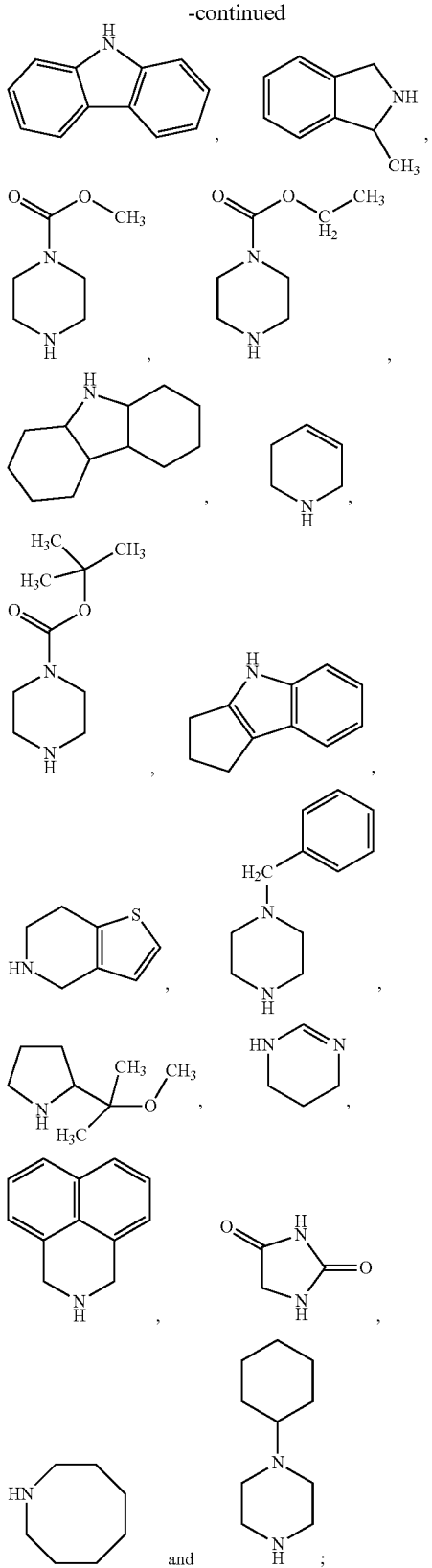

which is in each case bonded to the pyrazoline compound of general formula I in any position of the cyclic part of the aforementioned radicals including the NH-groups, preferably said radicals are bonded to the pyrazoline compound of general formula I at the nitrogen atom of the cyclic part of the aforementioned radicals;

optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

Also more particularly preferred are substituted pyrazoline compounds of general formula L, M or N,

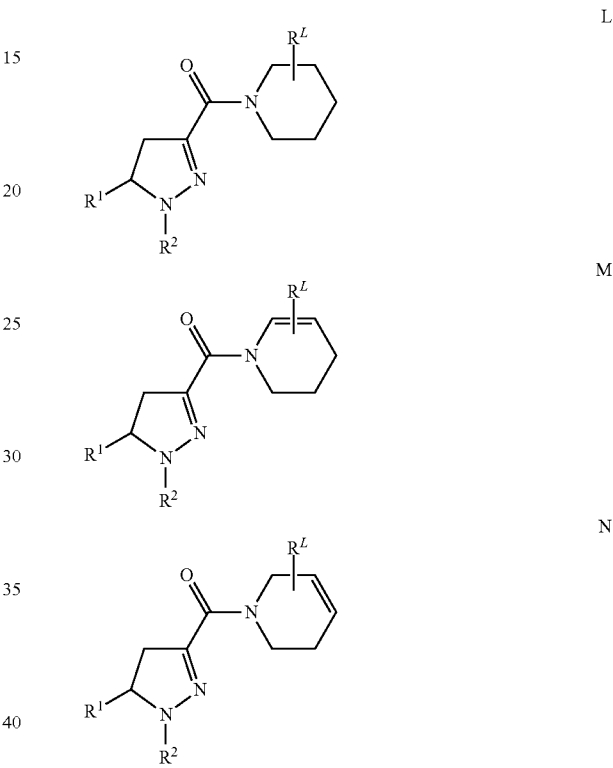

wherein
$R^L$ represents H, —OH or oxo (=O);
$R^1$ represents a phenyl radical that is substituted with a hydroxy, fluorine, chlorine, bromine or iodine atom or a —O—CH$_3$-group in the para-(4-)-position of the phenyl radical;
and $R^2$ represents a (2,4)-dichloro-phenyl radical;
optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

Most particularly preferred are substituted pyrazoline compounds of general formula I given above selected from the group consisting of

[10] 5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide

[13] 5-(4-Chloro-phenyl)-1-(2,4-dichloro-phenyl)-4,5-dihydro-1H-pyrazole-3-carboxylic acid [2-(S)-(1-methoxy-1-methyl-ethyl)-pyrrolidin-1-yl]-amide

[14] 5-(4-Chloro-phenyl)-1-(2,4-dichloro-phenyl)-4,5-dihydro-1H-pyrazole-3-carboxylic acid [2-(R)-(1-methoxy-1-methyl-ethyl)-pyrrolidin-1-yl]-amide

[15] 5-(4-Chloro-phenyl)-1-(2,4-dichloro-phenyl)-4,5-dihydro-1H-pyrazole-3-carboxylic acid [2-(1-methoxy-1-methyl-ethyl)-pyrrolidin-1-yl]-amide
[16] 5-(4-Chloro-phenyl)-1-(2,4-dichloro-phenyl)-4,5-dihydro-1H-pyrazole-3-carboxylic acid azepan-1-ylamide
[21] [5-(4-Chloro-phenyl)-1-(2,4-dichloro-phenyl)-4,5-dihydro-1H-pyrazole-3-yl]-(4-cyclohexyl-piperazin-1-yl)-methanone
[22] [5-(4-Chloro-phenyl)-1-(2,4-dichloro-phenyl)-4,5-dihydro-1H-pyrazole-3-yl]-(octahydro-isoquinolin-2-yl)-methanone
[24] 5-(4-Chloro-phenyl)-1-(2,4-dichloro-phenyl)-4,5-dihydro-1H-pyrazole-3-carboxylic acid (1,3-dioxo-1H,3H-benzo[de]isoquinolin-2-yl)-amide
[25] 5-(4-Chloro-phenyl)-1-(2,4-dichloro-phenyl)-4,5-dihydro-1H-pyrazole-3-carboxylic acid (1H,3H-benzo[de]isoquinolin-2-yl)-amide
[26] 5-(4-Chloro-phenyl)-1-(2,4-dichloro-phenyl)-4,5-dihydro-1H-pyrazole-3-carboxylic acid (4-cyclopentyl-piperazin-1-yl)-amide
[27] 5-(4-Chloro-phenyl)-1-(2,4-dichloro-phenyl)-4,5-dihydro-1H-pyrazole-3-carboxylic acid (2-methyl-2,3-dihydro-indol-1-yl)-amide
[28] 5-(4-Chloro-phenyl)-1-(2,4-dichloro-phenyl)-4,5-dihydro-1H-pyrazole-3-carboxylic acid (2,3-dihydro-indol-1-yl)-amide
[32] 5-(4-Chloro-phenyl)-1-(2,4-dichloro-phenyl)-4,5-dihydro-1H-pyrazole-3-carboxylic acid cyclohexylmethyl-amide
[35] 5-(4-Chloro-phenyl)-1-(2,4-dichloro-phenyl)-4,5-dihydro-1H-pyrazole-3-carboxylic acid (1-methyl-hexyl)-amide
[38] Azocan-1-yl-[5-(4-chloro-phenyl)-1-(2,4-dichloro-phenyl)-4,5-dihydro-1H-pyrazol-3-yl]-methanone
[39] [5-(4-Chloro-phenyl)-1-(2,4-dichloro-phenyl)-4,5-dihydro-1H-pyrazole-3-yl]-(1,3-dihydro-isoindol-2-yl)-methanone
[40] Azetidin-1-yl-[5-(4-chloro-phenyl)-1-(2,4-dichloro-phenyl)-4,5-dihydro-1H-pyrazol-3-yl]-methanone
[42] [1,4']Bipiperidin-1'-yl-[5-(4-chloro-phenyl)-1-(2,4-dichloro-phenyl)-4,5-dihydro-1H-pyrazol-3-yl]-methanone
[44] 4-[5-(4-Chloro-phenyl)-1-(2,4-dichloro-phenyl)-4,5-dihydro-1H-pyrazole-3-carbonyl]-piperazine-1-carboxylic acid ethyl ester
[45] [5-(4-Chloro-phenyl)-1-(2,4-dichloro-phenyl)-4,5-dihydro-1H-pyrazole-3-yl]-(3,4-dihydro-1H-isoquinolin-2-yl)-methanone
[48] 5-(4-Chloro-phenyl)-1-(2,4-dichloro-phenyl)-4,5-dihydro-1H-pyrazole-3-carboxylic acid (2,4-dioxo-imidazolidin-1-yl)-amide
[49] 5-(4-Chloro-phenyl)-1-(2,4-dichloro-phenyl)-4,5-dihydro-1H-pyrazole-3-carboxylic acid cyclododecylamide
[52] (4-Benzyl-piperazin-1-yl)-[5-(4-chloro-phenyl)-1-(2,4-dichloro-phenyl)-4,5-dihydro-1H-pyrazol-3-yl]-methanone
[56] [5-(4-Chloro-phenyl)-1-(2,4-dichloro-phenyl)-4,5-dihydro-1H-pyrazole-3-yl]-(6,7-dihydro-4H-thieno[3,2-c]pyridin-5-yl)-methanone
[58] 5-(4-Chloro-phenyl)-1-(2,4-dichloro-phenyl)-4,5-dihydro-1H-pyrazole-3-carboxylic acid (1,7,7-trimethyl-bicyclo[2.2.1]hept-2-yl)-amide
[63] 5-(4-Bromo-phenyl)-1-(2,4-dichloro-phenyl)-4,5-dihydro-1H-pyrazole-3-carboxylic acid (hexahydro-cyclopenta[c]pyrrol-2-yl)-amide
[64] 5-(4-Bromo-phenyl)-1-(2,4-dichloro-phenyl)-4,5-dihydro-1H-pyrazole-3-carboxylic acid (4-cyclopentyl-piperazin-1-yl)-amide
[65] 5-(4-Bromo-phenyl)-1-(2,4-dichloro-phenyl)-4,5-dihydro-1H-pyrazole-3-carboxylic acid (1H,3H-benzo[de]isoquinolin-2-yl)-amide
[66] 5-(4-Bromo-phenyl)-1-(2,4-dichloro-phenyl)-4,5-dihydro-1H-pyrazole-3-carboxylic acid (2,3-dihydro-indol-1-yl)-amide hydrochloride
[68] 5-(4-Bromo-phenyl)-1-(2,4-dichloro-phenyl)-4,5-dihydro-1H-pyrazole-3-carboxylic acid azepan-1-yl-amide
[71] 5-(4-Chloro-phenyl)-1-(2,4-dichloro-phenyl)-4,5-dihydro-1H-pyrazole-3-carboxylic acid (2-morpholin-4-yl-ethyl)-amide
[73] 5-(4-Chloro-phenyl)-1-(2,4-dichloro-phenyl)-4,5-dihydro-1H-pyrazole-3-carboxylic acid (3-dimethylamino-propyl)-amide
[74] [5-(4-Chloro-phenyl)-1-(2,4-dichloro-phenyl)-4,5-dihydro-1H-pyrazole-3-yl]-(3,6-dihydro-2H-pyridin-1-yl)-methanone
[75] [5-(4-Chloro-phenyl)-1-(2,4-dichloro-phenyl)-4,5-dihydro-1H-pyrazole-3-yl]-(5,6-dihydro-4H-pyrimidin-1-yl)-methanone
[76] 5-(4-Chloro-phenyl)-1-(2,4-dichloro-phenyl)-4,5-dihydro-1H-pyrazole-3-carboxylic acid (1,2,3,4-tetrahydro-naphthalen-1-yl)-amide
[78] [5-(4-Chloro-phenyl)-1-(2,4-dichloro-phenyl)-4,5-dihydro-1H-pyrazole-3-yl]-(2,3-dihydro-1H-cyclopenta[b]indol-4-yl)-methanone
[81] [5-(4-Chloro-phenyl)-1-(2,4-dichloro-phenyl)-4,5-dihydro-1H-pyrazole-3-yl]-(3,4-dihydro-2H-quinolin-1-yl)-methanone
[84] 5-(4-Chloro-phenyl)-1-(2,4-dichloro-phenyl)-4,5-dihydro-1H-pyrazole-3-carboxylic acid (2-cyclohexyl-ethyl)-amide
[85] [5-(4-Chloro-phenyl)-1-(2,4-dichloro-phenyl)-4,5-dihydro-1H-pyrazole-3-yl]-(dodecahydro-carbazol-9-yl)-methanone
[87] 5-(4-Chloro-phenyl)-1-(2,4-dichloro-phenyl)-4,5-dihydro-1H-pyrazole-3-carboxylic acid (2-cyclopentyl-ethyl)-amide
[88] 5-(4-Chloro-phenyl)-1-(2,4-dichloro-phenyl)-4,5-dihydro-1H-pyrazole-3-carboxylic acid bicyclo[2.2.1]hept-2-ylamide
[91] 1-(2,4-Dichloro-phenyl)-5-(4-fluoro-phenyl)-4,5-dihydro-1H-pyrazole-3-carboxylic acid (hexahydro-cyclopenta[c]pyrrol-2-yl)-amide hydrochloride
[92] 1-(2,4-Dichloro-phenyl)-5-(4-fluoro-phenyl)-4,5-dihydro-1H-pyrazole-3-carboxylic acid (4-cyclopentyl-piperazin-1-yl)-amide
[93] 1-(2,4-Dichloro-phenyl)-5-(4-fluoro-phenyl)-4,5-dihydro-1H-pyrazole-3-carboxylic acid (1H,3H-benzo[de]isoquinolin-2-yl)-amide
[94] 1-(2,4-Dichloro-phenyl)-5-(4-fluoro-phenyl)-4,5-dihydro-1H-pyrazole-3-carboxylic acid (2,3-dihydro-indol-1-yl)-amide
[96] 1-(2,4-Dichloro-phenyl)-5-(4-fluoro-phenyl)-4,5-dihydro-1H-pyrazole-3-carboxylic acid azepan-1-yl-amide
[100] 1-(2,4-Dichloro-phenyl)-5-(4-iodo-phenyl)-4,5-dihydro-1H-pyrazole-3-carboxylic acid (hexahydro-cyclopenta[c]pyrrol-2-yl)-amide
[101] 1-(2,4-Dichloro-phenyl)-5-(4-iodo-phenyl)-4,5-dihydro-1H-pyrazole-3-carboxylic acid (4-cyclopentyl-piperazin-1-yl)-amide
[102] 1-(2,4-Dichloro-phenyl)-5-(4-iodo-phenyl)-4,5-dihydro-1H-pyrazole-3-carboxylic acid (1H,3H-benzo[de]isoquinolin-2-yl)-amide

[103] 1-(2,4-Dichloro-phenyl)-5-(4-iodo-phenyl)-4,5-dihydro-1H-pyrazole-3-carboxylic acid (2,3-dihydro-indol-1-yl)-amide
[105] 1-(2,4-Dichloro-phenyl)-5-(4-iodo-phenyl)-4,5-dihydro-1H-pyrazole-3-carboxylic acid azepan-1-ylamide;
[109] 1-(2,4-Dichloro-phenyl)-5-(4-methoxy-phenyl)-4,5-dihydro-1H-pyrazole-3-carboxylic acid (hexahydro-cyclopenta[c]pyrrol-2-yl)-amide hydrochloride
[110] 1-(2,4-Dichloro-phenyl)-5-(4-methoxy-phenyl)-4,5-dihydro-1H-pyrazole-3-carboxylic acid (4-cyclopentyl-piperazin-1-yl)-amide
[111] 1-(2,4-Dichloro-phenyl)-5-(4-methoxy-phenyl)-4,5-dihydro-1H-pyrazole-3-carboxylic acid (1H,3H-benzo[de]isoquinolin-2-yl)-amide
[112] 1-(2,4-Dichloro-phenyl)-5-(4-methoxy-phenyl)-4,5-dihydro-1H-pyrazole-3-carboxylic acid (2,3-dihydro-indol-1-yl)-amide hydrochloride
[114] 1-(2,4-Dichloro-phenyl)-5-(4-methoxy-phenyl)-4,5-dihydro-1H-pyrazole-3-carboxylic acid azepan-1-ylamide hydrochloride
[145] 5-(4-Chloro-phenyl)-1-(2,4-dichloro-phenyl)-4,5-dihydro-1H-pyrazole-3-carboxylic acid azocan-1-ylamide hydrochloride
[146] 5-(4-bromo-phenyl)-1-(2,4-dichloro-phenyl)-4,5-dihydro-1H-pyrazole-3-carboxylic acid azocan-1-ylamide
[147] 5-(4-fluoro-phenyl)-1-(2,4-dichloro-phenyl)-4,5-dihydro-1H-pyrazole-3-carboxylic acid azocan-1-ylamide
[148] 5-(4-methoxy-phenyl)-1-(2,4-dichloro-phenyl)-4,5-dihydro-1H-pyrazole-3-carboxylic acid azocan-1-ylamide
[149] 5-(4-hydroxy-phenyl)-1-(2,4-dichloro-phenyl)-4,5-dihydro-1H-pyrazole-3-carboxylic acid azocan-1-ylamide hydrochloride
[150] 5-(4-iodo-phenyl)-1-(2,4-dichloro-phenyl)-4,5-dihydro-1H-pyrazole-3-carboxylic acid azocan-1-ylamide
[151] N-((1S,2S)-2-(benzyloxy)cyclohexyl)-5-(4-chlorophenyl)-1-(2,4-dichlorophenyl)-4,5-dihydro-1H-pyrazole-3-carboxamide
[158] 5-(4-Chloro-phenyl)-1-(2,4-dichloro-phenyl)-4,5-dihydro-1H-pyrazole-3-carboxylic acid adamantan-1-ylamide
[159] (R)-5-(4-Chloro-phenyl)-1-(2,4-dichloro-phenyl)-4,5-dihydro-1H-pyrazole-3-carboxylic acid adamantan-1-ylamide
[160] (S)-5-(4-Chloro-phenyl)-1-(2,4-dichloro-phenyl)-4,5-dihydro-1H-pyrazole-3-carboxylic acid adamantan-1-ylamide
[161] 5-(4-bromo-phenyl)-1-(2,4-dichloro-phenyl)-4,5-dihydro-1H-pyrazole-3-carboxylic acid adamantan-1-ylamide
[162] 5-(4-fluoro-phenyl)-1-(2,4-dichloro-phenyl)-4,5-dihydro-1H-pyrazole-3-carboxylic acid adamantan-1-ylamide
[163] 5-(4-methoxy-phenyl)-1-(2,4-dichloro-phenyl)-4,5-dihydro-1H-pyrazole-3-carboxylic acid adamantan-1-ylamide
[164] 5-(4-hydroxy-phenyl)-1-(2,4-dichloro-phenyl)-4,5-dihydro-1H-pyrazole-3-carboxylic acid adamantan-1-ylamide
[165] 5-(4-iodo-phenyl)-1-(2,4-dichloro-phenyl)-4,5-dihydro-1H-pyrazole-3-carboxylic acid adamantan-1-ylamide
[166] 5-(4-Chloro-phenyl)-1-(2,4-dichloro-phenyl)-4,5-dihydro-1H-pyrazole-3-carboxylic acid adamantan-2-ylamide
[167] 5-(4-bromo-phenyl)-1-(2,4-dichloro-phenyl)-4,5-dihydro-1H-pyrazole-3-carboxylic acid adamantan-2-ylamide
[168] 5-(4-fluoro-phenyl)-1-(2,4-dichloro-phenyl)-4,5-dihydro-1H-pyrazole-3-carboxylic acid adamantan-2-ylamide
[169] 5-(4-methoxy-phenyl)-1-(2,4-dichloro-phenyl)-4,5-dihydro-1H-pyrazole-3-carboxylic acid adamantan-2-ylamide
[170] 5-(4-hydroxy-phenyl)-1-(2,4-dichloro-phenyl)-4,5-dihydro-1H-pyrazole-3-carboxylic acid adamantan-2-ylamide
[171] 5-(4-iodo-phenyl)-1-(2,4-dichloro-phenyl)-4,5-dihydro-1H-pyrazole-3-carboxylic acid adamantan-2-ylamide
[173] 1-(2,4-Dichloro-phenyl)-5-(4-hydroxy-phenyl)-4,5-dihydro-1H-pyrazole-3-carboxylic acid azepan-1-ylamide hydrochloride
[174] 1-(2,4-Dichloro-phenyl)-5-(4-hydroxy-phenyl)-4,5-dihydro-1H-pyrazole-3-carboxylic acid (hexahydro-cyclopenta[c]pyrrol-2-yl)-amide hydrochloride
[175] 1-(2,4-Dichloro-phenyl)-5-(4-hydroxy-phenyl)-4,5-dihydro-1H-pyrazole-3-carboxylic acid (2,3-dihydro-indol-1-yl)-amide hydrochloride
[176] (R)-5-(4-Chloro-phenyl)-1-(2,4-dichloro-phenyl)-4,5-dihydro-1H-pyrazole-3-carboxylic acid azocan-1-ylamide hydrochloride
[177] (S)-5-(4-Chloro-phenyl)-1-(2,4-dichloro-phenyl)-4,5-dihydro-1H-pyrazole-3-carboxylic acid azocan-1-ylamide hydrochloride
[178] N-((1R,2R)-2-(benzyloxy)cyclohexyl)-5-(4-chlorophenyl)-1-(2,4-dichlorophenyl)-4,5-dihydro-1H-pyrazole-3-carboxamide
[179] 1-(2,4-Dichloro-phenyl)-5-(4-fluoro-phenyl)-4,5-dihydro-1H-pyrazole-3-carboxylic acid (2,3-dihydro-indol-1-yl)-amide hydrochloride
[181] (R)-5-(4-Chloro-phenyl)-1-(2,4-dichloro-phenyl)-4,5-dihydro-1H-pyrazole-3-carboxylic acid (2,3-dihydro-indol-1-yl)-amide hydrochloride
[182] (S)-5-(4-Chloro-phenyl)-1-(2,4-dichloro-phenyl)-4,5-dihydro-1H-pyrazole-3-carboxylic acid (2,3-dihydro-indol-1-yl)-amide hydrochloride
[183] (S)-5-(4-Chloro-phenyl)-1-(2,4-dichloro-phenyl)-4,5-dihydro-1H-pyrazole-3-carboxylic acid azepan-1-ylamide hydrochloride
[184] (S)-5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide hydrochloride
[185] (S)-5-(4-Chloro-phenyl)-1-(2,4-dichloro-phenyl)-4,5-dihydro-1H-pyrazole-3-carboxylic acid azepan-1-ylamide
[187] (R)-5-(4-Chloro-phenyl)-1-(2,4-dichloro-phenyl)-4,5-dihydro-1H-pyrazole-3-carboxylic acid azepan-1-ylamide hydrochloride
[188] (R)-5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide
[190] (R)-5-(4-Chloro-phenyl)-1-(2,4-dichloro-phenyl)-4,5-dihydro-1H-pyrazole-3-carboxylic acid (2,3-dihydro-indol-1-yl)-amide
[191] 5-(4-Chloro-phenyl)-1-(2,4-dichloro-phenyl)-4,5-dihydro-1H-pyrazole-3-carboxylic acid cycloheptylmethyl-amide and
[193] 5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide hydrochloride;

optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

In another aspect the present invention relates to a compound selected from the group consisting of

[7] N-oxide of 5-(4-Chloro-phenyl)-1-(2,4-dichloro-phenyl)-4,5-dihydro-1H-pyrazole-3-carboxylic acid piperidin-1-ylamide
[8] 5-(4-Chloro-phenyl)-1-(2,4-dichloro-phenyl)-4,5-dihydro-1H-pyrazole-3-carboxylic acid morpholin-4-ylamide
[9] 5-(4-Chloro-phenyl)-1-(2,4-dichloro-phenyl)-4,5-dihydro-1H-pyrazole-3-carboxylic acid morpholin-4-ylamide hydrochloride
[11] 5-(4-Chloro-phenyl)-1-(2,4-dichloro-phenyl)-4,5-dihydro-1H-pyrazole-3-carboxylic acid pyrrolidin-1-ylamide
[12] 5-(4-Chloro-phenyl)-1-(2,4-dichloro-phenyl)-4,5-dihydro-1H-pyrazole-3-carboxylic acid (2,6-dimethyl-piperidin-1-yl)-amide
[17] 5-(4-Chloro-phenyl)-1-(2,4-dichloro-phenyl)-4,5-dihydro-1H-pyrazole-3-carboxylic acid (4-methyl-cyclohexyl)-amide
[18] 5-(4-Chloro-phenyl)-1-(2,4-dichloro-phenyl)-4,5-dihydro-1H-pyrazole-3-carboxylic acid (2-methyl-cyclohexyl)-amide
[19] 5-(4-Chloro-phenyl)-1-(2,4-dichloro-phenyl)-4,5-dihydro-1H-pyrazole-3-carboxylic acid cycloheptylamide
[20] 5-(4-Chloro-phenyl)-1-(2,4-dichloro-phenyl)-4,5-dihydro-1H-pyrazole-3-carboxylic acid hexylamide
[23] 1-(2,4-Dichloro-phenyl)-5-(4-fluoro-phenyl)-4,5-dihydro-1H-pyrazole-3-carboxylic acid piperidin-1-ylamide
[29] 5-(4-Chloro-phenyl)-1-(2,4-dichloro-phenyl)-4,5-dihydro-1H-pyrazole-3-carboxyclic acid N'-butyl-N'-phenyl-hydrazide
[30] 5-(4-Chloro-phenyl)-1-(2,4-dichloro-phenyl)-4,5-dihydro-1H-pyrazole-3-carboxylic acid cyclobutylamide
[31] 5-(4-Chloro-phenyl)-1-(2,4-dichloro-phenyl)-4,5-dihydro-1H-pyrazole-3-carboxylic acid (4-tert-butyl-cyclohexyl)-amide
[33] 5-(4-Chloro-phenyl)-1-(2,4-dichloro-phenyl)-4,5-dihydro-1H-pyrazole-3-carboxylic acid N-cyclohexyl-N-ethyl-amide
[34] 5-(4-Chloro-phenyl)-1-(2,4-dichloro-phenyl)-4,5-dihydro-1H-pyrazole-3-carboxylic acid cyclooctylamide
[36] 5-(4-Chloro-phenyl)-1-(2,4-dichloro-phenyl)-4,5-dihydro-1H-pyrazole-3-carboxylic acid cyclopropylamide
[37] 5-(4-Chloro-phenyl)-1-(2,4-dichloro-phenyl)-4,5-dihydro-1H-pyrazole-3-carboxylic acid cyclopentylamide
[41] 5-(4-Chloro-phenyl)-1-(2,4-dichloro-phenyl)-4,5-dihydro-1H-pyrazole-3-carboxylic acid cyclohexylamide
[43] [5-(4-Chloro-phenyl)-1-(2,4-dichloro-phenyl)-4,5-dihydro-1H-pyrazole-3-yl]-(4-methyl-piperazin-1-yl)-methanone
[46] [5-(4-Chloro-phenyl)-1-(2,4-dichloro-phenyl)-4,5-dihydro-1H-pyrazole-3-yl]-(2-methyl-piperazin-1-yl)-methanone
[47] 5-(4-Chloro-phenyl)-1-(2,4-dichloro-phenyl)-4,5-dihydro-1H-pyrazole-3-carboxylic acid N-cyclohexyl-N-methyl-amide
[50] 5-(4-Chloro-phenyl)-1-(2,4-dichloro-phenyl)-4,5-dihydro-1H-pyrazole-3-carboxylic acid diisopropylamide
[51] 5-(4-Chloro-phenyl)-1-(2,4-dichloro-phenyl)-4,5-dihydro-1H-pyrazole-3-carboxylic acid dimethylamide
[53] 1-[5-(4-Chloro-phenyl)-1-(2,4-dichloro-phenyl)-4,5-dihydro-1H-pyrazole-3-carbonyl]-pyrrolidine-2-carboxylic acid
[54] [5-(4-Chloro-phenyl)-1-(2,4-dichloro-phenyl)-4,5-dihydro-1H-pyrazole-3-yl]-morpholin-4-yl-methanone
[55] 5-(4-Chloro-phenyl)-1-(2,4-dichloro-phenyl)-4,5-dihydro-1H-pyrazole-3-carboxylic acid cyclohexyl-isopropyl-amide
[57] 5-(4-Chloro-phenyl)-1-(2,4-dichloro-phenyl)-4,5-dihydro-1H-pyrazole-3-carboxylic acid (3-methyl-cyclohexyl)-amide
[59] [5-(4-Chloro-phenyl)-1-(2,4-dichloro-phenyl)-4,5-dihydro-1H-pyrazole-3-yl]-(5-ethyl-2-methyl-piperidin-1-yl)-methanone
[60] 5-(4-Bromo-phenyl)-1-(2,4-dichloro-phenyl)-4,5-dihydro-1H-pyrazole-3-carboxylic acid piperidin-1-ylamide hydrochloride
[61] 5-(4-Bromo-phenyl)-1-(2,4-dichloro-phenyl)-4,5-dihydro-1H-pyrazole-3-carboxylic acid pyrrolidin-1-ylamide
[62] 5-(4-Bromo-phenyl)-1-(2,4-dichloro-phenyl)-4,5-dihydro-1H-pyrazole-3-carboxylic acid (2,6-dimethyl-piperidin-1-yl)-amide
[67] 5-(4-Bromo-phenyl)-1-(2,4-dichloro-phenyl)-4,5-dihydro-1H-pyrazole-3-carboxylic acid morpholin-4-ylamide
[69] 5-(4-Bromo-phenyl)-1-(2,4-dichloro-phenyl)-4,5-dihydro-1H-pyrazole-3-carboxylic acid propylamide
[70] 5-(4-Chloro-phenyl)-1-(2,4-dichloro-phenyl)-4,5-dihydro-1H-pyrazole-3-carboxylic acid tert-butylamide
[72] 5-(4-Chloro-phenyl)-1-(2,4-dichloro-phenyl)-4,5-dihydro-1H-pyrazole-3-carboxylic acid butylamide
[79] 5-(4-Chloro-phenyl)-1-(2,4-dichloro-phenyl)-4,5-dihydro-1H-pyrazole-3-carboxylic acid (3,5-dimethyl-[1,2,4]triazol-4-yl)-amide
[80] [5-(4-Chloro-phenyl)-1-(2,4-dichloro-phenyl)-4,5-dihydro-1H-pyrazole-3-yl]-(2,6-dimethyl-morpholin-4-yl)-methanone
5-(4-chlorophenyl)-1-(2,4-dichlorophenyl)-N-((1R,2R)-2-hydroxycyclohexyl)-4,5-dihydro-1H-pyrazole-3-carboxamide
[83] 5-(4-chlorophenyl)-1-(2,4-dichlorophenyl)-N-((1S,2S)-2-hydroxycyclohexyl)-4,5-dihydro-1H-pyrazole-3-carboxamide
[86] [5-(4-Chloro-phenyl)-1-(2,4-dichloro-phenyl)-4,5-dihydro-1H-pyrazole-3-yl]-(4-propyl-piperidin-1-yl)-methanone
[89] 1-(2,4-Dichloro-phenyl)-5-(4-fluoro-phenyl)-4,5-dihydro-1H-pyrazole-3-carboxylic acid pyrrolidin-1-ylamide
[90] 1-(2,4-Dichloro-phenyl)-5-(4-fluoro-phenyl)-4,5-dihydro-1H-pyrazole-3-carboxylic acid (2,6-dimethyl-piperidin-1-yl)-amide
[95] 1-(2,4-Dichloro-phenyl)-5-(4-fluoro-phenyl)-4,5-dihydro-1H-pyrazole-3-carboxylic acid morpholin-4-ylamide
[97] 1-(2,4-Dichloro-phenyl)-5-(4-iodo-phenyl)-4,5-dihydro-1H-pyrazole-3-carboxylic acid piperidin-1-ylamide
[98] 1-(2,4-Dichloro-phenyl)-5-(4-iodo-phenyl)-4,5-dihydro-1H-pyrazole-3-carboxylic acid pyrrolidin-1-ylamide
[99] 1-(2,4-Dichloro-phenyl)-5-(4-iodo-phenyl)-4,5-dihydro-1H-pyrazole-3-carboxylic acid (2,6-dimethyl-piperidin-1-yl)-amide
[104] 1-(2,4-Dichloro-phenyl)-5-(4-iodo-phenyl)-4,5-dihydro-1H-pyrazole-3-carboxylic acid morpholin-4-ylamide
[106] 1-(2,4-Dichloro-phenyl)-5-(4-methoxy-phenyl)-4,5-dihydro-1H-pyrazole-3-carboxylic acid piperidin-1-ylamide hydrochloride
[107] 1-(2,4-Dichloro-phenyl)-5-(4-methoxy-phenyl)-4,5-dihydro-1H-pyrazole-3-carboxylic acid pyrrolidin-1-ylamide
[108] 1-(2,4-Dichloro-phenyl)-5-(4-methoxy-phenyl)-4,5-dihydro-1H-pyrazole-3-carboxylic acid (2,6-dimethyl-piperidin-1-yl)-amide
[113] 1-(2,4-Dichloro-phenyl)-5-(4-methoxy-phenyl)-4,5-dihydro-1H-pyrazole-3-carboxylic acid morpholin-4-ylamide
[130] 5-(4-Bromo)-1-(2,4-dichloro-phenyl)-4,5-dihydro-1H-pyrazole-3-carboxylic acid cycloheptylamide

[131] 5-(4-Fluorophenyl)-1-(2,4-dichloro-phenyl)-4,5-dihydro-1H-pyrazole-3-carboxylic acid cycloheptylamide
[132] 5-(4-methoxyphenyl)-1-(2,4-dichloro-phenyl)-4,5-dihydro-1H-pyrazole-3-carboxylic acid cycloheptylamide
[133] 5-(4-hydroxyphenyl)-1-(2,4-dichloro-phenyl)-4,5-dihydro-1H-pyrazole-3-carboxylic acid cycloheptylamide
[134] 5-(4-iodophenyl)-1-(2,4-dichloro-phenyl)-4,5-dihydro-1H-pyrazole-3-carboxylic acid cycloheptylamide
[135] 1-(2,4-Dichloro-phenyl)-5-(4-fluoro-phenyl)-4,5-dihydro-1H-pyrazole-3-carboxylic acid piperidin-1-ylamide hydrochloride
[186] (S)-5-(4-Chloro-phenyl)-1-(2,4-dichloro-phenyl)-4,5-dihydro-1H-pyrazole-3-carboxylic acid cycloheptylamide
[189] (R)-5-(4-Chloro-phenyl)-1-(2,4-dichloro-phenyl)-4,5-dihydro-1H-pyrazole-3-carboxylic acid cycloheptylamide
[192] 5-(4-Chloro-phenyl)-1-(2,4-dichloro-phenyl)-4,5-dihydro-1H-pyrazole-3-carboxylic acid (2,6-dimethyl-piperidin-1-yl)-amide hydrochloride
[194] 5-(4-Chloro-phenyl)-1-(2,4-dichloro-phenyl)-4,5-dihydro-1H-pyrazole-3-carboxylic acid pyrrolidin-1-ylamide hydrochloride
[195] [5-(4-Chloro-phenyl)-1-(2,4-dichloro-phenyl)-4,5-dihydro-1H-pyrazole-3-yl]-(4-methyl-piperazin-1-yl)-methanone hydrochloride
[136] 1-(2,4-dichlorophenyl)-N-((1S,2S)-2-hydroxycyclohexyl)-5-(4-methoxyphenyl)-4,5-dihydro-1H-pyrazole-3-carboxamide
[137] (R)-1-(2,4-dichlorophenyl)-N-((1S,2S)-2-hydroxycyclohexyl)-5-(4-methoxyphenyl)-4,5-dihydro-1H-pyrazole-3-carboxamide
[138] (S)-1-(2,4-dichlorophenyl)-N-((1S,2S)-2-hydroxycyclohexyl)-5-(4-methoxyphenyl)-4,5-dihydro-1H-pyrazole-3-carboxamide
[139] (R)-5-(4-chlorophenyl)-1-(2,4-dichlorophenyl)-N-((1S,2S)-2-hydroxycyclohexyl)-4,5-dihydro-1H-pyrazole-3-carboxamide
[140] (S)-5-(4-chlorophenyl)-1-(2,4-dichlorophenyl)-N-((1S,2S)-2-hydroxycyclohexyl)-4,5-dihydro-1H-pyrazole-3-carboxamide
[141] (R)-5-(4-chlorophenyl)-1-(2,4-dichlorophenyl)-N-((1R,2R)-2-hydroxycyclohexyl)-4,5-dihydro-1H-pyrazole-3-carboxamide
[142] (S)-5-(4-chlorophenyl)-1-(2,4-dichlorophenyl)-N-((1R,2R)-2-hydroxycyclohexyl)-4,5-dihydro-1H-pyrazole-3-carboxamide
[143] 1-(2,4-dichlorophenyl)-5-(4-fluorophenyl)-N-((1S,2S)-2-hydroxycyclohexyl)-4,5-dihydro-1H-pyrazole-3-carboxamide
[144] 1-(2,4-dichlorophenyl)-5-(4-iodophenyl)-N-((1S,2S)-2-hydroxycyclohexyl)-4,5-dihydro-1H-pyrazole-3-carboxamide
[152] 5-(4-Chloro-phenyl)-1-(2,4-dichloro-phenyl)-4,5-dihydro-1H-pyrazole-3-carboxylic acid (4-oxo-piperidin-1-yl)-amide
[153] 5-(4-Chloro-phenyl)-1-(2,4-dichloro-phenyl)-4,5-dihydro-1H-pyrazole-3-carboxylic acid (3,6-dihydro-2H-pyridin-1-yl)-amide
[154] 5-(4-Chloro-phenyl)-1-(2,4-dichloro-phenyl)-4,5-dihydro-1H-pyrazole-3-carboxylic acid (3-hydroxy-piperidin-1-yl)-amide
[155] 5-(4-Chloro-phenyl)-1-(2,4-dichloro-phenyl)-4,5-dihydro-1H-pyrazole-3-carboxylic acid (4-hydroxy-piperidin-1-yl)-amide
[156] 5-(4-Chloro-phenyl)-1-(2,4-dichloro-phenyl)-4,5-dihydro-1H-pyrazole-3-carboxylic acid (2-hydroxy-piperidin-1-yl)-amide
[157] 5-(4-Chloro-phenyl)-1-(2,4-dichloro-phenyl)-4,5-dihydro-1H-pyrazole-3-carboxylic acid (3,4-dihydro-2H-pyridin-1-yl)-amide [172] 1-(2,4-Dichloro-phenyl)-5-(4-hydroxy-phenyl)-4,5-dihydro-1H-pyrazole-3-carboxylic acid piperidin-1-ylamide hydrochloride
[196] (R)-5-(4-chlorophenyl)-1-(2,4-dichlorophenyl)-N-((1R,2R)-2-hydroxycyclohexyl)-4,5-dihydro-1H-pyrazole-3-carboxamide
[197] (S)-5-(4-chlorophenyl)-1-(2,4-dichlorophenyl)-N-((1R,2R)-2-hydroxycyclohexyl)-4,5-dihydro-1H-pyrazole-3-carboxamide
[198] (R)-5-(4-chlorophenyl)-1-(2,4-dichlorophenyl)-N-((1S,2S)-2-hydroxycyclohexyl)-4,5-dihydro-1H-pyrazole-3-carboxamide
[199] (S)-5-(4-chlorophenyl)-1-(2,4-dichlorophenyl)-N-((1S,2S)-2-hydroxycyclohexyl)-4,5-dihydro-1H-pyrazole-3-carboxamide
[200] 5-(4-bromophenyl)-1-(2,4-dichlorophenyl)-N-((1S,2S)-2-hydroxycyclohexyl)-4,5-dihydro-1H-pyrazole-3-carboxamide
[201] 5-(4-bromophenyl)-1-(2,4-dichlorophenyl)-N-((1R,2R)-2-hydroxycyclohexyl)-4,5-dihydro-1H-pyrazole-3-carboxamide
[202] 1-(2,4-dichlorophenyl)-N-((1S,2S)-2-hydroxycyclohexyl)-5-(4-methoxyphenyl)-4,5-dihydro-1H-pyrazole-3-carboxamide
[203] 1-(2,4-dichlorophenyl)-N-((1R,2R)-2-hydroxycyclohexyl)-5-(4-methoxyphenyl)-4,5-dihydro-1H-pyrazole-3-carboxamide;

optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

Another object of the present invention is a compound selected from the group consisting of
[115] 5-(4-Chloro-phenyl)-1-(2,4-dichloro-phenyl)-4,5-dihydro-1H-pyrazole-3-carboxylic acid methyl ester
[116] 5-(4-Bromo-phenyl)-1-(2,4-dichloro-phenyl)-4,5-dihydro-1H-pyrazole-3-carboxylic acid methyl ester
[117] 1-(2,4-Dichloro-phenyl)-5-(4-fluoro-phenyl)-4,5-dihydro-1H-pyrazole-3-carboxyclic acid methyl ester
[118] 1-(2,4-Dichloro-phenyl)-5-(4-methoxy-phenyl)-4,5-dihydro-1H-pyrazole-3-carboxyclic acid methyl ester
[119] 1-(2,4-Dichloro-phenyl)-5-(4-iodo-phenyl)-4,5-dihydro-1H-pyrazole-3-carboxyclic acid methyl ester
[120] 5-(4-Chloro-phenyl)-1-(2,4-dichloro-phenyl)-4,5-dihydro-1H-pyrazole-3-carboxylic acid ethyl ester
[121] 5-(4-Bromo-phenyl)-1-(2,4-dichloro-phenyl)-4,5-dihydro-1H-pyrazole-3-carboxylic acid ethyl ester
[122] 1-(2,4-Dichloro-phenyl)-5-(4-fluoro-phenyl)-4,5-dihydro-1H-pyrazole-3-carboxyclic acid ethyl ester
[123] 1-(2,4-Dichloro-phenyl)-5-(4-iodo-phenyl)-4,5-dihydro-1H-pyrazole-3-carboxyclic acid ethyl ester
[124] 1-(2,4-Dichloro-phenyl)-5-(4-methoxy-phenyl)-4,5-dihydro-1H-pyrazole-3-carboxyclic acid ethyl ester
[125] 1-(2,4-Dichloro-phenyl)-5-(4-iodo-phenyl)-4,5-dihydro-1H-pyrazole-3-carboxyclic acid
[126] 1-(2,4-Dichloro-phenyl)-5-(4-fluoro-phenyl)-4,5-dihydro-1H-pyrazole-3-carboxyclic acid
[127] 1-(2,4-Dichloro-phenyl)-5-(4-methoxy-phenyl)-4,5-dihydro-1H-pyrazole-3-carboxyclic acid
[128] 5-(4-Bromo-phenyl)-1-(2,4-dichloro-phenyl)-4,5-dihydro-1H-pyrazole-3-carboxylic acid and
[129] 5-(4-Chloro-phenyl)-1-(2,4-dichloro-phenyl)-4,5-dihydro-1H-pyrazole-3-carboxylic acid

[180] 1-(2,4-Dichloro-phenyl)-5-(4-hydroxy-phenyl)-4,5-dihydro-1H-pyrazole-3-carboxylic acid.

In another aspect the present invention relates to a compound selected from the group consisting of

[60A] 5-(4-Bromo-phenyl)-1-(2,4-dichloro-phenyl)-4,5-dihydro-1H-pyrazole-3-carboxylic acid piperidin-1-ylamide

[66A] 5-(4-Bromo-phenyl)-1-(2,4-dichloro-phenyl)-4,5-dihydro-1H-pyrazole-3-carboxylic acid (2,3-dihydro-indol-1-yl)-amide

[82A] 5-(4-Chloro-phenyl)-1-(2,4-dichloro-phenyl)-4,5-dihydro-1H-pyrazole-3-carboxylic acid (2-(R)-hydroxy-cyclohexyl)-amide

[83A] 5-(4-Chloro-phenyl)-1-(2,4-dichloro-phenyl)-4,5-dihydro-1H-pyrazole-3-carboxylic acid (2-(S)-hydroxy-cyclohexyl)-amide

[91A] 1-(2,4-Dichloro-phenyl)-5-(4-fluoro-phenyl)-4,5-dihydro-1H-pyrazole-3-carboxylic acid (hexahydro-cyclopenta[c]pyrrol-2-yl)-amide

[106A] 1-(2,4-Dichloro-phenyl)-5-(4-methoxy-phenyl)-4,5-dihydro-1H-pyrazole-3-carboxylic acid piperidin-1-ylamide

[109A] 1-(2,4-Dichloro-phenyl)-5-(4-methoxy-phenyl)-4,5-dihydro-1H-pyrazole-3-carboxylic acid (hexahydro-cyclopenta[c]pyrrol-2-yl)-amide

[112A] 1-(2,4-Dichloro-phenyl)-5-(4-methoxy-phenyl)-4,5-dihydro-1H-pyrazole-3-carboxylic acid (2,3-dihydro-indol-1-yl)-amide and

[114A] 1-(2,4-Dichloro-phenyl)-5-(4-methoxy-phenyl)-4,5-dihydro-1H-pyrazole-3-carboxylic acid azepan-1-ylamide;

optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof.

The afore mentioned compounds, e.g. the afore mentioned carboxylic acids and carboxylic esters, are intermediates in the synthesis of compounds of general formula I and in addition exhibit the same pharmacological activity as the compounds of general formula I.

In another aspect the present invention also provides a process for the preparation of substituted pyrazoline compounds of general formula I given above, wherein at least one compound of general formula II,

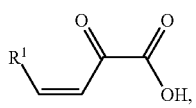

II wherein $R^1$ has the meaning given above, is reacted with at least one compound of general formula III,

III or a corresponding salt thereof, wherein $R^2$ has the meaning given above, in a reaction medium, optionally in an inert atmosphere, optionally in the presence of at least one acid, to yield at least one compound of general formula IV,

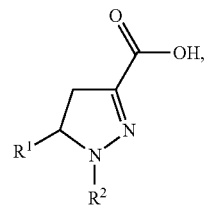

IV wherein $R^1$ and $R^2$ have the meaning given above, which is optionally isolated and/or purified, and at least one compound of general formula IV is reacted with an activating agent in a reaction medium, optionally in an inert atmosphere, to yield at least one compound of general formula V,

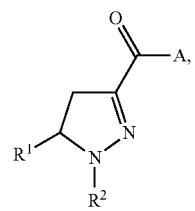

V wherein $R^1$ and $R^2$ have the meaning given above and A represents a leaving group, which is optionally purified and/or isolated, and at least one compound of general formula V is reacted with at least one compound of general formula $R^3$—H, wherein $R^3$ has the meaning given above, in a reaction medium, optionally in an inert atmosphere, optionally in the presence of at least one base selected from the group consisting of diisopropylethylamine, triethylamine, pyridine, dimethylaminopyridine and N-methylmorpholine, to yield at least one compound of general formula I, wherein $R^1$, $R^2$ and $R^3$ have the meaning given above, which is optionally purified and/or isolated;

or at least one compound of general formula IV is reacted with at least one compound of general formula $R^3$—H, wherein $R^3$ represents a —$NR^4R^5$ moiety, wherein $R^4$ and $R^5$ have the meaning given above, in a reaction medium, in the presence of at least one coupling agent, optionally in the presence of at least one base, to yield at least one compound of general formula I, wherein $R^1$ and $R^2$ have the meaning given above and $R^4$ represents a —$NR^4R^5$ moiety, which is optionally purified and/or isolated.

Also preferred is the process for the preparation of a compound of general formula I given above, wherein at least one compound of general formula $R^1$—C(=O)—H (general formula VII), wherein $R^1$ has the meaning given above, is reacted with at least one compound of general formula VI,

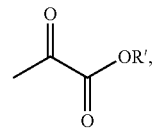

VI wherein R' represents a linear or branched $C_{1-6}$-alkyl radical, a potassium cation or a sodium cation, in a reaction medium, optionally in an inert atmosphere, optionally in the presence of at least one base, to yield at least one compound of general formula II,

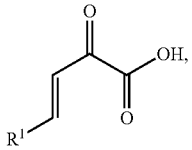

wherein $R^1$ has the meaning given above, which is optionally purified and/or isolated,
and at least one compound of general formula II is reacted with an activating agent in a reaction medium, optionally in an inert atmosphere, to yield at least one compound of general formula VIII,

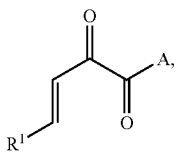

wherein $R^1$ has the meaning given above and A represents a leaving group, which is optionally purified and/or isolated,
and at least one compound of general formula VIII is reacted with at least one compound of general formula $R^3$—H, wherein $R^3$ has the meaning given above, in a reaction medium, optionally in an inert atmosphere, optionally in the presence of at least one base selected from the group consisting of diisopropylethylamine, triethylamine, pyridine, dimethylaminopyridine and N-methylmorpholine, to yield at least one compound of general formula IX,

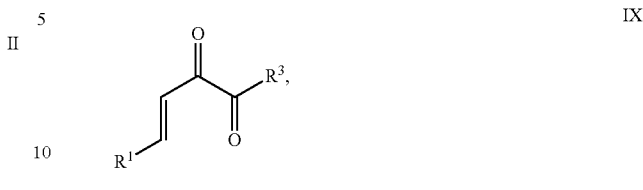

wherein $R^1$ and $R^3$ have the meaning given above, which is optionally purified and/or isolated;
or at least one compound of general formula II is reacted with at least one compound of general formula $R^3$—H, wherein $R^3$ represents a —$NR^4R^5$ moiety, wherein $R^4$ and $R^5$ have the meaning given above, in a reaction medium, in the presence of at least one coupling agent, optionally in the presence of at least one base, to yield at least one compound of general formula IX, wherein $R^3$ represents a —$NR^4R^5$ moiety, which is optionally purified and/or isolated,
and at least one compound of general formula IX is reacted with at least one compound of general formula III,

wherein $R^2$ has the meaning given above, in a reaction medium, optionally in an inert atmosphere, optionally in the presence of at least one acid, to yield at least one compound of general formula I, wherein $R^1$, $R^2$ and $R^3$ have the meaning given above, which is optionally purified and/or isolated.

The inventive process is also illustrated in scheme I given below:

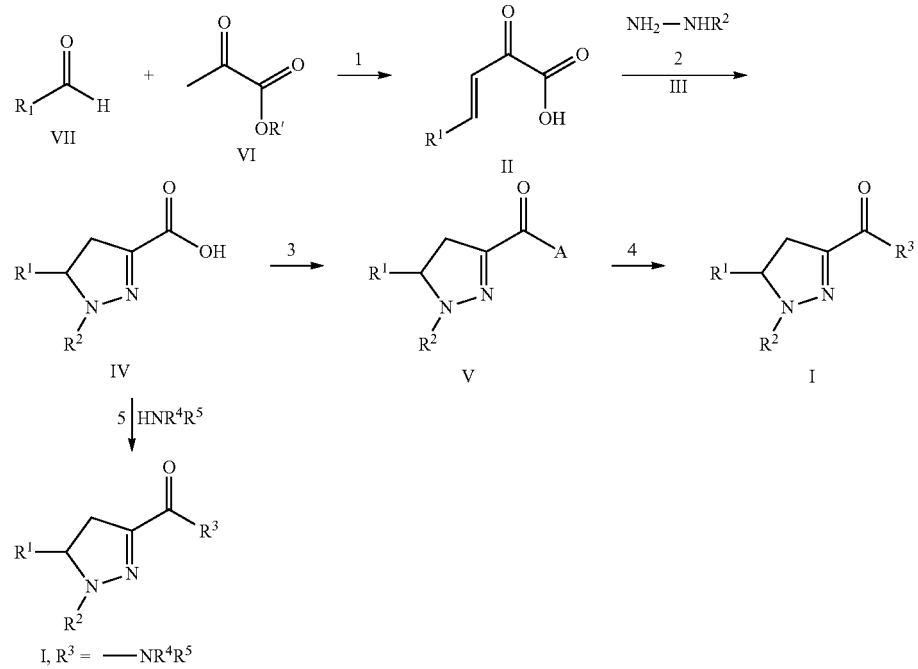

In step 1 a compound of general formula VI is reacted with a compound of general formula VII in a protic reaction medium, preferably in a reaction medium selected from the group consisting of methanol, ethanol, isopropanol, n-butanol, water and mixtures thereof, in the presence of at least one base, preferably in the presence of an alkali metal hydroxide such as sodium hydroxide or potassium hydroxide or an alkali metal methoxide such as sodium methoxide, as described, for example, in Synthetic Communications, 26(11), 2229-33, (1996). The respective description is hereby incorporated by reference and forms part of the disclosure. Reaction temperature as well as the duration of the reaction may vary over a broad range. Preferred reaction temperatures range from −10° C. to the boiling point of the reaction medium. Suitable reaction times may vary for example from several minutes to several hours.

Preferably the reaction between a compound of general formula VI and general formula VII can also be carried out under acid catalysed conditions, more preferably by refluxing the above mentioned compounds in dichloromethane in the presence of copper(II)trifluoromethanesulfonate as described, for example, in Synlett, (1), 147-149, 2001. The respective description is hereby incorporated by reference and forms part of the disclosure.

In step 2 a compound of general formula II is reacted with a compound of general formula III in a reaction medium, preferably in a reaction medium selected from the group consisting of methanol, ethanol, isopropanol, n-butanol, diethylether, tert-butyl-methylether, dioxane, tetrahydrofuran or mixtures of at least two of these afore mentioned reaction media. Also preferably, said reaction may be carried out in the presence of an acid, whereby the acid may be organic such as acetic acid and/or inorganic such as hydrochloric acid. Alternatively the reaction may also be carried out in the presence of a base such as piperidine, piperazine, sodium hydroxide, potassium hydroxide, sodium methoxide or sodium ethoxide or mixtures of at least two of these bases.

Reaction temperature as well as the duration of the reaction may vary over a broad range. Suitable reaction temperatures range from room temperature, i.e. approximately 25° C. to the boiling point of the reaction medium. Suitable reaction times may vary for example from several minutes to several hours.

In step 3 the carboxylic group of the compound of general formula IV may be activated for further reactions by the introduction of a suitable leaving group according to conventional methods well known to those skilled in the art. Preferably the compounds of general formula IV are transferred into an acid chloride, an acid anhydride, a mixed anhydride, a $C_{1-4}$ alkyl ester or an activated ester such as p-nitrophenylester. Suitable activating agent therefore are selected from the group consisting of thionyl chloride, oxalyl chloride and ethylchloroformate.

If said activated compound of general formula V is an acid chloride, wherein A represents a chlorine atom, that compound is preferably prepared by the reaction of the corresponding acid of general formula IV with thionyl chloride or oxalyl chloride, whereby said chlorinating agent is also used as the reaction medium, in the presence of at least one base, preferably in the presence of a base selected from the group consisting of triethylamine, N-methylmorpholine, pyridine, dimethylaminopyridine and diisopropylethylamine. Also preferably an additional reaction medium may be used. Suitable reaction media include hydrocarbons such as benzene, toluene or xylene, halogenated hydrocarbons such as dichloromethane, chloroform or carbon tetrachloride, ethers such as diethyl ether, dioxane, tetrahydrofuran or dimethoxyethane or dimethylformamide and mixtures thereof. More preferably toluene in the presence of a catalytic amount of dimethylformamide is used as reaction medium. Preferred reaction temperature range from 0° C. to the boiling point of the solvent and reaction times vary from several minutes to several hours.

If said activated compound of general formula V is a mixed anhydride, wherein A represents —O—C(=O)—O—$C_2H_5$, said anhydride may preferably be prepared, for example, by reaction of the corresponding acid of general formula IV with ethylchloroformate in the presence of a base such as triethylamine, pyridine or diisopropylethylamine, in a suitable solvent such as dichloromethane, optionally in an inert atmosphere, at a temperature between −50° C. and 50° C.

In step 4 the reaction between a compound of general formula V with a compound of general formula H—$R^3$ to yield a compound of general formula I, wherein $R^3$ represents a —$NR^4R^5$ moiety, is preferably carried out in the presence of a base such as triethylamine in a reaction medium such as methylenchloride. The temperature is preferably in the range from 0° C. to the boiling point of the reaction medium. The reaction time may vary over a broad range, e.g. from several hours to several days.

Alternatively the reaction of a compound of general formula V with a compound of general formula H—$R^3$ to yield compounds of general formula I may be carried out according to conventional methods well known to those skilled in the art, e.g. from Pascual, A., J. Prakt Chem., 1999, 341(7), 695-700; Lin, S. et al., Heterocycles, 2001, 55(2), 265-277; Rao, P. et al., J. Org. Chem., 2000, 65(22), 7323-7344, Pearson D. E and Buehler, C. A., Synthesis, 1972, 533-542 and references cited therein. The respective descriptions are hereby incorporated by reference and form part of the present disclosure.

Preferably said reaction is carried out in the presence of a Lewis acid, which is preferably selected from the group consisting of $FeCl_3$, $ZnCl_2$ and $AlCl_3$, in a suitable reaction medium such as toluene, benzene, tetrahydrofuran or similar reaction media. The temperature is preferably in the range from 0° C. to the boiling point of the reaction medium, more preferably from 15 to 25° C. The reaction time may vary over a broad range, e.g. from several minutes to several hours.

In step 5 a compound of general formula IV is reacted with a compound of general formula H—$R^3$, wherein $R^3$ represents a —$NR^4R^5$ moiety, in a reaction medium, preferably in a reaction medium selected from the group consisting of diethylether, tetrahydrofuran, acetonitrile, methanol, ethanol, (1,2)-dichlorethane, dimethylformamide, dichlormethane and mixtures thereof, in the presence of at least one coupling agent, preferably in the presence of a coupling agent selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisoproylcarbodiimide, 1,1'-carbonyl-diimidazole (CDI), N-[(dimethyamino)-1H-1,2,3-triazolo[4,5-b]pyridino-1-ylmethylen]-N-methylmethanaminium hexafluorophosphate N-oxid (HATU), O-(benzotriazol-1-yl)-N,N,N',N'-tetramethyluroniom hexafluorophosphate (HBTU), O-(benzotriazol-1-yl)-N,N,N',N'-tetramethyluronium-tetrafluoroborate (TBTU), 1-hydroxy-benzotriazole (HOBt) and 1-hydroxy-7-azabenzotriazol (HOAt), optionally in the presence of a base, preferably in the presence of a base selected from the group consisting of pyridine, dimethylaminopyridine, N-methylmorpholine, triethylamine and diisopropylethylamine to yield a compound of general formula I, wherein $R^3$ represents a —$NR^4R^5$ moiety.

Preferably said reaction is carried out in the presence of EDCI and HOBt, optionally in the presence of N-methylmorpholine or triethylamine, in an aprotic reaction medium such as dimethylformamide or tetrahydrofuran, at a temperature between 20° C. and 30° C. for 15 to 24 hours as described in Tetrahedron Lett. 2004, 45, 4977. The respective description is hereby incorporated by reference and forms part of the disclosure. Polymer-supported EDCI (P-EDCI) can also suitably be used for this process instead of EDCI as described in Tetrahedron Lett. 1998, 39, 1487 and Tetrahedron Lett. 2002, 43, 7685. The respective descriptions are hereby incorporated by reference and form part of the disclosure.

Alternatively said reaction can be carried out by using HBTU in the presence of a base such as diisopropylethylamine in an aprotic solvent, such as acetonitrile, preferably at a temperature between 20 and 30° C. for 15 to 24 hours.

A further inventive process to obtain compounds of general formula IV is illustrated in scheme II given below.

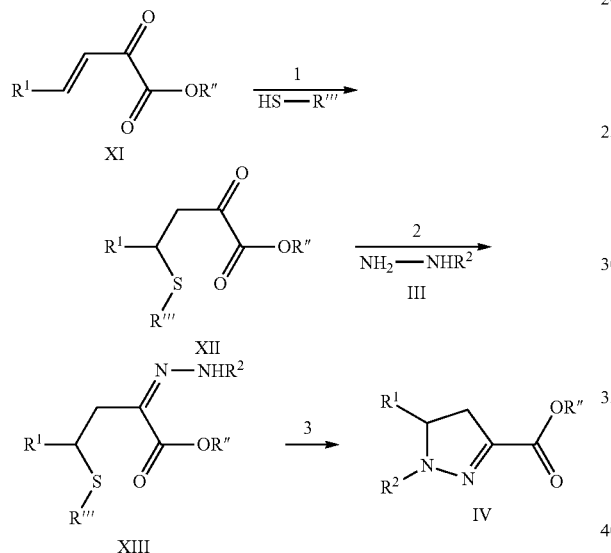

Scheme II

In step 1 a compound of general formula XI, wherein $R^1$ has the meaning given above and R" represents a hydrogen atom or a $C_{1-6}$-alkyl radical, is reacted with a compound of general formula HS—R'", wherein R'" represents an unsubstituted or at least mono-substituted phenyl radical, in a reaction medium, preferably in an dry aprotic reaction medium, more preferably in toluene, optionally in the presence of an organic base, preferably in the presence of an organic base selected from the group consisting of triethylamine, pyridine, diisopropylethylamine, dimethylaminopyridine and N-methylmorpholine, preferably at a temperature between −50° C. and 50° C., preferably for 4 to 24 hours, to yield a compound of general formula XII, wherein $R^1$, R" and R'" have the meaning given above.

In step 2 a compound of general formula XII is reacted with a compound of general formula III, wherein $R^2$ has the meaning given above, in a reaction medium, preferably in a protic reaction medium, more preferably in methanol, optionally in the presence of an inorganic base, preferably in the presence of $KHSO_4$, preferably at a temperature between 0° C. and 100° C., preferably for 4 to 15 hours, to yield a compound of general formula XIII, wherein $R^1$, $R^2$, R" and R" have the meaning given above.

In step 3 the compound of general formula XIII is cyclized intramolecularly in a reaction medium, preferably in a dry aprotic reaction medium, more preferably in dimethylformamide, preferably under an inert atmosphere, in the presence of a base, preferably in the presence of a metal hydride salt, more preferably in the presence of sodium hydride and/or potassium hydride to yield a compound of general formula IV. If R" represents a $C_{1-6}$-alkyl radical, the compound of general formula IV, wherein R" represents a hydrogen atom, is obtained after saponification of the cyclized compound according to methods known to those skilled in the art.

The sequence illustrated in scheme 1 is also described in, for example, Tetrahedron 2005, 81, 5235-5240 and Tetrahedron Asymmetry 2001, 12, 1923-1928. The respective descriptions are hereby incorporated by reference and form part of the disclosure.

A compound of general formula IV can also be obtained as described in scheme III given below.

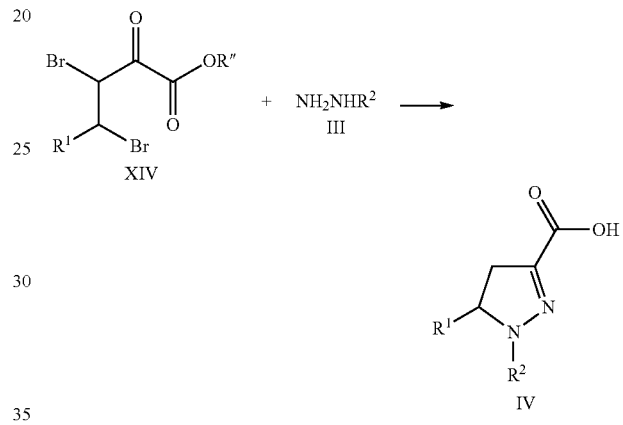

Scheme III

The compound of general formula XIV, wherein $R^1$ has the meaning given above and R" represents a hydrogen atom or a $C_{1-6}$-alkyl radical, is obtained by the bromination of a compound of general formula XI in a reaction medium, preferably in an aprotic reaction medium, more preferably in dichloromethane, with bromine at a temperature between 0° C. and 30° C. for several hours as described in Tetrahedron Lett. 1998, 39 (44), 8163-8166; J. Chem. Soc. Perkin Trans 1, 1999, 21, 3069-3070; Tetrahedron 1999, 55 (36), 11127-11142 and J. Heterocyclic Chem. 1986, 23, 1199. The respective descriptions are hereby incorporated by reference and form part of the disclosure. Preferably a compound of general formula XIV is reacted with bromine in the presence of an aprotic solvent, preferably in the presence of dichloromethane, at ambient temperature for 1 to 2 hours.

The compound of general formula XIV is reacted with a compound of general formula III, wherein $R^2$ has the meaning given above, and cyclized intramolecularly in a reaction medium, preferably in a dry aprotic reaction medium, more preferably in dimethylformamide or in a mixture of dioxane, water and acetic acid, at a temperature between 0° C. and 250° C. to yield a compound of general formula IV as described in Chemistry of Heterocyclic Compounds 1997, 33(6); Indian J. Chem. 20B, 1981, 1090; Indian J. Chem. 29B, 1990, 887 and J. Indian Chem. Soc. 1997, 74(3), 202-205. The respective descriptions are hereby incorporated by reference and form part of the disclosure. If R" represents a $C_{1-6}$-alkyl radical, the compound of general formula IV, wherein R" represents a hydrogen atom, is obtained after saponification of the cyclized compound according to methods known to those skilled in the art.

A compound of general formula IV can also be obtained by the process described in scheme IV.

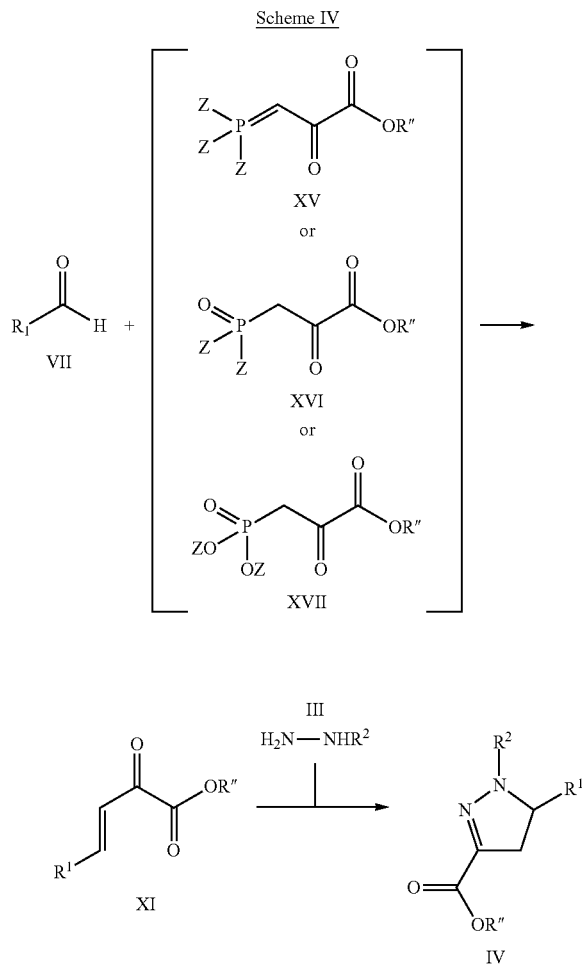

An aldehyde of general formula VII, wherein $R^1$ has the meaning given above, is reacted with either a phosphonium ylide of general formula XV, a phosphine oxide of general formula XVI or a phosphonate of general formula XVII, wherein in each case R" represents a hydrogen atom or a $C_{1-6}$-alkyl radical and Z represents an unsubstituted or at least mono-substituted phenyl radical, in a reaction medium, preferably in an aprotic reaction medium, more preferably in tetrahydrofuran, optionally in the presence of at least one base, preferably in the presence of a base selected from the group consisting of potassium tert-butylat, n-butyllithium, sodium hydride and lithium diisopropylamide, to yield a compound of general formula XI which is reacted with a compound of general formula III, wherein $R^2$ has the meaning given above, and cyclized intramolecularly to yield a compound of general formula IV as described above. The process is also described in Tetrahedron 1994, 50 (44), 12727-12742 and Zhurnal Obshchei Khimii 1986, 56 (2), 347-353. The respective descriptions are hereby incorporated by reference and form part of the disclosure. If R" represents a $C_{1-6}$-alkyl radical, the compound of general formula IV, wherein R" represents a hydrogen atom, is obtained after saponification of the cyclized compound according to methods known to those skilled in the art.

Another method for the preparation of compounds of general formula XI is illustrated in scheme V below.

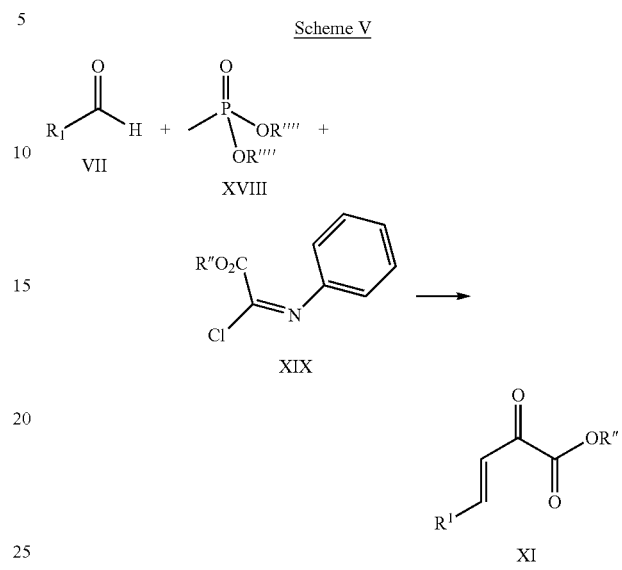

A compound of general formula VII, wherein $R^1$ has the meaning given above, is reacted with a phosphonate of general formula XVIII, wherein R"" represents a $C_{1-6}$-alkyl radical, preferably an ethyl radical, and a compound of general formula XIX, wherein R" represents a hydrogen atom or a $C_{1-6}$-alkyl radical to yield a compound of general formula XI, wherein $R^1$ and R" have the meaning given above. The process is described in J. Chem. Soc. Perkin Trans 1, 1995, 741-742. Preferably the reaction is carried out by the addition of phosphonate of general formula XVIII to a solution of n-butyllithium in a dry reaction medium, preferably in tetrahydrofuran, at a temperature between $-100°$ C. and $-50°$ C., followed by the addition of N-phenylalcoxycarbonylacetimidoyl chloride of general formula XIX and aldehyde of general formula VII and stirring at a temperature between 0° C. and 30° C. for several hours. The respective description is hereby incorporated by reference and forms part of the disclosure.

A compound of general formula IV can also be obtained according to the process described in scheme VI.

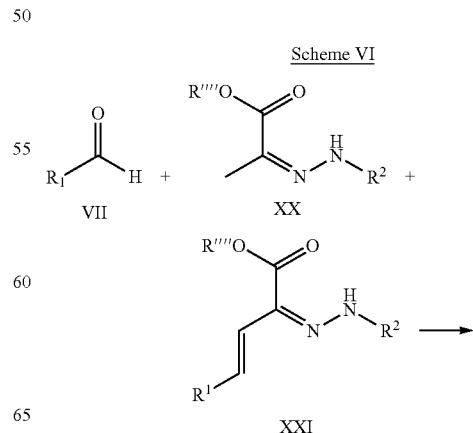

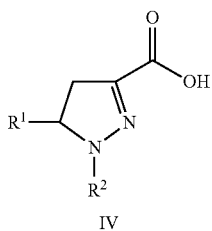

A compound of general formula VII, wherein R¹ has the meaning given above, is reacted with a compound of general formula XX, wherein R² has the meaning given above and R"" represents a $C_{1-6}$-alkyl radical, is reacted in a reaction medium, preferably in ethanol, in the presence of a base, preferably sodium acetate, at a temperature between 30° C. and 90° C., or in a reaction medium, preferably in ethanol, in the presence of glacial acetic acid at a temperature between 0° C. and 50° C. to yield a compound of general formula XXI, wherein R¹ and R² have the meaning given above and R"" represents a $C_{1-6}$-alkyl radical. The compound of general formula XXI is converted into the compound of general formula IV in a reaction medium, preferably in ethanol and/or water, in the presence of an acid, preferably in the presence of hydrochloric acid, at a temperature between 50° C. and 120° C. to yield a compound of general formula IV. The process is described in J. Chem. Engineering Data 1984, 29(2), 225-229 and Indian J. Chem. 27B, 1988, 3, 245-249. The respective descriptions are hereby incorporated by reference and form part of the disclosure.

A compound of general formula IV can also be obtained according to the process described in scheme VII.

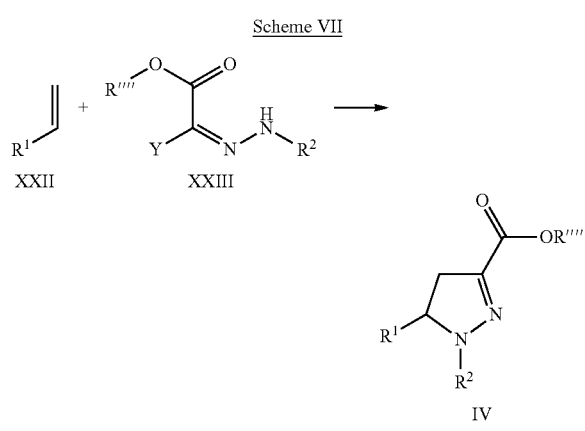

A compound of general formula XXII, wherein R¹ has the meaning given above, is reacted with a compound of general formula XXIII, wherein R² has the meaning given above, R"" represents a $C_{1-6}$-alkyl radical and Y represents a chlorine or bromine atom, in a reaction medium, preferably in an aprotic or protic reaction medium, more preferably in toluene and/or chloroform and/or ethanol, in the presence of a base, preferably an organic base, more preferably an organic base selected from the group consisting of triethylamine, pyridine, diisopropylethylamine, dimethylaminopyridine, 1,4-diazabicyclo[2.2.2]octane and N-methylmorpholine, at a temperature between 0° C. and 150° C. to yield a compound of general formula IV. If regioisomers are obtained during the reaction, these regioisomers can be separated by conventional chromatographic techniques. The compound of general formula IV, wherein R"" represents a $C_{1-6}$-alkyl radical is converted into the corresponding acid by using standard methods which are known to those skilled in the art. The process is disclosed in Bull. Chem. Soc. Japan 1984, 57 (3), 787-790 and Chem. Lett. 1982, 543-546. The respective descriptions are hereby incorporated by reference and form part of the disclosure.

The compound of general formula XXIII can be prepared according to the processes described in scheme VIII.

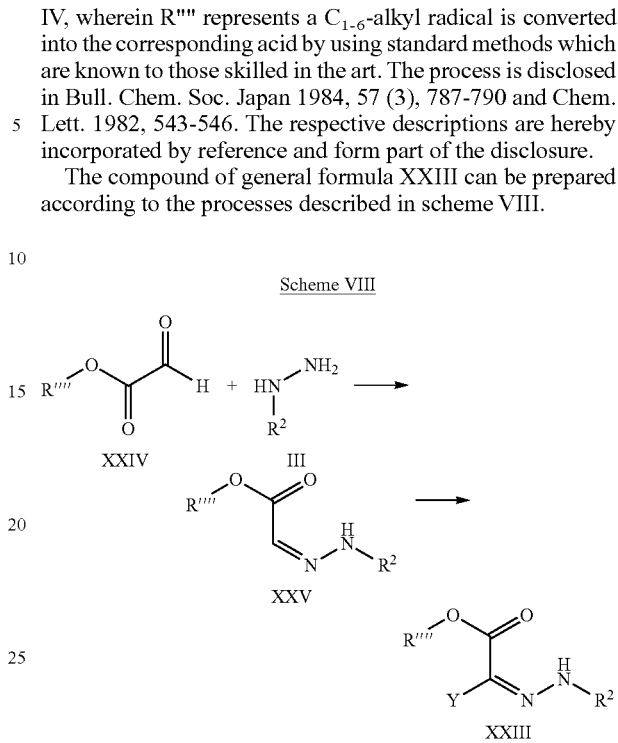

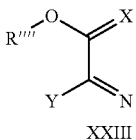

XXIII

The compound of general formula XXIV, wherein R'''' represents a $C_{1-6}$-alkyl radical, is reacted in a reaction medium, preferably in a mixture of water and ethanol, in the presence of at least one acid, preferably in the presence of acetic acid, at a temperature between 70° C. and 120° C. with a compound of general formula III, wherein $R^2$ has the meaning given above, to yield a compound of general formula XXV, wherein $R^2$ has the meaning given above and R'''' represents a $C_{1-6}$-alkyl radical, which is reacted with N-chloro-succinimide or N-bromo-succinimide in a reaction medium, preferably in an aprotic reaction medium, more preferably in dimethylformamide at a temperature between 0° C. and 30° C. to yield a compound of general formula XXIII. The process is described in Synth. Commun. 2001, 31(1), 111-115 and Tetrahedron 1994, 50 (25), 7543-7556. The respective descriptions are hereby incorporated by reference and form part of the disclosure.

The compound of general formula XXIII can also be prepared by the reaction of a compound of general formula XXVI, wherein R'''' represents a $C_{1-6}$-alkyl radical, with a compound of general formula XXVII, wherein $R^2$ has the meaning given above and subsequent bromination of the resulting compound of general formula XXVIII, wherein $R^2$ has the meaning given above and R'''' represents a $C_{1-6}$-alkyl radical, by using bromine in the presence of acetic acid as described in Synthesis 1975, 333 and J. Chem. Soc. Perkin Trans. 1, 1977, 2092. The respective descriptions are hereby incorporated by reference and form part of the disclosure. The diazonium salt of general formula XXVII can preferably be obtained by the addition of an aqueous solution of sodium nitrite to a compound of general formula $R^2$—$NH_2$ in aqueous hydrochloride acid, wherein $R^2$ has the meaning given above. Alternatively this transformation can also be achieved in the presence of a compound of general formula XXVI by adjusting the pH of the reaction medium to 4 by the addition of sodium acetate at a temperature between 0° C. and 30° C.

The compound of general formula XXIII can also be prepared by the reaction of a compound of general formula XXIX, wherein X has the meaning given above, R'''' represents a $C_{1-6}$-alkyl radical and Y represents a chlorine or bromine atom, with dimethylsulfide, in a reaction medium, preferably in ethanol, at a temperature between 70° C. and 120° C. Optionally the dimethylsulfonium salt is isolated and further reacted with a compound of general formula XXVII, wherein $R^2$ has the meaning given above, in the presence of sodium acetate and acetic acid at a temperature between 0° C. and 30° C. as described in Heterocycles 1991, 32(6), 1101-1107. The respective description is hereby incorporated by reference and forms part of the disclosure.

The compound of general formula XXIII can also be prepared by the reaction of a compound of general formula XXXXVIII, wherein X has the meaning given above, R'''' represents a $C_{1-6}$-alkyl radical and Y represents a leaving group, preferably a leaving group selected from the group consisting of chlorine and bromine, with a compound of general formula XXVII, wherein $R^2$ has the meaning given above, in the presence of a protic solvent, preferably in the presence of a protic solvent selected from the group consisting of methanol and ethanol, or in the presence of an aprotic solvent, preferably in the presence of tetrahydrofuran, in the presence of a base, preferably in the presence of sodium acetate, or in the presence of an acid, preferably in the presence of acetic acid. The method is described in J. Chem. Soc. Perkin Transaction 1 1998, 24, 4103-4106; Tetrahedron Asymmetry 2000, 11(9), 1975-1983; Tetrahedron 1998, 54(49), 14859-14868; Synthesis 1996, 9, 1076-1078 and Synthesis 1995, 12, 1483-1484. The respective descriptions are hereby incorporated by reference and form part of the disclosure.

Another method for the preparation of a compound of general formula IV is described in scheme IX.

Scheme IX

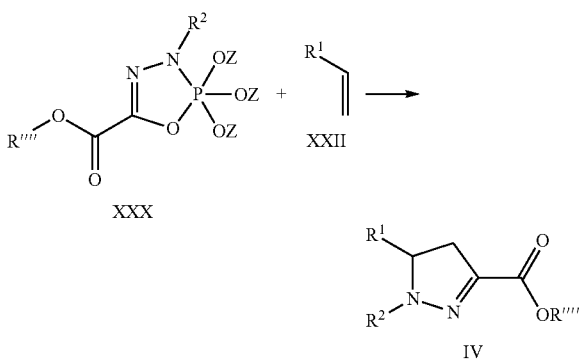

A compound of general formula XXX, wherein $R^2$ has the meaning given above, Z represents an unsubstituted or at least mono-substituted phenyl radical, preferably an unsubstituted phenyl radical, and R'''' represents a $C_{1-6}$-alkyl radical, preferably an ethyl radical, is reacted with a compound of general formula XXII, wherein $R^1$ has the meaning given above, in a reaction medium, preferably in xylene, at a temperature between 50° C. and 200° C. for 2 to 30 hours to yield a compound of general formula IV. The process is described in Chem. Lett. 1983, 507-510 and Bull. Chem. Soc. Japan 1984, 57(9), 2689-2690. The respective descriptions are hereby incorporated by reference and form part of the disclosure. The compound of general formula IV, wherein R'''' represents a $C_{1-6}$-alkyl radical, is converted into the corresponding acid by using standard methods which are known to those skilled in the art.

A process for the preparation of a compound of general formula XXX is described in scheme X.

Scheme X

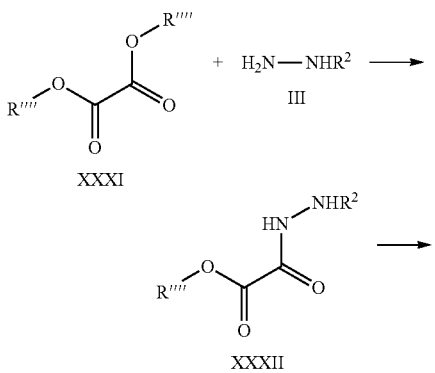

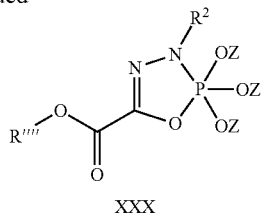

XXX

A compound of general formula XXXI, wherein R'''' is a $C_{1-6}$-alkyl radical, is reacted with a compound of general formula III, wherein $R^2$ has the meaning given above, to yield a compound of general formula XXXII, wherein $R^2$ has the meaning given above and R'''' represents a $C_{1-6}$-alkyl radical. Subsequently, the compound of general formula XXXIII is reacted with phosphorous pentachloride or $POCl_3$ in a reaction medium, preferably in toluene, at a temperature between 0° C. and 50° C., followed by the addition of a phenolic compound, preferably O-trimethylsilyl-p-cresol, in refluxing toluene to yield a compound of general formula XXX.

Another method for the preparation of a compound of general formula IV is described in scheme XI.

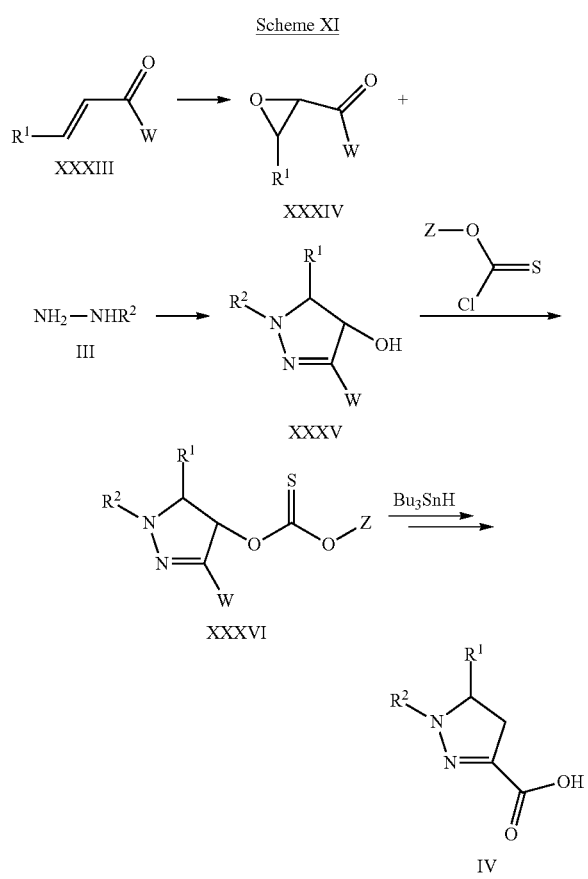

Scheme XI

A compound of general formula XXXIII, wherein $R^1$ has the meaning given above and W represents —C(=O)—OH, —C(=O)—OR'''' or —CN, whereby R'''' represents a $C_{1-6}$-alkyl radical, is converted to a compound of general formula XXXIV, wherein $R^1$ and W have the meaning given above, by means of epoxidation with a reagent selected from the group consisting of perbenzoic acid, preferably m-chloro-perbenzoic acid, sodium peroxocarbonate, hydrogen peroxide, dioxirane and hydroperoxide. The compound of general formula XXIV is reacted with a compound of general formula III, wherein $R^2$ has the meaning given above, in a reaction medium, preferably in ethanol, to yield a compound of general formula XXXV, wherein $R^1$, $R^2$ and W have the meaning given above. Subsequently, the compound of general formula XXXV is converted into the corresponding xanthate of general formula XXXVI, wherein $R^1$, $R^2$ and W have the meaning given above, by reaction with an unsubstituted or at least mono-substituted phenylthionochloroformate of general formula ZO—C(=S)—Cl, wherein Z represents an unsubstituted or at least mono-substituted phenyl radical. The compound of general formula XXXVI is reacted with tributyltinhydride optionally followed by saponification and/or hydrolysis to yield a compound of general formula IV, wherein $R^1$ and $R^2$ have the meaning given above. The process is described in Synlett 1990, 11, 705-706. The respective description is hereby incorporated by reference and forms part of the disclosure.

Yet another method for the preparation of a compound of general formula IV is described in scheme XII.

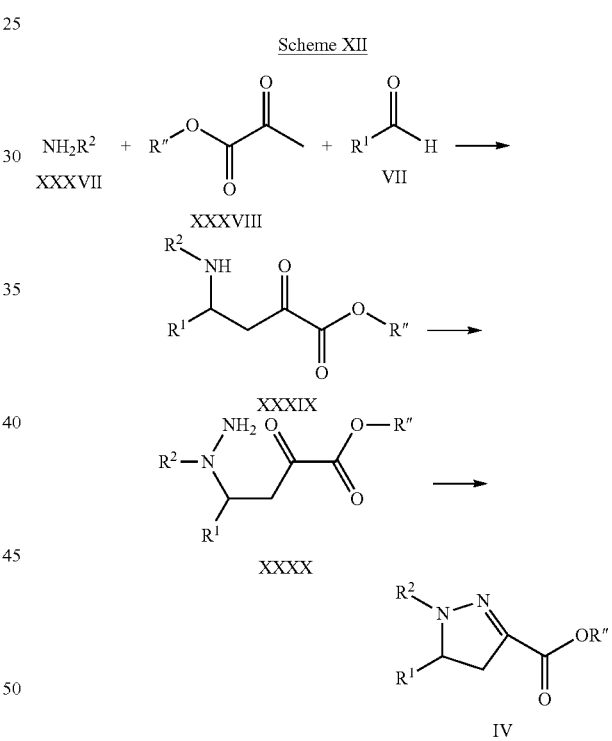

Scheme XII

A compound of general formula XXXVII, wherein $R^2$ has the meaning given above, is reacted with a compound of general formula XXXVIII, wherein R" represents a hydrogen atom or a $C_{1-6}$-alkyl radical, and a compound of general formula VII, wherein $R^1$ has the meaning given above, to yield a compound of general formula XXXIX, wherein $R^1$ and $R^2$ have the meaning given above and R" represents a hydrogen atom or a $C_{1-6}$-alkyl radical. The compound of general formula XXXIX is converted into the compound of general formula XXXX by using O-substituted hydroxylamines according to the method described in J. Org. Chem. 2002, 67, 6237-6239. The respective description is hereby incorporated by reference and forms part of the disclosure. Alternatively, this transformation can be achieved by using nitrites and subsequent reduction according to methods known to those skilled in the art. Upon cyclization of a compound of general formula XXXX according to the methods described above a compound of general formula IV is obtained. If R" represents a $C_{1-6}$-alkyl radical, the compound of general formula IV, wherein R" represents hydrogen, is obtained after saponification of the cyclized compound according to methods known to those skilled in the art.

A further inventive process to obtain compounds of general formula IV is illustrated in scheme XIII given below.

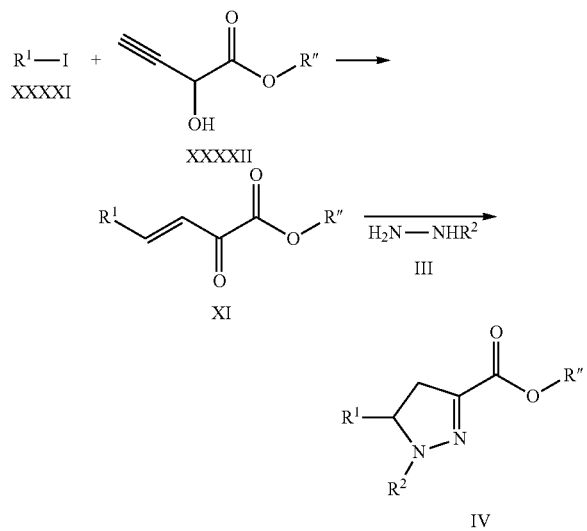

The compound of general formula XXXXI, wherein $R^1$ has the meaning given above, is reacted with a compound of general formula XXXXII, wherein R" represents a hydrogen atom or a $C_{1-6}$-alkyl radical, in a reaction medium, preferably in a dry aprotic reaction medium, more preferably in tetrahydrofuran, in the presence of a catalyst, preferably in the presence of a catalyst based on palladium, more preferably in the presence of a catalyst selected from the group consisting of palladium chloride [PdCl$_2$], palladium acetate [Pd(OAc)$_2$], tetrakistriphenylphosphin palladium [Pd(PPh$_3$)$_4$], bistriphenylphosphin palladium dichloride [Pd(PPh$_3$)$_2$Cl$_2$] and bistriphenylphosphin palladium acetate [Pd(PPh$_3$)$_2$(OAc)$_2$], in the presence of a copper(I) salt, preferably in the presence of copper iodide, in the presence of a base, preferably in the presence of an organic base, more preferably in the presence of an organic base selected from the group consisting of triethylamine, N-methylmorpholine, pyridine, dimethylaminopyridine and diisopropylethylamine, optionally in an inert atmosphere, at a temperature between 20° C. and 120° C. for 5 to 15 hours to yield a compound of general formula XI, wherein $R^1$ has the meaning given above and R" represents a hydrogen atom or a $C_{1-6}$-alkyl radical. The compound of general formula XI is without isolation and/or purification further reacted with a compound of general formula III, wherein $R^2$ has the meaning given above, at a temperature between 20° C. and 120° C. for 5 to 10 hours. The process is described in Angew. Chem. Int. Ed. 2000, 39(7), 1253-1256. The respective description is hereby incorporated by reference and forms part of the disclosure. If R" represents a $C_{1-6}$-alkyl radical, the compound of general formula IV is obtained after saponification of the cyclized compound according to methods known to those skilled in the art.

The compounds of general formula I, wherein $R^3$ represents —$NR^4R^5$, can also be obtained by the reaction sequence described in scheme XIV.

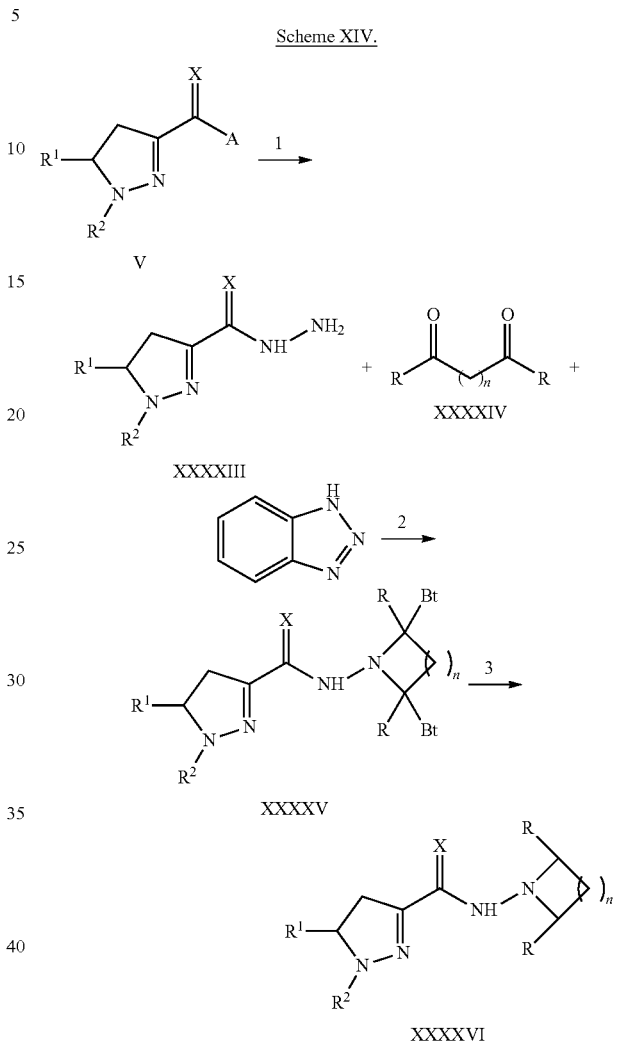

In step 1 a compound of general formula V is reacted with hydrazine hydrate in the presence of an aprotic or protic solvent, preferably in the presence of ethanol, at reflux temperature to yield a compound of general formula XXXXIII, wherein $R^1$, $R^2$ and X have the meaning as defined above.

In step 2 a compound of general formula XXXXIII is reacted with a compound of general formula XXXXIV, wherein R represents a hydrogen atom or a linear or branched $C_{1-12}$ alkyl radical and n is 0, 1, 2, 3, 4, 5, 6, 7, 8, 9 or 10, in the presence of benzotriazole to yield a compound of general formula XXXXV, wherein R, n, $R^1$, $R^2$ and X have the meaning as defined above and Bt represents a benzotriazolyl radical. A compound of general formula XXXXV can be transformed into a compound of general formula XXXXVI, wherein R, n, $R^1$, $R^2$ and X have the meaning as defined above, in the presence of a reducing agent, preferably in the presence of sodium borohydride, in the presence of an aprotic solvent, preferably in the presence of tetrahydrofuran. Alternatively, the benzotriazole moiety in compounds of general formula XXXXV can be replaced by a linear or branched $C_{1-10}$ alkyl group via reaction with the respective alkyl Grignard reagents The process is disclosed J. Org. Chem. 1990, 55, 3205-3209. The respective description is hereby incorporated by reference and forms part of the disclosure.

The compounds of general formula I, wherein $R^3$ represents —$NR^4R^5$, can also be obtained by the reaction sequence described in scheme XVI.

Scheme XV.

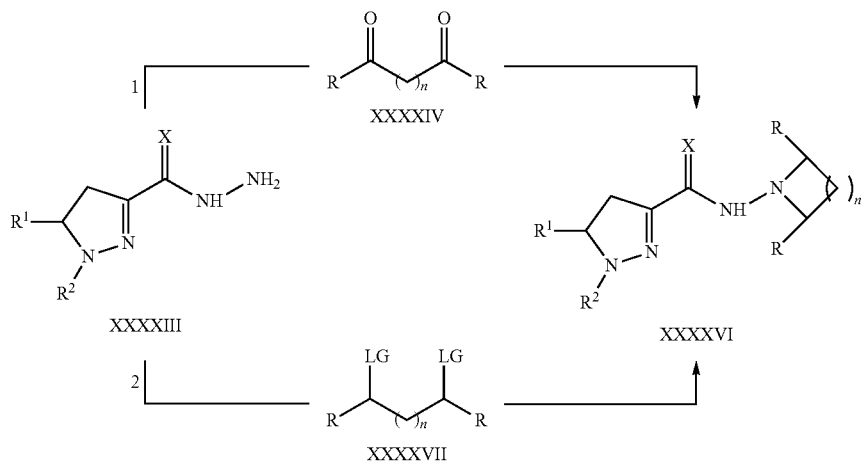

In step 1 a compound of general formula XXXXIII is reacted with a compound of general formula XXXXIV, wherein R represents a hydrogen atom or a linear or branched $C_{1-12}$ alkyl radical and n is 0, 1, 2, 3, 4, 5, 6, 7, 8, 9 or 10, in the presence of a reducing agent, preferably in the presence of a reducing agent selected from the group consisting of sodium borohydride, sodium cyanoborohydride or triacetoxyborohydride, to yield a compound of general formula XXXXVI, wherein R, n, $R^1$, $R^2$ and X have the meaning as defined above.

In step 2 a compound of general formula XXXXIII is reacted with a compound of general formula XXXXVII, wherein R represents a hydrogen atom or a linear or branched $C_{1-12}$ alkyl radical, n is 0, 1, 2, 3, 4, 5, 6, 7, 8, 9 or 10 and LG represents a leaving group, preferably a leaving group selected from the group consisting of chlorine and bromine, more preferably LG represents bromine, in the presence of a base, preferably in the presence of potassium carbonate, to yield a compound of general formula XXXXVI, wherein R, n, $R^1$, $R^2$ and X have the meaning as defined above.

The afore mentioned reactions involving the synthesis of the 4,5-dihydro-pyrazole ring or the reaction of a compound comprising said ring are preferably carried out under an inert atmosphere, preferably under a nitrogen or argon atmosphere, to avoid oxidation of the ring-system.

During some synthetic reactions described above the protection of sensitive or reactive groups may be necessary and/or desirable. This can be performed by using conventional protective groups like those described in Protective groups in Organic Chemistry, ed. J. F. W. McOmie, Plenum Press, 1973; T. W. Greene & P. G. M. Wuts and Protective Groups in Organic Chemistry, John Wiley & sons, 1991. The respective parts of the description is hereby incorporated by reference and forms part of the disclosure. The protective groups may be eliminated when convenient by means well-known to those skilled in the art.

If the substituted pyrazoline compounds of general formula I are obtained in form of a mixture of stereoisomers, particularly enantiomers or diastereomers, said mixtures may be separated by standard procedures known to those skilled in the art, e.g. chromatographic methods or crystallisation with chiral reagents. It is also possible to obtain pure stereoisomers via stereoselective synthesis.

In a further aspect the present invention also provides a process for the preparation of salts of substituted pyrazoline compounds of general formula I and stereoisomers thereof, wherein at least one compound of general formula I having at least one basic group is reacted with at least one inorganic and/or organic acid, preferably in the presence of a suitable reaction medium. Suitable reaction media include, for example, any of the ones given above. Suitable inorganic acids include hydrochloric acid, hydrobromic acid, phosphoric acid, sulfuric acid, nitric acid, suitable organic acids are e.g. citric acid, maleic acid, fumaric acid, tartaric acid, or derivatives thereof, p-toluenesulfonic acid, methanesulfonic acid or camphersulfonic acid.

In yet a further aspect the present invention also provides a process for the preparation of salts of substituted pyrazoline compounds of general formula I or stereoisomers thereof, wherein at least one compound of general formula I having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or unbranched $C_{1-4}$-alkyl-radical. Suitable reaction media are, for example, any of the ones given above.

In the presence of several acidic or basic groups, mono- or poly-salts may be formed. Compounds of the formula I having an acidic group, for example a free carboxyl group, and a basic group, for example an amino group, may also be present in the form of inner salts, i.e., in zwitterionic form, or a part of the molecule may be present in the form of an inner salt and another part in the form of a normal salt.

Solvates, preferably hydrates, of the substituted pyrazoline compounds of general formula I, of corresponding stereoisomers, of corresponding N-oxides or of corresponding salts thereof may also be obtained by standard procedures known to those skilled in the art.

Substituted pyrazoline compounds of general formula I, which comprise nitrogen-atom containing saturated, unsaturated or aromatic rings may also be obtained in the form of their N-oxides by methods well known to those skilled in the art.

The purification and isolation of the inventive substituted pyrazoline compounds of general formula I, of a corresponding stereoisomer, or salt, or N-oxide, or solvate or any intermediate thereof may, if required, be carried out by conventional methods known to those skilled in the art, e.g. chromatographic methods or recrystallisation.

The compounds of general formula I given above may also act as prodrugs, i.e. they represent a drug precursor, which following administration to a patient releases a drug in vivo via some kind of chemical and/or physiological process (e.g., a prodrug on being brought to a physiological pH and/or through an enzyme action is converted to a desired drug form; see, e.g., R. B. Silverman, 1992, "The Organic Chemistry of Drug Design and Drug Action", Academic Press, Chp. 8). In particular, the compounds of general formula I give rise to a compound of general formula I, wherein $R^3$ represents a —OH moiety, upon administration to a patient.

Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group.

The substituted pyrazoline compounds of general formula I given above, their stereoisomers, corresponding N-oxides, corresponding salts thereof and corresponding solvates are toxicologically acceptable and are therefore suitable as pharmaceutical active substances for the preparation of medicaments.

It has been found that the substituted pyrazoline compounds of general formula I given above, stereoisomers thereof, N-oxides thereof, corresponding salts and corresponding solvates have a high affinity to cannabinoid receptors, particularly cannabinoid 1 ($CB_1$)-receptors, i.e. they are selective ligands for the ($CB_1$)-receptor and act as modulators, e.g. antagonists, inverse agonists or agonists, on these receptors. In particular, these pyrazoline compounds show little or no development of tolerance during treatment, particularly with respect to food intake, i.e. if the treatment is interrupted for a given period of time and then continued afterwards, the inventively used pyrazoline compounds will again show the desired effect. After ending the treatment with the pyrazoline compounds, the positive influence on the body weight is found to continue.

Furthermore, these substituted pyrazoline compounds show relatively weak Herg channel affinity, thus a low risk of prolongation of the QT-interval is to be expected for these compounds.

In summary, the inventively used substituted pyrazoline compounds are distinguished by a broad spectrum of beneficial effects, while at the same time showing relatively little undesired effects, i.e. effects which do not positively contribute to or even interfere with the well being of the patient.

Thus, an other aspect of the present invention relates to a medicament comprising at least one substituted pyrazoline compound of general formula I, optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof, and optionally at least one physiologically acceptable auxiliary agent.

Preferably said medicament is suitable for the modulation (regulation) of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferably said medicament is suitable for the prophylaxis and/or treatment of psychosis.

Also particularly preferably said medicament is suitable for the prophylaxis and/or treatment of food intake disorders, preferably bulimia, anorexia, cachexia, obesity and/or type II diabetus mellitus (non-insuline dependent diabetes mellitus), more preferably obesity. The inventive medicament also seems to be active in the prophylaxis and/or treatment of appetency disorders, e.g. the pyrazoline compounds of general formula I also reduce the desire for sweets.

Also particularly preferred is the use of at least one of the pyrazoline compounds as defined herein and optionally one or more pharmaceutically acceptable excipients, for the preparation of a medicament for the treatment of metabolic syndrome.

The metabolic syndrome and definitions thereof are described in detail by Eckel et al., The Lancet, Vol. 365 (2005), 1415-1428, included herewith by reference. One of the respective definitions was established by the WHO in 1998 (as described in Alberti et al., Diabet. Med. 1998, 15, pages 539-53, the respective description thereof is herewith incorporated by reference and forms part of the present disclosure). The other, more widely accepted, definition of the metabolic syndrome was established by the Adult Treatment Panel (ATP III) of the US National Cholesterol Education Program (NCEP) in 2001, as described in JAMA 2001; 285; 2486-97, the respective description thereof is herewith incorporated by reference and forms part of the present disclosure.

The metabolic syndrome is characterized by an interaction of several physiological parameters such as triglycerides, lipids, blood pressure, glucose levels and insulin levels.

Even though obesity may play a critical role in the development of metabolic syndrome, many of its aspects are weight independent, especially some lipid parameters. Especially the positive influence on the weight independent aspects of the metabolic syndrome (see e.g. Pagotto and Pasquali, The Lancet, Vol. 365 (2005), 1363, 1364, included herewith by reference) like some blood parameters, especially lipid parameters is one of the major and surprising advantages of the inventively used substituted pyrazoline compounds.

Another aspect of the invention is the use of one or more pyrazoline compounds as defined herein for the manufacture of a medicament for improvement of cardiovascular and/or metabolic risk factors, such as one or more of the following factors:
Elevated triglycerides, whereby elevated levels of triglycerides are preferably understood as being >150 mg/dl,
Low HDL cholesterol, whereby low levels of HDL cholesterol are preferably understood as being <40 mg/dl in men and <50 mg/dl in women,
Hypertension, whereby hypertension is preferably understood as being >130/85 mmHg,
Impaired fasting glucose, whereby impaired fasting glucose levels are preferably understood as being >110 mg/dl,
Insulin Resistance
Dyslipidemia.

Another aspect of the invention is the use of one or more pyrazoline compounds as defined herein for the manufacture of a medicament for the treatment of the weight independent aspects of metabolic syndrome.

Another aspect of the invention is a method for improving cardiovascular and/or metabolic risk factors, such as one or more of the following factors:

Elevated triglycerides, whereby elevated levels of triglycerides are preferably understood as being >150 mg/dl, Low HDL cholesterol, whereby low levels of HDL cholesterol are preferably understood as being <40 mg/dl in men and <50 mg/dl in women, Hypertension, whereby hypertension is preferably understood as being >130/85 mmHg, Impaired fasting glucose, whereby impaired fasting glucose levels are preferably understood as being >110 mg/dl, Insulin Resistance Dyslipidemia, in a subject, preferably a human.

Another aspect of the invention is a method for treating of the weight independent aspects of metabolic syndrome.

Also particularly preferably said medicament is suitable for the prophylaxis and/or treatment of cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, more preferably for the prophylaxis and/or treatment of one or more types of cancer selected from the group consisting of colon cancer, bowel cancer and prostate cancer.

Particularly preferably said medicament is suitable for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction and/or nicotine abuse and/or nicotine addiction.

Thus, the inventive medicament is active in the treatment of abstinence, craving reduction and relapse prevention of alcohol intake. The inventive medicament can also be used in the prophylaxis and/or treatment of smoking addiction, cessation and/or dependence including treatment for craving reduction and relapse prevention of tobacco smoking.

Medicaments and/or drugs, which are frequently the subject of misuse include opioids, barbiturates, cannabis, cocaine, amphetamines, phencyclidine, hallucinogens and benzodiazepines.

The medicament is also suitable for the prophylaxis and/or treatment of one or more disorders selected from the group consisting of bone disorders, preferably osteoporosis (e.g. osteoporosis associated with a genetic predisposition, sex hormone deficiency, or ageing), cancer-associated bone disease or Paget's disease of bone; schizophrenia, anxiety, depression, epilepsy, neurodegenerative disorders, cerebellar disorders, spinocerebellar disorders, cognitive disorders, cranial trauma, head trauma, stroke, panic attacks, peripheral neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, medicament-induced movement disorders, dystonia, endotoxemic shock, hemorrhagic shock, hypotension, insomnia, immunologic disorders, sclerotic plaques, vomiting, diarrhoea, asthma, memory disorders, pruritus, pain, or for potentiation of the analgesic effect of narcotic and non-narcotic analgesics, or for influencing intestinal transit.

The medicament is also suitable for the prophylaxis and/or treatment of one or more disorders selected from the group consisting of dementia and related disorders, preferably for the prophylaxis and/or treatment of one or more types of dementia selected from the group consisting of memory loss, vascular dementia, mild cognitive impairment, frontotemporal dementia and Pick's disease; binge eating disorders; juvenile obesity; drug induced obesity; atypical depression; behavioural addictions; attention deficit disorders; Tourette's syndrome; suppression of reward-related behaviours; e.g. conditioned place avoidance such as suppression of cocaine- and morphine induced conditioned place preference; impulsivity; sexual dysfunction; preferably for the prophylaxis and/or treatment of one or more types of sexual dysfunction selected from the group consisting of erectile difficulty and female sexual dysfunction; seizure disorders; nausea; emesis; neuroinflammatory disease, preferably for the prophylaxis and/or treatment of one or more types of neuroinflammatory diseases selected from the group consisting of multiple sclerosis, demyelinisation related disorders, Guillan-Barré syndrome, viral encephalitis and cerebrovascular accidents; neurological disorders; muscle spasticity; traumatic brain injury; spinal cord injury; inflammation and immunomodulatory disorders, preferably for the treatment and/or prophylaxis of one or more types of inflammation and immunomodulatory disorders selected from the group consisting of cutaneous T-cell lymphoma, rheumatoid arthritis, systemic lupus erythematosus, sepsis, sarcoidosis, idiopathic pulmonary fibrosis, bronchopulmonary dysplasia, retinal disease, scleroderma, renal ischemia, myocardial infarction, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, chronic obstructive pulmonary disease and bronchitis; cerebral apoplexy; craniocerebral trauma; neuropathic pain disorders; gastric ulcers; atheriosclerosis and liver cirrhosis.

Another aspect of the present invention is the use of at least one substituted pyrazoline compound of general formula I given above as suitable active substances, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the modulation of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of psychosis.

Also particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of food intake disorders, preferably bulimia, anorexia, cachexia, obesity and/or type II diabetus mellitus (non-insuline dependent diabetes mellitus), more preferably obesity.

Also particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, more preferably for the prophylaxis and/or treatment of one or more types of cancer selected from the group consisting of colon cancer, bowel cancer and prostate cancer.

Also particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction and/or nicotine abuse and/or nicotine addiction.

Medicaments/drugs, which are frequently the subject of misuse include opioids, barbiturates, cannabis, cocaine, amphetamines, phencyclidine, hallucinogens and benzodiazepines.

Also preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of one or more disorders selected from the group consisting of bone disorders, preferably osteoporosis (e.g. osteoporosis associated with a genetic predisposition, sex hormone deficiency, or ageing), cancer-associated bone disease or Paget's disease of bone; schizophrenia, anxiety, depression, epilepsy, neurodegenerative disorders, cerebellar disorders, spinocerebellar disorders, cognitive disorders, cranial trauma, head trauma, stroke, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, medicament-induced movement disorders, dystonia, endotoxemic shock, hemorrhagic shock, hypotension, insomnia, immunologic disorders, sclerotic plaques, vomiting, diarrhoea, asthma, memory disorders, pruritus, pain, or for potentiation of the analgesic effect of narcotic and non-narcotic analgesics, or for influencing intestinal transit.

Also particularly preferred is the use of at least one of the respective substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding solvate thereof, and optionally one or more pharmaceutically acceptable excipients, for the preparation of a medicament for the prophylaxis and/or treatment of one or more disorders selected from the group consisting of dementia and related disorders, preferably for the prophylaxis and/or treatment of one or more types of dementia selected from the group consisting of memory loss, vascular dementia, mild cognitive impairment, frontotemporal dementia and Pick's disease; binge eating disorders; juvenile obesity; drug induced obesity; atypical depression; behavioural addictions; attention deficit disorders; Tourette's syndrome; suppression of reward-related behaviours; e.g. conditioned place avoidance such as suppression of cocaine- and morphine induced conditioned place preference; impulsivity; sexual dysfunction; preferably for the prophylaxis and/or treatment of one or more types of sexual dysfunction selected from the group consisting of erectile difficulty and female sexual dysfunction; seizure disorders; nausea; emesis; neuroinflammatory disease, preferably for the prophylaxis and/or treatment of one or more types of neuroinflammatory diseases selected from the group consisting of multiple sclerosis, demyelinisation related disorders, Guillan-Barré syndrome, viral encephalitis and cerebrovascular accidents; neurological disorders; muscle spasticity; traumatic brain injury; spinal cord injury; inflammation and immunomodulatory disorders, preferably for the treatment and/or prophylaxis of one or more types of inflammation and immunomodulatory disorders selected from the group consisting of cutaneous T-cell lymphoma, rheumatoid arthritis, systemic lupus erythematosus, sepsis, sarcoidosis, idiopathic pulmonary fibrosis, bronchopulmonary dysplasia, retinal disease, scleroderma, renal ischemia, myocardial infarction, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, chronic obstructive pulmonary disease and bronchitis; cerebral apoplexy; craniocerebral trauma; neuropathic pain disorders; gastric ulcers; atheriosclerosis and liver cirrhosis.

Dementia is a disease characterized by the progressive deterioration in cognitive and social adaptive functions that can eventually interfere with the patient's ability to live independently. Dementia also constitutes of impairment in short- and long-term memory plus additional symptoms, such as problems with abstract thinking, judgment, or personality. An estimated 18 million patients suffer from dementia worldwide. The most common forms of dementia include Alzheimer's disease and vascular dementia. Other forms are frontotemporal dementia and Pick's disease.

Dementia can also be of vascular origin. Vascular dementia (atherosclerotic cerebrovascular disease) is considered to be the second most common dementia of late life, affecting approximately 10-15% of all cases. AD and vascular dementia can exist in isolation or together (mixed dementia). In vascular dementia, atherosclerotic changes in cerebral vessels can lead to reduced local blood flow that results in multiple small strokes (multi-infarct dementia). Vascular dementia is pharmacologically treated by stroke prophylaxis, and by treatment of the cognitive deficit.

Alzheimer's disease (AD), the most common and important form of dementia, is a neurodegenerative disorder that is characterized by progressive impairment of cognitive functions, such as abstract reasoning and memory. Currently, an estimated 2 million people in the United States and 12 million worldwide are afflicted by this disease. Due to increasing life expectancy, it is predicted that there will be over 100 million AD patients worldwide by the year 2050. AD is one of the most prevalent illnesses in the elderly. The majority of AD patients are in their sixties or older. More than 5% of all persons over the age of 70 have significant memory loss due to AD.

AD is mainly characterized through a gradual development of forgetfulness. In further advanced disease stages, other failures in cerebral function become increasingly apparent. This includes impairment of speech, writing, and arithmetic skills. Visiospacial orientation, such as parking the car, dressing properly, and giving and understanding directions to a location, can become defective or impaired. In late stage disease, patients forget how to use common objects and tools while retaining necessary motor power and co-ordination for these activities.

Schizophrenia is characterized by profound disruption in cognition and emotion, affecting the most fundamental human attributes: language, thought, perception, affect, and sense of self. Positive symptoms include psychotic manifestations, such as hearing internal voices or experiencing other sensations not connected to an obvious source (hallucinations) and assigning unusual significance or meaning to normal events or holding fixed false personal beliefs (delusions). Negative symptoms are characterized by affective flattening and lack of initiative or goals (avolition), loss of usual interests or pleasures (anhedonia), disturbances of sleep and eating, dysphoric mood (depressed, anxious, irritable, or angry mood) and difficulty concentrating or focusing attention.

Major depression is a multifaceted disorder characterized by primarily by dysphoric mood and loss of interest or pleasure in activities that were once enjoyable. Other physical and psychological symptoms include inability to concentrate, motor disturbances (psychomotor retardation or agitation), feelings of worthlessness, inappropriate guilt, thoughts of suicide, and disturbances in appetite and sleep.

Anxiety disorders are a group of syndromes that include generalized anxiety disorder, panic disorder, phobias, obsessive-compulsive disorder, and post traumatic stress disorder. Although each disorder has its own distinct features, all share common symptoms of excessive worrying, intense fears and dread, hypervigilance and/or somatic symptoms, in the absence of a dangerous situation.

Normal sexual function requires, among others, the ability to achieve and maintain penile erection. Major anatomic structures of the penis that are involved in erectile function include the corpus cavernosum, corpus spinosum, and the tunica albuginea (a collagenous sheath that surrounds each corpus). Thecorpora are composed of a mass of smooth muscle (trabecula) which contains a network of endothelial-lined vessels (lacunar spaces). Penile tumescence and erection is caused by relaxation of the arteries and corporal smooth muscles, while closing emissary veins, leading to increased blood flow into the lacunar network. Central and peripheral innervation contributes to regulation of the erectile response.

Erectile dysfunction (ED) may result from failure to initiate, fill, or store adequate blood volume within the lacunar network of the penis. Depending on the underlying dysfunction, ED may be vasculogenic, neurogenic, endocrinologic, diabetic, psychogenic, or medication-related.

ED affects 10-25% of middle-aged and elderly men, and has a profound impact on the well-being of affected men. It is currently treated using PDE5 inhibitors such as vardenafil, tadalifil, and sildenafil. Intraurethral alpostadil (prostaglandin EI) may be used in patients that fail on oral agents. In addition, vacuum constriction devices (VCD) are a well-established, noninvasive therapy.

Female sexual dysfunction (FSD) is highly prevalent, age-related, and progressive. It affects 30 to 50% of women. FSD denotes a range of medical problems and is categorized according to disorders of (1) desire, (2) arousal, (3) orgasm and (4) sexual pain, and symptoms include diminished vaginal lubrication, pain and discomfort with intercourse, decreased arousal, and difficulty achieving orgasm. On a molecular level, vasoactive intestinal peptide (VIP), nitic oxide (NO), and sex hormones such as estrogens and androgens have been suggested to be important in female sexual function. Current treatment approaches include estrogen replacement therapy, methyl testosterone, PDE5 inhibitors such as sildenafil, the NO-donor L-arginine, prostaglandin EI, phentolamine, and the dopamine agonists apomorphine.

The medicament according to the present invention may be in any form suitable for the application to humans and/or animals, preferably humans including infants, children and adults and can be produced by standard procedures known to those skilled in the art. The medicament can be produced by standard procedures known to those skilled in the art, e.g. from the table of contents of "Pharmaceutics: The Science of Dosage Forms", Second Edition, Aulton, M. E. (ED. Churchill Livingstone, Edinburgh (2002); "Encyclopedia of Pharmaceutical Technology", Second Edition, Swarbrick, J. and Boylan J. C. (Eds.), Marcel Dekker, Inc. New York (2002); "Modern Pharmaceutics", Fourth Edition, Banker G. S, and Rhodes C. T. (Eds.) Marcel Dekker, Inc. New York 2002 y "The Theory and Practice of Industrial Pharmacy", Lachman L., Lieberman H. And Kanig J. (Eds.), Lea & Febiger, Philadelphia (1986). The respective descriptions are hereby incorporated by reference and form part of the disclosure. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilising agents, solubilizing agents, and buffers, may be included in such injectable compositions. These medicaments may for example be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, granules, capsules, lozenges, aqueous or oily solutions, suspensions, emulsions, or dry powdered forms suitable for reconstitution with water or other suitable liquid medium before use, for immediate or retarded release. The multiparticulate forms, such as pellets or granules, may e.g. be filled into a capsule, compressed into tablets or suspended in a suitable liquid.

Suitable controlled release formulations, materials and methods for their preparation are known from the prior art, e.g. from the table of contents of "Modified-Release Drug Delivery Technology", Rathbone, M. J. Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York, (2000); "Controlled Drug Delivery", Vol, I, Basic Concepts, Bruck, S. D. (Ed.), CRD Press Inc., Boca Raton (1983) y de Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728. The respective descriptions are hereby incorporated by reference and form part of the disclosure.

Medicaments according to the present invention may also comprise an enteric coating, so that their dissolution is dependent on pH-value. Due to said coating the medicament can pass the stomach undissolved and the respective pyrazoline compound of general formula I is liberated in the intestinal tract. Preferably the enteric coating is soluble at a pH value of 5 to 7.5. Suitable materials and methods for the preparation are known from the prior art.

Typically, the medicaments according to the present invention may contain 1-60% by weight of one or more substituted pyrazoline compounds as defined herein and 40-99% by weight of one or more auxiliary substances (additives).

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000, even more preferably 1 to 150 milligrams of active substance to be administered during one or several intakes per day.

Pharmacological Methods
I. In-Vitro Determination of Affinity to CB1/CB2-Receptors
a)
The in-vitro determination of the affinity of the inventive substituted pyrazoline compounds to $CB_1/CB_2$-Rezeptors is carried out as described in the publication of Ruth A. Ross, Heather C. Brockie et al., "Agonist-inverse agonist characterization at $CB_1$ and $CB_2$ cannabinoid receptors of L-759633, L759656 and AM630", British Journal of Pharmacology, 126, 665-672, (1999), whereby the transfected human $CB_1$ and $CB_2$ receptors of Receptor Biology, Inc. are used. The radioligand used for both receptors is [$^3$H]-CP55940. The respective parts of the description is hereby incorporated by reference and forms part of the present disclosure.
b)
Rat Cerebellum CB1 Binding
Binding affinity to CB1 receptor was evaluated according to a modification of the method described by Govaerts et al., Eur J Pharmac Sci 23, 233-243 (2004). The respective parts of the description is hereby incorporated by reference and forms part of the present disclosure.

Briefly, cerebellum from male wistar rats (250-300 g) were carefully dissected on ice and homogenates were prepared with Potter-Helveheim in a cold 50 mM Tris-HCl solution containing 5 mM $MgCl_2$, 1 mM EDTA and 0.25 M sucrose, pH 7.4. The suspension was centrifuged at 1,000×g for 5 minutes. The supernatants were collected and centrifuged 50,000×g for 15 minutes. The resulting pellets were then resuspended in Tris-HCl buffer without sucrose, homogenized and incubated for 15 min at 37° C. in an orbital shaker bath and centrifuged again at 50,000×g for 15 min. Pellets were weighted, resuspended in Tris-HCl buffer without sucrose, homogenized with Ultraturrax at 13,500 rpm for 3×5 seconds and alicuoted in 0.9 ml volumes in Eppendorf tubes. Alicuotes were centrifuged at 20,800×g for 5 minutes, supernatants discarded and pellets were frozen at –80° C. until use. Total protein concentration was determined using the Bio-Rad Lowry method based kit. Competitive binding experiments were performed in presence of 1 nM [$^3$H]-CP 55,940 in siliconized glass tubes containing 100 µg protein/tube resuspended in 1 ml final volume of 50 mM Tris-HCl, 5 mM $MgCl_2$, 1 mM EDTA, 0.5% (w/v) bovine serum albumin, pH 7.4. Compounds were present at various concentrations and the non specific binding was determined in the presence of 10 µM HU-210. After 1 hour incubation at 30° C., the suspension was rapidly filtered through 0.5% PEI pre-treated GF/B fiber filters on a 96-well harvester and washed 3 times with 3 ml ice-cold binding buffer without bovine serum albumin. Radioactivity on filters was measured with Wallac Winspectral 1414 counter by liquid scintillation in 6 ml Ecoscint H (National Diagnostics, U.K.). Assays were made in triplicates.

Binding data were analyzed by non-linear regression with the software GraphPad Prism Version 3.03.

II. In-Vivo Bioassay System for Determination of Cannabinoid Activity
Mouse Tetrad Model Substances with affinity for cannabinoid receptors are known to produce a wide range of pharmacological effects. It is also known that intravenous administration of a substance with affinity for cannabinoid receptors in mice produces analgesia, hypothermia, sedation and catalepsy. Individually, none of these effects can be considered as proof that a tested substance has affinity for cannabinoid-receptors, since all of these effects are common for various classes of centrally active agents. However, substances, which show all of these effects, i.e. substances that are active in this so-called tetrad model are considered to have affinity for the cannabinoid receptors. It has further been shown that cannabinoid receptor antagonists are highly effective in blocking the effects of a cannabinoid agonist in the mouse tetrad model.

The tetrad model is described, for example, in the publication of A. C. Howlett et al, International Union of Pharmacology XXVII. Classification of Cannabinoid Receptors, Pharmacol Rev 54, 161-202, 2002 and David R. Compton et al., "In-vivo Characterization of a Specific Cannabinoid Receptor Antagonist (SR141716A): Inhibition of Tetrahydrocannbinol-induced Responses and Apparent Agonist Activity", J. Pharmacol. Exp. Ther. 277, 2, 586-594, 1996. The corresponding parts of the description are hereby incorporated by reference.

Material and Methods
Male NMRI mice with a weight of 20-30 g (Harlan, Barcelona, Spain) are used in all of the following experiments.

Before testing in the behavioural procedures given below, mice are acclimatised to the experimental setting. Pre-treatment control values are determined for analgesia hot plate latency (in seconds), rectal temperature, sedation and catalepsy.

In order to determine the agonistic activity of the substance to be tested, the mice are injected intravenously with the substance to be tested or the vehicle alone. 15 minutes after injection, latency in hot plate analgesia is measured. Rectal temperature, sedation and catalepsy are measured 20 minutes after injection.

In order to determine the antagonistic activity the identical procedure is used as for the determination of the agonistic effects, but with the difference that the substance to be evaluated for its antagonistic activity is injected 5 minutes before the intravenous injection of 1.25 mg/kg Win-55,212 a known cannabinoid-receptor agonist.

Hot Plate Analgesia

The hot plate analgesia is determined according to the method described in Woolfe D. et al. "The evaluation of analgesic action of pethidine hydrochloride (Demerol)", J. Pharmacol. Exp. Ther. 80, 300-307, 1944. The respective description is hereby incorporated by reference and forms part of the present disclosure.

The mice are placed on a hot plate (Harvard Analgesimeter) at 55±0.5° C. until they show a painful sensation by licking their paws or jumping and the time for these sensations to occur is recorded. This reading is considered the basal value (B). The maximum time limit the mice are allowed to remain on the hot plate in absence of any painful response is 40 seconds in order to prevent skin damage. This period is called the cut-off time (PC).

Fifteen minutes after the administration of the substance to be tested, the mice are again placed on the hot plate and the afore described procedure is repeated. This period is called the post-treatment reading (PT).

The degree of analgesia is calculated from the formula:

$$\% \text{ MPE of Analgesia} = (PT-B)/(PC-B) \times 100$$

MPE=Maximum possible effect.

Determination of Sedation and Ataxia

Sedation and ataxia is determined according to the method described in Desmet L. K. C. et al. "Anticonvulsive properties of Cinarizine and Flunarizine in Rats and Mice", Arzneim.-Forsch. (Frug Res) 25, 9, 1975. The respective description is hereby incorporated by reference and forms part of the present disclosure.

The chosen scoring system is
0: no ataxia;
1: doubtful;
2: obvious calmness and quiet;
3 pronounced ataxia;
prior to as well as after treatment.

The percentage of sedation is determined according to the formula:

$$\% \text{ of sedation} = \text{arithmetic mean}/3 \times 100$$

Hypothermia:

Hypothermia is determined according to the method described in David R. Compton et al. "In-vivo Characterization of a Specific Cannabinoid Receptor Antagonist (SR141716A) Inhibition of Tetrahydrocannbinol-induced Responses and Apparent Agonist Activity", J. Pharmacol Exp Ther. 277, 2, 586-594, 1996. The respective description is hereby incorporated by reference and forms part of the present disclosure.

The base-line rectal temperatures are determined with a thermometer (Yello Springs Instruments Co., Panlabs) and a thermistor probe inserted to 25 mm before the administration of the substance to be tested. Rectal temperature is again measured 20 minutes after the administration of the substances to be tested. The temperature difference is calculated for each animal, whereby differences of $\geq -2°$ C. are considered to represent activity.

Catalepsy:

Catalepsy is determined according to the method described in Alpermann H. G. et al. "Pharmacological effects of Hoe 249: A new potential antidepressant", Drugs Dev. Res. 25, 267-282. 1992. The respective description is hereby incorporated by reference and forms part of the present disclosure.

The cataleptic effect of the substance to be tested is evaluated according to the duration of catalepsy, whereby the animals are placed head downwards with their kinlegs upon the top of the wooden block.

The chosen scoring system is:
Catalepsy for:
more than 60 seconds=6; 50-60 seconds=5, 40-50 seconds=4, 30-40 seconds=3, 20-30 seconds=2, 5-10 seconds=1, and less than 5 seconds=0.

The percentage of catalepsy is determined according to the following formula:

$$\% \text{ Catalepsy} = \text{arithmetic mean}/6 \times 100$$

III. In Vivo Testing for Antiobesic Activity a) Accute Treatment

Normally handled rats were habituated to a reversed cycle 12/12 h, and the tested compound as well as saline was acutely orally administered. After administration the cumulated food intake (g) was measured at 6 h and 24 h. Following that the difference in body weight between control and compound treated animals was measured. This is a variation of the test according to Colombo et al. as described below.

b) Long-Term Treatment

The in-vivo testing for antiobesic activity of the inventive pyrazoline compounds is carried out as described in the publication of G. Colombo et al., "Appetite Suppression and Weight Loss after the Cannabinoid Antagonist SR 141716"; Life Sciences, 63 (8), 113-117, (1998). The respective part of the description is hereby incorporated by reference and forms part of the present disclosure.

IV. In Vivo Testing for Antidepressant Activity

The in-vivo testing for antidepressant activity of the inventive pyrazoline compounds in the water despair test is carried out as described in the publication of E. T. Tzavara et al., "The CB1 receptor antagonist SR141716A selectively increases monoaminergic neurotransmission in the medial prefrontal cortex: implications for therapeutic actions"; Br. J. Pharmacol. 2003, 138(4):544:53. The respective part of the description is hereby incorporated by reference and forms part of the present disclosure.

V. In Vitro Determination of Antagonism to CB1-Receptor

Membrane Preparation:

Chinese hamster ovary (CHO) cells stably expressing recombinant human cannabinoid 1 receptor (CB1) were cultured in nutrient mixture Ham's F 12 supplemented with 10% heat-inactivated fetal bovine serum, 2 mM L-glutamine, 50 U/ml penicillin, 50 U/ml streptomycin and 0.5 mg/ml geneticin. In order to obtain cells, culture flasks were washed twice with phosphate buffered saline and scraped. Then, cells were collected by centrifugation (200×g, 10 min) and stored dry at −80° C. Cells were homogenized in ice-cold 20 mM HEPES, 10 mM EDTA (pH 7.5) and centrifuged at 40,000×g for 15 min at 4° C. The membrane pellet was resuspended in 20 mM HEPES, 0.1 mM EDTA (pH 7.5) and centrifuged for 15 min at 4° C. The final membrane pellet was resuspended in 20 mM HEPES, 0.1 mM EDTA (pH 7.5), and divided in aliquots and stored at −80° C. until use.

[$^{35}$S]GTPγS Binding Assay:

The reaction was performed in 96-well plates. Membranes (15 μg protein/well) were incubated for 60 min at 30° C. in buffer (50 mM HEPES, 100 mM KCl, 5 mM MgCl$_2$, 1 mM EDTA, 0.1% wt/vol bovine serum albumin, 5 μM GDP, saponin (10 μg/ml), 0.5 nM [$^{35}$S]GTPγS, pH 7.4) with compound at a final concentration of 1 μM in either the absence or presence of agonist WIN 55, 212-2 between 3 nM and 3 μM. The incubation was terminated by rapid filtration through Millipore Multiscreen glass fiber FB, and rinsed two-times with ice-cold assay buffer. Filter plates were dried and 30 μl of scintillation liquid was added. Radioactivity was determined using a Wallac Microbeta Trilux. Each experiment was performed at least in duplicate. A WIN 55, 212-2 dose-response experiment either alone or in the presence of Rimonabant (1 μM) was systematically performed.

Calculations:

The average of basal [$^{35}$S]GTPγS binding was subtracted from all binding data. In order to compare the antagonism results from one screening campaign to another one, the difference between the maximal agonist effect of WIN 55, 212-2 alone, and the maximal antagonism effect due to WIN 55, 212-2 plus Rimonabant (1 μM) was defined as 100%.

Further Methods:

Alcohol Intake

The following protocol may be used to evaluate the effects of alcohol intake in alcohol preferring (P) female rats (e.g. bred at Indiana University) with an extensive drinking history. The following reference provides detailed a description of P rats: Lumeng, L, et al., "Different sensitivities to ethanol in alcohol-preferring and -nonpreferring rats," Pharmacol, Biochem Behav., 16, 125-130 (1982).

Female rats are given 2 hours of access to alcohol (10% v/v and water, 2-bottle choice) daily at the onset of the dark cycle. The rats are maintained on a reverse cycle to facilitate experimenter interactions. The animals are initially assigned to four groups equated for alcohol intakes: Group 1-vehicle; Group 2-positive control (e.g. 5.6 mg/kg AM251; Group3-low dose test compound; and Group 4-high dose of test compound. Test compounds are generally mixed into a vehicle of 30% (w/v)-cyclodextrin in distilled water at a volume of 1-2 ml/kg. Vehicle injections are given to all groups for the first two days of the experiment. This is followed by 2 days of drug injections (to the appropriate groups) and a final day of vehicle injections. On the drug injection days, drugs are given sc 30 minutes prior to a 2-hour alcohol access period. Alcohol intake for all animals is measured during the test period and a comparison is made between drug and vehicle-treated animals to determine effects of the compounds on alcohol drinking behavior.

Additional drinking studies can be done utilizing female C57B1/6 mice (Charles River). Several studies have shown that this strain of mice will readily consume alcohol with little to no manipulation required (Middaugh et al., "Ethanol Consumption by C57BU6 Mice: Influence of Gender and Procedural Variables" Alcohol, 17 (3), 175-183, 1999; Le et al., "Alcohol Consumption by C57BL/6, BALA/c, and DBA/2 Mice in a Limited AccessParadigm" PharmacologyBiochemistry and Behavior, 47, 375-378, 1994).

For example, upon arrival mice are individually housed and given unlimited access to powdered rat chow, water and a 10% (w/v) alcohol solution. After 2-3 weeks of unlimited access, water is restricted for 20 hours and alcohol is restricted to only 2 hours access daily. This is done in a manner that the access period was the last 2 hours of the dark part of the light cycle.

Once drinking behavior is stabilized, testing can commence. Mice are considered stable when the average alcohol consumption for 3 days is 20% of the average for all 3 days. Day 1 of test consists of all mice receiving vehicle injection (sc or ip). Thirty to 120 minutes post injection access is given to alcohol and water. Alcohol consumption for that day is calculated (g/kg) and groups are assigned so that all groups have equivocal alcohol intake. On day 2 and 3, mice are injected with vehicle or drug and the same protocol as the previous day is followed. Day 4 iss wash out and no injections are given. Data is analyzed using repeated measures ANOVA. Change in water or alcohol consumption is compared back to vehicle for each day of the test. Positive results would be interpreted as a compound that was able to significantly reduce alcohol consumption while having no effect on water Oxygen Consumption Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (e.g. 300-380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e., sc, ip, iv). Drugs are prepared in methylcellulose, water or other specified vehicle (examples include PEG400, 30% beta-cyclo dextran and propylene glycol). Oxygen consumption and ambulatory activity are measured every 10 minutes for an additional 1-6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min02 consumption values, excluding periods of high ambulatory activity (ambulatory activity count >100) and excluding the first 5 values of the pre-dose period and the first value from the post-dose period. Change in oxygen consumption is reported as percent and is calculated by dividing the post-dosing resting oxygen consumption by the pre-dose oxygen consumption*100. Experiments will typically be done with n=4-6 rats and results reported are mean+/−SEM.

Interpretation:

An increase in oxygen consumption of >10% is considered a positive result. Historically, vehicle-treated rats have no change in oxygen consumption from pre-dose basal.

Nicotine Dependence

An intravenous nicotine self-administration model or place preference model may be used to assess the effects of a test compound on nicotine dependence (see, e.g., Vastola, et al. Physiol. Behav. 77:107-114, 2002; Brower, et al., Brain Res. 930:12-20, 2002).

Place Preference

Sprague-Dawley rats are used in this study (Vastola, et al., 2002). Animals are housed in a temperature-controlled, 12 h/12 h illumination cycle with ad libitum access to food and water. Conditioning and testing are conducted in a chamber divided into two compartments with a door separating the two compartments. Behavior of the animals is recorded by video camera.

Animals are habituated to the injection procedure for several days. The animals are then placed into the test chamber and given free access to both compartments. The initial preference for a particular compartment is determined. For the conditioning trials, animals are injected with nicotine and restricted to the nonpreferred compartment, or the animals are injected with saline and restricted to the preferred compartment. On test day, the door separating the compartments is removed, the animal is placed in the center of the chamber and allowed to move freely between compartments. Time spent in each compartment is scored. Preferential occupancy of the nicotine compartment follows from the conditioned reinforcing effects of nicotine.

Self-Administration

Self-administration in animals is a predictor of a compound's abuse potential in humans. Modifications to this procedure may also be used to identify compounds that prevent or block the reinforcing properties of drags that have abuse potential. A compound that extinguishes the self-administration of a drag may prevent that drag's abuse or its dependence.

Sprague-Dawley rats are used in this study. Initially, animals are housed in a temperature-controlled, 12 h/12 h illumination cycle with ad libitum access to food and water. The animals are then implanted with jugular catheters which exit through the animal's back, and each animal is placed in an individual operant chamber (Brower, et al., 2002). The catheters are connected to a computer-driven syringe pump which is located outside of the chamber. The chamber contains two levers with a green light located above each lever. The light is illuminated when nicotine is available.

In a self-administration test, animals are placed in the operant chambers and the levers are randomly designated as an active and inactive lever. Each response on the active lever produces an infusion of nicotine. Presses on the inactive lever have no effect, but are also recorded. Animals are then trained to self-administer nicotine over a set period of time by having drag access during each daily session. Illumination of the chamber house light signals the beginning of the session and the availability of nicotine. When the session ends, the house light is turned off. Initially, a nicotine infusion occurs with every press of the active lever. Once lever-pressing behavior has been established, the number of presses to produce a nicotine infusion is increased. After stable nicotine self-administration is obtained, the effect of a test compound on the nicotine-reinforced behavior may be evaluated. Administration of this test compound prior to the session can either potentiate, extinguish, or produce no change to the self-administrating behavior. Tests are conducted every two days, and the order of the administration of the test compound doses is controlled.

Alzheimer/Dementia Experiments
Morris Water Maze Task

The Morris water maze is a behavioral in vivo test to measure spatial orientation learning and memory through a complex learning task. It is highly suitable for testing compounds that enhance learning and memory. A circular water tank or pool (diameter 2 m, height 0.7 m) is filled with water, and a 10 cm2 platform is placed 1-1.5 cm below the water surface at a defined location within the pool. The escape platform is not visible for an animal swimming in the water tank. For the experiment, a rat or mouse is placed into the pool to swim freely.

The animals have the task to localize the submerged platform, and the time and distance required for successful retrieval is measured. Multiple extra-maze cues are provided by the furniture in the room, including desks, computer equipment, a second water tank, the presence of the experimenter, and by a radio on a shelf that is playing softly.

Before administration of the test compound, animals are usually trained in the task 4 times a day for 5 days. Test compounds are administered orally or intraperitoneally on the day of the experiment at a defined time (e.g., 30 minutes before the first swim test). Control animals are dosed with the corresponding vehicle not containing test compound. Active compounds yield shorter times and distances to localize the platform (i.e., the better the animal remembers the location of the platform, the shorter the distance covered and the faster the platform is reached).

The test can also be carried out using transgenic or cognitively impaired animals. Cognitive impairment is induced either by old age or experimentally through brain lesions, such as bilateral lesions of the entorhinal cortex in rats. Such lesions can be induced by intracerebral injections of the excitotoxin ibotenic acid.

Object Recognition Task

The object recognition task is used to assess the effects of compounds on the cognitive performance of rodents. A rat is placed in an open field, in which two identical objects are located. The rats inspects both objects during the initial trial of the test. After a certain retention interval (e.g., 24 hours), a second trial is carried out. Here, one of the two objects used in the first trial (the 'familiar' object) and a novel object are placed in the open field, and the inspection time at each of the objects is measured. Good retention is reflected by higher exploration times towards the novel compared with the 'familiar' object.

Administration of the putative cognition enhancer prior to the first trial predominantly allows assessment of the effects on acquisition, and on the consolidation processes. Administration of the test compound after the first trial allows to assess the effects on consolidation processes, whereas administration before the second trial allows to measure effects on retrieval processes.

Passive Avoidance Task

The passive avoidance task assesses memory performance in rats and mice. The inhibitory avoidance uses an apparatus consisting of a box with two compartments separated by a guillotine door that can be operated by the experimenter. One compartment is illuminated with bright light, and the other compartment is dark. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. During the habituation sessions and the retention session, the rat is allowed to explore the apparatus for 300 seconds.

The rat is placed in the light compartment, facing the wall opposite to the guillotine door. After an accommodation period of 15 seconds, the guillotine door is opened so that all parts of the apparatus can be visited freely. Rats normally avoid brightly lit areas and will enter the dark compartment within a few seconds.

In the shock session, the guillotine door between the compartments is lowered as soon as the rat has entered the dark compartment with all paws, and a scrambled 1 mA footshock is administered for 2 seconds. Then the rat is removed from the apparatus and returned into its home cage. The procedure during the retention session is identical to that of the habituation sessions.

The step-through latency, that is, the first latency of entering the dark compartment (in seconds) during the retention session is an index of the memory performance of the animal: a better retention is assumed if the latency to enter the dark compartment is longer. A test compound is given 30 minutes before the shock session, together with 1 mg/kg scopolamine. Scopolamine impairs the memory performance during the retention session 24 hours later. If the test compound increases the enter latency compared with the scopolamine-treated controls, it is considered to possess cognition enhancing activity. T-maze Spontaneous Alternation Task The T-maze spontaneous alternation task (TeMCAT) assesses the spatial memory performance in mice. The start arm and the two goal arms of the T-maze are provided with guillotine doors that can be operated manually by the experimenter. A mouse is put into the start arm at the beginning of training. In the first trial, either the left or right goal arm is blocked by lowering the respective guillotine door (forced trial).

After the mouse has been released from the start arm, it will explore the maze, eventually entering the open goal arm, and return to the start position, where it will be confined for 5 seconds, by lowering the guillotine door. Then, the animal can choose freely between the left and right goal arm (all guillotine-doors opened) during 14 additional trials (free choice trials). As soon as a mouse has entered one goal arm, the other arm is closed. The mouse eventually returns to the start arm and is free to visit whichever arm it wants after having been confined to the start arm for 5 seconds. After completion of 14 free choice trials in one session, the animal is removed from the maze.

Out of the 14 trials the alternations in percent are calculated. This percentage and the total time needed to complete the first forced trial and the subsequent 14 free choice trials (in seconds) is analyzed. In addition, cognitive deficits can be induced by injection of scopolamine 30 minutes before the start of the training session. A cognition enhancer, administered before the training session, will at least partially, antagonize the scopolamine-induced reduction in the spontaneous alternation rate.

Depression Model

A forced swim or tail suspension model may be used to assess the efficacy of antidepressant compounds (see, e.g., Porsolt, et al., Nature 266:730-732, 1977; Stern, et al., Psychopharmacology 85:367-370, 1985).

Forced Swim Test

Rats or mice are placed in a cylinder filled with water 23-25° C. from which no escape is possible. Initially, animals struggle and try to escape, but eventually adopt a characteristic immobile posture and make no further attempts to escape except for small movements needed their head above water. Animals are dosed with a compound and the activity (swimming or climbing) or immobility is measured by an observer. The immobility is considered by some to reflect a 'behavioral despair' in which animals cease to struggle to escape the aversive situation. A wide variety of clinically used antidepressants (TCAs, MAOIs, SSRIs, atypicals) decrease immobility in this test and has a good predictive validity in that it detects antidepressants with different mechanisms of action but its construct validity is weak. At least two distinct active behavioral patterns are produced by pharmacologically selective antidepressant drugs. Serotonin-selective reuptake inhibitors increase swimming behavior, whereas drugs acting primarily to increase extracellular levels of norepinephrine or dopamine increase climbing behavior. There are false positives (psychostimulants) but relatively few false negatives ([beta]-adrenergic agonists). The test is sensitive to muscle-relaxant (benzodiazepines) and sedative (neuroleptics) effects, leading to enhanced immobility. False positives and false negatives can often be screened by measuring if the compound produces locomotor stimulation or sedation.

Tail Suspension Test

When suspended by the tail, mice will initially struggle and try to escape and then alternate between active escape attempts and immobililty. In this test, animals are dosed with a compound and the immobility is measured by an observer for 6 min. Porsolt describes the immobile behavior as 'behavioral despair' which animals cease to struggle to escape the aversive situation. A large variety of clinically antidepressants (tricyclics, MAOIs, SSRIs, and atypicals) reduce immobility in this model. The test has a good predictive validity for antidepressant activity and works for most antidepressant classes including but has some false positives (psychostimulants). The test is sensitive to muscle-relaxant (benzodiazepines) and sedative (neuroleptics) effects, which lead to enhanced immobility. False positives and false negatives can often be screened by measuring if the compound produces locomotor stimulation or sedation. Strain differences in the tail suspension test have been found in mice. The tail suspension test has some face validity but its construct validity is rather weak.

Schizophrenia Model

A prepulse inhibition model may be used to assess the efficacy of antipsychotic compounds (see Swerdlow and Geyer, Schizophrenia Bulletin 24: 285-301, 1998).

Prepulse Inhibition

Prepulse inhibition is the process whereby a relatively mild stimulus, the prepulse, suppresses the response to a strong, startle-eliciting stimulus when the prepulse precedes the startle stimulus by a brief duration (about 10 to 500 milliseconds). Prepulse inhibition is a cross-species phenomenon (ie, it is present in mammals ranging from mice to humans), yet it is relatively absent among schizophrenic patients. The deficit in PPI in schizophrenic patients is thought to reflect the loss of sensorimotor gating that may lead to sensory flooding and cognitive fragmentation. In this test, mice or rats are administered compounds and individually placed into a holder on a transducer platform to measure whole body startle. The holder is housed in a startle chamber with background white noise. Following a brief habituation period, animals are given multiple trials of a weak auditory prepulse stimululs, followed by a strong auditory startle stimulus. Four types of trials are given: prepulse plus startle, prepulse alone, startle alone, and no stimulation. PPI is measured as the amount of inhibition of startle following the prepulse and is expressed as the percentage of basic startle. As a control, measurements are taken in the no stimulation and prepulse alone trials. PPI is considered a test with good predictive, face and construct validity for schizophrenia. Putative antipsychotics can be tested alone to determine if they enhance PPI. Alternately, antipsychotics can be screened to determine if they block various agents that disrupt PPI (apomorphine, d-amphetamine, PCP, ketamine, DOI). Finally, mutant mice with or without drugs can be screened using the PPI procedure.

Anxiety Model

An elevated plus maze model may be used to assess the efficacy of anxiolytic compounds (see Fellow and File, Pharm. Biochem. Behav. 24, 525-529, 1986).

Elevated Plus Maze

The elevated plus maze is widely used as an anxiety paradigm that examines the conflict between the drive to explore and the aversiveness of heights and open spaces of rats or mice. The maze is a cross made up of two open and two closed arms that is raised above the ground. The combination of light, the open arms, and the height is thought to produce unconditioned fear or anxiety responses in mice or rats. The test apparatus is an open top maze constructed of opaque plastic with alternating open and enclosed arms. For rats, each arm is 45-55 cm long and 8-12 cm wide, with the sides of the enclosed arms 35-45 cm high, the juncture approximately 10×10 cm, and the maze is elevated 45-55 cm above the floor. The mouse elevated plus maze consists of two closed arms (15×6×30 cm) and two open arms (1×6×30 cm) forming a cross, with a quadrangular center (6×6 cm).

The maze is placed 50 cm above the floor. Testing is performed in a room free of noise and distraction. On test days animals are administered drug or vehicle. If a pretreatment period is necessary, the animals are returned to the home cage for the duration of the pretreatment time; otherwise, the animals are placed in a clear plastic holding chamber singly or with cage mates for 1-10 minutes prior to test time. Rats are then placed in the center of the maze always oriented in the same direction, either consistently facing an open arm or an enclosed arm. For 5-10 minutes, entries into each arm and the time spent in each arm are recorded by the observer(s) or by videotape or a computer receiving input from a video camera mounted above the maze. To count as an entry, all four paws must be inside the arm. If necessary, additional measures of anxiety-related behaviors will be recorded, i.e., time spent motionless, time spent in the center, time spent grooming, and the number of rears, stretching postures or feces produced. Following testing the animals are returned to the home cages. When animals are placed in the center of the maze, they spend most of their time in the closed arms, avoiding the open arms. Anxiolytic drugs, such as benzodiazepines, will increase the amount of time animals spend in the open arms. The test is also sensitive to anxiogenic drugs, which lends strong support for its predictive validity.

Erectile Dysfunction

Drugs affecting erectile function may be tested by measuring the effect on apomorphine-evoked increases in intracavernous pressure in the awake rat as described by Andersson, et al., (J. Urol. 161: 1707-17] 2, 1999). One end of a polyethylene tubing is implanted into the cavernosal space of the penis of male Sprague-Dawley rats. After recovery from the surgery, intracavernous pressure is recorded using a pressure transducer connected to a multichannel pen-recorder. Erections are induced by administration of apomorphine (100-250 ug/kg s.c.) with or without test compound, and the results are compared for the treated group and the non-treated group.

Female Sexual Dysfunction

Systems to test compounds for the treatment of female sexual dysfunction include in vitro and in situ models using vaginal or clitoral smooth muscle preparations, histological evaluation, and vaginal blood flow assessments. In vivo studies of sexual responses focus on behavioral paradigms involving lordotic posturing and receptivity, as well as indices of motivation using a dual chamber pacing method (see, e.g., Hale, et al., Int. J. Impot. Res. 15 Suppl 5: S75-79, 2003).

The present invention is illustrated below with the aid of examples. These illustrations are given solely by way of example and do not limit the general spirit of the present invention.

EXAMPLES

Preparation of 4-(4-chlorophenyl)-2-oxo-3-butenoic acid

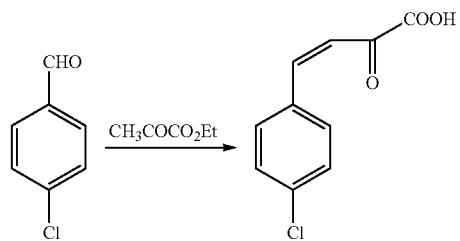

p-Chlorobenzaldehyde (13.3 g, 95 mmol) and ethyl pyruvate (10 g, 86 mmol) were dissolved in 150 mL of absolute ethanol. The solution was cooled to 0° C. and an aqueous solution of NaOH (3.8 g in 45 mL water) was added drop wise keeping the temperature below or equal to 10° C., whereby a yellow-orange coloured precipitate was formed. The reaction mixture was stirred for 1 hour at 0° C. and an additional 1.5 hours at room temperature (approximately 25° C.). Afterwards the reaction mixture was cooled down to approximately 5° C. and the insoluble sodium salt of 4-(4-chlorophenyl)-2-oxo-3-butenoic acid was isolated by filtration.

The filtrate was left in the refrigerator overnight, whereby more precipitate was formed, which was filtered off, combined with the first fraction of the salt and washed with diethyl ether. The sodium salt of 4-(4-chlorophenyl)-2-oxo-3-butenoic acid was then treated with a solution of 2N HCl, stirred for some minutes and solid 4-(4-chlorophenyl)-2-oxo-3-butenoic acid was separated via filtration and dried to give 12.7 g of the desired product (70% of theoretical yield).

IR (KBr, cm$^{-1}$): 3500-2500, 1719.3, 1686.5, 1603.4, 1587.8, 1081.9.

$^1$H NMR (CDCl$_3$, 300 MHz) δ 7.4 (d, J=8.4 Hz, 2H), 7.5 (d, J=16.1 Hz, 1H), 7.6 (d, J=8.4 Hz, 2H), 8.1 (d, J=16.1 Hz, 1H).

Preparation of 5-(4-chlorophenyl)-1-(2,4-dichlorophenyl)-4,5-dihydro-pyrazole-3-carboxylic acid

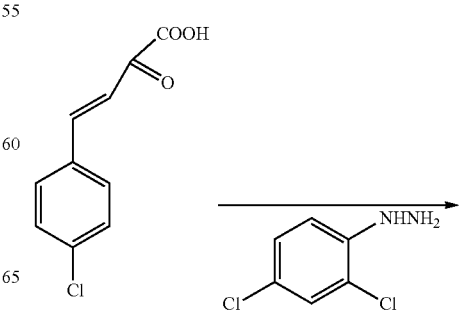

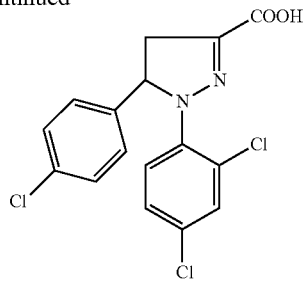

4-(4-Chlorophenyl)-2-oxo-3-butenoic acid (12.6 g, 60 mmol), 2,4-dichlorophenylhydrazine hydrochloride (12.8 g, 60 mmol) and glacial acetic acid (200 mL) were mixed under a nitrogen atmosphere and heated to reflux for 4 hours, cooled down to room temperature (approximately 25° C.) and poured into ice, whereby a sticky mass was obtained, which was extracted with methylene chloride. The combined methylene chloride fractions were washed with water, dried over sodium sulfate, filtered and evaporated to dryness to give a pale yellow solid (12.7 g, 57% of theoretical yield).

IR (KBr, cm$^{-1}$): 3200-2200, 1668.4, 1458, 1251.4, 1104.8.
$^1$H NMR (CDCl$_3$, 300 MHz) δ 3.3 (dd, 1H), 3.7 (dd, 1H), 5.9 (dd, 1H), 7.09-7.25 (m, 7H).

Preparation of 5-(4-chlorophenyl)-1-(2,4-dichlorophenyl)-4,5-dihydro-pyrazole-3-carboxylic acid chloride

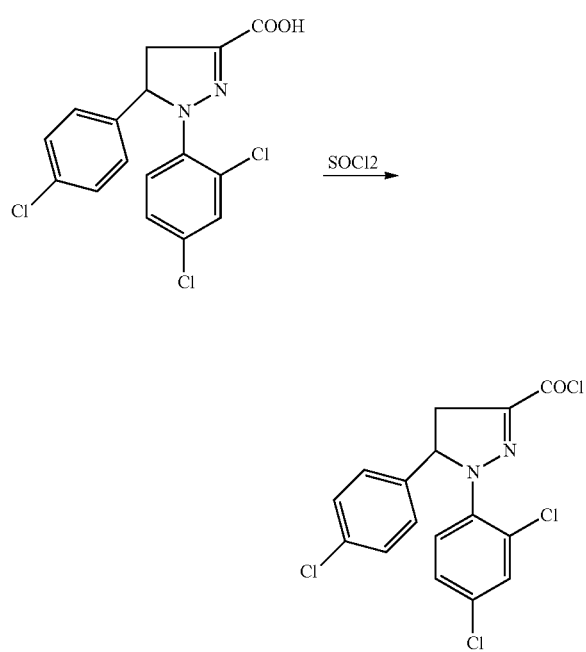

5-(4-Chlorophenyl)-1-(2,4-dichlorophenyl)-4,5-dihydropyrazole-3-carboxylic acid (5.54 g, 15 mmols) was dissolved in 120 mL of dry toluene and thionyl chloride (2.14 g, 18 mmol) was added. The mixture was heated to 80° C. for 2.5 hours. The solvent was removed under reduced pressure and the resulting crude residue (6.06 g, 100%) was used without any further purification.

IR (KBr, cm$^{-1}$): 1732, 1700, 1533, 1478, 1212, 826

Example 1

Preparation of 5-(4-Chloro-phenyl)-1-(2,4-dichloro-phenyl)-4,5-dihydro-1H-pyrazole-3-carboxylic acid piperidin-1-ylamide

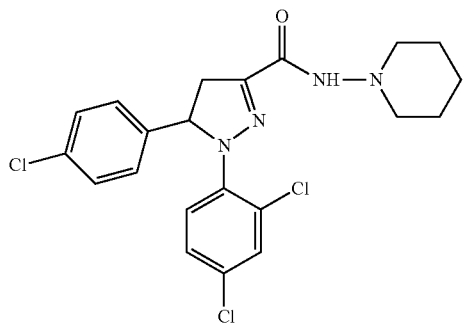

N-Aminopiperidine (0.6 mL, 5.6 mmol) and triethylamine (4 mL) were dissolved in methylene chloride (25 mL) under nitrogen atmosphere. The resulting mixture was -cooled to 0° C. and a solution of 5-(4-chlorophenyl)-1-(2,4-dichlorophenyl)-4,5-dihydro-pyrazole-3-carboxylic acid chloride in methylene chloride (15 mL) was added drop wise. The resulting reaction mixture was stirred at room temperature (approximately 25° C.) overnight. The reaction mixture was washed with water, followed by a saturated aqueous solution of sodium bicarbonate, again with water, dried over sodium sulfate, filtered and evaporated to dryness in a rotavapor. The resulting crude solid was crystallised from ethanol. The crystallised solid was removed via filtration and the mother liquors were concentrated to yield a second fraction of crystallised product. The two fractions were combined to give a total amount of 1.7 g (57% of theoretical yield) of the title compound having a melting point of 183-186° C.

IR (KBr, cm$^{-1}$): 3222.9, 2934.9, 1647.4, 1474.7, 1268.3, 815.6.

$^1$H NMR (CDCl$_3$, δ): 1.4 (m, 2H), 1.7 (m, 4H), 2.8 (m, 4H), 3.3 (dd, J=6, 1 y 18.3 Hz, 1H), 3.7 (dd, J=12, 5 and 18.3 Hz, 1H), 5.7 (dd, J=6, 1 and 12.5 Hz, 1H), 7.0-7.2 (m, 6H), 7.4 (s, 1H).

The following compounds were prepared according to the processes described for the preparation of compound I above. Those skilled in the art are familiar with the starting materials that are needed to obtain said compounds.

Example 7

N-oxide of N-piperidinyl-5-(4-chlorophenyl)-1-(2,4-dichlorophenyl)-4,5-dihydropyrazole-3-carboxamide Under nitrogen gas as an inert atmosphere N-piperidinyl-5-(4-chlorophenyl)-1-(2,4-dichlorophenyl)-4,5-dihydropyrazole-3-carboxamide (0.15 g, 0.33 mmol) was dissolved in 7 mL of dichloromethane. The resulting solution was ice-cooled to 0° C. and m-chloroperbenzoic acid (0.204 g, 0.83 mmol) was added in several portions. After stirring for 15 minutes a control via thin layer chromatography showed that no starting material was present. A saturated solution of sodium bicarbonate was then slowly added, the organic phase separated, washed with water, dried over sodium sulfate and filtered. The filtered solution was evaporated to dryness and the crude product was purified via column chromatography yielding 78 mg (50% of theoretical yield) of the N-oxide of N-piperidinyl-5-(4-chlorophenyl)-1-(2,4-dichlorophenyl)-4,5-dihydropyrazole-3-carboxamide in form of a white solid having a melting point of 115-120° C.

IR (KBr, cm$^{-1}$): 3202, 1678, 1654, 1474, 1309, 1107.

$^1$H-NMR (CDCl$_3$, δ): 1.6 (m, 2H), 1.8-2.0 (m, 4H), 2.55 (m, 2H), 3.3 (dd, J=6.3 Hz and 18.2 Hz, 1H), 3.7 (m, 3H), 5.8 (dd, J=6.3 Hz and 12.5 Hz, 1H), 7.0-7.3 (m, 7H), 8.5 (s, 1H.)

Example 120

[5-(4-Chloro-phenyl)-1-(2,4-dichloro-phenyl)-4,5-dihydro-1H-pyrazol-3-carboxylic acid ethyl ester 5-(4-chlorophenyl)-1-(2,4-dichlorophenyl)-4,5-dihydro-pyrazole-3-carboxylic acid (0.55 g, 1.50 mmol) was dissolved in 20 mL of toluene and (2 mL) ethanol and (0.05 g) of p-toluenesulfonic acid monohydrate were added. The mixture was heated at 80° C. for 72 hours. After cooling to room temperature, the reaction mixture washed with sodium hydrogen carbonate solution and water, dried over sodium sulphate and evaporated to dryness to give the title compound in form of oil.

IR (film, cm$^{-1}$): 2981, 1728, 1704, 1478, 1246.

The compounds according to the following examples 68 to 172 have been prepared by the methods described for the preparation of Example 1. The other examples were prepared or can be prepared by the methods described above.

Example 68

5-(4-Bromo-phenyl)-1-(2,4-dichloro-phenyl)-4,5-dihydro-1H-pyrazole-3-carboxylic acid azepan-1-ylamide Preparation of 4-(4-bromophenyl)-2-oxo-3-butenoic acid This compound was obtained following the same method described in Example 1 starting from p-bromobenzaldehyde.

$^1$H NMR (400 MHz, CDCl$_3$,): 67.55 (2H, m, ArH,), 7.61 (3H, m, Ar H), 8.09 (1H, d, J=16.4 Hz)

$^{13}$C NMR (100 MHz, CDCl$_3$): δ 118.1 (CH), 127.2 (C), 130.7 (CH), 132.7 (CH), 149.7 (C+CH), 160.0 (CO), 182.2 (CO).

Preparation of 5-(4-bromophenyl)-1-(2,4-dichlorophenyl)-4,5-dihydro-pyrazole-3-carboxylic acid IR (KBr, cm$^{-1}$): 3200-2200, 1685, 1571, 1549, 1480, 1112

$^1$H NMR (400 MHz, CDCl$_3$)): δ 3.27 (1H, dd, J 18.0, 6.4 Hz, ArH,), 3.71 (1H, dd, J 18, 12.8 Hz, Ar H), 5.88 (1H, dd, J 12.8, 6.4 Hz, CH), 7.02 (2H, d, J=7.6 Hz, ArH), 7.08 (1H, m, ArH), 7.19 (1H, d J 8.4 Hz, ArH), 7.26 (1H, m, ArH), 7.37 (2H, d, 7.6 Hz, ArH)

$^{13}$C NMR (100 MHz, CDCl$_3$): δ 40.4 (CH$_2$), 67.4 (CH), 122.7 (C), 126.0 (CH), 126.5 (C), 127.6 (CH), 128.3 (CH), 130.2 (CH), 131.2 (C), 132.2 (CH), 138.4 (C), 138.5 (C), 140.2 (C), 165.7 (C).

Preparation of 5-(4-bromophenyl)-1-(2,4-dichlorophenyl)-4,5-dihydro-pyrazole-3-carboxylic acid chloride IR (KBr, cm$^{-1}$): 1737, 1534, 1477, 1212, 1127.

Preparation of 5-(4-Bromo-phenyl)-1-(2,4-dichlorophenyl)-4,5-dihydro-1H-pyrazole-3-carboxylic acid azepan-1-ylamide This compound was obtained following the same method described in Example 1 starting from 5-(4-bromophenyl)-1-(2,4-dichlorophenyl)-4,5-dihydro-pyrazole-3-carboxylic acid chloride and azepan-1-amine.

$^1$H NMR (300 MHz, CHLOROFORM-d) δ ppm 1.75 (br. s., 4H) 2.00 (br. s., 4H) 3.26 (dd, J=18.16, 6.15 Hz, 1H) 3.71 (dd, J=18.16, 12.45 Hz, 1H) 3.65 (br. s., 4H) 5.82 (dd, J=12.45, 6.15 Hz, 1H) 6.97 (d, J=8.35 Hz, 2H) 7.10 (d, J=2.20 Hz, 1H) 7.16-7.22 (m, 1H) 7.24 (d, J=2.20 Hz, 1H) 7.35 (d, J=8.50 Hz, 2H)

MS (M+H)$^+$: 510

Example 96

1-(2,4-Dichloro-phenyl)-5-(4-fluoro-phenyl)-4,5-dihydro-1H-pyrazole-3-carboxylic acid azepan-1-ylamide Preparation of 4-(4-fluorophenyl)-2-oxo-3-butenoic acid $^1$H NMR (400 MHz, CDCl$_3$,): δ 7.15 (2H, apt, J=8.4 Hz, ArH,), 7.53 (1H, d, J=16.0 Hz, CH), 7.70 (2H, m, ArH), 8.11 (1H, d, J=16.0 Hz)

$^{13}$C NMR (100 MHz, CDCl$_3$): δ 116.5 (CH, d, J$_F$ 24 Hz), 117.4 (CH, d, J$_F$ 8.7 Hz), 130.1 (C, d, J$_F$ 2.4 Hz), 131.7 (CH, d, J$_F$ 9.1 Hz), 149.9 (CH), 162.0 (C, d, J$_F$ 320 Hz), 166.7 (CO), 182.4 (CO).

Preparation of 5-(4-fluorophenyl)-1-(2,4-dichlorophenyl)-4,5-dihydro-pyrazole-3-carboxylic acid IR (KBr, cm$^{-1}$): 3200-2200, 1687.5, 1478, 1230, 1107

$^1$H NMR (400 MHz, CDCl$_3$): δ 3.30 (1H, dd, J 18.0, 6.4 Hz, ArH,), 3.72 (1H, dd, J 18, 12.8 Hz, Ar H), 5.93 (1H, dd, J 12.8, 6.4 Hz, CH), 6.92 (2H, t, J=8.4 Hz, ArH), 7.09-7.12 (3H, m, ArH), 7.22 (1H, bs, ArH), 7.26 (1H, m, ArH)

$^{13}$C NMR (100 MHz, CDCl$_3$): δ 40.7 (CH$_2$), 67.8 (CH), 115.9 (CH, d, J$_F$ 21 Hz), 126.1 (CH), 126.5 (C), 127.6 (CH), 128.3 (CH, d, J$_F$ 8.2 Hz), 130.1 (CH), 131.2 (C), 135.1 (C, d, J$_F$ 3 Hz), 138.6 (C), 140.1 (C), 160.6 (C, d, J$_F$ 240 Hz), 166.3 (C).

Preparation of 5-(4-fluorophenyl)-1-(2,4-dichlorophenyl)-4,5-dihydro-pyrazole-3-carboxylic acid chloride IR (KBr, cm$^{-1}$): 1733, 1548, 1511, 1478, 1212, 832.

Preparation of 1-(2,4-Dichloro-phenyl)-5-(4-fluorophenyl)-4,5-dihydro-1H-pyrazole-3-carboxylic acid azepan-1-ylamide $^1$H NMR (300 MHz, CHLOROFORM-d) δ ppm 1.75 (br. s., 4H) 2.00 (br. s., 4H) 3.28 (dd, J=18.16, 6.08 Hz, 1H) 3.68 (dd, J=18.16, 12.38 Hz, 1H) 3.68 (br. s., 4H) 5.84 (dd, J=12.38, 6.08 Hz, 1H) 6.90 (t, J=8.57 Hz, 2H) 7.08 (m, 3H) 7.14-7.19 (m, 1H) 7.24 (d, J=2.20 Hz, 1H)

MS (M+H)$^+$: 449

Example 106

1-(2,4-Dichloro-phenyl)-5-(4-methoxy-phenyl)-4,5-dihydro-1H-pyrazole-3-carboxylic acid piperidin-1-ylamide hydrochloride Preparation of 4-(4-methoxyphenyl)-2-oxo-3-butenoic acid $^1$H NMR (400 MHz, CDCl$_3$): δ 3.88 (3H, s, OCH$_3$), 6.95 (2H, d, J=6.8 Hz), 7.45 (2H, d, J 15.6; H), 7.65 (2H, d, J=6.8 Hz), 8.09 (2H, d, J=15.6 Hz).

Preparation of 5-(4-methoxyphenyl)-1-(2,4-dichlorophenyl)-4,5-dihydro-pyrazole-3-carboxylic acid IR (KBr, cm$^{-1}$) 3200-2200, 1685, 1513, 1478, 1248, 1105
$^1$H NMR (400 MHz, CDCl$_3$): δ 1.45 (2H, m, CH$_2$), 1.75 (4H, m), 2.84 (4H, m), 3.45 (1H, dd J 4.8, 18 Hz), 3.61 (1H, dd J 11.2, 19.6 Hz), 5.93 (1H, dd J 4.8, 11.2 Hz), 6.57 (2H, ap s), 7.13 (2H, m), 7.32 (1H, m), 7.40 (1H, m)
$^{13}$C NMR (100 MHz, CDCl$_3$): δ 23.4 (CH$_2$), 25.3 (CH$_2$), 40.5 (CH$_2$), 57.3 (CH$_2$), 63.7 (CH), 125.7 (CH), 125.8 (CH), 126.1 (CH), 127.1 (C), 127.8 (CH), 130.1 (CH), 131.1 (C), 139.6 (C), 139.9 (C), 146.1 (C), 158.9 (CO).

Preparation of 5-(4-methoxyphenyl)-1-(2,4-dichlorophenyl)-4,5-dihydro-pyrazole-3-carboxylic acid chloride IR (KBr, cm$^{-1}$): 1735, 1513, 1477, 1249, 1129

Preparation of 1-(2,4-Dichloro-phenyl)-5-(4-methoxy-phenyl)-4,5-dihydro-1H-pyrazole-3-carboxylic acid piperidin-1-ylamide hydrochloride $^1$H NMR (300 MHz, CHLOROFORM-d) δ ppm 1.67 (br. s., 2H) 2.10 (br. s., 4H) 3.25 (dd, J=18.02, 6.01 Hz, 1H) 3.64 (dd, J=18.02, 12.60 Hz, 1H) 3.72 (s, 3H) 3.89 (br. s., 4H) 5.85 (dd, J=12.60, 6.01 Hz, 1H) 6.72 (d, J=8.79 Hz, 2H) 7.00 (d, J=8.64 Hz, 2H) 7.07 (dd, J=8.64, 2.20 Hz, 1H) 7.22 (d, J=8.64 Hz, 1H) 7.22 (d, J=2.20 Hz, 1H) 9.63 (br. s., 1H)
MS (M+H)$^+$: 447

Example 109

1-(2,4-Dichloro-phenyl)-5-(4-methoxy-phenyl)-4,5-dihydro-1H-pyrazole-3-carboxylic acid (hexahydro-cyclopenta[c]pyrrol-2-yl)-amide hydrochloride $^1$H NMR (300 MHz, CHLOROFORM-d) δ ppm 1.61-1.91 (m, 6H) 2.96 (br. s., 2H) 3.27 (dd, J=18.09, 5.86 Hz, 1H) 3.49 (m, 2H) 3.64 (dd, J=18.09, 12.60 Hz, 1H) 3.72 (s, 3H) 3.90 (br. s., 2H) 5.82 (dd, J=12.60, 5.86 Hz, 1H) 6.71 (d, J=8.64 Hz, 2H) 7.00 (d, J=8.64 Hz, 2H) 7.06 (dd, J=8.72, 2.27 Hz, 1H) 7.21 (m, 2H) 9.25 (br. s., 1H)
MS (M+H)$^+$: 473

Example 172

1-(2,4-Dichloro-phenyl)-5-(4-hydroxy-phenyl)-4,5-dihydro-1H-pyrazole-3-carboxylic acid piperidin-1-ylamide hydrochloride The free base of compound 106 (0.82 mmol) was dissolved in dichloromethane (10 ml) and a solution of 1 M BBr$_3$ (5 eq) in dichloromethane was slowly added at 0° C. and the reaction mixture was stirred at room temperature for 8 h. The solid formed was filtered off and the solvent was evaporated. A solution of 2 N HCl in diethyl ether was added to form the hydrochloride.

$^1$H NMR (300 MHz, METHANOL-d$_4$) δ ppm 1.69 (br. s., 2H) 2.00 (br. s., 4H) 3.24 (dd, J=17.94, 6.23 Hz, 1H) 3.55 (br. s., 4H) 3.69 (dd, J=17.94, 12.38 Hz, 1H) 5.86 (dd, J=12.38, 6.23 Hz, 1H) 6.61 (d, J=8.50 Hz, 2H) 7.00 (d, J=8.50 Hz, 2H) 7.17 (dd, J=8.64, 2.20 Hz, 1H) 7.26-7.38 (m, 2H)
MS (M+H)$^+$: 433

Example 174

1-(2,4-Dichloro-phenyl)-5-(4-hydroxy-phenyl)-4,5-dihydro-1H-pyrazole-3-carboxylic acid (hexahydro-cyclopenta[c]pyrrol-2-yl)-amide hydrochloride The free base of compound 109 (0.82 mmol) was dissolved in dichloromethane (10 ml) and a solution of 1 M BBr$_3$ (5 eq) in dichloromethane was slowly added at 0° C. and the reaction mixture was stirred at room temperature for 8 h. The solid formed was filtered off and the solvent was evaporated. A solution of 2 N HCl in diethyl ether was added to form the hydrochloride.

$^1$H NMR (300 MHz, METHANOL-d$_4$) δ ppm 1.68 (br. s., 2H) 1.81 (br. s., 4H) 2.98 (br. s., 2H) 3.06-3.21 (m, 2H) 3.26 (dd, J=18.02, 6.30 Hz, 1H) 3.71 (dd, J=18.02, 12.45 Hz, 1H) 4.06 (m, 2H) 5.88 (dd, J=12.45, 6.30 Hz, 1H) 6.63 (d, J=8.64 Hz, 2 H) 7.02 (d, J=8.64 Hz, 2H) 7.18 (dd, J=8.64, 2.34 Hz, 1H) 7.37 (d, J=2.20 Hz, 1H) 7.34 (d, J=8.79 Hz, 1H)
MS (M+H)$^+$: 459

| No | STRUCTURE | Name | $^1$H-NMR | MS (M + H)$^+$ |
|---|---|---|---|---|
| 7 | 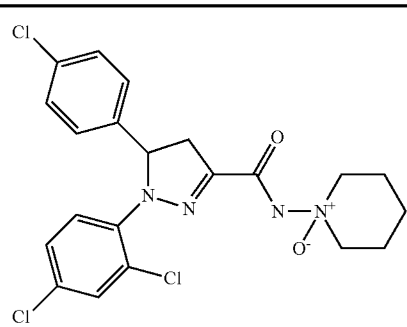 | N-oxide of 5-(4-Chloro-phenyl)-1-(2,4-dichloro-phenyl)-4,5-dihydro-1H-pyrazole-3-carboxylic acid piperidin-1-ylamide | 1H NMR (300 MHz, CHLOROFORM-d) δ ppm 1.6 (m, 2H) 1.8-2.0 (m, 4H) 2.55 (m, 2 H) 3.3 (dd, J = 18.2, 6.3 Hz, 1H) 3.7 (m, 3H) 5.8 (dd, J = 12.5, 6.3 Hz, 1H) 7.0-7.3 (m, 7 H) 8.5 (s, 1H). | |

-continued

| No | STRUCTURE | Name | ¹H-NMR | MS (M + H)⁺ |
|---|---|---|---|---|
| 8 | 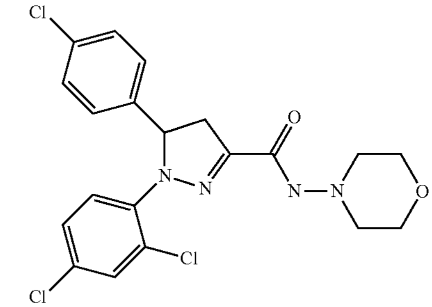 | 5-(4-Chloro-phenyl)-1-(2,4-dichloro-phenyl)-4,5-dihydro-1H-pyrazole-3-carboxylic acid morpholin-4-ylamide | 1H NMR (300 MHz, CHLOROFORM-d) δ ppm 3.00 (m, 4H) 3.32 (dd, J = 18.31, 6.30 Hz, 1H) 3.69 (dd, J = 18.31, 12.30 Hz, 1H) 3.90 (m, 4H) 5.75 (dd, J = 12.30, 6.30 Hz, 1H) 7.07 (m, 4H) 7.17 (m, 3H) 7.68 (s, 1H) | 453 |
| 9 | 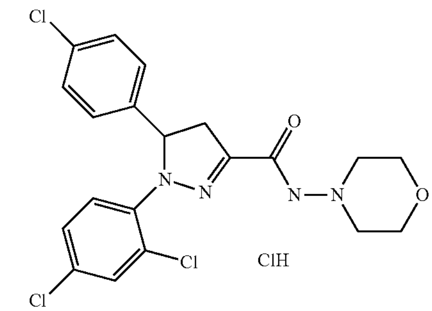 | 5-(4-Chloro-phenyl)-1-(2,4-dichloro-phenyl)-4,5-dihydro-1H-pyrazole-3-carboxylic acid morpholin-4-ylamide hydrochloride | | 453 |
| 10 | 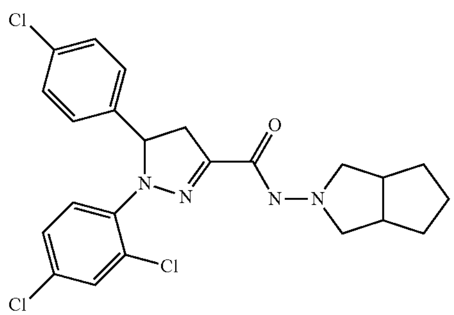 | 5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide | 1H NMR (400 MHz, CHLOROFORM-d) δ ppm 1.61 (m, 6H) 2.77 (m, 4H) 3.31 (dd, J = 18.17, 6.06 Hz, 1H) 3.47 (s, 2H) 3.68 (dd. J = 18.17, 12.11 Hz, 1H) 5.75 (dd, J = 12.11, 6.06 Hz, 1H) 7.05 (m, 3H) 7.16 (t, J = 8.60 Hz, 2H) 7.25 (m, 2H) 7.75 (br, 1H) | 477 |
| 11 | 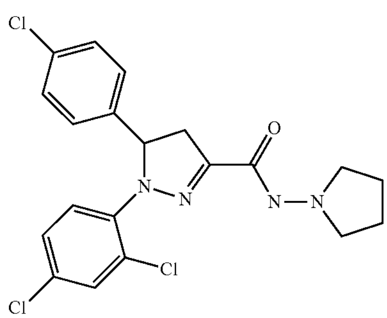 | 5-(4-Chloro-phenyl)-1-(2,4-dichloro-phenyl)-4,5-dihydro-1H-pyrazole-3-carboxylic acid pyrrolidin-1-ylamide | 1H NMR (400 MHz, CHLOROFORM-d) δ ppm 2.06 (s, 4H) 3.28 (m, 5H) 3.69 (dd, J = 17.98, 12.50 Hz, 1H) 5.79 (dd, J = 12.50, 5.86 Hz, 1H) 7.06 (m, 3H) 7.18 (m, 3H) 7.25(m, 1H) 8.22 (br, 1H) | 437 |
| 12 | 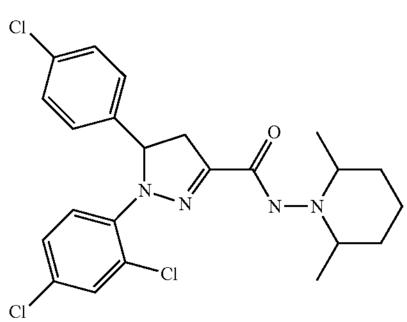 | 5-(4-Chloro-phenyl)-1-(2,4-dichloro-phenyl)-4,5-dihydro-1H-pyrazole-3-carboxylic acid (2,6-dimethyl-piperidin-1-yl)-amide | 1H NMR (400 MHz, CHLOROFORM-d) δ ppm 1.16 (m, 6H) 1.59 (m, 2H) 1.71 (m, 4H) 2.39 (m, 2H) 3.35 (dd, J = 18.56, 4.88 Hz, 1H) 3.70 (dd, J = 18.56, 12.50 Hz, 1H) 5.71 (dd, J = 12.50, 6.06 Hz, 1H) 6.84 (br, 1H) 7.06 (m, 4H) 7.18 (d, J = 8.21 Hz, 2H) 7.26 (m, 1H) | 479 |

-continued

| No | STRUCTURE | Name | ¹H-NMR | MS (M + H)⁺ |
|---|---|---|---|---|
| 13 | 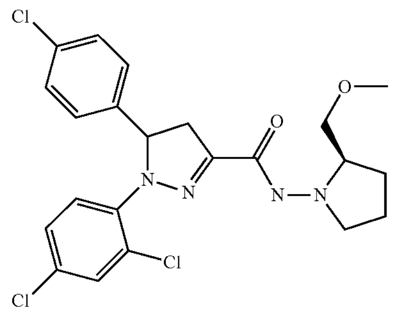 | 5-(4-Chloro-phenyl)-1-(2,4-dichloro-phenyl)-4,5-dihydro-1H-pyrazole-3-carboxylic acid (2-methoxymethyl-pyrrolidin-1-yl)-amide | 1H NMR (400 MHz, CHLOROFORM-d) δ ppm 1.88 (m, 1H) 2.06 (m, 2H) 2.20 (m, 1H) 3.30 (dd, J = 18.37, 5.86 Hz, 1H) 3.37 (m, 1H) 3.40 (s, 3H) 3.59 (m, 2H) 3.71 (m, 3H) 5.82 (dd, J = 12.50, 5.86 Hz, 1H) 7.05 (m, 3H) 7.19 (d, J = 8.60 Hz, 2H) 7.24 (m, 2H) | 481 |
| 14 | 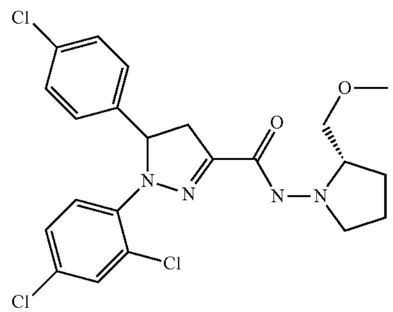 | 5-(4-Chloro-phenyl)-1-(2,4-dichloro-phenyl)-4,5-dihydro-1H-pyrazole-3-carboxylic acid (2-methoxymethyl-pyrrolidin-1-yl)-amide | 1H NMR (400 MHz, CHLOROFORM-d) δ ppm 1.79 (m, 1H) 1.98 (m, 2H) 2.13 (m, 1H) 3.32 (dd, J = 18.76, 6.25 Hz, 1H) 3.36 (m, 1H) 3.38 (s, 3H) 3.51 (m, 2H) 3.64 (m, 2H) 3.70 (dd, J = 18.76, 12.31 Hz, 1H) 5.77 (dd, J = 12.31, 6.25 Hz, 1H) 7.07 (td, J = 8.99, 2.34 Hz, 3H) 7.18 (d, J = 8.21 Hz, 2H) 7.24 (m, 2H) | 481 |
| 15 | 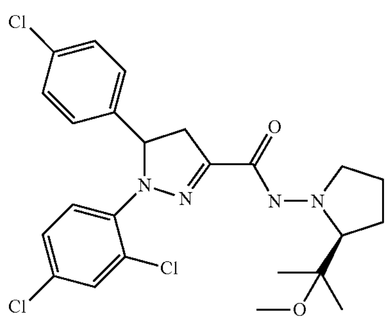 | 5-(4-Chloro-phenyl)-1-(2,4-dichloro-phenyl)-4,5-dihydro-1H-pyrazole-3-carboxylic acid [2-(1-methoxy-1-methyl-ethyl)-pyrrolidin-1-yl]-amide | 1H NMR (300 MHz, DMSO-d₆) δ ppm 1.07 (m, 6H) 1.71 (m, 3H) 1.82 (d, J = 7.03 Hz, 2H) 2.89 (m, 1H) 3.01 (m, 1H) 3.07 (m, 3H) 3.18 (m, 1H) 3.64 (dd, J = 18.02, 11.86 Hz, 1H) 5.79 (m, 1H) 7.12 (m, 2H) 7.28 (m, 3H) 7.46 (m, 2H) 9.33 (s, 1H) | 509 |
| 16 | 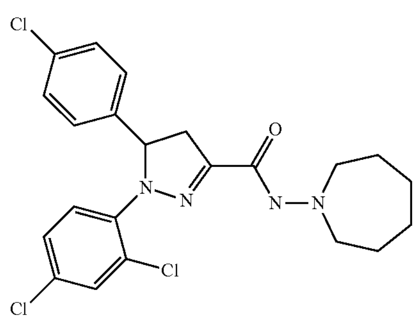 | 5-(4-Chloro-phenyl)-1-(2,4-dichloro-phenyl)-4,5-dihydro-1H-pyrazole-3-carboxylic acid azepan-1-ylamide | 1H NMR (300 MHz, CHLOROFORM-d) δ ppm 1.63 (m, 4H) 1.80 (m, 4H) 3.22 (dd, J = 18.31, 6.15 Hz, 1H) 3.30 (m, 4H) 3.61 (dd, J = 18.31, 12.30 Hz, 1H) 5.70 (dd, J = 12.30, 6.15 Hz, 1H) 6.99 (m, 3H) 7.10 (m, 3H) 7.19 (m, 1H) | 465 |
| 17 | 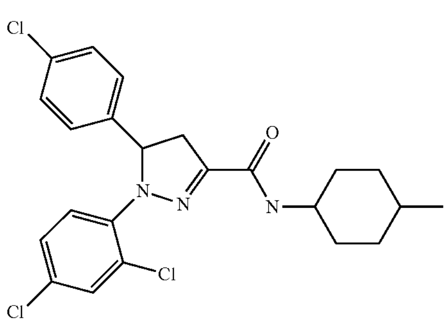 | 5-(4-Chloro-phenyl)-1-(2,4-dichloro-phenyl)-4,5-dihydro-1H-pyrazole-3-carboxylic acid (4-methyl-cyclohexyl)-amide | | 464 |

| No | Name | ¹H-NMR | MS (M + H)⁺ |
|---|---|---|---|
| 18 | 5-(4-Chloro-phenyl)-1-(2,4-dichloro-phenyl)-4,5-dihydro-1H-pyrazole-3-carboxylic acid (2-methyl-cyclohexyl)-amide | | 464 |
| 19 | 5-(4-Chloro-phenyl)-1-(2,4-dichloro-phenyl)-4,5-dihydro-1H-pyrazole-3-carboxylic acid cycloheptylamide | 1H NMR (300 MHz, DMSO-d₆) δ ppm 1.53 (m, 10H) 1.79 (m, 2H) 3.05 (dd, J = 18.16, 5.71 Hz, 1H) 3.64 (dd, J = 18.16, 11.94 Hz, 1H) 3.85 (m, 1H) 5.80 (dd, J = 11.94, 5.71 Hz, 1H) 7.13 (m, 2H) 7.27 (m, 2H) 7.43 (d, J = 2.34 Hz, 1H) 7.51 (d, J = 8.79 Hz, 1H) 8.10 (d, J = 8.35 Hz, 1H) | 464 |
| 20 | 5-(4-Chloro-phenyl)-1-(2,4-dichloro-phenyl)-4,5-dihydro-1H-pyrazole-3-carboxylic acid hexylamide | 1H NMR (300 MHz, DMSO-d₆) δ ppm 0.85 (m, 3H) 1.25 (m, 6H) 1.47 (m, 2H) 3.05 (dd, J = 18.16, 5.79 Hz, 1H) 3.17 (m, 2H) 3.65 (dd, J = 18.16, 11.86 Hz, 1H) 5.81 (dd, J = 11.86, 5.79 Hz, 1H) 7.14 (d, J = 8.50 Hz, 2H) 7.27 (m, 3H) 7.45 (m, 2H) 8.32 (t, J = 5.86 Hz, 1H) | 452 |
| 21 | [5-(4-Chloro-phenyl)-1-(2,4-dichloro-phenyl)-4,5-dihydro-1H-pyrazol-3-yl]-(4-cyclohexyl-piperazin-1-yl)-methanone | | 519 |
| 22 | [5-(4-Chloro-phenyl)-1-(2,4-dichloro-phenyl)-4,5-dihydro-1H-pyrazol-3-yl]-(octahydro-isoquinolin-2-yl)-methanone | | 490 |

-continued

| No | STRUCTURE | Name | ¹H-NMR | MS (M + H)⁺ |
|---|---|---|---|---|
| 23 | 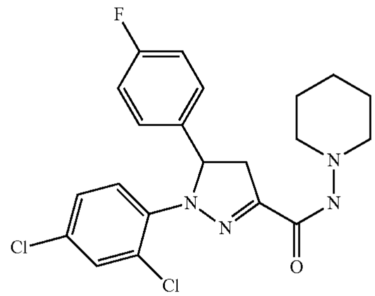 | 1-(2,4-Dichloro-phenyl)-5-(4-fluoro-phenyl)-4,5-dihydro-1H-pyrazole-3-carboxylic acid piperidin-1-ylamide | 1H NMR (300 MHz, CHLOROFORM-d) δ ppm 1.48 (s, 2H) 1.84 (s, 4H) 3.25 (s, 4H) 3.28 (dd, J = 18.16, 6.15 Hz, 1H) 3.61 (dd, J = 18.16, 12.38 Hz, 1H) 5.73 (dd, J = 12.38, 6.15 Hz, 1H) 6.83 (t, J = 8.57 Hz, 2H) 7.02 (m, 4H) 7.18 (m, 1H) 8.21 (br, 1H) | 435 |
| 24 | 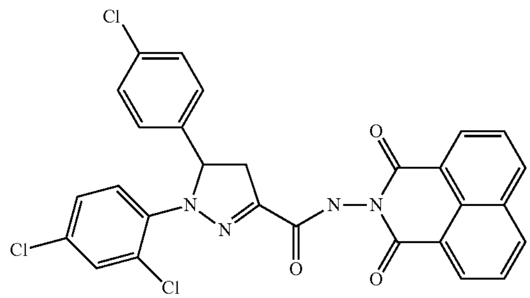 | 5-(4-Chloro-phenyl)-1-(2,4-dichloro-phenyl)-4,5-dihydro-1H-pyrazole-3-carboxylic acid (1,3-dioxo-1H,3H-benzo[de]isoquinolin-2-yl)-amide | 1H NMR (300 MHz, DMSO-d₆) δ ppm 3.16 (dd, J = 18.02, 6.45 Hz, 1H) 3.79 (dd, J = 18.02, 12.01 Hz, 1H) 5.98 (dd, J = 12.01, 6.45 Hz, 1H) 7.24 (d, J = 8.06 Hz, 2H) 7.36 (m, 3H) 7.55 (m, 2H) 7.92 (m, 2H) 8.55 (m, 4H) 11.08 (s, 1H) | 563 |
| 25 | 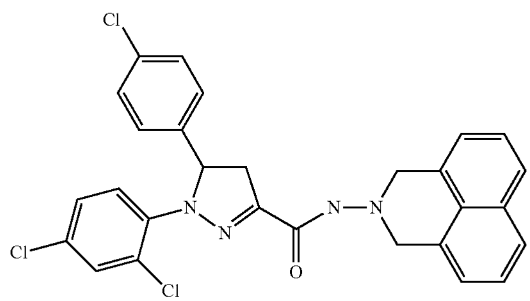 | 5-(4-Chloro-phenyl)-1-(2,4-dichloro-phenyl)-4,5-dihydro-1H-pyrazole-3-carboxylic acid (1H, 3H-benzo[de]isoquinolin-2-yl)-amide | 1H NMR (300 MHz, DMSO-d₆) δ ppm 3.13 (dd, J = 18.09, 5.86 Hz, 1H) 3.71 (dd, J = 18.09, 11.86 Hz, 1H) 4.35 (s, 4H) 5.84 (dd, J = 11.86, 5.86 Hz, 1H) 7.19 (d, J = 8.50 Hz, 2H) 7.31 (m, 5H) 7.47 (m, 4H) 7.79 (d, J = 8.20 Hz, 2H) 9.77 (s, 1H) | 535 |
| 26 | 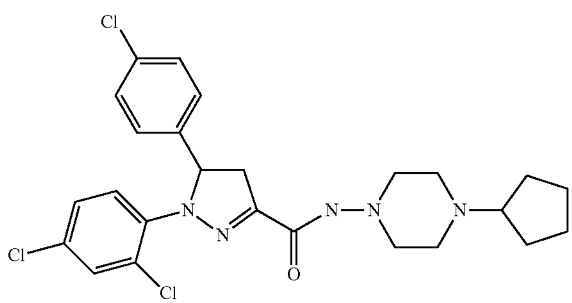 | 5-(4-Chloro-phenyl)-1-(2,4-dichloro-phenyl)-4,5-dihydro-1H-pyrazole-3-carboxylic acid (4-cyclopentyl-piperazin-1-yl)-amide | | 520 |
| 27 | 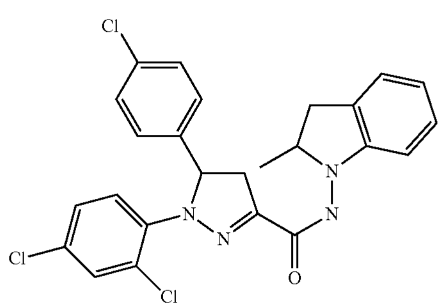 | 5-(4-Chloro-phenyl)-1-(2,4-dichloro-phenyl)-4,5-dihydro-1H-pyrazole-3-carboxylic acid (2-methyl-2,3-dihydro-indol-1-yl)-amide | | 499 |

-continued

| No | STRUCTURE | Name | ¹H-NMR | MS (M + H)⁺ |
|---|---|---|---|---|
| 28 | 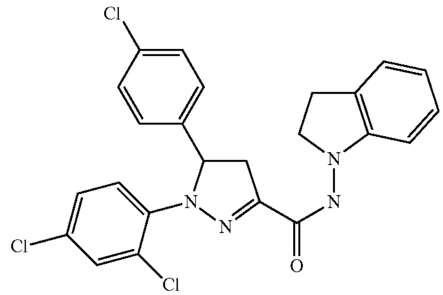 | 5-(4-Chloro-phenyl)-1-(2,4-dichloro-phenyl)-4,5-dihydro-1H-pyrazole-3-carboxylic acid (2,3-dihydro-indol-1-yl)-amide | 1H NMR (300 MHz, DMSO-$d_6$) δ ppm 2.96 (t, J = 8.20 Hz, 2H) 3.11 (dd, J = 18.02, 5.71 Hz, 1H) 3.59 (t, J = 8.20 Hz, 2H) 3.73 (dd, J = 18.02, 12.01 Hz, 1H) 5.87 (dd, J = 12.01, 5.71 Hz, 1H) 6.58 (d, J = 7.76 Hz, 1H) 6.75 (t, J = 7.32 Hz, 1H) 7.10 (m, 4H) 7.29 (m, 3H) 7.45 (d, J = 2.34 Hz, 1H) 7.54 (d, J = 8.79 Hz, 1H) 10.20 (s, 1H) | 485 |
| 29 | 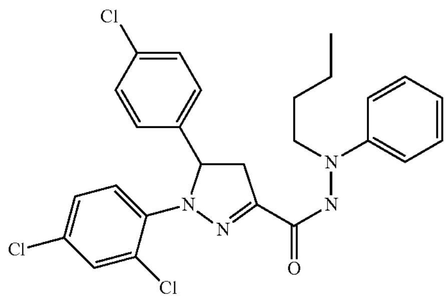 | 5-(4-Chloro-phenyl)-1-(2,4-dichloro-phenyl)-4,5-dihydro-1H-pyrazole-3-carboxylic acid N'-butyl-N'-phenyl-hydrazide | 1H NMR (300 MHz, CHLOROFORM-d) δ ppm 0.98 (t, J = 7.32 Hz, 3H) 1.45 (m, 2H) 1.69 (m, 2H) 3.36 (dd, J = 18.31, 6.84 Hz, 1H) 3.57 (m, 2H) 3.75 (dd, J = 18.31, 12.21 Hz, 1H) 5.77 (dd, J = 12.21, 6.84 Hz, 1H) 6.90 (m, 3H) 7.10 (m, 4H) 7.26 (m, 5H) 8.22 (s, 1H) | 515 |
| 30 | 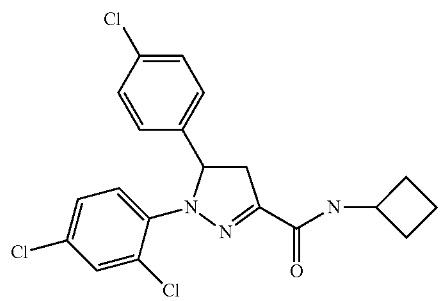 | 5-(4-Chloro-phenyl)-1-(2,4-dichloro-phenyl)-4,5-dihydro-1H-pyrazole-3-carboxylic acid cyclobutylamide | 1H NMR (300 MHz, DMSO-$d_6$) δ ppm 1.61 (m, 2H) 2.14 (m, 4H) 3.05 (dd, J = 18.16, 5.57 Hz, 1H) 3.63 (dd, J = 18.16, 11.94 Hz, 1H) 4.33 (m, 1H) 5.81 (dd, J = 11.94, 5.57 Hz, 1H) 7.13 (m, 2H) 7.27 (m, 3H) 7.43 (d, J = 2.34 Hz, 1H) 7.52 (d, J = 8.79 Hz, 1H) 8.53 (d, J = 8.06 Hz, 1H) | 422 |
| 31 | 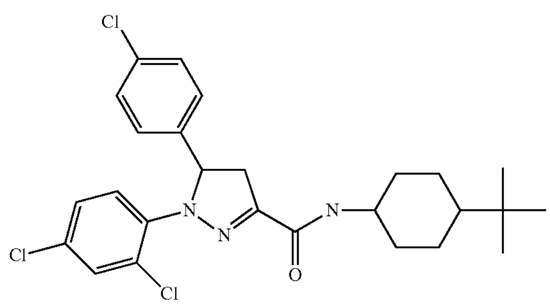 | 5-(4-Chloro-phenyl)-1-(2,4-dichloro-phenyl)-4,5-dihydro-1H-pyrazole-3-carboxylic acid (4-tert-butyl-cyclohexyl)-amide | | 506 |
| 32 | 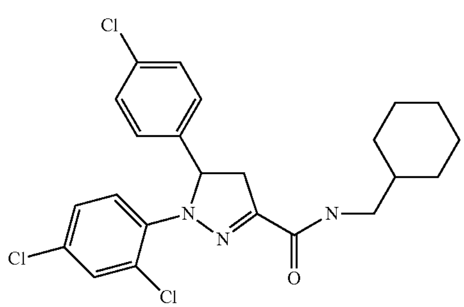 | 5-(4-Chloro-phenyl)-1-(2,4-dichloro-phenyl)-4,5-dihydro-1H-pyrazole-3-carboxylic acid cyclohexylmethyl-amide | 1H NMR (400 MHz, CHLOROFORM-d) δ ppm 0.99 (m, 2H) 1.21 (m, 4H) 1.69 (m, 1H) 1.76 (m, 4H) 3.15 (dd, J = 17.98, 6.06 Hz, 1H) 3.32 (dt, J = 12.60, 6.40 Hz, 2H) 3.67 (dd, J = 17.98, 12.11 Hz, 1H) 5.73 (dd, J = 12.11, 6.06 Hz, 1H) 6.75 (t, J = 6.06 Hz, 1H) 7.06 (m, 3H) 7.12 (m, 1H) 7.17 (d, J = 8.60 Hz, 2H) 7.26 (m, 1H) | 464 |

-continued

| No | STRUCTURE | Name | ¹H-NMR | MS (M + H)⁺ |
|---|---|---|---|---|
| 33 | 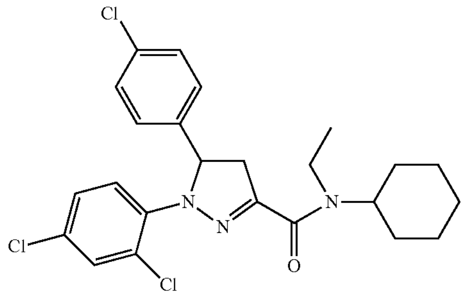 | 5-(4-Chloro-phenyl)-1-(2,4-dichloro-phenyl)-4,5-dihydro-1H-pyrazole-3-carboxylic acid cyclohexyl-ethyl-amide | | 478 |
| 34 | 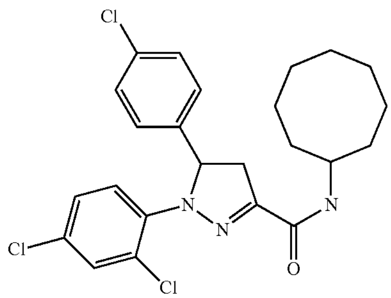 | 5-(4-Chloro-phenyl)-1-(2,4-dichloro-phenyl)-4,5-dihydro-1H-pyrazole-3-carboxylic acid cyclooctylamide | 1H NMR (400 MHz, CHLOROFORM-d) δ ppm 1.59 (m, 12H) 1.91 (m, 2H) 3.32 (dd, J = 18.37, 5.86 Hz, 1H) 3.66 (dd, J = 18.37, 12.11 Hz, 1H) 4.10 (ddd, J = 8.60, 4.01, 3.71 Hz, 1H) 5.72 (dd, J = 12.11, 5.86 Hz, 1H) 6.65 (d, J = 8.60 Hz, 1H) 7.07 (m, 3H) 7.15 (m, 3H) 7.25 (m, 1H) | 478 |
| 35 | 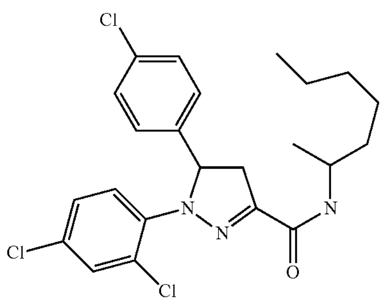 | 5-(4-Chloro-phenyl)-1-(2,4-dichloro-phenyl)-4,5-dihydro-1H-pyrazole-3-carboxylic acid (l-methyl-hexyl)-amide | 1H NMR (400 MHz, CHLOROFORM-d) δ ppm 0.89 (m, J = 6.94 Hz, 3H) 1.21 (m, J = 6.64 Hz, 3H) 1.34 (m, 6H) 1.50 (m, 2H) 3.32 (ddd, J = 18.37, 6.06, 1.76 Hz, 1H) 3.67 (ddd, J = 18.37, 12.02, 3.32 Hz, 1H) 4.08 (m, 1H) 5.73 (dt, J = 12.02, 6.06 Hz, 1H) 6.48 (dd, J = 8.01, 5.67 Hz, 1H) 7.08 (m, 3H) 7.11 (m, 1H) 7.16 (m, 2H) 7.25 (m, 1H) | 466 |
| 36 | 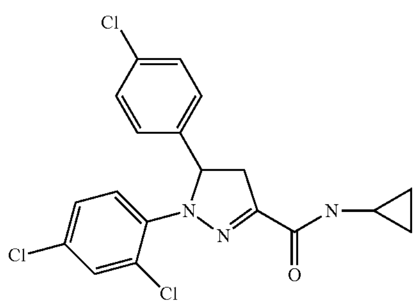 | 5-(4-Chloro-phenyl)-1-(2,4-dichloro-phenyl)-4,5-dihydro-1H-pyrazole-3-carboxylic acid cyclopropylamide | 1H NMR (300 MHz, DMSO-d₆) δ ppm 0.63 (m, 4H) 2.77 (m, 1H) 3.06 (dd, J = 18.02, 5.57 Hz, 1H) 3.64 (dd, J = 18.02, 11.86 Hz, 1H) 5.81 (dd, J = 11.86, 5.57 Hz, 1H) 7.13 (d, J = 8.50 Hz, 2H) 7.26 (m, 3H) 7.42 (d, J = 2.34 Hz, 1H) 7.49 (d, J = 8.64 Hz, 1H) 8.36 (d, J = 4.39 Hz, 1H) | 408 |
| 37 | 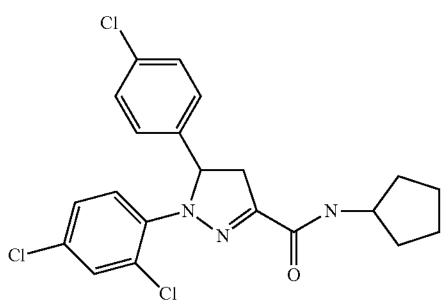 | 5-(4-Chloro-phenyl)-1-(2,4-dichloro-phenyl)-4,5-dihydro-1H-pyrazole-3-carboxylic acid cyclopentylamide | 1H NMR (400 MHz, CHLOROFORM-d) δ ppm 1.44-1.75 (m, 6H) 2.06 (td, J = 13.09, 5.86 Hz, 2H) 3.32 (dd, J = 18.37, 6.25 Hz, 1H) 3.66 (dd, J = 18.37, 12.11 Hz, 1H) 4.31 (m, 1H) 5.73 (dd, J = 12.11, 6.25 Hz, 1H) 6.62 (d, J = 7.82 Hz, 1H) 7.06 (m, 3H) 7.12 (s, 1H) 7.17 (m, 2H) 7.25 (m, 1H) | 436 |

-continued

| No | STRUCTURE | Name | ¹H-NMR | MS (M + H)⁺ |
|---|---|---|---|---|
| 38 | 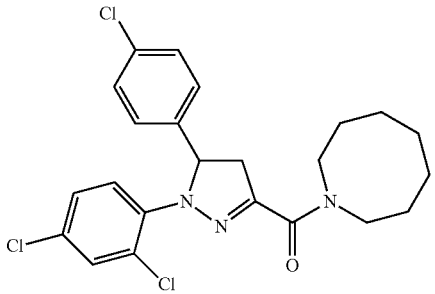 | Azocan-1-yl-[5-(4-chloro-phenyl)-1-(2,4-dichloro-phenyl)-4,5-dihydro-1H-pyrazol-3-yl]-methanone | 1H NMR (400 MHz, CHLOROFORM-d) δ ppm 1.61 (m, 6H) 1.82 (m, 4H) 3.37 (dd, J = 17.98, 5.86 Hz, 1H) 3.62 (m, 2H) 3.72 (dd, J = 17.98, 11.72 Hz, 1H) 3.87 (m, 2H) 5.65 (dd, J = 11.72, 5.86 Hz, 1H) 7.06 (m, 4H) 7.17 (m, 2H) 7.25 (m, 1H) | 464 |
| 39 | 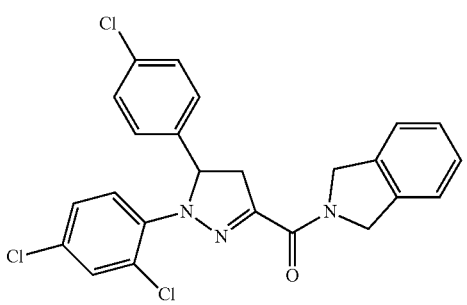 | [5-(4-Chloro-phenyl)-1-(2,4-dichloro-phenyl)-4,5-dihydro-1H-pyrazol-3-yl]-(1,3-dihydro-isoindol-2-yl)-methanone | 1H NMR (400 MHz, CHLOROFORM-d) δ ppm 3.44 (dd, J = 17.98, 6.25 Hz, 1H) 3.78 (dd, J = 17.98, 12.11 Hz, 1H) 4.98 (d, J = 3.13 Hz, 2H) 5.24 (d, J = 16.02 Hz, 1H) 5.32 (d, J = 16.02 Hz, 1H) 5.70 (dd, J = 12.11, 6.25 Hz, 1H) 7.10 (m, 3H) 7.17 (m, 3H) 7.32 (m, 5H) | 470 |
| 40 | 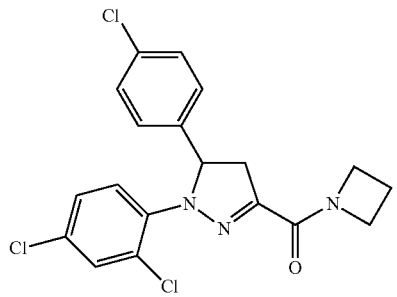 | Azetidin-1-yl-[5-(4-chloro-phenyl)-1-(2,4-dichloro-phenyl)-4,5-dihydro-1H-pyrazol-3-yl]-methanone | 1H NMR (300 MHz, DMSO-d₆) δ ppm 2.26 (m, J = 7.58,2H) 3.01 (dd, J = 18.02, 6.30 Hz, 1H) 3.64 (dd, J = 18.02, 12.01 Hz, 1H) 3.99 (ddd, J = 7.43, 4.10, 3.85 Hz, 2H) 4.38 (q, J = 7.67 Hz, 1H) 4.53 (m, 1H) 5.77 (dd, J = 12.01, 6.30 Hz, 1H) 7.17 (m, 2H) 7.27 (m, 4H) 7.46 (d, J = 2.20 Hz, 1H) | 408 |
| 41 | 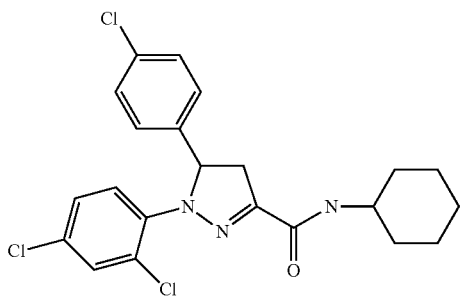 | 5-(4-Chloro-phenyl)-1-(2,4-dichloro-phenyl)-4,5-dihydro-1H-pyrazole-3-carboxylic acid cyclohexylamide | | 450 |
| 42 | 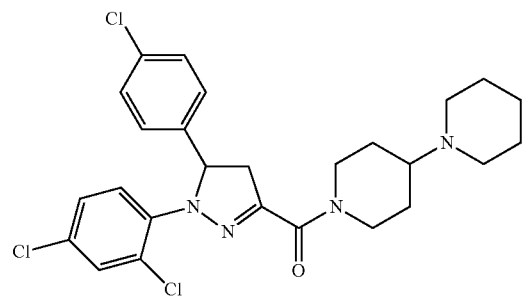 | [1,4']Bipiperidinyl-1'-yl-[5-(4-chloro-phenyl)-1-(2,4-dichloro-phenyl)-4,5-dihydro-1H-pyrazol-3-yl]-methanone | | 519 |

-continued

| No | STRUCTURE | Name | ¹H-NMR | MS (M + H)⁺ |
|---|---|---|---|---|
| 43 | 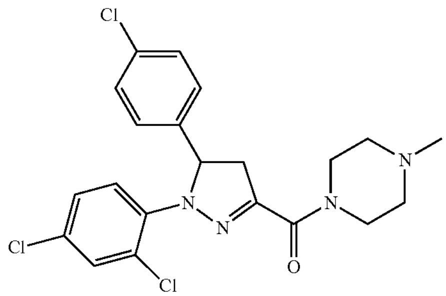 | [5-(4-Chloro-phenyl)-1-(2,4-dichloro-phenyl)-4,5-dihydro-1H-pyrazol-3-yl]-(4-methyl-piperazin-1-yl)-methanone | 1H NMR (300 MHz, DMSO-d₆) δ ppm 2.18 (s, 3H) 2.35 (m, 4H) 3.11 (dd, J = 17.80, 6.96 Hz, 1H) 3.52 (m, 1H) 3.61 (m, 1H) 3.70 (dd, J = 17.80, 11.64 Hz, 1H) 3.87 (m, 2H) 5.71 (dd, J = 11.64, 6.96 Hz, 1H) 7.22 (m, 4H) 7.31 (m, 2H) 7.48 (d, J = 1.61 Hz, 1H) | 451 |
| 44 | 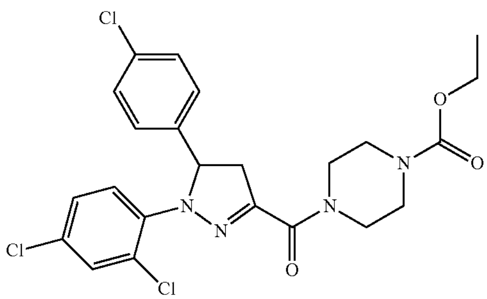 | 4-[5-(4-Chloro-phenyl)-1-(2,4-dichloro-phenyl)-4,5-dihydro-1H-pyrazole-3-carbonyl]-piperazine-1-carboxylic acid ethyl ester | | 509 |
| 45 | 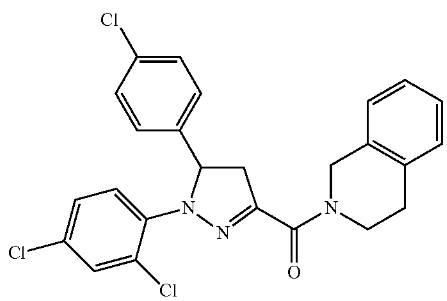 | [5-(4-Chloro-phenyl)-1-(2,4-dichloro-phenyl)-4,5-dihydro-1H-pyrazol-3-yl]-(3,4-dihydro-1H-isoquinolin-2-yl)-methanone | | 484 |
| 46 | 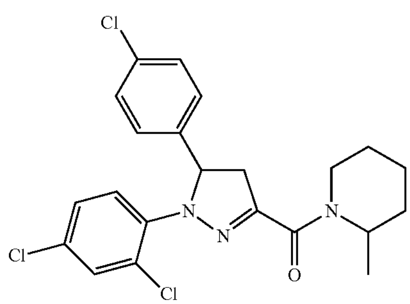 | [5-(4-Chloro-phenyl)-1-(2,4-dichloro-phenyl)-4,5-dihydro-1H-pyrazol-3-yl]-(2-methyl-piperidin-1-yl)-methanone | | 450 |
| 47 | 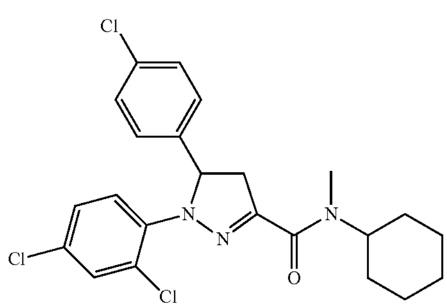 | 5-(4-Chloro-phenyl)-1-(2,4-dichloro-phenyl)-4,5-dihydro-1H-pyrazole-3-carboxylic acid cyclohexyl-methyl-amide | 1H NMR (300 MHz, DMSO-d₆) δ ppm 1.22 (m, 4H) 1.57 (m, 3H) 1.73 (m, 3H) 2.97 (s, 3H) 3.10 (dd, J = 17.80, 7.03 Hz, 1H) 3.71 (dd, J = 17.80, 11.64 Hz, 1H) 4.28 (m, 1H) 5.71 (m, 1H) 7.22 (m, 4H) 7.30 (m, 2H) 7.48 (m, 1H) | 464 |

-continued

| No | STRUCTURE | Name | ¹H-NMR | MS (M + H)⁺ |
|---|---|---|---|---|
| 48 | 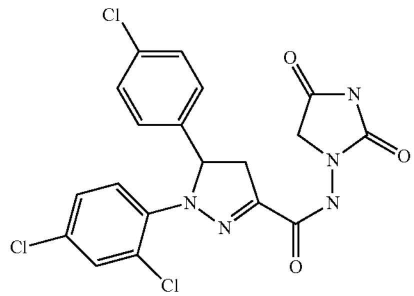 | 5-(4-Chloro-phenyl)-1-(2,4-dichloro-phenyl)-4,5-dihydro-1H-pyrazole-3-carboxylic acid (2,4-dioxo-imidazolidin-1-yl)-amide | | 466 |
| 49 | 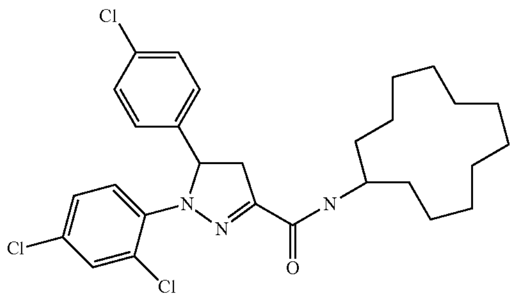 | 5-(4-Chloro-phenyl)-1-(2,4-dichloro-phenyl)-4,5-dihydro-1H-pyrazole-3-carboxylic acid cyclododecylamide | 1H NMR (300 MHz, DMSO-d₆) δ ppm 1.29 (m, 20H) 1.63 (m, 2H) 3.06 (dd, J = 18.09, 5.93 Hz, 1H) 3.65 (dd, J = 18.09, 11.86 Hz, 1H) 4.04 (m, 1H) 5.81 (dd, J = 11.86, 5.93 Hz, 1H) 7.14 (m, 2H) 7.28 (m, 3H) 7.43 (d, J = 2.34 Hz, 1H) 7.50 (d, J = 8.79 Hz, 1H) 8.00 (d, J = 8.79 Hz, 1H) | 534 |
| 50 | 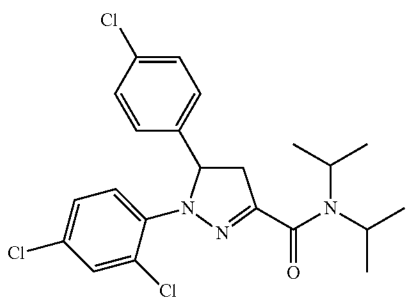 | 5-(4-Chloro-phenyl)-1-(2,4-dichloro-phenyl)-4,5-dihydro-1H-pyrazole-3-carboxylic acid diisopropylamide | 1H NMR (300 MHz, DMSO-d₆) δ ppm 1.20 (m, 6H) 1.36 (m, 6H) 3.09 (dd, J = 17.65, 6.66 Hz, 1H) 3.60 (br, 1H) 3.67 (dd, J = 17.65, 11.43 Hz, 1H) 4.52 (br, 1H) 5.69 (dd, J = 11.43, 6.66 Hz, 1H) 7.20 (m, 4H) 7.32 (m, 2H) 7.46 (d, J = 2.05 Hz, 1H) | 452 |
| 51 | 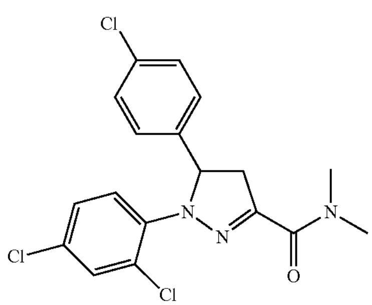 | 5-(4-Chloro-phenyl)-1-(2,4-dichloro-phenyl)-4,5-dihydro-1H-pyrazole-3-carboxylic acid dimethylamide | | 396 |
| 52 | 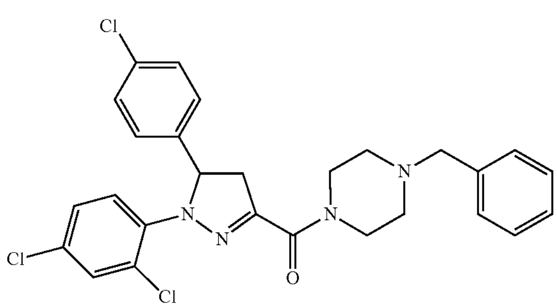 | (4-Benzyl-piperazin-1-yl)-[5-(4-chloro-phenyl)-1-(2,4-dichloro-phenyl)-4,5-dihydro-1H-pyrazol-3-yl]-methanone | | 527 |

| No | Name | ¹H-NMR | MS (M + H)⁺ |
|---|---|---|---|
| 53 | 1-[5-(4-Chloro-phenyl)-1-(2,4-dichloro-phenyl)-4,5-dihydro-1H-pyrazole-3-carbonyl]-pyrrolidine-2-carboxylic acid | | 466 |
| 54 | [5-(4-Chloro-phenyl)-1-(2,4-dichloro-phenyl)-4,5-dihydro-1H-pyrazol-3-yl]-morpholin-4-yl-methanone | 1H NMR (300 MHz, DMSO-d₆) δ ppm 3.12 (dd, J = 17.87, 6.37 Hz, 1H) 3.62 (m, 6H) 3.72 (dd, J = 17.87, 11.06 Hz, 1H) 3.93 (m, 2H) 5.71 (dd, J = 11.06, 6.37 Hz, 1H) 7.22 (m, 4H) 7.31 (m, 2H) 7.48 (s, 1H) | 438 |
| 55 | 5-(4-Chloro-phenyl)-1-(2,4-dichloro-phenyl)-4,5-dihydro-1H-pyrazole-3-carboxylic acid cyclohexyl-isopropyl-amide | | 492 |
| 56 | [5-(4-Chloro-phenyl)-1-(2,4-dichloro-phenyl)-4,5-dihydro-1H-pyrazol-3-yl]-(6,7-dihydro-4H-thieno[3,2-c]pyridin-5-yl)-methanone | | 490 |
| 57 | 5-(4-Chloro-phenyl)-1-(2,4-dichloro-phenyl)-4,5-dihydro-1H-pyrazole-3-carboxylic acid (3-methyl-cyclohexyl)-amide | | 464 |

-continued

| No | STRUCTURE | Name | ¹H-NMR | MS (M + H)⁺ |
|---|---|---|---|---|
| 58 | 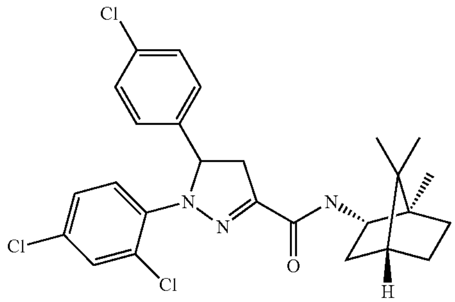 | 5-(4-Chloro-phenyl)-1-(2,4-dichloro-phenyl)-4,5-dihydro-1H-pyrazole-3-carboxylic acid (1,7,7-trimethyl-bicyclo[2.2.1]hept-2-yl)-amide | | 504 |
| 59 | 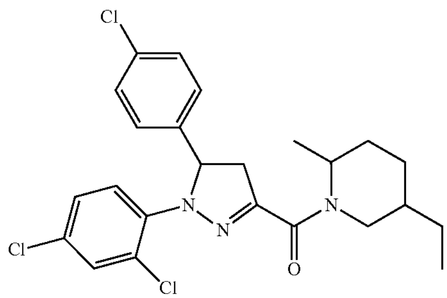 | [5-(4-Chloro-phenyl)-1-(2,4-dichloro-phenyl)-4,5-dihydro-1H-pyrazol-3-yl]-(5-ethyl-2-methyl-piperidin-1-yl)-methanone | | 478 |
| 60 | 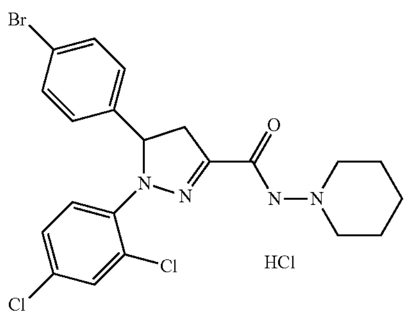 | 5-(4-Bromo-phenyl)-1-(2,4-dichloro-phenyl)-4,5-dihydro-1H-pyrazole-3-carboxylic acid piperidin-1-ylamide hydrochloride | 1H NMR (300 MHz, METHANOL-$d_4$) δ ppm 1.68 (m, 2H) 1.92-2.03 (m, 4H) 3.24 (dd, J = 18.02, 6.52 Hz, 1H) 3.49 (br. s., 4H) 3.76 (dd, J = 18.02, 12.52 Hz, 1H) 5.95 (dd, J = 12.52, 6.52 Hz, 1H) 7.14 (d, J = 8.50 Hz, 2 H) 7.21 (dd, J = 8.72, 2.42 Hz, 1H) 7.40 (m, 3 H) 7.37 (d, J = 2.42 Hz, 1H) | 495 |
| 61 | 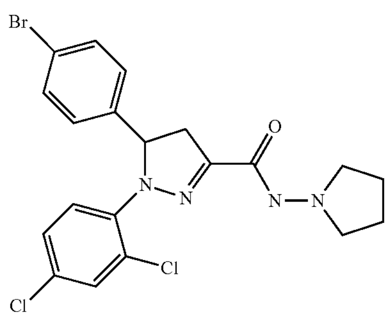 | 5-(4-Bromo-phenyl)-1-(2,4-dichloro-phenyl)-4,5-dihydro-1H-pyrazole-3-carboxylic acid pyrrolidin-1-ylamide | | 482 |
| 62 | 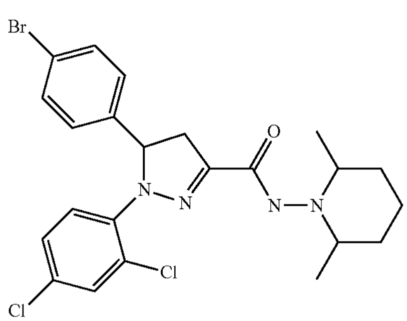 | 5-(4-Bromo-phenyl)-1-(2,4-dichloro-phenyl)-4,5-dihydro-1H-pyrazole-3-carboxylic acid (2,6-dimethyl-piperidin-1-yl)-amide | | 524 |

-continued

| No | STRUCTURE | Name | ¹H-NMR | MS (M + H)⁺ |
|---|---|---|---|---|
| 63 | 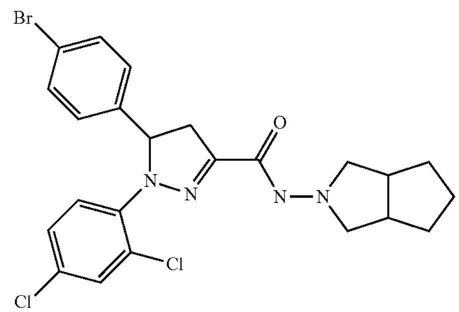 | 5-(4-Bromo-phenyl)-1-(2,4-dichloro-phenyl)-4,5-dihydro-1H-pyrazole-3-carboxylic acid (hexahydro-cyclopenta-[c]pyrrol-2-yl)-amide | 1H NMR (300 MHz, CHLOROFORM-d) δ ppm 1.54-1.85 (m, 6H) 2.91 (br. s., 2H) 3.25 (dd, J = 18.16, 6.08 Hz, 1H) 3.29 (br. s., 2 H) 3.68 (dd, J = 18.16, 12.52 Hz, 1H) 3.79 (br. s., 2H) 5.81 (dd, J = 12.52, 6.08 Hz, 1H) 6.98 (d, J = 8.50 Hz, 2H) 7.09 (dd, J = 8.64, 2.34 Hz, 1H) 7.20-7.25 (m, 2H) 7.34 (d, J = 8.35 Hz, 2H) 9.04 (br. s., 1H) | 522 |
| 64 | 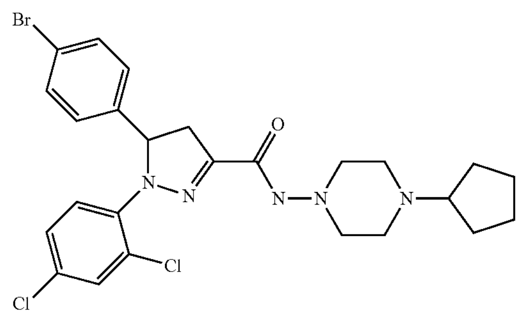 | 5-(4-Bromo-phenyl)-1-(2,4-dichloro-phenyl)-4,5-dihydro-1H-pyrazole-3-carboxylic acid (4-cyclopentyl-piperazin-1-yl)-amide | | 565 |
| 65 | 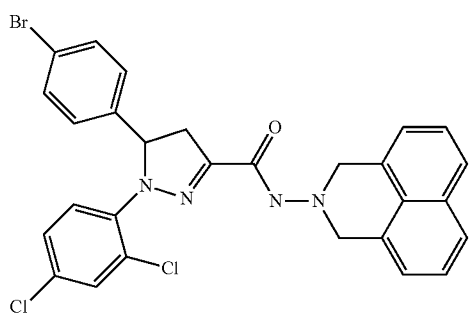 | 5-(4-Bromo-phenyl)-1-(2)4-dichloro-phenyl)-4,5-dihydro-1H-pyrazole-3-carboxylic acid (1H, 3H-benzo[de]-isoquinolin-2-yl)-amide | | 580 |
| 66 | 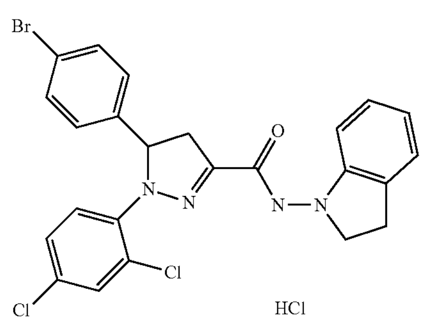 | 5-(4-Bromo-phenyl)-1-(2,4-dichloro-phenyl)-4,5-dihydro-1H-pyrazole-3-carboxylic acid (2,3-dihydro-indol-1-yl)-amide hydrochloride | 1H NMR (300 MHz, METHANOL-d₄) δ ppm 3.05 (t, J = 7.98 Hz, 2H) 3.28 (dd, J = 18.09, 5.86 Hz, 1H) 3.64 (t, J = 8.50 Hz, 2H) 3.77 (dd, J = 18.09, 12.16 Hz, 1H) 5.93 (dd, J = 12.16, 5.86 Hz, 1H) 6.71 (d, J = 7.76 Hz, 1 H) 6.84 (t, J = 7.40 Hz, 1H) 7.07-7.21 (m, 5 H) 7.31 (d, J = 2.34 Hz, 1H) 7.44 (d, J = 8.64 Hz, 1H) 7.40 (d, J = 8.50 Hz, 2H) | 529 |
| 67 | 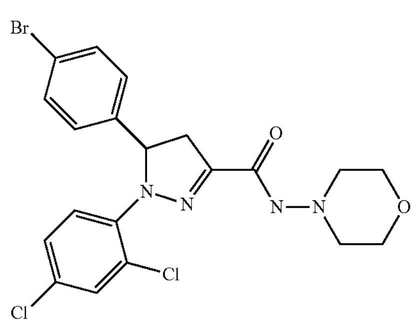 | 5-(4-Bromo-phenyl)-1-(2,4-dichloro-phenyl)-4,5-dihydro-1H-pyrazole-3-carboxylic acid morpholin-4-ylamide | | 498 |

-continued

| No | STRUCTURE | Name | ¹H-NMR | MS (M + H)⁺ |
|---|---|---|---|---|
| 68 | 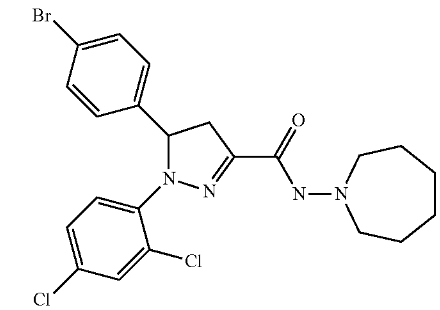 | 5-(4-Bromo-phenyl)-1-(2,4-dichloro-phenyl)-4,5-dihydro-1H-pyrazole-3-carboxylic acid azepan-1-ylamide | 1H NMR (300 MHz, CHLOROFORM-d) δ ppm 1.75 (br. s., 4H) 2.00 (br. s., 4H) 3.26 (dd, J = 18.16, 6.15 Hz, 1H) 3.71 (dd, J = 18.16, 12.45 Hz, 1H) 3.65 (br. s., 4H) 5.82 (dd, J = 12.45, 6.15 Hz, 1H) 6.97 (d, J = 8.35 Hz, 2H) 7.10 (d, J = 2.20 Hz, 1H) 7.16-7.22 (m, 1H) 7.24 (d, J = 2.20 Hz, 1H) 7.35 (d, J = 8.50 Hz, 2H) | 510 |
| 69 | 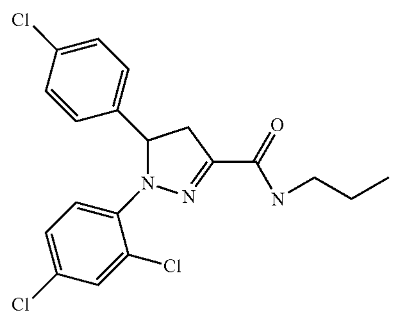 | 5-(4-Chloro-phenyl)-1-(2,4-dichloro-phenyl)-4,5-dihydro-1H-pyrazole-3-carboxylic acid propylamide | | 410 |
| 70 | 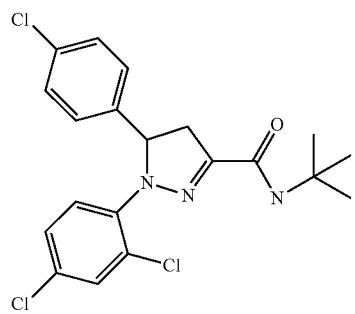 | 5-(4-Chloro-phenyl)-1-(2,4-dichloro-phenyl)-4,5-dihydro-1H-pyrazole-3-carboxylic acid tert-butylamide | | 424 |
| 71 | 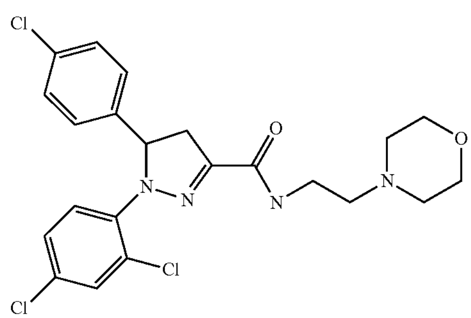 | 5-(4-Chloro-phenyl)-1-(2,4-dichloro-phenyl)-4,5-dihydro-1H-pyrazole-3-carboxylic acid (2-morpholin-4-yl-ethyl)-amide | | 481 |
| 72 | 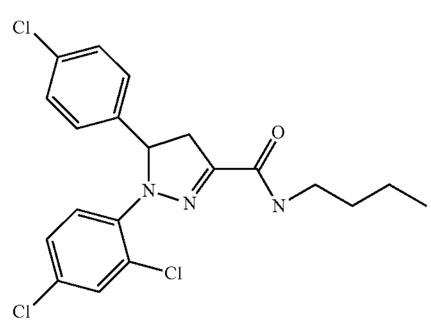 | 5-(4-Chloro-phenyl)-1-(2,4-dichloro-phenyl)-4,5-dihydro-1H-pyrazole-3-carboxylic acid butylamide | | 424 |

-continued

| No | STRUCTURE | Name | ¹H-NMR | MS (M + H)⁺ |
|---|---|---|---|---|
| 73 | 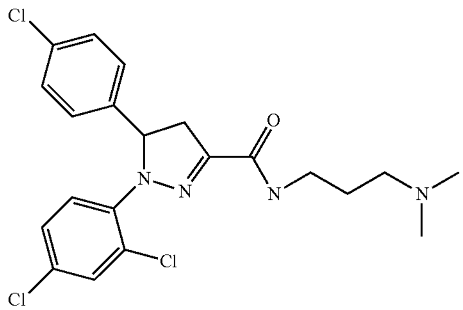 | 5-(4-Chloro-phenyl)-1-(2,4-dichloro-phenyl)-4,5-dihydro-1H-pyrazole-3-carboxylic acid (3-dimethylamino-propyl)-amide | | 453 |
| 74 | 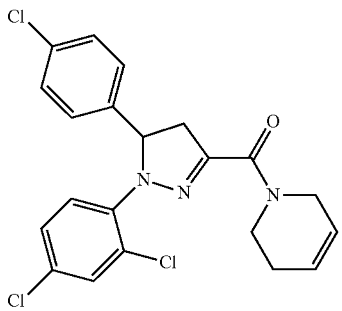 | [5-(4-Chloro-phenyl)-1-(2,4-dichloro-phenyl)-4,5-dihydro-1H-pyrazol-3-yl]-(3,6-dihydro-2H-pyridin-1-yl)-methanone | | 434 |
| 75 | 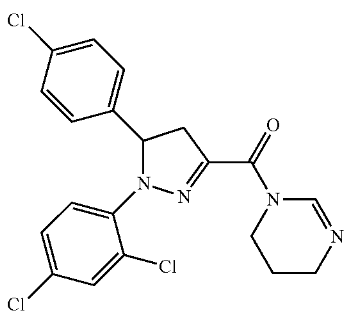 | [5-(4-Chloro-phenyl)-1-(2,4-dichloro-phenyl)-4,5-dihydro-1H-pyrazol-3-yl]-(5,6-dihydro-4H-pyrimidin-1-yl)-methanone | | 435 |
| 76 | 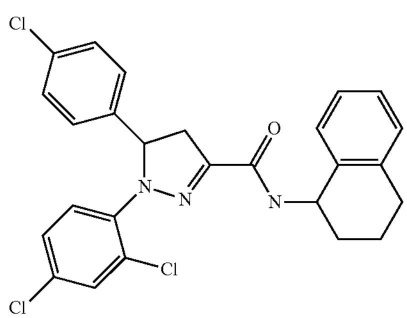 | 5-(4-Chloro-phenyl)-1-(2,4-dichloro-phenyl)-4,5-dihydro-1H-pyrazole-3-carboxylic acid (1,2,3,4-tetrahydro-naphthalen-1-yl)-amide | | 498 |
| 77 | 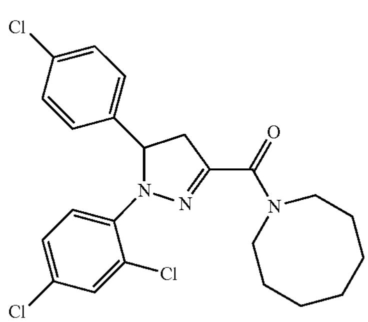 | Azocan-1-yl-[5-(4-chloro-phenyl)-1-(2,4-dichloro-phenyl)-4,5-dihydro-1H-pyrazol-3-yl]-methanone | | 464 |

| No | STRUCTURE | Name | ¹H-NMR | MS (M + H)⁺ |
| --- | --- | --- | --- | --- |
| 78 | 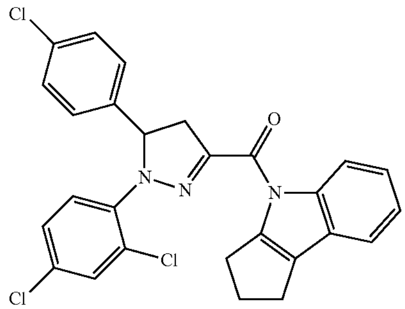 | [5-(4-Chloro-phenyl)-1-(2,4-dichloro-phenyl)-4,5-dihydro-1H-pyrazol-3-yl]-(2,3-dihydro-1H-cyclopenta[b]indol-4-yl)-methanone | | 508 |
| 79 | 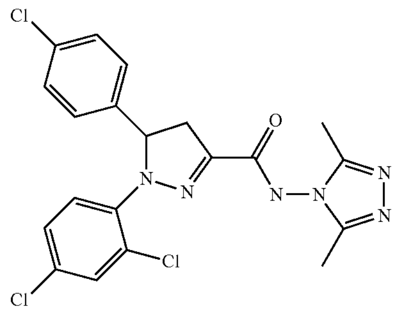 | 5-(4-Chloro-phenyl)-1-(2,4-dichloro-phenyl)-4,5-dihydro-1H-pyrazole-3-carboxylic acid (3,5-dimethyl-[1,2,4]triazol-4-yl)-amide | | 463 |
| 80 | 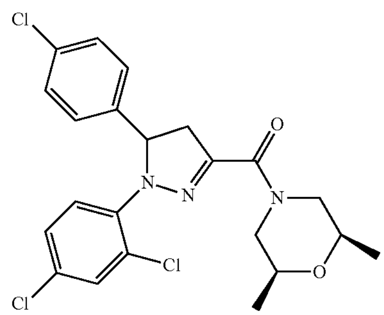 | [5-(4-Chloro-phenyl)-1-(2,4-dichloro-phenyl)-4,5-dihydro-1H-pyrazol-3-yl]-(2,6-dimethyl-morpholin-4-yl)-methanone | | 466 |
| 81 | 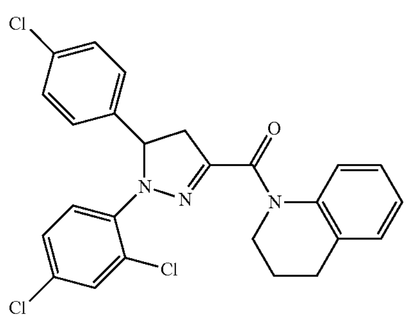 | [5-(4-Chloro-phenyl)-1-(2,4-dichloro-phenyl)-4,5-dihydro-1H-pyrazol-3-yl]-(3,4-dihydro-2H-quinolin-1-yl)-methanone | | 484 |
| 82 | 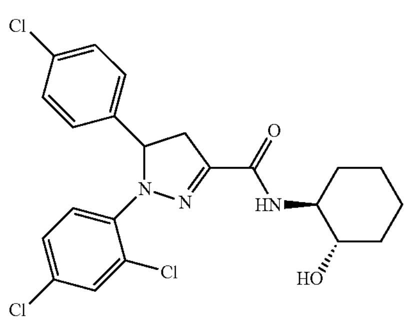 | 5-(4-chlorophenyl)-1-(2,4-dichlorophenyl)-N-((1R,2R)-2-hydroxycyclohexyl)-4,5-dihydro-1H-pyrazole-3-carboxamide | 1H NMR (300 MHz, METHANOL-d₄) δ ppm 1.36 (m, 4H) 1.75 (m, 2H) 2.02 (m, 2H) 3.24 (dd, J = 5.71, 18.08 Hz, 1H) 3.50 (m, 1H) 3.70 (dd, J = 18.10, 12.01 Hz, 1H) 3.74 (m, 1H) 5.91 (dd, J = 12.01, 5.71 Hz, 1H) 7.12-7.32 (m, 6H) 7.45 (t, J = 8.28 Hz, 1H) | 466 |

-continued

| No | STRUCTURE | Name | ¹H-NMR | MS (M + H)⁺ |
|---|---|---|---|---|
| 83 | 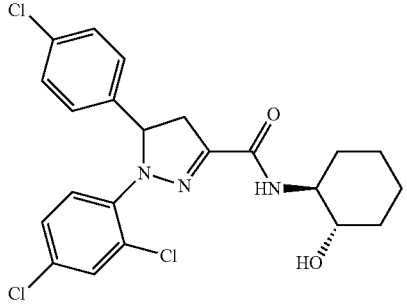 | 5-(4-chlorophenyl)-1-(2,4-dichlorophenyl)-N-((1S,2S)-2-hydroxycyclohexyl)-4,5-dihydro-1H-pyrazole-3-carboxamide | 1H NMR (300 MHz, METHANOL-d₄) δ ppm 1.36 (m, 4H) 1.75 (m, 2H) 2.02 (m, 2H) 3.24 (dd, J = 5.71, 18.08 Hz, 1H) 3.50 (m, 1H) 3.70 (dd, J = 18.10, 12.01 Hz, 1H) 3.74 (m, 1H) 5.91 (dd, J = 12.01, 5.71 Hz, 1H) 7.12-7.32 (m, 6H) 7.45 (t, J = 8.28 Hz, 1H) | 466 |
| 84 | 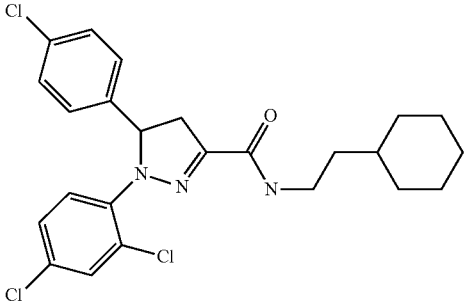 | 5-(4-Chloro-phenyl)-1-(2,4-dichloro-phenyl)-4,5-dihydro-1H-pyrazole-3-carboxylic acid (2-cyclohexyl-ethyl)-amide | | 478 |
| 85 | 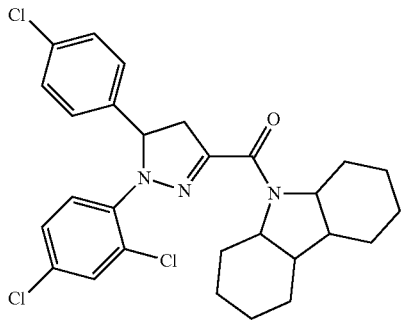 | [5-(4-Chloro-phenyl)-1-(2,4-dichloro-phenyl)-4,5-dihydro-1H-pyrazol-3-yl]-(dodecahydro-carbazol-9-yl)-methanone | | 530 |
| 86 | 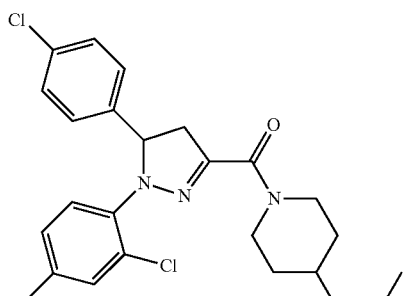 | [5-(4-Chloro-phenyl)-1-(2,4-dichloro-phenyl)-4,5-dihydro-1H-pyrazol-3-yl]-(4-propyl-piperidin-1-yl)-methanone | | 478 |
| 87 | 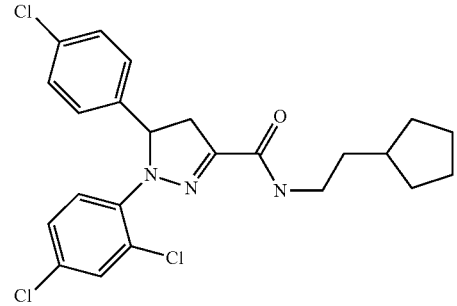 | 5-(4-Chloro-phenyl)-1-(2,4-dichloro-phenyl)-4,5-dihydro-1H-pyrazole-3-carboxylic acid (2-cyclopentyl-ethyl)-amide | | 464 |

-continued

| No | STRUCTURE | Name | ¹H-NMR | MS (M + H)⁺ |
|---|---|---|---|---|
| 88 | 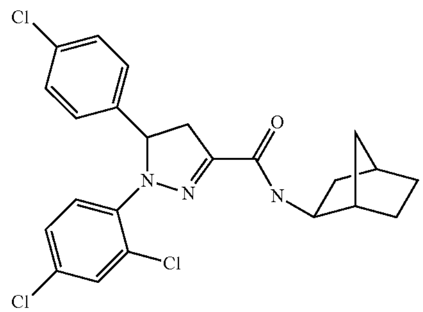 | 5-(4-Chloro-phenyl)-1-(2,4-dichloro-phenyl)-4,5-dihydro-1H-pyrazole-3-carboxylic acid bicyclo[2.2.1]hept-2-ylamide | | 462 |
| 89 | 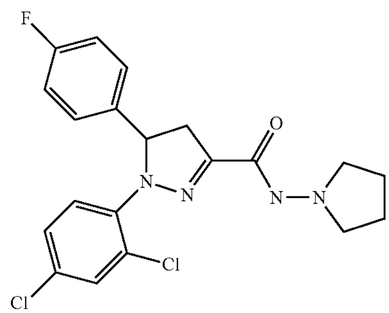 | 1-(2,4-Dichloro-phenyl)-5-(4-fluoro-phenyl)-4,5-dihydro-1H-pyrazole-3-carboxylic acid pyrrolidin-1-ylamide | | 421 |
| 90 | 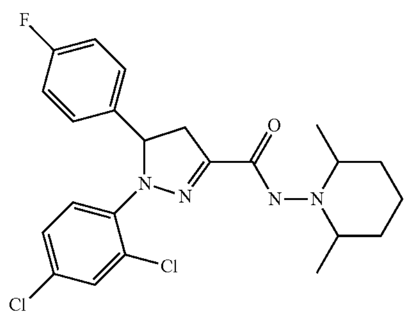 | 1-(2,4-Dichloro-phenyl)-5-(4-fluoro-phenyl)-4,5-dihydro-1H-pyrazole-3-carboxylic acid (2,6-dimethyl-piperidin-1-yl)-amide | | 463 |
| 91 | 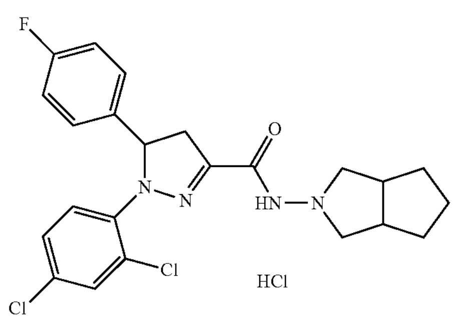 | 1-(2,4-Dichloro-phenyl)-5-(4-fluoro-phenyl)-4,5-dihydro-1H-pyrazole-3-carboxylic acid (hexahydro-cyclopenta[c]pyrrol-2-yl)-amide hydrochloride | 1H NMR (300 MHz, DMSO-d₆) δ ppm 1.48 (d, J = 8.20 Hz, 2H) 1.52-1.68 (m, 4H) 2.66 (br. s., 2H) 2.87 (m, 2H) 3.11 (dd, J = 18.02, 6.30 Hz, 1H) 3.54 (m, 2H) 3.66 (dd, J = 18.02, 12.01 Hz, 1H) 5.85 (dd, J = 12.01, 6.30 Hz, 1 H) 7.06 (t, J = 8.79 Hz, 2H) 7.16-7.24 (m, 2 H) 7.30 (dd, J = 8.72, 2.27 Hz, 1H) 7.47 (m, 2 H) 10.58 (br. s., 1H) | 461 |
| 91A | 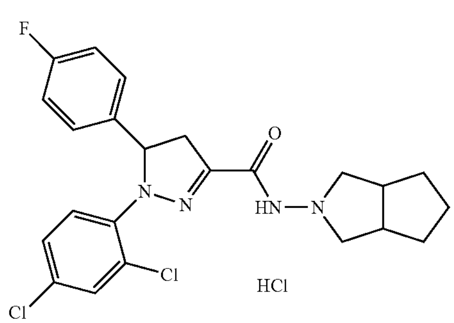 | 1-(2,4-Dichloro-phenyl)-5-(4-fluoro-phenyl)-4,5-dihydro-1H-pyrazole-3-carboxylic acid (hexahydro-cyclopenta[c]pyrrol-2-yl)-amide | | |

-continued

| No | STRUCTURE | Name | ¹H-NMR | MS (M + H)⁺ |
|---|---|---|---|---|
| 92 | 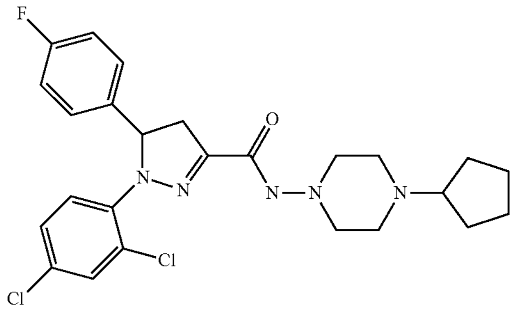 | 1-(2,4-Dichloro-phenyl)-5-(4-fluoro-phenyl)-4,5-dihydro-1H-pyrazole-3-carboxylic acid (4-cyclopentyl-piperazin-1-yl)-amide | | 504 |
| 93 | 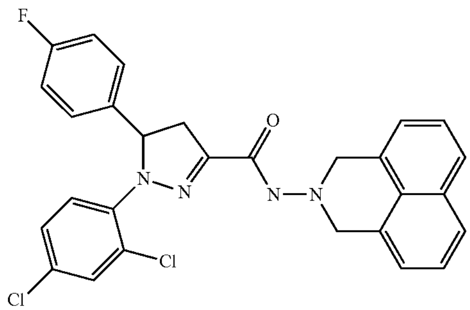 | 1-(2,4-Dichloro-phenyl)-5-(4-fluoro-phenyl)-4,5-dihydro-1H-pyrazole-3-carboxylic acid (1H,3H-benzo[de]isoquinolin-2-yl)-amide | | 519 |
| 94 | 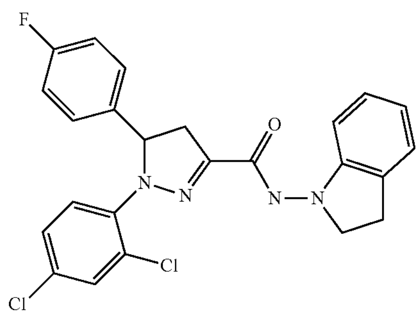 | 1-(2,4-Dichloro-phenyl)-5-(4-fluoro-phenyl)-4,5-dihydro-1H-pyrazole-3-carboxylic acid (2,3-dihydro-indol-1-yl)-amide | | 469 |
| 95 | 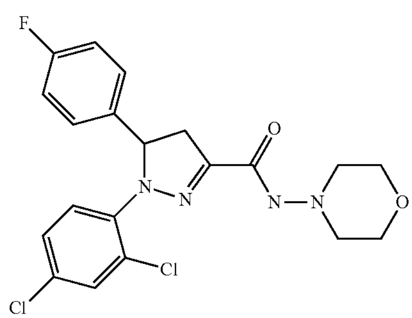 | 1-(2,4-Dichloro-phenyl)-5-(4-fluoro-phenyl)-4,5-dihydro-1H-pyrazole-3-carboxylic acid morpholin-4-ylamide | | 437 |
| 96 | 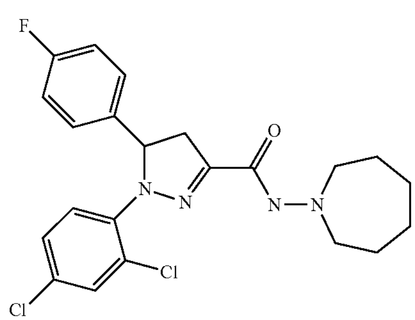 | 1-(2,4-Dichloro-phenyl)-5-(4-fluoro-phenyl)-4,5-dihydro-1H-pyrazole-3-carboxylic acid azepan-1-ylamide | 1H NMR (300 MHz, CHLOROFORM-d) δ ppm 1.75 (br. s., 4H) 2.00 (br. s., 4H) 3.28 (dd, J = 18.16, 6.08 Hz, 1H) 3.68 (dd, J = 18.16, 12.38 Hz, 1H) 3.68 (br. s., 4H) 5.84 (dd, J = 12.38, 6.08 Hz, 1H) 6.90 (t, J = 8.57 Hz, 2H) 7.08 (m, 3H) 7.14-7.19 (m, 1H) 7.24 (d, J = 2.20 Hz, 1H) | 449 |

-continued

| No | STRUCTURE | Name | ¹H-NMR | MS (M + H)⁺ |
|---|---|---|---|---|
| 97 | 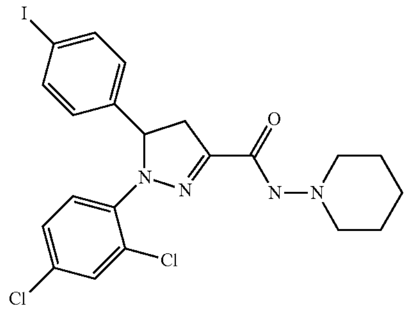 | 1-(2,4-Dichloro-phenyl)-5-(4-iodo-phenyl)-4,5-dihydro-1H-pyrazole-3-carboxylic acid piperidin-1-ylamide | | 543 |
| 98 | 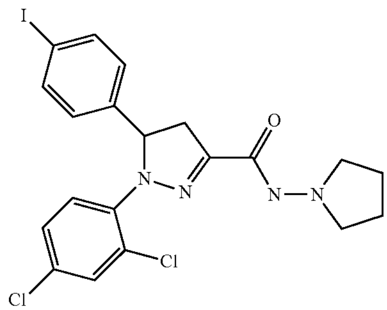 | 1-(2,4-Dichloro-phenyl)-5-(4-iodo-phenyl)-4,5-dihydro-1H-pyrazole-3-carboxylic acid pyrrolidin-1-ylamide | | 529 |
| 99 | 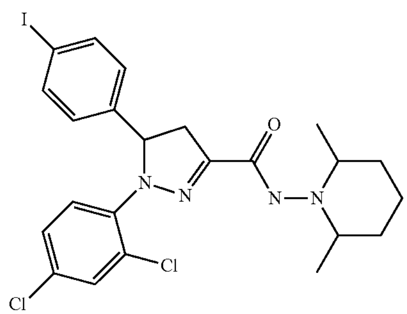 | 1-(2,4-Dichloro-phenyl)-5-(4-iodo-phenyl)-4,5-dihydro-1H-pyrazole-3-carboxylic acid (2,6-dimethyl-piperidin-1-yl)-amide | | 571 |
| 100 | 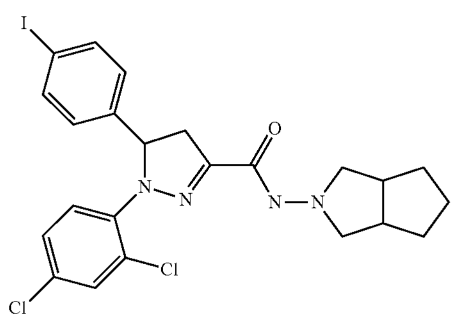 | 1-(2,4-Dichloro-phenyl)-5-(4-iodo-phenyl)-4,5-dihydro-1H-pyrazole-3-carboxylic acid (hexahydro-cyclopenta[c]pyrrol-2-yl)-amide | | 569 |
| 101 | 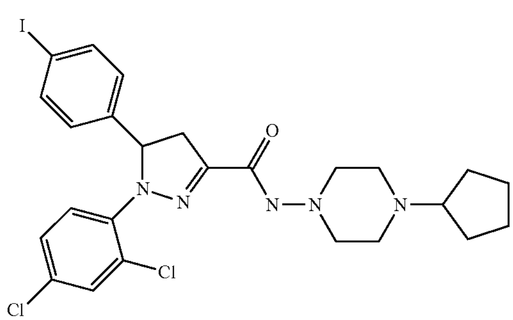 | 1-(2,4-Dichloro-phenyl)-5-(4-iodo-phenyl)-4,5-dihydro-1H-pyrazole-3-carboxylic acid (4-cyclopentyl-piperazin-1-yl)-amide | | 612 |

-continued

| No | STRUCTURE | Name | ¹H-NMR | MS (M + H)⁺ |
|---|---|---|---|---|
| 102 | 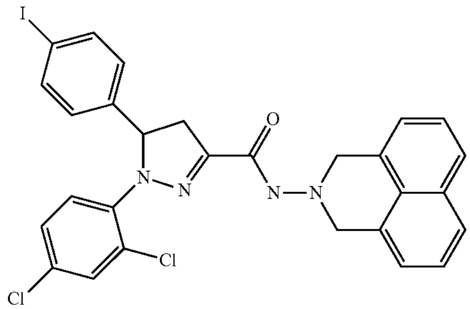 | 1-(2,4-Dichloro-phenyl)-5-(4-iodo-phenyl)-4,5-dihydro-1H-pyrazole-3-carboxylic acid (1H,3H-benzo[de]isoquinolin-2-yl)-amide | | 627 |
| 103 | 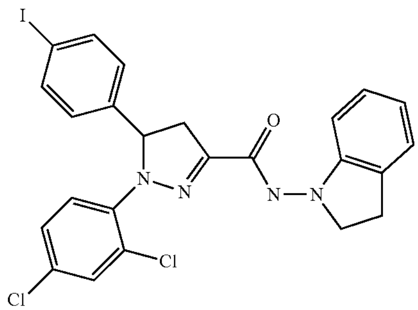 | 1-(2,4-Dichloro-phenyl)-5-(4-iodo-phenyl)-4,5-dihydro-1H-pyrazole-3-carboxylic acid (2,3-dihydro-indol-1-yl)-amide | | 577 |
| 104 | 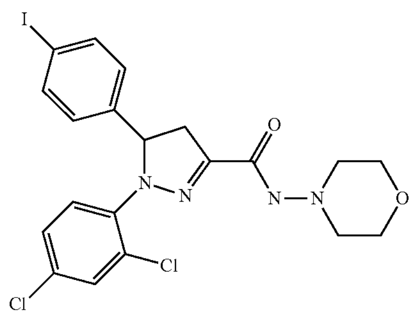 | 1-(2,4-Dichloro-phenyl)-5-(4-iodo-phenyl)-4,5-dihydro-1H-pyrazole-3-carboxylic acid morpholin-4-ylamide | | 545 |
| 105 | 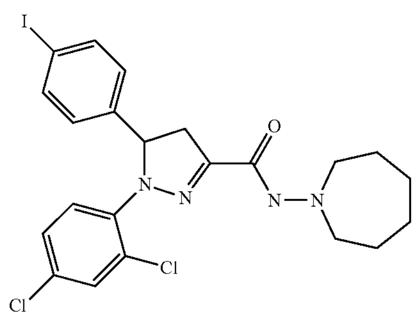 | 1-(2,4-Dichloro-phenyl)-5-(4-iodo-phenyl)-4,5-dihydro-1H-pyrazole-3-carboxylic acid azepan-1-ylamide | | 557 |
| 106 | 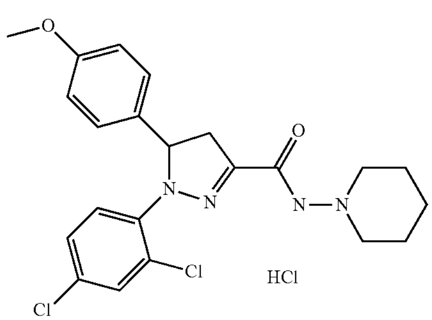 | 1-(2,4-Dichloro-phenyl)-5-(4-methoxy-phenyl)-4,5-dihydro-1H-pyrazole-3-carboxylic acid piperidin-1-ylamide hydrochloride | 1H NMR (300 MHz, CHLOROFORM-d) δ ppm 1.67 (br. s., 2H) 2.10 (br. s., 4H) 3.25 (dd, J = 18.02, 6.01 Hz, 1H) 3.64 (dd, J = 18.02, 12.60 Hz, 1H) 3.72 (s, 3H) 3.89 (br. s., 4H) 5.85 (dd, J = 12.60, 6.01 Hz, 1H) 6.72 (d, J = 8.79 Hz, 2H) 7.00 (d, J = 8.64 Hz, 2H) 7.07 (dd, J = 8.64, 2.20 Hz, 1H) 7.22 (d, J = 8.64 Hz, 1H) 7.22 (d, J = 2.20 Hz, 1H) 9.63 (br. s., 1H) | 447 |

| No | Name | ¹H-NMR | MS (M + H)⁺ |
|---|---|---|---|
| 107 | 1-(2,4-Dichloro-phenyl)-5-(4-methoxyphenyl)-4,5-dihydro-1H-pyrazole-3-carboxylic acid pyrrolidin-1-ylamide | | 433 |
| 108 | 1-(2,4-Dichloro-phenyl)-5-(4-methoxyphenyl)-4,5-dihydro-1H-pyrazole-3-carboxylic acid (2,6-dimethyl-piperidin-1-yl)-amide | | 475 |
| 109 | 1-(2,4-Dichloro-phenyl)-5-(4-methoxyphenyl)-4,5-dihydro-1H-pyrazole-3-carboxylic acid (hexahydro-cyclopenta[c]pyrrol-2-yl)-amide hydrochloride | 1H NMR (300 MHz, CHLOROFORM-d) δ ppm 1.61-1.91 (m, 6H) 2.96 (br. s., 2H) 3.27 (dd, J = 18.09, 5.86 Hz, 1H) 3.49 (m, 2H) 3.64 (dd, J = 18.09, 12.60 Hz, 1H) 3.72 (s, 3 H) 3.90 (br. s., 2H) 5.82 (dd, J = 12.60, 5.86 Hz, 1H) 6.71 (d, J = 8.64 Hz, 2H) 7.00 (d, J = 8.64 Hz, 2H) 7.06 (dd, J = 8.72, 2.27 Hz, 1 H) 7.21 (m, 2H) 9.25 (br. s., 1H) | 473 |
| 109 A | 1-(2,4-Dichloro-phenyl)-5-(4-methoxyphenyl)-4,5-dihydro-1H-pyrazole-3-carboxylic acid (hexahydro-cyclopenta[c]pyrrol-2-yl)-amide | | |

-continued

| No | STRUCTURE | Name | ¹H-NMR | MS (M + H)⁺ |
|---|---|---|---|---|
| 110 | 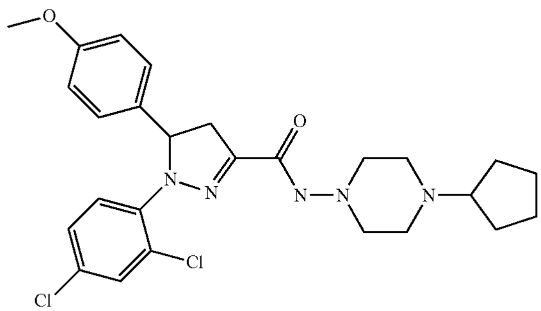 | 1-(2,4-Dichloro-phenyl)-5-(4-methoxy-phenyl)-4,5-dihydro-1H-pyrazole-3-carboxylic acid (4-cyclopentyl-piperazin-1-yl)-amide | | 516 |
| 111 | 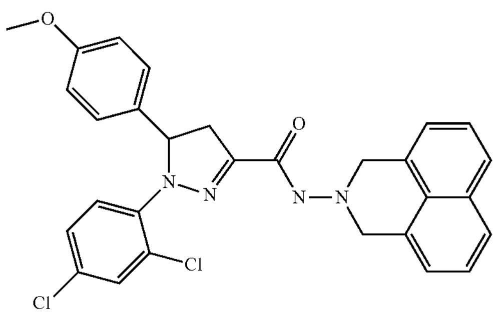 | 1-(2,4-Dichloro-phenyl)-5-(4-methoxy-phenyl)-4,5-dihydro-1H-pyrazole-3-carboxylic acid (1H,3H-benzo[de]isoquinolin-2-yl)-amide | | 531 |
| 112 | 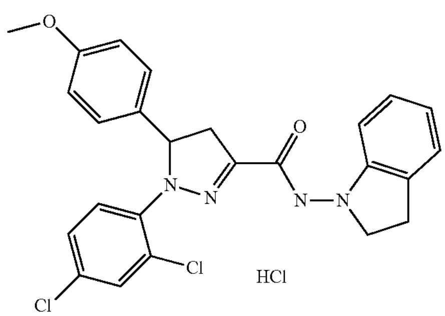 | 1-(2,4-Dichloro-phenyl)-5-(4-methoxy-phenyl)-4,5-dihydro-1H-pyrazole-3-carboxylic acid (2,3-dihydro-indol-1-yl)-amide \hydrochloride | | 481 |
| 113 | 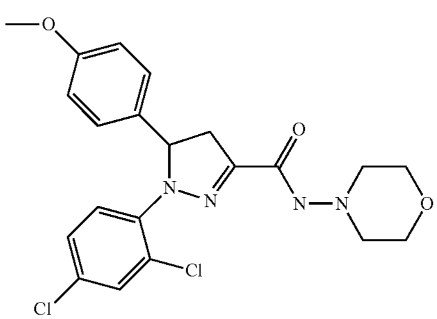 | 1-(2,4-Dichloro-phenyl)-5-(4-methoxy-phenyl)-4,5-dihydro-1H-pyrazole-3-carboxylic acid morpholin-4-ylamide | | 449 |
| 114 | 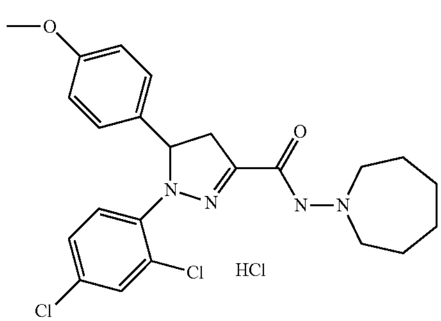 | 1-(2,4-Dichloro-phenyl)-5-(4-methoxy-phenyl)-4,5-dihydro-1H-pyrazole-3-carboxylic acid azepan-1-ylamide hydrochloride | 1H NMR (300 MHz, METHANOL-d₄) δ ppm 1.77 (br. s., 4H) 1.98 (br. s., 4H) 3.27 (dd, J = 6.15 Hz, 1H) 3.63 (m, 5H) 3.70 (s, 3H) 5.90 (dd, J = 12.45, 6.15 Hz, 1H) 6.76 (d, J = 8.64 Hz, 2H) 7.16 (dd, J = 8.64, 2.20 Hz, 1H) 7.10 (d, J = 8.64 Hz, 2H) 7.33 (m, 2H) | 461 |

-continued

| No | STRUCTURE | Name | ¹H-NMR | MS (M + H)⁺ |
|---|---|---|---|---|
| 115 | 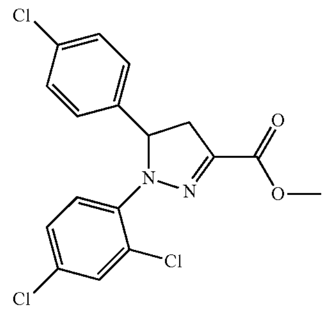 | 5-(4-Chloro-phenyl)-1-(2,4-dichloro-phenyl)-4,5-dihydro-1H-pyrazole-3-carboxylic acid methyl ester | | 383 |
| 116 | 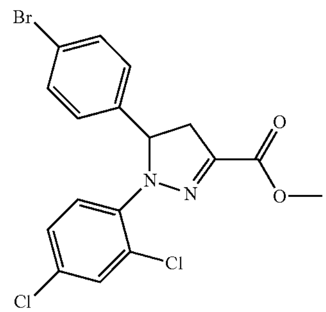 | 5-(4-Bromo-phenyl)-1-(2,4-dichloro-phenyl)-4,5-dihydro-1H-pyrazole-3-carboxylic acid methyl ester | | 427 |
| 117 | 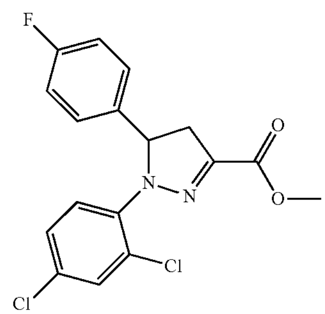 | 1-(2,4-Dichloro-phenyl)-5(4-fluoro-phenyl)-4,5-dihydro-1H-pyrazole-3-carboxylic acid methyl ester | | 367 |
| 118 | 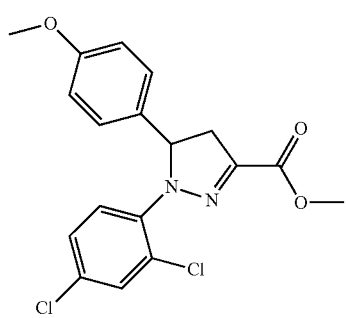 | 1-(2,4-Dichloro-phenyl)-5-(4-methoxy-phenyl)-4,5-dihydro-1H-pyrazole-3-carboxylic acid methyl ester | | 379 |
| 119 | 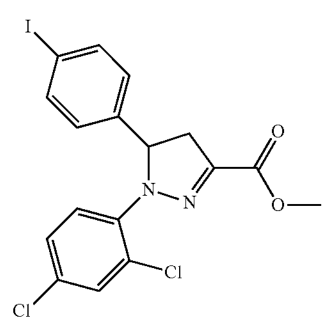 | 1-(2,4-Dichloro-phenyl)-5-(4-iodo-phenyl)-4,5-dihydro-1H-pyrazole-3-carboxylic acid methyl ester | | 475 |

-continued

| No | STRUCTURE | Name | ¹H-NMR | MS (M + H)⁺ |
|---|---|---|---|---|
| 120 | 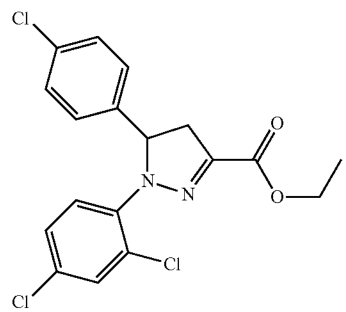 | 5-(4-Chloro-phenyl)-1-(2,4-dichloro-phenyl)-4,5-dihydro-1H-pyrazole-3-carboxylic acid ethyl ester | | 397 |
| 121 | 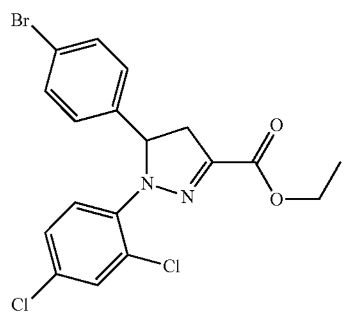 | 5-(4-Bromo-phenyl)-1-(2,4-dichloro-phenyl)-4,5-dihydro-1H-pyrazole-3-carboxylic acid ethyl ester | | 441 |
| 122 | 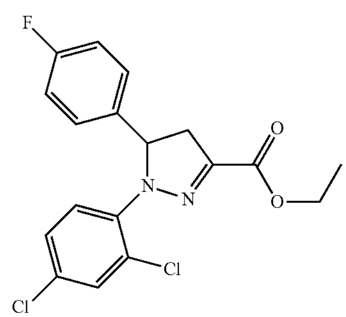 | 1-(2,4-Dichloro-phenyl)-5-(4-fluoro-phenyl)-4,5-dihydro-1H-pyrazole-3-carboxylic acid ethyl ester | | 381 |
| 123 | 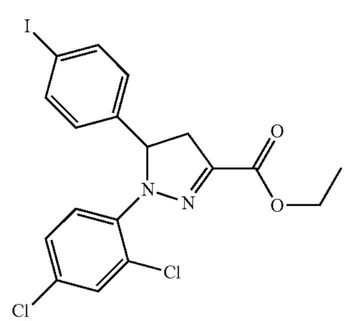 | 1-(2,4-Dichloro-phenyl)-5-(4-iodo-phenyl)-4,5-dihydro-1H-pyrazole-3-carboxylic acid ethyl ester | | 489 |
| 124 | 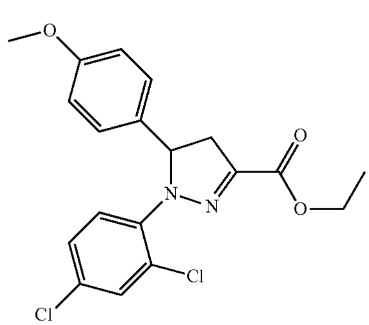 | 1-(2,4-Dichloro-phenyl)-5-(4-methoxy-phenyl)-4,5-dihydro-1H-pyrazole-3-carboxylic acid ethyl ester | | 393 |

-continued

| No | STRUCTURE | Name | ¹H-NMR | MS (M + H)⁺ |
|---|---|---|---|---|
| 125 | 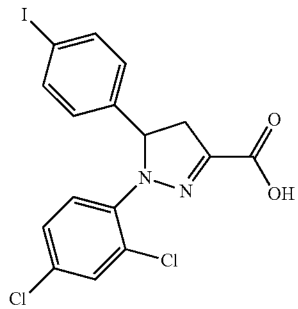 | 1-(2,4-Dichloro-phenyl)-5-(4-iodo-phenyl)-4,5-dihydro-1H-pyrazole-3-carboxylic acid | | 461 |
| 126 | 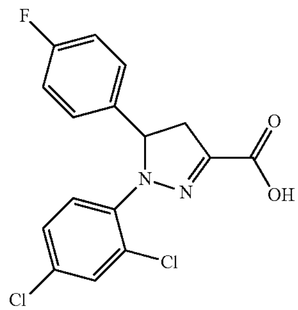 | 1-(2,4-Dichloro-phenyl)-5-(4-fluoro-phenyl)-4,5-dihydro-1H-pyrazole-3-carboxylic acid | | 353 |
| 127 | 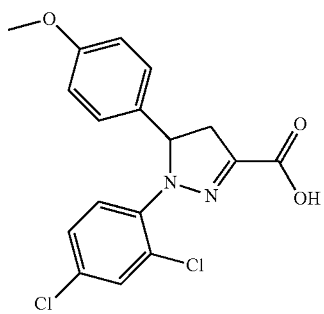 | 1-(2,4-Dichloro-phenyl)-5-(4-methoxy-phenyl)-4,5-dihydro-1H-pyrazole-3-carboxylic acid | | 365 |
| 128 | 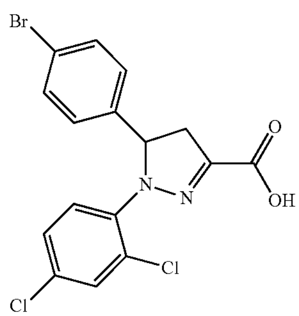 | 5-(4-Bromo-phenyl)-1-(2,4-dichloro-phenyl)-4,5-dihydro-1H-pyrazole-3-carboxylic acid | | 413 |
| 129 | 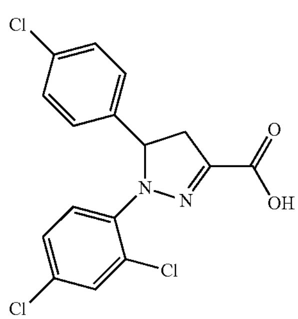 | 5-(4-Chloro-phenyl)-1-(2,4-dichloro-phenyl)-4,5-dihydro-1H-pyrazole-3-carboxylic acid | | 369 |

-continued

| No | STRUCTURE | Name | ¹H-NMR | MS (M + H)⁺ |
|---|---|---|---|---|
| 130 | 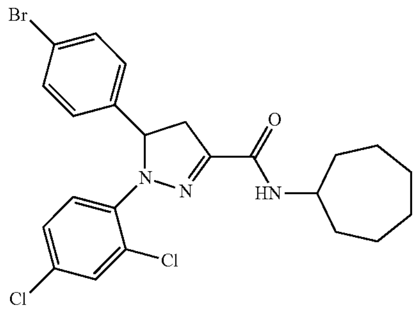 | 5-(4-Bromo-phenyl)-1-(2,4-dichloro-phenyl)-4,5-dihydro-1H-pyrazole-3-carboxylic acid cycloheptylamide | 1H NMR (300 MHz, METHANOL-d₄) δ ppm 1.49-1.78 (m, 10H) 1.95 (br. s., 2 H) 3.21 (dd, J = 18.09, 5.79 Hz, 1H) 3.67 (dd, J = 18.09, 12.08 Hz, 1H) 3.99 (m, 1 H) 5.86 (dd, J = 12.08, 5.79 Hz, 1H) 7.09 (d, J = 8.50 Hz, 2H) 7.15 (dd, J = 8.79, 2.34 Hz, 1H) 7.30 (d, J = 2.34 Hz, 1H) 7.33-7.44 (m, 3H) | 508 |
| 131 | 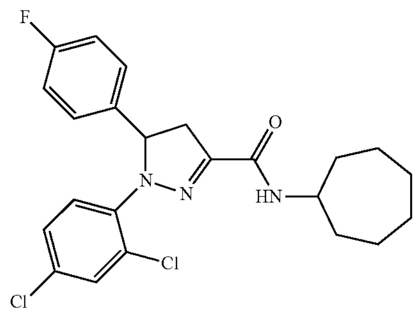 | 5-(4-Fluorophenyl)-1-(2,4-dichloro-phenyl)-4,5-dihydro-1H-pyrazole-3-carboxylic acid cycloheptylamide | 1H NMR (300 MHz, DMSO-d₆) δ ppm 1.36-1.67 (m, 10H) 1.72-1.87 (m, 2H) 3.05 (dd, J = 18.02, 5.64 Hz, 1H) 3.63 (dd, J = 18.02, 11.79 Hz, 1H) 3.79-3.92 (m, J = 8.95, 1H) 5.80 (dd, J = 11.79, 5.64 Hz, 1H) 7.04 (t, J = 8.79 Hz, 2H) 7.12-7.18 (m, 2H) 7.26 (dd, J = 8.79, 2.34 Hz, 1H) 7.43 (d, J = 2.34 Hz, 1H) 7.50 (d, J = 8.79 Hz, 1H) 8.10 (d, J = 8.20 Hz, 1H) | 448 |
| 132 | 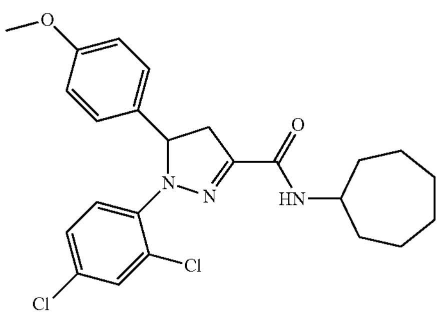 | 5-(4-methoxyphenyl)-1-(2,4-dichloro-phenyl)-4,5-dihydro-1H-pyrazole-3-carboxylic acid cycloheptylamide | | 460 |
| 133 | 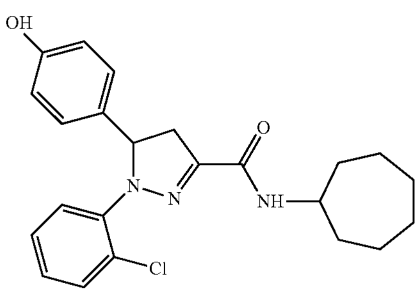 | 5-(4-hydroxyphenyl)-1-(2,4-dichloro-phenyl)-4,5-dihydro-1H-pyrazole-3-carboxylic acid cycloheptylamide | | 412 |
| 134 | 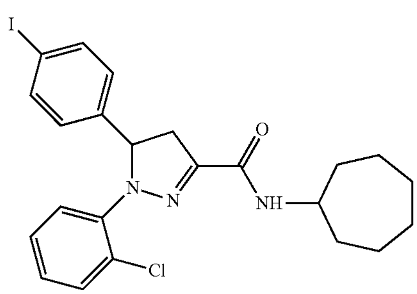 | 5-(4-iodophenyl)-1-(2,4-dichloro-phenyl)-4,5-dihydro-1H-pyrazole-3-carboxylic acid cycloheptylamide | | 522 |

-continued

| No | STRUCTURE | Name | ¹H-NMR | MS (M + H)⁺ |
|---|---|---|---|---|
| 135 | 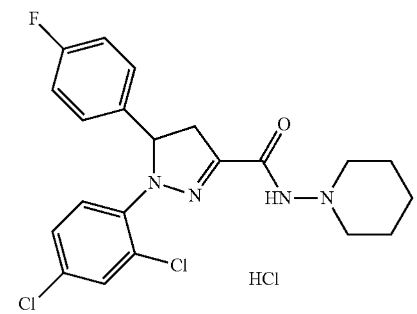 | 1-(2,4-Dichloro-phenyl)-5-(4-fluoro-phenyl)-4,5-dihydro-1H-pyrazole-3-carboxylic acid piperidin-1-ylamide hydrochloride | 1H NMR (300 MHz, DMSO-d$_6$) δ ppm 1.42 (br. s., 2H) 1.72 (br. s., 4H) 3.08 (dd, J = 18.02, 6.23 Hz, 1H) 3.14 (br. s., 4 H) 3.69 (dd, J = 18.02, 12.08 Hz, 1H) 5.84 (dd, J = 12.08, 6.23 Hz, 1H) 7.06 (t, J = 8.79 Hz, 2H) 7.20 (dd, J = 8.72, 5.49 Hz, 2H) 7.30 (dd, J = 8.72, 2.42 Hz, 1H) 7.40-7.53 (m, 2H) 10.54 (br. s., 1H) | 435 |
| 136 | 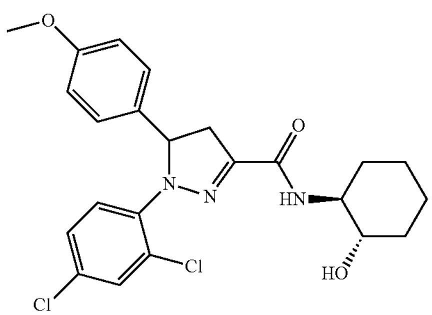 | 1-(2,4-dichlorophenyl)-N-((1S,2S)-2-hydroxycyclohexyl)-5-(4-methoxyphenyl)-4,5-dihydro-1H-pyrazole-3-carboxamide | | 462 |
| 137 | 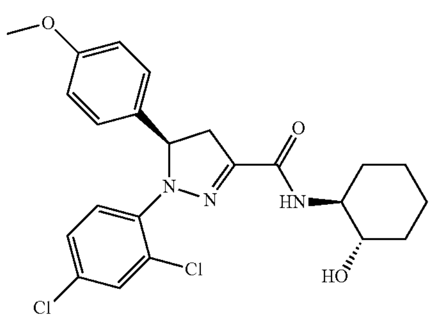 | (R)-1-(2,4-dichlorophenyl)-N-((1S,2S)-2-hydroxycyclohexyl)-5-(4-methoxyphenyl)-4,5-dihydro-1H-pyrazole-3-carboxamide | | 462 |
| 138 | 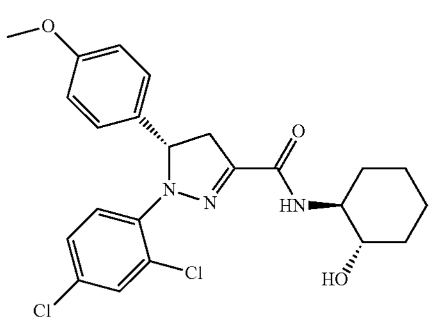 | (S)-1-(2,4-dichlorophenyl)-N-((1S,2S)-2-hydroxycyclohexyl)-5-(4-methoxyphenyl)-4,5-dihydro-1H-pyrazole-3-carboxamide | | 462 |
| 139 | 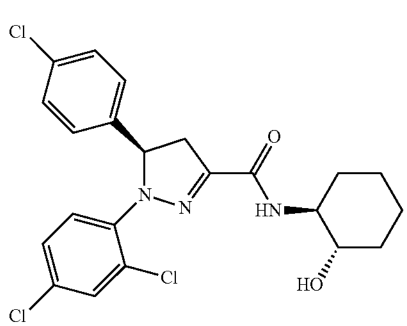 | (R)-5-(4-chlorophenyl)-1-(2,4-dichlorophenyl)-N-((1S,2S)-2-hydroxycyclohexyl)-4,5-dihydro-1H-pyrazole-3-carboxamide | | 466 |

| No | Name | MS (M + H)+ |
|---|---|---|
| 140 | (S)-5-(4-chlorophenyl)-1-(2,4-dichlorophenyl)-N-((1S,2S)-2-hydroxycyclohexyl)-4,5-dihydro-1H-pyrazole-3-carboxamide | 466 |
| 141 | (R)-5-(4-chlorophenyl)-1-(2,4-dichlorophenyl)-N-((1R,2R)-2-hydroxycyclohexyl)-4,5-dihydro-1H-pyrazole-3-carboxamide | 466 |
| 142 | (S)-5-(4-chlorophenyl)-1-(2,4-dichlorophenyl)-N-((1R,2R)-2-hydroxycyclohexyl)-4,5-dihydro-1H-pyrazole-3-carboxamide | 466 |
| 143 | 1-(2,4-dichlorophenyl)-5-(4-fluorophenyl)-N-((1S,2S)-2-hydroxycyclohexyl)-4,5-dihydro-1H-pyrazole-3-carboxamide | 450 |
| 144 | 1-(2,4-dichlorophenyl)-5-(4-iodophenyl)-N-((1S,2S)-2-hydroxycyclohexyl)-4,5-dihydro-1H-pyrazole-3-carboxamide | 558 |

| No | Name | ¹H-NMR | MS (M + H)⁺ |
|---|---|---|---|
| 145 | 5-(4-Chloro-phenyl)-1-(2,4-dichloro-phenyl)-4,5-dihydro-1H-pyrazole-3-carboxylic acid azocan-1-ylamide hydrochloride | 1H NMR (300 MHz, METHANOL-d₄) δ ppm 1.76 (br. s., 6H) 2.01 (br. s., 4H) 3.26 (dd, J = 18.02, 6.52 Hz, 1H) 3.65 (m, 4H) 3.76 (dd, J = 18.02, 12.52 Hz, 1H) 5.96 (dd, J = 12.52, 6.52 Hz, 1H) 7.16-7.28 (m, 5H) 7.40 (d, J = 8.64 Hz, 1H) 7.37 (d, J = 2.34 Hz, 1H) | 479 |
| 146 | 5-(4-bromo-phenyl)-1-(2,4-dichloro-phenyl)-4,5-dihydro-1H-pyrazole-3-carboxylic acid azocan-1-ylamide | | 523 |
| 147 | 5-(4-fluoro-phenyl)-1-(2,4-dichloro-phenyl)-4,5-dihydro-1H-pyrazole-3-carboxylic acid azocan-1-ylamide | | 463 |
| 148 | 5-(4-methoxy-phenyl)-1-(2,4-dichloro-phenyl)-4,5-dihydro-1H-pyrazole-3-carboxylic acid azocan-1-ylamide | 1H NMR (300 MHz, CHLOROFORM-d) δ ppm 1.53-1.62 (m, 2H) 1.68 (br. s., 8 H) 3.10 (m, 4H) 3.34 (dd, J = 18.31, 6.01 Hz, 1H) 3.64 (dd, J = 18.31, 12.01 Hz, 1H) 3.72 (s, 3H) 5.68 (dd, J = 12.01, 6.01 Hz, 1H) 6.70 (d, J = 8.64 Hz, 2H) 7.03 (m, 3H) 7.08-7.13 (m, 1H) 7.23 (d, J = 2.34 Hz, 1H) 7.93 (br. s., 1H) | 475 |
| 149 | 5-(4-hydroxy-phenyl)-1-(2,4-dichloro-phenyl)-4,5-dihydro-1H-pyrazole-3-carboxylic acid azocan-1-ylamide hydrochloride | | 461 |

| No | STRUCTURE | Name | ¹H-NMR | MS (M + H)⁺ |
|---|---|---|---|---|
| 150 | 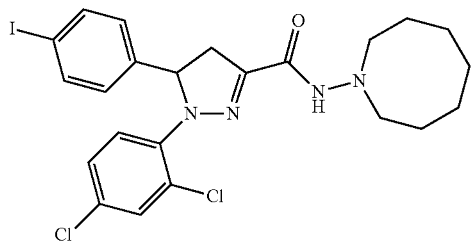 | 5-(4-iodo-phenyl)-1-(2,4-dichloro-phenyl)-4,5-dihydro-1H-pyrazole-3-carboxylic acid azocan-1-ylamide | | 571 |
| 151 | 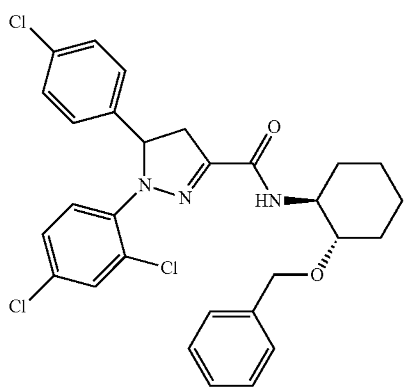 | N-((1S,2S)-2-(benzyloxy)cyclohexyl)-5-(4-chlorophenyl)-1-(2,4-dichlorophenyl)-4,5-dihydro-1H-pyrazole-3-carboxamide | | 556 |
| 152 | 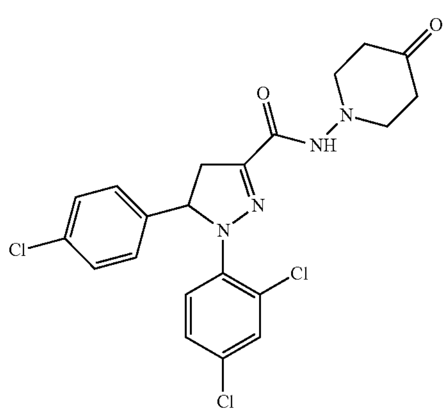 | 5-(4-Chloro-phenyl)-1-(2,4-dichloro-phenyl)-4,5-dihydro-1H-pyrazole-3-carboxylic acid (4-oxo-piperidin-1-yl)-amide | | 465 |
| 153 | 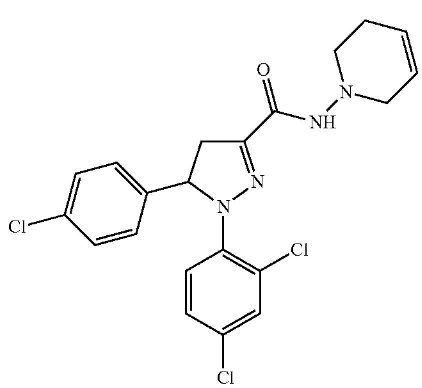 | 5-(4-Chloro-phenyl)-1-(2,4-dichloro-phenyl)-4,5-dihydro-1H-pyrazole-3-carboxylic acid (3,6-dihydro-2H-pyridin-1-yl)-amide | 1H NMR (250 MHz, DMSO-d₆) δ ppm 2.20 (br. s., 2H) 2.96 (t, J = 5.63 Hz, 2H) 3.08 (dd, J = 17.98, 5.76 Hz, 1H) 3.37 (br. s., 2H) 3.67 (dd, J = 17.98, 11.80 Hz, 1H) 5.58-5.74 (m, 2H) 5.81 (dd, J = 11.80, 5.76 Hz, 1H) 7.13-7.24 (m, 2H) 7.30 (d, J = 8.23 Hz, 3H) 7.51 (d, J = 8.78 Hz, 1H) 7.45 (d, J = 2.47 Hz, 1H) 9.41 (s, 1H) | 449 |

-continued

| No | STRUCTURE | Name | ¹H-NMR | MS (M + H)⁺ |
|---|---|---|---|---|
| 154 | 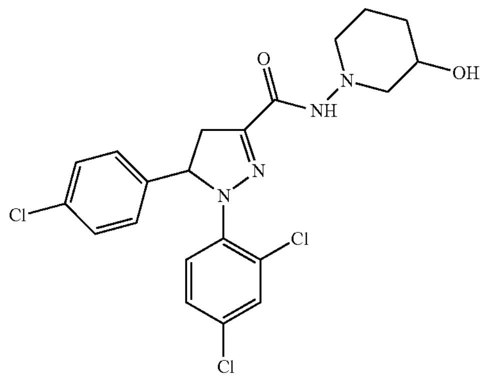 | 5-(4-Chloro-phenyl)-1-(2,4-dichloro-phenyl)-4,5-dihydro-1H-pyrazole-3-carboxylic acid (3-hydroxy-piperidin-1-yl)-amide | 1H NMR (300 MHz, DMSO-d$_6$) δ ppm 1.05 (d, J = 10.26 Hz, 1H) 1.43 (d, J = 10.55 Hz, 1H) 1.52-1.82 (m, 2H) 2.57 (m, 1H) 2.83 (m, 1H) 3.04 (m, 2H) 3.41-3.70 (m, 2H) 4.75 (t, J = 3.66 Hz, 1H) 5.78 (dd, J = 11.57, 5.42 Hz, 1H) 7.14 (d, J = 8.20 Hz, 2H) 7.28 (d, J = 7.91 Hz, 3H) 7.37-7.57 (m, 2H) 9.33 (s, 1H) | 467 |
| 155 | 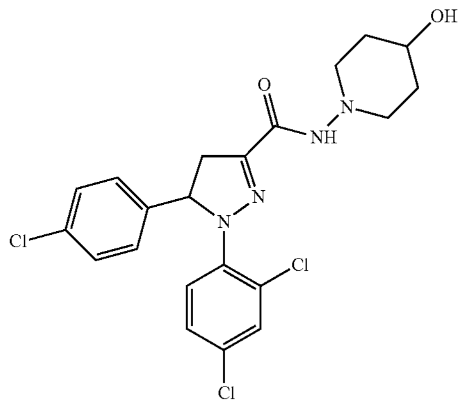 | 5-(4-Chloro-phenyl)-1-(2,4-dichloro-phenyl)-4,5-dihydro-1H-pyrazole-3-carboxylic acid (4-hydroxy-piperidin-1-yl)-amide | 1H NMR (250 MHz, CHLOROFORM-d) δ ppm 1.91 (m, 2H) 2.08 (m, 2H) 2.89 (m, 2H) 3.15 (m, 2H) 3.40 (dd, J = 18.39, 6.31 Hz, 1H) 3.76 (dd, J = 18.39, 12.08 Hz, 1H) 3.91 (d, J = 3.57 Hz, 1H) 5.80 (dd, J = 12.08, 6.31 Hz, 1H) 7.09-7.20 (m, 4H) 7.24 (m, 2H) 7.33 (m, 1H) 7.55 (s, 1H) | 467 |
| 156 | 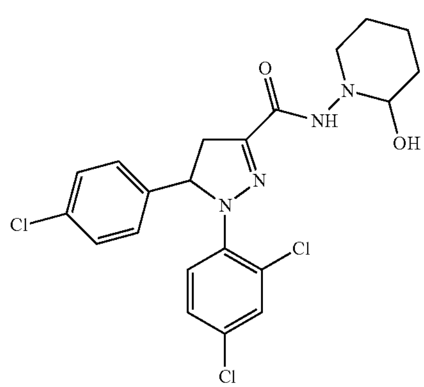 | 5-(4-Chloro-phenyl)-1-(2,4-dichloro-phenyl)-4,5-dihydro-1H-pyrazole-3-carboxylic acid (2-hydroxy-piperidin-1-yl)-amide | | 467 |
| 157 | 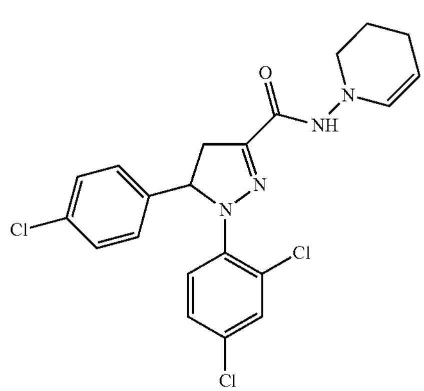 | 5-(4-Chloro-phenyl)-1-(2,4-dichloro-phenyl)-4,5-dihydro-1H-pyrazole-3-carboxylic acid (3,4-dihydro-2H-pyridin-1-yl)-amide | | 449 |

-continued

| No | STRUCTURE | Name | ¹H-NMR | MS (M + H)⁺ |
|---|---|---|---|---|
| 158 | 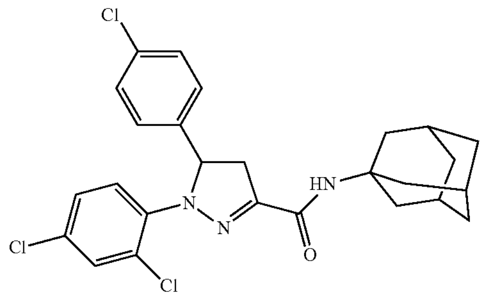 | 5-(4-Chloro-phenyl)-1-(2,4-dichloro-phenyl)-4,5-dihydro-1H-pyrazole-3-carboxylic acid adamantan-1-ylamide | | 502 |
| 159 | 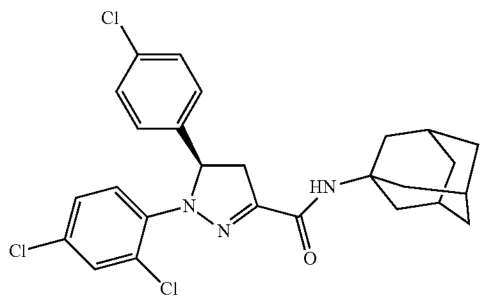 | (R)-5-(4-Chloro-phenyl)-1-(2,4-dichloro-phenyl)-4,5-dihydro-1H-pyrazole-3-carboxylic acid adamantan-1-ylamide | | 502 |
| 160 | 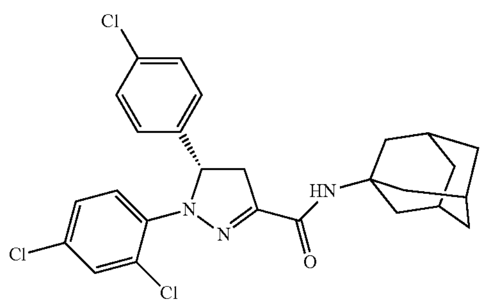 | (S)-5-(4-Chloro-phenyl)-1-(2,4-dichloro-phenyl)-4,5-dihydro-1H-pyrazole-3-carboxylic acid adamantan-1-ylamide | | 502 |
| 161 | 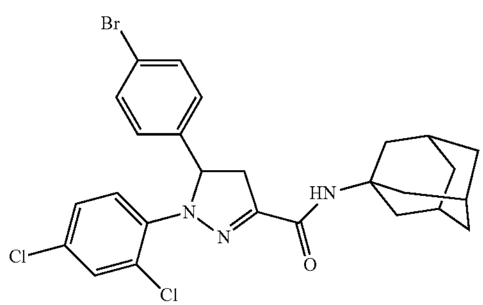 | 5-(4-bromo-phenyl)-1-(2,4-dichloro-phenyl)-4,5-dihydro-1H-pyrazole-3-carboxylic acid adamantan-1-ylamide | | 546 |
| 162 | 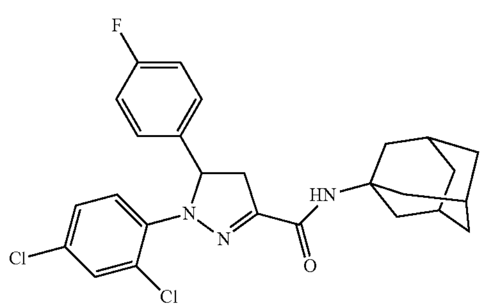 | 5-(4-fluoro-phenyl)-1-(2,4-dichloro-phenyl)-4,5-dihydro-1H-pyrazole-3-carboxylic acid adamantan-1-ylamide | | 486 |

-continued

| No | STRUCTURE | Name | ¹H-NMR | MS (M + H)⁺ |
|---|---|---|---|---|
| 163 | 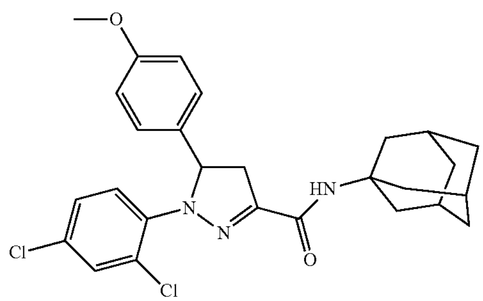 | 5-(4-methoxy-phenyl)-1-(2,4-dichloro-phenyl)-4,5-dihydro-1H-pyrazole-3-carboxylic acid adamantan-1-ylamide | | 498 |
| 164 | 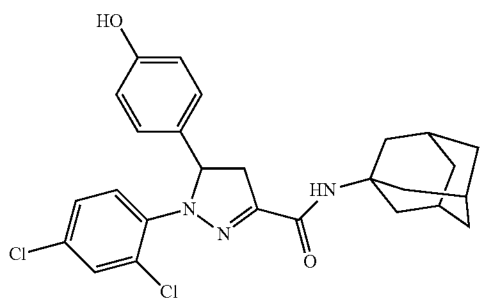 | 5-(4-hydroxy-phenyl)-1-(2,4-dichloro-phenyl)-4,5-dihydro-1H-pyrazole-3-carboxylic acid adamantan-1-ylamide | | 484 |
| 165 | 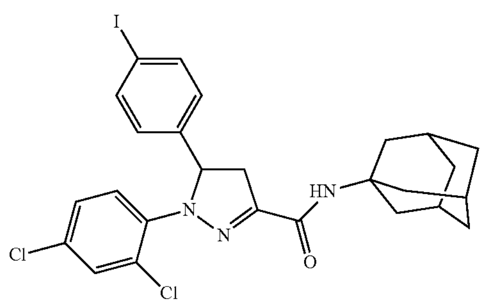 | 5-(4-iodo-phenyl)-1-(2,4-dichloro-phenyl)-4,5-dihydro-1H-pyrazole-3-carboxylic acid adamantan-1-ylamide | | 594 |
| 166 | 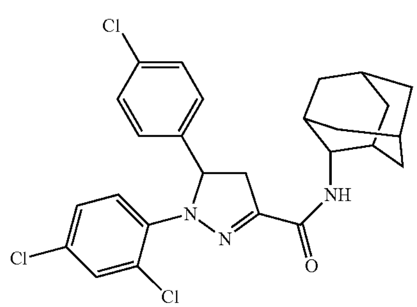 | 5-(4-Chloro-phenyl)-1-(2,4-dichloro-phenyl)-4,5-dihydro-1H-pyrazole-3-carboxylic acid adamantan-2-ylamide | | 502 |
| 167 | 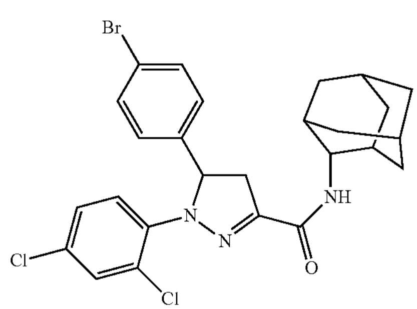 | 5-(4-bromo-phenyl)-1-(2,4-dichloro-phenyl)-4,5-dihydro-1H-pyrazole-3-carboxylic acid adamantan-2-ylamide | | 546 |

-continued

| No | STRUCTURE | Name | ¹H-NMR | MS (M + H)⁺ |
|---|---|---|---|---|
| 168 | 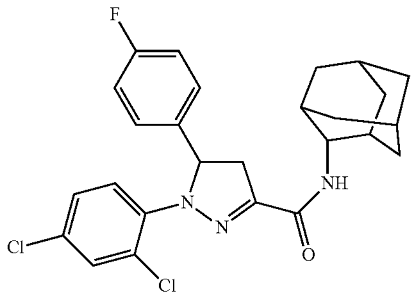 | 5-(4-fluoro-phenyl)-1-(2,4-dichloro-phenyl)-4,5-dihydro-1H-pyrazole-3-carboxylic acid adamantan-2-ylamide | | 486 |
| 169 | 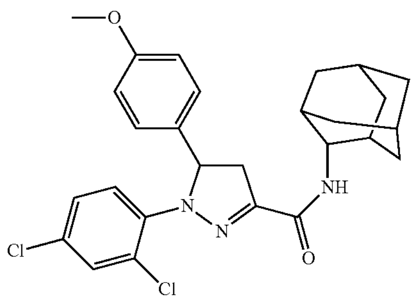 | 5-(4-methoxy-phenyl)-1-(2,4-dichloro-phenyl)-4,5-dihydro-1H-pyrazole-3-carboxylic acid adamantan-2-ylamide | | 498 |
| 170 | 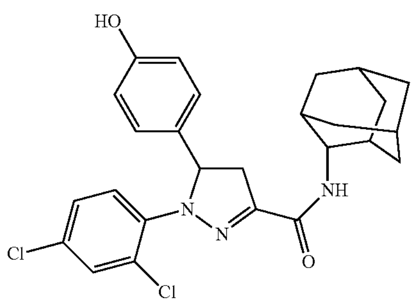 | 5-(4-hydroxy-phenyl)-1-(2,4-dichloro-phenyl)-4,5-dihydro-1H-pyrazole-3-carboxylic acid adamantan-2-ylamide | | 484 |
| 171 | 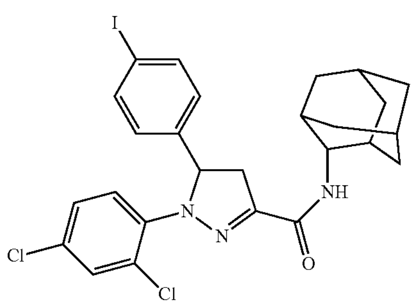 | 5-(4-iodo-phenyl)-1-(2,4-dichloro-phenyl)-4,5-dihydro-1H-pyrazole-3-carboxylic acid adamantan-2-ylamide | | 594 |
| 172 | 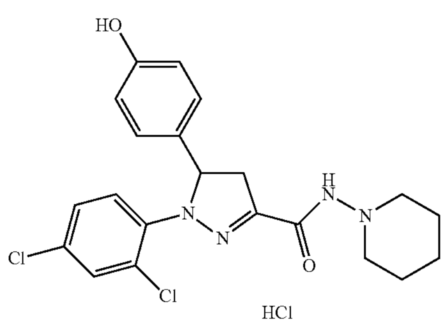 | 1-(2,4-Dichloro-phenyl)-5-(4-hydroxy-phenyl)-4,5-dihydro-1H-pyrazole-3-carboxylic acid piperidin-1-ylamide hydrochloride | 1H NMR (300 MHz, METHANOL-d₄) δ ppm 1.69 (br. s., 2H) 2.00 (br. s., 4H) 3.24 (dd, J = 17.94, 6.23 Hz, 1H) 3.55 (br. s., 4H) 3.69 (dd, J = 17.94, 12.38 Hz, 1H) 5.86 (dd, J = 12.38, 6.23 Hz, 1H) 6.61 (d, J = 8.50 Hz, 2H) 7.00 (d, J = 8.50 Hz, 2H) 7.17 (dd, J = 8.64, 2.20 Hz, 1H) 7.26-7.38 (m, 2H) | 433 |

US 8,207,156 B2

-continued

| No | STRUCTURE | Name | ¹H-NMR | MS (M + H)⁺ |
|---|---|---|---|---|
| 173 | 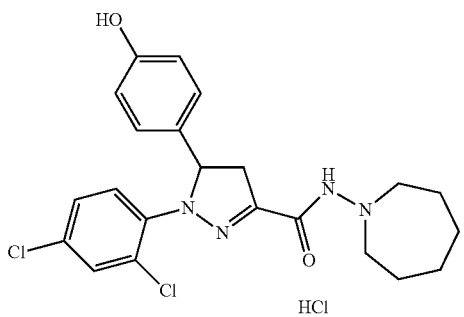 | 1-(2,4-Dichloro-phenyl)-5-(4-hydroxy-phenyl)-4,5-dihydro-1H-pyrazole-3-carboxylic acid azepan-1-ylamide hydrochloride | 1H NMR (300 MHz, DMSO-d₆) δ ppm 0.81 (d, J = 7.18 Hz, 3H) 1.59 (br. s., 4H) 1.78 (br. s., 4H) 3.36 (br. s., 4H) 3.76 (dq, J = 11.28, 7.18 Hz, 1H) 5.81 (d, J = 11.28 Hz, 1H) 6.59 (d, J = 8.50 Hz, 2H) 6.89 (d, J = 8.50 Hz, 2H) 7.31 (dd, J = 8.79, 2.34 Hz, 1H) 7.49 (d, J = 2.34 Hz, 1H) 7.56 (d, J = 8.64 Hz, 1H) 9.43 (br. s., 1H) 10.90 (br. s., 1H) | 447 |
| 174 | 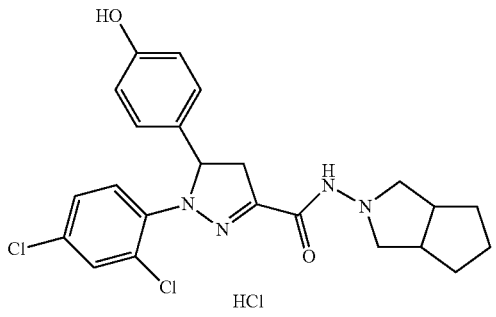 | 1-(2,4-Dichloro-phenyl)-5-(4-hydroxy-phenyl)-4,5-dihydro-1H-pyrazole-3-carboxylic acid (hexahydro-cyclopenta[c]pyrrol-2-yl)-amide hydrochloride | 1H NMR (300 MHz, METHANOL-d₄) ppm 1.68 (br. s., 2H) 1.81 (br. s., 4H) 2.98 (br. s., 2H) 3.06-3.21 (m, 2H) 3.26 (dd, J = 18.02, 6.30 Hz, 1H) 3.71 (dd, J = 18.02, 12.45 Hz, 1H) 4.06 (m, 2H) 5.88 (dd, J = 12.45, 6.30 Hz, 1H) 6.63 (d, J = 8.64 Hz, 2H) 7.02 (d, J = 8.64 Hz, 2H) 7.18 (dd, J = 8.64, 2.34 Hz, 1H) 7.37 (d, J = 2.20 Hz, 1H) 7.34 (d, J = 8.79 Hz, 1H) | 459 |
| 175 | 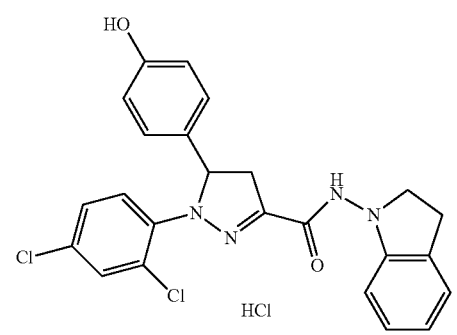 | 1-(2,4-Dichloro-phenyl)-5-(4-hydroxy-phenyl)-4,5-dihydro-1H-pyrazole-3-carboxylic acid (2,3-dihydro-indol-1-yl)-amide hydrochloride | | 467 |
| 176 | 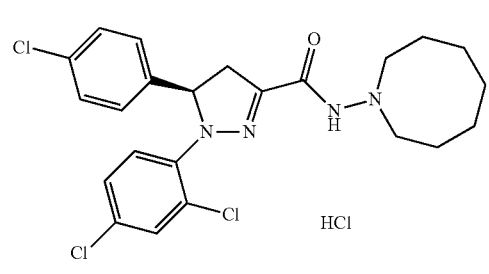 | (R)-5-(4-Chloro-phenyl)-1-(2,4-dichloro-phenyl)-4,5-dihydro-1H-pyrazole-3-carboxylic acid azocan-1-ylamide hydrochloride | 1H NMR (300 MHz, METHANOL-d₄) δ ppm 1.76 (br. s., 6H) 2.01 (br. s., 4H) 3.26 (dd, J = 18.02, 6.52 Hz, 1H) 3.65 (m, 4H) 3.76 (dd, J = 18.02, 12.52 Hz, 1H) 5.96 (dd, J = 12.52, 6.52 Hz, 1H) 7.16-7.28 (m, 5H) 7.40 (d, J = 8.64 Hz, 1H) 7.37 (d, J = 2.34 Hz, 1H) | 479 |

-continued

| No | STRUCTURE | Name | ¹H-NMR | MS (M + H)⁺ |
|---|---|---|---|---|
| 177 | 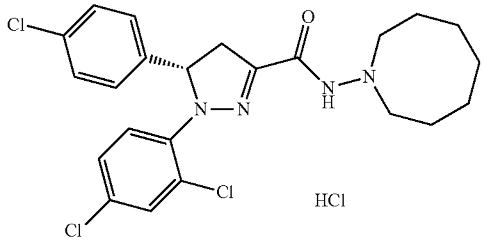 | (S)-5-(4-Chloro-phenyl)-1-(2,4-dichloro-phenyl)-4,5-dihydro-1H-pyrazole-3-carboxylic acid azocan-1-ylamide hydrochloride | 1H NMR (300 MHz, METHANOL-d₄) δ ppm 1.76 (br. s., 6H) 2.01 (br. s., 4H) 3.26 (dd, J = 18.02, 6.52 Hz, 1H) 3.65 (m, 4H) 3.76 (dd, J = 18.02, 12.52 Hz, 1H) 5.96 (dd, J = 12.52, 6.52 Hz, 1H) 7.16-7.28 (m, 5H) 7.40 (d, J = 8.64 Hz, 1H) 7.37 (d, J = 2.34 Hz, 1H) | 479 |
| 184 | 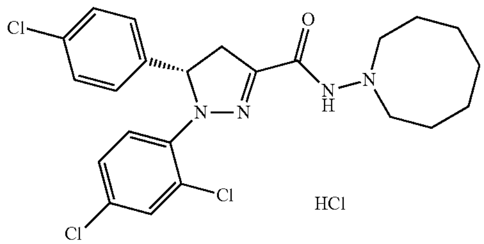 | (S)-5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide hydrochloride | | 477 |
| 188 | 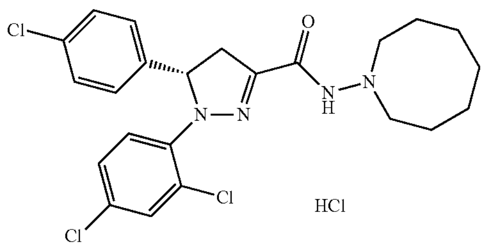 | (R)-5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide | | 477 |
| 193 | 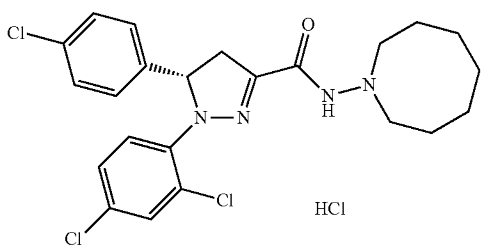 | 5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide hydrochloride | | 477 |
| 196 | 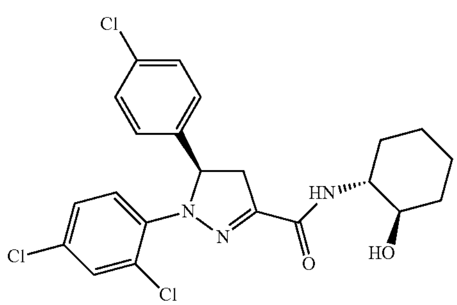 | (R)-5-(4-chlorophenyl)-1-(2,4-dichlorophenyl)-N-((1R,2R)-2-hydroxycyclohexyl)-4,5-dihydro-1H-pyrazole-3-carboxamide | | 466 |

-continued

| No | STRUCTURE | Name | ¹H-NMR | MS (M + H)⁺ |
|---|---|---|---|---|
| 197 | 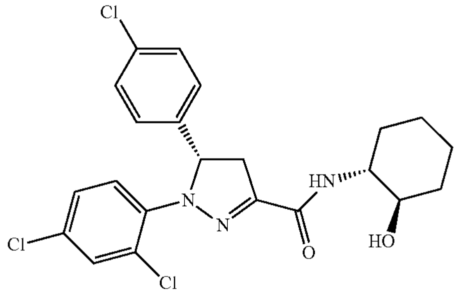 | (S)-5-(4-chlorophenyl)-1-(2,4-dichlorophenyl)-N-((1R,2R)-2-hydroxycyclohexyl)-4,5-dihydro-1H-pyrazole-3-carboxamide | | 466 |
| 198 | 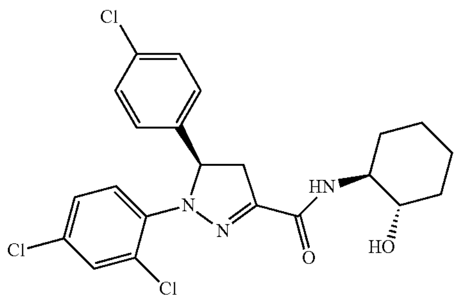 | (R)-5-(4-chlorophenyl)-1-(2,4-dichlorophenyl)-N-((1S,2S)-2-hydroxycyclohexyl)-4,5-dihydro-1H-pyrazole-3-carboxamide | | 466 |
| 199 | 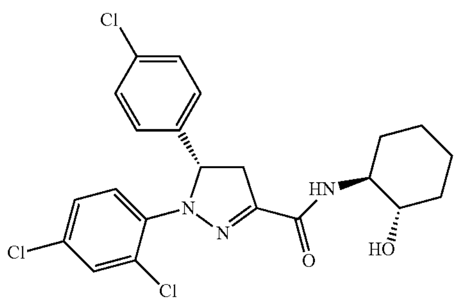 | (S)-5-(4-chlorophenyl)-1-(2,4-dichlorophenyl)-N-((1S,2S)-2-hydroxycyclohexyl)-4,5-dihydro-1H-pyrazole-3-carboxamide | | 466 |
| 200 | 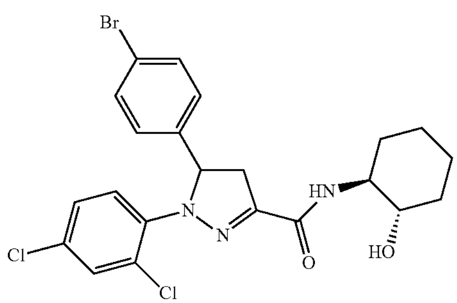 | 5-(4-bromophenyl)-1-(2,4-dichlorophenyl)-N-((1S,2S)-2-hydroxycyclohexyl)-4,5-dihydro-1H-pyrazole-3-carboxamide | | 510 |
| 201 | 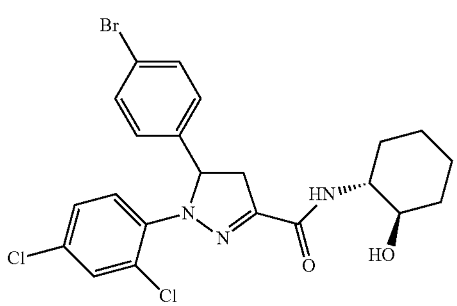 | 5-(4-bromophenyl)-1-(2,4-dichlorophenyl)-N-((1R,2R)-2-hydroxycyclohexyl)-4,5-dihydro-1H-pyrazole-3-carboxamide | | 510 |

| No | STRUCTURE | Name | ¹H-NMR | MS (M + H)⁺ |
|---|---|---|---|---|
| 202 | 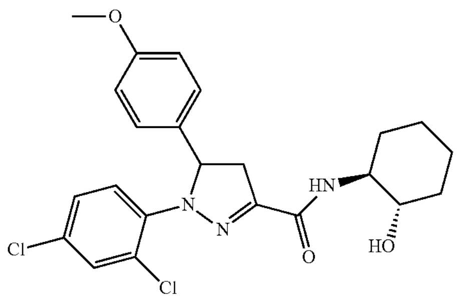 | 1-(2,4-dichlorophenyl)-N-((1S,2S)-2-hydroxycyclohexyl)-5-(4-methoxyphenyl)-4,5-dihydro-1H-pyrazole-3-carboxamide | | 462 |
| 203 | 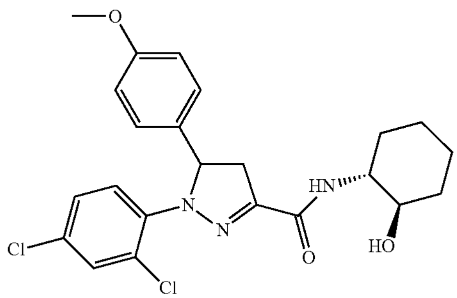 | 1-(2,4-dichlorophenyl)-N-((1R,2R)-2-hydroxycyclohexyl)-5-(4-methoxyphenyl)-4,5-dihydro-1H-pyrazole-3-carboxamide | | 462 |

[178] N-((1R,2R)-2-(benzyloxy)cyclohexyl)-5-(4-chlorophenyl)-1-(2,4-dichlorophenyl)-4,5-dihydro-1H-pyrazole-3-carboxamide [M+H]⁺=556

[179] 1-(2,4-Dichloro-phenyl)-5-(4-fluoro-phenyl)-4,5-dihydro-1H-pyrazole-3-carboxylic acid (2,3-dihydro-indol-1-yl)-amide hydrochloride [M+H]⁺=469

[180] 1-(2,4-Dichloro-phenyl)-5-(4-hydroxy-phenyl)-4,5-dihydro-1H-pyrazole-3-carboxylic acid [M+H]⁺=351

[181] (R)-5-(4-Chloro-phenyl)-1-(2,4-dichloro-phenyl)-4,5-dihydro-1H-pyrazole-3-carboxylic acid (2,3-dihydro-indol-1-yl)-amide hydrochloride [M+H]⁺=485

[182] (S)-5-(4-Chloro-phenyl)-1-(2,4-dichloro-phenyl)-4,5-dihydro-1H-pyrazole-3-carboxylic acid (2,3-dihydro-indol-1-yl)-amide hydrochloride [M+H]⁺=485

[183] (S)-5-(4-Chloro-phenyl)-1-(2,4-dichloro-phenyl)-4,5-dihydro-1H-pyrazole-3-carboxylic acid azepan-1-ylamide hydrochloride [M+H]⁺=465

[184] (S)-5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide hydrochloride [M+H]⁺=477

[185] (S)-5-(4-Chloro-phenyl)-1-(2,4-dichloro-phenyl)-4,5-dihydro-1H-pyrazole-3-carboxylic acid azepan-1-ylamide [M+H]⁺=465

[186] (S)-5-(4-Chloro-phenyl)-1-(2,4-dichloro-phenyl)-4,5-dihydro-1H-pyrazole-3-carboxylic acid cycloheptylamide [M+H]⁺=464

[187] (R)-5-(4-Chloro-phenyl)-1-(2,4-dichloro-phenyl)-4,5-dihydro-1H-pyrazole-3-carboxylic acid azepan-1-ylamide hydrochloride [M+H]⁺=465

[188] (R)-5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide [M+H]⁺=477

[189] (R)-5-(4-Chloro-phenyl)-1-(2,4-dichloro-phenyl)-4,5-dihydro-1H-pyrazole-3-carboxylic acid cycloheptylamide [M+H]⁺=464

[190] (R)-5-(4-Chloro-phenyl)-1-(2,4-dichloro-phenyl)-4,5-dihydro-1H-pyrazole-3-carboxylic acid (2,3-dihydro-indol-1-yl)-amide [M+H]⁺=485

[191] 5-(4-Chloro-phenyl)-1-(2,4-dichloro-phenyl)-4,5-dihydro-1H-pyrazole-3-carboxylic acid cycloheptylmethyl-amide [M+H]⁺=478

[192] 5-(4-Chloro-phenyl)-1-(2,4-dichloro-phenyl)-4,5-dihydro-1H-pyrazole-3-carboxylic acid (2,6-dimethyl-piperidin-1-yl)-amide hydrochloride [M+H]⁺=479

[193] 5-(4-Chloro-phenyl)-1-(2,4-dichloro-phenyl)-4,5-dihydro-1H-pyrazole-3-carboxylic acid (hexahydro-cyclopenta[c]pyrrol-2-yl)-amide hydrochloride [M+H]⁺=477

[194] 5-(4-Chloro-phenyl)-1-(2,4-dichloro-phenyl)-4,5-dihydro-1H-pyrazole-3-carboxylic acid pyrrolidin-1-ylamide hydrochloride [M+H]⁺=437

[195] [5-(4-Chloro-phenyl)-1-(2,4-dichloro-phenyl)-4,5-dihydro-1H-pyrazole-3-yl]-(4-methyl-piperazin-1-yl)-methanone hydrochloride [M+H]⁺=451

[60A] 5-(4-Bromo-phenyl)-1-(2,4-dichloro-phenyl)-4,5-dihydro-1H-pyrazole-3-carboxylic acid piperidin-1-ylamide

[66A] 5-(4-Bromo-phenyl)-1-(2,4-dichloro-phenyl)-4,5-dihydro-1H-pyrazole-3-carboxylic acid (2,3-dihydro-indol-1-yl)-amide

[82A] 5-(4-Chloro-phenyl)-1-(2,4-dichloro-phenyl)-4,5-dihydro-1H-pyrazole-3-carboxylic acid (2-(R)-hydroxy-cyclohexyl)-amide

[83A] 5-(4-Chloro-phenyl)-1-(2,4-dichloro-phenyl)-4,5-dihydro-1H-pyrazole-3-carboxylic acid (2-(S)-hydroxy-cyclohexyl)-amide

[91A] 1-(2,4-Dichloro-phenyl)-5-(4-fluoro-phenyl)-4,5-dihydro-1H-pyrazole-3-carboxylic acid (hexahydro-cyclopenta[c]pyrrol-2-yl)-amide

[106A] 1-(2,4-Dichloro-phenyl)-5-(4-methoxy-phenyl)-4,5-dihydro-1H-pyrazole-3-carboxylic acid piperidin-1-ylamide

[109A] 1-(2,4-Dichloro-phenyl)-5-(4-methoxy-phenyl)-4,5-dihydro-1H-pyrazole-3-carboxylic acid (hexahydro-cyclopenta[c]pyrrol-2-yl)-amide

[112A] 1-(2,4-Dichloro-phenyl)-5-(4-methoxy-phenyl)-4,5-dihydro-1H-pyrazole-3-carboxylic acid (2,3-dihydro-indol-1-yl)-amide

[114A] 1-(2,4-Dichloro-phenyl)-5-(4-methoxy-phenyl)-4,5-dihydro-1H-pyrazole-3-carboxylic acid azepan-1-ylamide;

I. In-Vitro Determination of Affinity to CB1/CB2-Receptors

The binding data for some of the inventive compounds was obtained as described above in the section pharmacological methods, part I, and is given in the following table (table 1).

TABLE 1

| Compound according to example | $IC_{50}$ [nM] | Inhibition [%], $10^{-7}$ M | Inhibition [%], $10^{-8}$ M |
|---|---|---|---|
| 7 | 146 | 71.2 | −12.8 |
| 8 |  | 21.9 | −8.2 |
| 11 | 630 |  |  |
| 12 | 250 |  |  |
| 13 |  | 31.8 | 14.3 |
| 16 | 26.3 |  |  |
| 18 | 25.1 |  |  |
| 22 | 79.4 |  |  |
| 23 | 39.8 |  |  |
| 27 | 117 | 50.7 | 32.9 |
| 29 | >1000 |  |  |
| 31 | >1000 |  |  |
| 32 | 84 | 52.7 | 12 |
| 34 | 56.2 |  |  |
| 37 | 280 |  |  |
| 41 |  | 3.4 | −5.2 |
| 52 | 251.2 |  |  |
| 57 | 39.8 |  |  |
| 60 | 27 |  |  |
| 60A | 44 | 65.8 | 33.3 |
| 63 | 25.1 |  |  |
| 64 | 562.3 |  |  |
| 66 | 100 |  |  |
| 68 | 39.8 |  |  |
| 69 | 354.8 |  |  |
| 72 |  | 19.6 | −10.2 |
| 73 |  | −18.9 | 15.7 |
| 74 | 794.3 |  |  |
| 75 | >1000 |  |  |
| 76 | 398.1 |  |  |
| 80 | 501.2 |  |  |
| 81 | 707.9 |  |  |
| 87 |  | 15.2 | −2.4 |
| 91 | 47 | 79.1 | 43 |
| 91A | 84 | 75.3 | 34.9 |
| 96 | 56 | 74.8 | 43.3 |
| 106 | 32 | 76.1 | 23.4 |
| 106A | 20 |  |  |
| 109 | 16 | 80.6 | 44 |
| 109A | 15 | 74.2 | 33.5 |
| 112 | 106 | 61.8 | 46.3 |
| 114 | 24 | 68.7 | 47.6 |
| 114A | 18 | 79.3 | 41.4 |
| 115 |  | −4.3 | 1.9 |
| 120 |  | 7.1 | −4.1 |
| 127 |  | 7.8 | 7.4 |
| 130 | 52 | 67.7 | 33.1 |
| 131 | 115 | 70.2 | 42.9 |
| 132 |  | 37.8 | 18.2 |
| 133 |  | 31.4 | 13.8 |
| 135 | 83 | 78.5 | 40.2 |
| 145 |  | 57.6 | 12.3 |
| 146 | 12 | 71.8 | 35.2 |
| 147 | 54 | 63.4 | 24.0 |
| 148 |  | 80.3 | 56.1 |
| 151 | 32 | 82.3 | 67.5 |
| 172 |  | 1.4 | 5.6 |
| 176 |  | 71.3 | 29.5 |
| 177 |  | 22.2 | −5.4 |
| 178 | 119 | 58 | 41.2 |
| 179 |  | 33.9 | 11.5 |
| 180 |  | 9.3 | 4.7 |
| 181 | 24 | 50.6 | 33.7 |
| 182 |  | 31.7 | 18.8 |
| 183 |  | 31.9 | 3.2 |
| 184 |  | 24.8 | 5.7 |
| 185 |  | 34.1 | −11.6 |
| 186 |  | 28.1 | 3.2 |
| 187 | 7.9 |  |  |
| 188 | 15.8 |  |  |
| 189 | 15.8 |  |  |
| 190 | 100 |  |  |
| 191 |  | 67.4 | 30.2 |
| 192 | 501.2 |  |  |
| 193 | 70.8 |  |  |
| 194 |  | 41.7 | 22.9 |
| 195 |  | 5.8 | 4.7 |

The antagonism of the pyrazoline compounds of general formula I to the CB1-receptor was determined according to the method described in Pharmacological methods, part V (table 2).

TABLE 2

| Compound according to example | Antagonism [%] |
|---|---|
| 8 | 54 |
| 9 | 53 |
| 10 | 119 |
| 12 | 78 |
| 15 | 6 |
| 17 | 65 |
| 18 | 78 |
| 20 | 61 |
| 21 | 66 |
| 22 | 62 |
| 23 | 91 |
| 24 | 27 |
| 25 | 7 |
| 26 | 52 |
| 27 | 31 |
| 28 | 63 |
| 30 | 54 |
| 33 | 2 |
| 34 | 60 |
| 35 | 68 |
| 36 | −5 |
| 37 | 81 |
| 38 | 45 |
| 39 | 62 |
| 40 | 32 |
| 41 | 69 |
| 42 | −13 |
| 43 | 25 |
| 44 | 39 |
| 45 | 59 |
| 46 | 53 |
| 47 | 28 |
| 49 | 14 |
| 50 | 18 |
| 51 | 21 |
| 53 | 14 |
| 54 | 46 |
| 55 | 30 |
| 56 | 44 |
| 57 | 81 |
| 58 | 47 |
| 59 | 60 |
| 61 | 75 |
| 62 | 67 |
| 63 | 119 |
| 64 | 63 |
| 66 | 86 |
| 67 | 52 |
| 68 | 98 |
| 74 | 44 |
| 75 | 42 |
| 76 | 57 |
| 80 | 56 |
| 81 | 20 |

TABLE 2-continued

| Compound according to example | Antagonism [%] |
|---|---|
| 106A | 112 |
| 115 | 23 |
| 120 | 30 |
| 126 | 30 |
| 128 | 18 |
| 191 | 82 |
| 192 | 63 |
| 193 | 115 |
| 194 | 82 |

What is claimed is:

1. A method for the treatment of obesity, the method comprising administering, to a patient, a medicament comprising a substituted pyrazoline compound of formula I

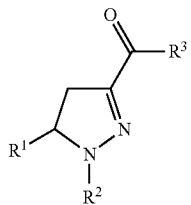

wherein $R^1$ represents an unsubstituted or at least mono-substituted phenyl radical;

$R^2$ represents an unsubstituted or at least mono-substituted phenyl radical;

$R^3$ represents an unsubstituted or at least mono-substituted radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydroindolizinyl, decahydroquinolinyl, dodecahydrocarbazolyl, 9H-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-azabicyclo[3.2.1]octyl, 8-aza-spiro[4.5]decanyl and (2,3)-dihydro-1H-cyclopenta[b]-indolyl, a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$C_{1-6}$-alkyl substituted with one or more hydroxy groups, —$C_{1-6}$-alkyl substituted with one or more chlorine atoms, —$C_{1-6}$-alkyl substituted with one or more methoxy or ethoxy groups, —O—$C_{1-6}$-alkyl substituted with one or more methoxy or ethoxy groups, —S—$C_{1-6}$-alkyl, —C(=O)—O—$C_{1-6}$-alkyl, —O—C(=O)—$C_{1-6}$-alkyl, —$SCF_3$, —$SCF_2H$, —$SCFH_2$, —SH, —$SO_3H$, —NH—C(=O)—$C_{1-6}$-alkyl, —N($C_{1-6}$-alkyl)-C(=O)—$C_{1-6}$-alkyl, —CHO, —C(=O)—$C_{1-6}$-perfluoroalkyl, —C(=S)—NH—$C_{1-6}$-alkyl, —$CF_2H$, —$CFH_2$, —C(=O)—NH—$NR^CR^D$, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —$NR^AR^B$, —($C_{1-5}$-alkylene)-$NR^AR^B$, —S(=O)$_2$—NH—$C_{1-6}$-alkyl, —S(=O)$_2$—NH-phenyl, cyclopropyl, cyclobutyl, cyclopentyl, cyclohexyl, pyrrolidinyl, piperidinyl, thiophenyl, phenoxy and benzyl; whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —$CF_3$, —CN, —$NO_2$, —$C_{1-6}$-alkyl, —O—$C_{1-6}$-alkyl, —O—$CF_3$ and —S—$CF_3$;

a —$NR^4R^5$ moiety or a —O—$R^6$ moiety;

$R^4$ represents a hydrogen atom or a saturated or unsaturated, unsubstituted or at least mono-substituted aliphatic radical;

$R^5$ represents an unsubstituted or at least mono-substituted radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)octyl, —O-methyl, —O-ethyl, —O-n-propyl, —O-isopropyl, —O-n-butyl, —O-isobutyl, —O-tert-butyl, —O-n-pentyl and —O-n-hexyl;

a substituted radical selected from the group consisting of methyl, ethyl, n-propyl, isopropyl, n-butyl, sec-butyl, tert-butyl, n-pentyl, n-hexyl, n-heptyl and n-octyl, which is substituted with 1, 2, 3, 4, 5, 6, 7, 8 or 9 substituents independently selected from the group consisting of —NH—$C_{1-6}$-alkyl, —N($C_{1-6}$-alkyl)$_2$, —C(=O)—O—$C_{1-6}$-alkyl and —NH—C(=O)—$C_{1-6}$-alkyl;

an unsubstituted or at least mono-substituted radical selected from the group consisting of adamantyl, cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3, 4)-tetrahydroisoquinolinyl, octahydro-cyclopenta[c]pyrrolyl, (1,3,4,7,9a)-hexahydro-2H-quinolizinyl, (1,2,3,5,6,8a)-hexahydroindolizinyl, decahydroquinolinyl, dodecahydro-carbazolyl, 9H-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl,
adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-azaspiro[4.5]decanyl and (2,3)-dihydro-1H-cyclopenta[b]-indolyl,
a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$C_{1-6}$-alkyl substituted with one or more hydroxy groups, —$C_{1-6}$-alkyl substituted with one or more chlorine atoms, —$C_{1-6}$-alkyl substituted with one or more methoxy or ethoxy groups, —O—$C_{1-6}$-alkyl substituted with one or more methoxy or ethoxy groups, —S—$C_{1-6}$-alkyl, —C(=O)—O—$C_{1-6}$-alkyl, —O—C(=O)—$C_{1-6}$-alkyl, —SCF$_3$, —SCF$_2$H, —SCFH$_2$, —SH, —SO$_3$H, —NH—C(=O)—$C_{1-6}$-alkyl, —N($C_{1-6}$-alkyl)-C(=O)—$C_{1-6}$-alkyl, —CHO, —C(=O)—$C_{1-6}$-perfluoroalkyl, —C(=S)—NH—$C_{1-6}$-alkyl, —CF$_2$H, —CFH$_2$, —C(=O)—NH—NR$^C$R$^D$, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —NR$^A$R$^B$, —($C_{1-5}$-alkylene)-NR$^A$R$^B$, —S(=O)$_2$—NH—$C_{1-6}$-alkyl, —S(=O)$_2$—NH-phenyl, cyclopropyl, cyclobutyl, cyclopentyl, cyclohexyl, pyrrolidinyl, piperidinyl, thiophenyl, —O-Benzyl, phenoxy and benzyl;
whereby in each case the cyclic moieties cyclopropyl, cyclobutyl, cyclopentyl, phenyl, cyclohexyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —CF$_3$, —CN, —NO$_2$, —$C_{1-6}$-alkyl, —O—$C_{1-6}$-alkyl, —O—CF$_3$ and —S—CF$_3$;
a saturated or unsaturated, unsubstituted or at least mono-substituted, optionally at least one heteroatom as a ring member containing cycloaliphatic radical, which is bonded via an unsubstituted or at least mono-substituted alkylene group, alkenylene group or alkinylene group may be condensed with an unsubstituted or at least mono-substituted mono- or polycyclic ring system or may be bridged by at least one unsubstituted or at least mono-substituted alkylene group;
a —NR$^7$R$^8$ moiety; a —P(=O)(OR$^9$)$_2$ moiety; a —C(=O)—OR$^{10}$ moiety; a —C(=O)—NH—R$^{11}$ moiety or a —C(=O)—R$^{12}$ moiety;
R$^6$ represents an unsubstituted or at least mono-substituted $C_{5-16}$ alkyl radical, $C_{2-16}$ alkenyl radical or $C_{2-16}$ alkinyl radical;
or a saturated or unsaturated, unsubstituted or at least mono-substituted, optionally at least one heteroatom as a ring member containing cycloaliphatic radical, which may be condensed with an unsubstituted or at least mono-substituted mono- or polycyclic ring system or may be bridged by at least one unsubstituted or at least mono-substituted alkylene group;
a —P(=O)(OR$^9$)$_2$ moiety; a —C(=O)—OR$^{10}$ moiety; a —C(=O)—NH—R$^{11}$ moiety or a —C(=O)—R$^{12}$ moiety;
R$^7$ represents a hydrogen atom or a saturated or unsaturated, unsubstituted or at least mono-substituted aliphatic radical;
R$^8$ represents an unsubstituted or at least mono-substituted radical selected from the group consisting of 2-pentyl, 3-pentyl, neo-pentyl, 2-hexyl, 3-hexyl, 2-heptyl, 3-heptyl, 4-heptyl, 2-octyl, 3-octyl, 4-octyl, 2-(6-methyl)-heptyl, 2-(5-methyl)-heptyl, 2-(5-methyl)-hexyl, 2-(4-methyl)-hexyl, 2-(7-methyl)-octyl, 2-(6-methyl)-octyl, —O-methyl, —O-ethyl, —O-n-propyl, —O-isopropyl, —O-n-butyl, —O-isobutyl, —O-tert-butyl, —O-n-pentyl and —O-n-hexyl;
a substituted radical selected from the group consisting of methyl, ethyl, n-propyl, isopropyl, n-butyl, sec-butyl, tert-butyl, n-pentyl, n-hexyl, n-heptyl and n-octyl, which is substituted with 1, 2, 3, 4, 5, 6, 7, 8 or 9 substituents independently selected from the group consisting of —NH—$C_{1-6}$-alkyl, —N($C_{1-6}$-alkyl)$_2$, —C(=O)—O—$C_{1-6}$-alkyl and —NH—C(=O)—$C_{1-6}$-alkyl;
an unsubstituted or at least mono-substituted radical selected from the group consisting of cyclononyl, cyclodecyl, cycloundecyl, cyclododecyl, cyclotridecyl, cyclotetradecyl, aziridinyl, azetidinyl, imidazolidinyl, thiomorpholinyl, pyrazolidinyl, tetrahydrofuranyl, tetrahydrothiophenyl, azepanyl, diazepanyl, azocanyl, (2,5)-dihydrofuranyl, (2,5)-dihydrothiophenyl, (2,3)-dihydrofuranyl, (2,3)-dihydrofuranyl, (2,5)-dihydro-1H-pyrrolyl, (2,3)-dihydro-1H-pyrrolyl, tetrahydrothiopyranyl, tetrahydropyranyl, (3,4)-dihydro-2H-pyranyl, (3,4)-dihydro-2H-thiopyranyl, (1,2,3,6)-tetrahydropyridinyl, (1,2,3,4)-tetrahydropyridinyl, (1,2,5,6)-tetrahydropyridinyl, [1,3]-oxazinanyl, hexahydropyrimidinyl, (5,6)-dihydro-4H-pyrimidinyl, oxazolidinyl, (1,3)-dioxanyl, (1,4)-dioxanyl, (1,3)-dioxolanyl, indolinyl, isoindolinyl, decahydronaphthyl, (1,2,3,4)-tetrahydroquinolinyl, (1,2,3,4)-tetrahydroisoquinolinyl, octahydro-cyclopenta[c]pyrrolyl, (1,3,4,7,9a)-hexahydro-2H-quinolizinyl, (1,2,3,5,6,8a)-hexahydroindolizinyl, decahydroquinolinyl, dodecahydro-carbazolyl, 9H-carbazolyl, decahydroisoquinolinyl, (6,7)-dihydro-4H-thieno[3,2-c]pyridinyl, (2,3)-dihydro-1H-benzo[de]isoquinolinyl, (1,2,3,4)-tetrahydroquinoxazlinyl, adamantyl, [1,2,3,4]-tetrahydronaphthyl, bicyclo[2.2.1]heptyl, bicyclo[3.1.1]heptyl, norbornenyl, 8-aza-bicyclo[3.2.1]octyl, 8-azaspiro[4.5]decanyl and (2,3)-dihydro-1H-cyclopenta[b]-indolyl,
a substituted radical selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl, homopiperazinyl and morpholinyl, which is substituted with 1, 2, 3, 4 or 5 substituent(s) independently selected from the group consisting of thioxo (=S), —$C_{1-6}$-alkyl substituted with one or more hydroxy groups, —$C_{1-6}$-alkyl substituted with one or more chlorine atoms, —$C_{1-6}$-alkyl substituted with one or more methoxy or ethoxy groups, —O—$C_{1-6}$-alkyl substituted with one or more methoxy or ethoxy groups, —S—$C_{1-6}$-alkyl, —C(=O)—

$O$—$C_{1-6}$-alkyl, —O—C(=O)—$C_{1-6}$-alkyl, —$SCF_3$, —$SCF_2H$, —$SCFH_2$, —SH, —$SO_3H$, —NH—C(=O)—$C_{1-6}$-alkyl, —N($C_{1-6}$-alkyl)-C(=O)—$C_{1-6}$-alkyl, —CHO, —C(=O)—$C_{1-6}$-perfluoroalkyl, —C(=S)—NH—$C_{1-6}$-alkyl, —$CF_2H$, —$CFH_2$, —C(=O)—NH—$NR^CR^D$, —S(=O)$_2$-phenyl, —($C_{1-5}$-alkylene)-S—$C_{1-6}$-alkyl, —($C_{1-5}$-alkylene)-S(=O)—$C_{1-6}$-alkyl, —($C_{1-5}$-alkylene)-S(=O)$_2$—$C_{1-6}$-alkyl, —$NR^AR^B$, —($C_{1-5}$-alkylene)-$NR^AR^B$, —S(=O)$_2$—NH—$C_{1-6}$-alkyl, —S(=O)$_2$—NH-phenyl, cyclopropyl, cyclobutyl, cyclopentyl, cyclohexyl, pyrrolidinyl, piperidinyl, thiophenyl, phenoxy and benzyl; whereby in each case the cyclic moieties cyclopropyl, cyclobutyl, cyclopentyl, cyclohexyl, phenyl, pyrrolidinyl, piperidinyl, thiophenyl, phenoxy and benzyl can optionally be substituted with 1, 2, 3, 4 or 5 substituent(s) independently selected from the group consisting of F, Cl, Br, I, —OH, —$CF_3$, —CN, —$NO_2$, —$C_{1-6}$-alkyl, —O—$C_{1-6}$-alkyl, —O—$CF_3$ and —S—$CF_3$;

or a saturated or unsaturated, unsubstituted or at least mono-substituted, optionally at least one heteroatom as a ring member containing cycloaliphatic radical, which is bonded via an unsubstituted or at least mono-substituted alkylene group, alkenylene group or alkinylene group may be condensed with an unsubstituted or at least mono-substituted mono- or polycyclic ring system or may be bridged by at least one unsubstituted or at least mono-substituted alkylene group;

$R^9$, $R^{10}$, $R^{11}$ and $R^{12}$, independently of one another, in each case represent a saturated or unsaturated, unsubstituted or at least mono-substituted aliphatic radical;

or an unsubstituted or at least mono-substituted aryl or heteroaryl radical, which may be condensed with an unsubstituted or at least mono-substituted mono- or polycyclic ring system or may be bonded via an unsubstituted or at least mono-substituted alkylene group, alkenylene group or alkinylene group;

$R^A$ and $R^B$, independently of one another, in each case represent —$C_{1-6}$-alkyl or $R^A$ and $R^B$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more identical or different $C_{1-6}$ alkyl radicals; and $R^C$ and $R^D$, independently of one another, in each case represent hydrogen, —$C_{1-6}$-alkyl, —C(=O)—O—$C_{1-6}$-alkyl, $C_{3-8}$-cycloalkyl, —($C_{1-5}$-alkylene)-$C_{3-8}$-cycloalkyl, —($C_{1-6}$-alkylene)-O—$C_{1-6}$-alkyl or —$C_{1-6}$-alkyl substituted with one or more hydroxy groups or $R^C$ and $R^D$ in each case together with the bridging nitrogen atom form a radical selected from the group consisting of pyrrolidinyl, imidazolidinyl, piperazinyl, piperidinyl, thiomorpholinyl, morpholinyl, azepanyl and diazepanyl which may be at least mono-substituted with one or more substituents independently selected from the group consisting —$C_{1-6}$-alkyl, —C(=O)—$C_{1-6}$-alkyl, —C(=O)—O—$C_{1-6}$-alkyl, —C(=O)—NH—$C_{1-6}$-alkyl, —C(=S)—NH—$C_{1-6}$-alkyl, oxo (=O), —$C_{1-6}$-alkyl substituted with one or more hydroxy groups, —($C_{1-6}$-alkylene)-O—$C_{1-6}$-alkyl and —C(=O)—$NH_2$;

optionally in a form of one of its stereoisomers or a racemate or in a form of a mixture of at least two of its stereoisomers, in any mixing ratio, or a corresponding N-oxide thereof, or a physiologically acceptable salt thereof.

\* \* \* \* \*